US011149320B1

(12) United States Patent
Brambati et al.

(10) Patent No.: US 11,149,320 B1
(45) **Date of Patent: *Oct. 19, 2021**

(54) ASSAYS FOR THE DETECTION OF SARS-COV-2

(71) Applicant: DiaSorin S.p.A., Saluggia (IT)

(72) Inventors: Chiara Brambati, Saluggia (IT); Simone Bocchetta, Saluggia (IT); Giulia Minnucci, Saluggai (IT)

(73) Assignee: DiaSorin S.p.A., Saluggia (IT)

( * ) Notice: Subject to any disclaimer, the term of this patent is extended or adjusted under 35 U.S.C. 154(b) by 0 days.

This patent is subject to a terminal disclaimer.

(21) Appl. No.: 17/078,249

(22) Filed: Oct. 23, 2020

Related U.S. Application Data

(63) Continuation-in-part of application No. 16/837,364, filed on Apr. 1, 2020, now Pat. No. 10,815,539.

(30) Foreign Application Priority Data

Mar. 31, 2020 (IT) ........................ 102020000006754

(51) Int. Cl.
*C12Q 1/68* (2018.01)
*C12Q 1/70* (2006.01)

(52) U.S. Cl.
CPC .................................... *C12Q 1/701* (2013.01)

(58) Field of Classification Search
CPC ........................................................ C12Q 1/68
USPC ........................................................ 435/6.12
See application file for complete search history.

(56) References Cited

U.S. PATENT DOCUMENTS

| | | | |
|---|---|---|---|
| 4,683,202 | A | 7/1987 | Mullis |
| 6,974,670 | B2 | 12/2005 | Notomi et al. |
| 7,175,985 | B1 | 2/2007 | Kanda et al. |
| 7,348,141 | B2 | 3/2008 | French et al. |
| 7,393,638 | B2 | 7/2008 | Chou |
| 7,399,588 | B2 | 7/2008 | Minekawa et al. |
| 7,494,790 | B2 | 2/2009 | Notomi et al. |
| 7,527,967 | B2 | 5/2009 | Chao et al. |
| 7,566,533 | B2 | 7/2009 | Jacobs et al. |
| 7,582,740 | B2 | 9/2009 | Briese et al. |
| 7,622,112 | B2 | 11/2009 | Berry et al. |
| 7,638,280 | B2 | 12/2009 | Kanda et al. |
| 7,709,188 | B2 | 5/2010 | Kostrikis |
| 7,736,850 | B2 | 6/2010 | Van Der Werf et al. |

(Continued)

FOREIGN PATENT DOCUMENTS

| | | | |
|---|---|---|---|
| CN | 111057798 A | * | 4/2020 |
| CN | 111273026 A | * | 6/2020 |

(Continued)

OTHER PUBLICATIONS

Al Johani, S. et al. (2016) "*MERS-CoV Diagnosis: An Update*," J. Infect. Public Health 9(3):216-219.

(Continued)

*Primary Examiner* — Aaron A Priest
(74) *Attorney, Agent, or Firm* — Jeffrey I. Auerbach; AuerbachSchrot LLC

(57) ABSTRACT

The present invention is directed to methods for assaying for the presence of SARS-CoV-2 in a sample, including a clinical sample, and to oligonucleotides, reagents, and kits useful in such assays. In particular, the present invention is directed to such assays that are rapid, accurate and specific for the detection of SARS-CoV-2.

30 Claims, 2 Drawing Sheets

Specification includes a Sequence Listing.

(56) References Cited

U.S. PATENT DOCUMENTS

| | | | |
|---|---|---|---|
| 7,998,673 | B2 | 8/2011 | French et al. |
| 8,142,997 | B2 | 3/2012 | Scholl et al. |
| 8,343,718 | B2 | 1/2013 | Van Der Werf et al. |
| 8,445,650 | B2 | 3/2013 | Simpson et al. |
| 8,541,003 | B2 | 9/2013 | Anderson et al. |
| 8,784,829 | B2 | 7/2014 | Morsey et al. |
| 8,906,622 | B2 | 12/2014 | Morley et al. |
| 9,067,205 | B2 | 6/2015 | Ludowise et al. |
| 9,132,423 | B2 | 9/2015 | Battrell et al. |
| 9,909,168 | B2 | 3/2018 | Notomi et al. |
| 9,945,856 | B2 | 4/2018 | van der Hoek |
| 10,619,151 | B2 | 4/2020 | Stehr et al. |
| 10,689,716 | B1 | 6/2020 | Daunert et al. |
| 2005/0095618 | A1 | 5/2005 | Tsui et al. |
| 2005/0136480 | A1 | 6/2005 | Brahmachari et al. |
| 2005/0208066 | A1 | 9/2005 | Chao et al. |
| 2006/0286124 | A1 | 12/2006 | Burt et al. |
| 2007/0092938 | A1 | 4/2007 | Kwang et al. |
| 2007/0099178 | A1 | 5/2007 | Minekawa et al. |
| 2008/0081047 | A1 | 4/2008 | Berry et al. |
| 2008/0090224 | A1 | 4/2008 | Yu et al. |
| 2010/0233250 | A1 | 9/2010 | Baras et al. |
| 2010/0279273 | A1 | 11/2010 | Bergeron et al. |
| 2010/0285457 | A1 | 11/2010 | Peiris et al. |
| 2011/0159001 | A1 | 6/2011 | Lanzavecchia |
| 2011/0262892 | A1 | 10/2011 | Aoyagi et al. |
| 2012/0045469 | A1 | 2/2012 | Baras et al. |
| 2012/0291565 | A1 | 11/2012 | Ludowise et al. |
| 2016/0238601 | A1 | 8/2016 | Baric et al. |
| 2018/0237842 | A1 | 8/2018 | Buersgens et al. |
| 2018/0326044 | A1 | 11/2018 | Carter |
| 2018/0371534 | A1 | 12/2018 | Minnucci et al. |
| 2019/0249168 | A1 | 8/2019 | Stehr et al. |
| 2020/0063173 | A1 | 2/2020 | Buersgens et al. |

FOREIGN PATENT DOCUMENTS

| | | |
|---|---|---|
| EP | 1020534 | 7/2000 |
| EP | 1642978 | 4/2006 |
| EP | 1694829 | 8/2010 |
| EP | 1690207 | 9/2010 |
| EP | 2275534 | 1/2011 |
| EP | 2361974 | 8/2011 |
| EP | 1697507 | 9/2012 |
| EP | 2597162 | 5/2013 |
| EP | 2709760 | 6/2019 |
| EP | 2499498 | 7/2019 |
| WO | WO 2004/097021 | 11/2004 |
| WO | WO 2005/054469 | 6/2005 |
| WO | WO 2005/056584 | 6/2005 |
| WO | WO 2005/057464 | 6/2005 |
| WO | WO 2006/068663 | 6/2006 |
| WO | WO 2008/155316 | 12/2008 |
| WO | WO 2009/085025 | 7/2009 |
| WO | WO 2009/128963 | 10/2009 |
| WO | WO 2010/063685 | 6/2010 |
| WO | WO 2011/059443 | 5/2011 |
| WO | WO 2017/108663 | 6/2017 |

OTHER PUBLICATIONS

Basile, K. et al. (2018) "*Point-Of-Care Diagnostics for Respiratory Viral Infections*," Exp. Rev. Molec. Diagnos. 18(1):75-83.

Basiri, A. et al. (2020) "*Microfluidic Devices for Detection of RNA Viruses*," Rev Med Virol. e2154:1-11.

Bengston, H.N. et al. (2014) "*A Differential Fluorescent Receptor for Nucleic Acid Analysis*," Chembiochem. 15(2):228-231.

Bodulev, O.L. et al. (2020) "*Isothermal Nucleic Acid Amplification Techniques and Their Use in Bioanalysis*," Biochemistry (Mosc) 85(2):147-166.

Bordi, L. et al. (2020) "*Rapid and Sensitive Detection of SARS-Cov-2 RNA Using the Simplexa™ COVID-19 Direct Assay*," J. Clin. Virol. 128:104416:1-5.

Brüssow, H. (2020) "*The Novel Coronavirus—A Snapshot of Current Knowledge*," Microbial Biotechnology 0:(0):1-6.

Bustin, S.A. et al. (2020) "*RT-qPCR Testing of SARS-CoV-2: A Primer*," Intl. J. Molec. Sci. 21:3004:1-9; Chang, G.-J.J. et al. (1994) "*An Integrated Target Sequence and Signal Amplification Assay, Reverse Transcriptase-PCR-Enzyme-Linked Immunosorbent Assay, To Detect and Characterize Flaviviruses*," J. Clin. Microbiol. 32(2):477-483.

Chan, J.F. et al. (2013) "*Interspecies Transmission and Emergence of Novel Viruses: Lessons From Bats and Birds*," Trends Microbiol. 21(10):544-555.

Chan, J.F. et al. (2020) "*Genomic Characterization of the 2019 Novel Human-Pathogenic Coronavirus Isolated From a Patient With Atypical Pneumonia After Visiting Wuhan*," Emerg. Microbes. Infect. 9(1):221-236.

Chan, J.F. et al. (2020) "*Improved Molecular Diagnosis of COVID-19 by the Novel, Highly Sensitive and Specific COVID-19-RdRp/Hel Real-Time Reverse Transcription-Polymerase Chain Reaction Assay Validated In Vitro and With Clinical Specimens*," J Clin. Microbiol. JCM.00310-20. doi: 10.1128/JCM.00310-20; pp. 1-33.

Chan, J.F. et al. (2020) "*A Familial Cluster of Pneumonia Associated With the 2019 Novel Coronavirus Indicating Person-To-Person Transmission: A Study of a Family Cluster*," Lancet 2020; 395: 514-23.

Chang, G.-J.J. et al. (1994) "*An Integrated Target Sequence and Signal Amplification Assay, Reverse Transcriptase-PCR-Enzyme-Linked Immunosorbent Assay, To Detect and Characterize Flaviviruses*," J. Clin. Microbiol. 32(2):477-483.

Chen, Y, et al. (2020) "*Emerging Coronaviruses: Genome Structure, Replication, and Pathogenesis*," J. Med. Virol. 92:418-423.

Chen, Y. et al. (2020) "*Structure Analysis of the Receptor Binding of 2019-Ncov*," Biochem. Biophys. Res. Commun. 525:135-140.

Cordes, A.K. et al. (2020) "*Rapid Random Access Detection of the Novel SARS-Coronavirus-2 (SARS-CoV-2, Previously 2019-nCoV) Using an Open Access Protocol for the Panther Fusion*," J. Clin. Virol. 125:104305 doi: 10.1016/j.jcv.2020.104305; pp. 1-2.

Corman, V.M. et al. (2020) "*Detection of 2019 Novel Coronavirus (2019-nCoV) By Real-Time RT-PCR*," Eurosurveill. 25(3):2000045; pp. 1-8.

Cradic, K. et al. (2020) ("*Clinical Evaluation and Utilization of Multiple Molecular In Vitro Diagnostic Assays for the Detection of SARS-CoV-2*," Am. J. Clin. Pathol. 154(2):201-207.

Daher, R.K. et al. (2016) "*Recombinase Polymerase Amplification for Diagnostic Applications*," Clin. Chem. 62(7):947-958.

DHHS Press Release (Mar. 13, 2020) "*HHS Funds Development of COVID-19-19 Diagnostic Tests*," https://www.hhs.gov/about/news/2020/03/13/hhs-funds-development-covid-19-diagostic-tests.html 2 pages.

DiaSorin Liaison MDX Product Brochure (2018); pp. 1-4.

DiaSorin Press Release (Mar. 30, 2020) "*DiaSorin Molecular COVID-19 Test Has Received FDA Emergency Use Authorization*," https://molecular.diasorin.com/international/wp-content/uploads/2020/03/DiaSorin-Molecular-COVID-19-EUA-APPROVED.pdf (3 pages).

Dreier, J. et al. (2005) "*Use of Bacteriophage MS2 as an Internal Control in Viral Reverse Transcription-PCR Assays*," J. Clin. Microbiol. 43(9):4551-4557.

Drosten et al. (2003) "*Identification of a Novel Coronavirus in Patients With Severe Acute Respiratory Syndrome*," New Engl. J. Med. 348:1967-1976.

Dunbar, S. et al. (2019) "*Amplification Chemistries in Clinical Virology*," J. Clin. Virol. 115:18-31.

Eiken Chemical Co., Ltd. (2020) "*Eiken Chemical Launches the Loopamp 2019 nCoV Detection Kit*," Press Release; pp. 1-2.

Fakruddin, M. et al. (2013) "*Nucleic Acid Amplification: Alternative Methods of Polymerase Chain Reaction*," J. Pharm. Bioallied Sci. 5(4):245-252.

Fang, Y. et al. (2020) "*Transmission Dynamics of the COVID-19 Outbreak and Effectiveness of Government Interventions: A Data-Driven Analysis*," J. Med. Virol. doi: 10.1002/jmv.25750.

Farzan, V.M. et al. (2017) "*Specificity of SNP Detection With Molecular Beacons Is Improved by Stem and Loop Separation With Spacers*," Analyst 142:945-950.

(56) References Cited

OTHER PUBLICATIONS

Finetti-Sialer, M.M. et al. (2005) "*Isolate-Specific Detection of Grapevine fanleaf virus from Xiphinema index Through DNA-Based Molecular Probes*," Phytopathology 95(3):262-268.
Fluorophores and BHQ (2019) Biosearch Technologies; 1 page.
French, D.J. et al. (2001) "*HyBeacon Probes: A New Tool for DNA Sequence Detection and Allele Discrimination*," Mol. Cell. Probes 15(6):363-374.
French, D.J. et al. (2006) "*HyBeacons®: A Novel DNA Probe Chemistry for Rapid Genetic Analysis*," Intl. Cong. Series 1288:707-709.
French, D.J. et al. (2008) "*HyBeacon Probes for Rapid DNA Sequence Detection and Allele Discrimination*," Methods Mol Biol. 429:171-85.
Gasparic, M.B et al. (2010) "*Comparison of Nine Different Real-Time PCR Chemistries for Qualitative and Quantitative Applications in GMO Detection*," Anal. Bioanal. Chem. 396(6):2023-2029.
GenBank Accession No. NC_002645.1 (Human coronavirus 229E) (2018) 12 pages.
GenBank Accession No. NC_004718.3 (SARS-coronavirus) (2018) 18 pages.
GenBank Accession No. NC_005831.2 (Human Coronavirus NL63) (2018) 11 pages.
GenBank Accession No. NC_006213.1 (Human coronavirus OC43 strain ATCC VR-759) (2019) 13 pages.
GenBank Accession No. NC_006577.2 (Human coronavirus HKU1) (2018) 14 pages.
GenBank Accession No. NC_019843.3 (Middle East Respiratory Syndrome coronavirus) (2018) 16 pages.
GenBank Accession No. NC_045512.2 (SARS-CoV-2) (2020) 16 pages.
Ghannam, M,G, et al. (2020) "*Biochemistry, Polymerase Chain Reaction (PCR)*," StatPearls Publishing, Treasure Is.; pp. 1-4.
Goel, G. et al. (2005) "*Molecular Beacon: A Multitask Probe*," J. Appl. Microbiol. 99(3):435-442.
Gong, S.R. et al. (2018) "*The Battle Against SARS and MERS Coronaviruses: Reservoirs and Animal Models*," Animal Model Exp. Med. 1(2):125-13.
Goo, N.I. et al. (2016) "*Rolling Circle Amplification As Isothermal Gene Amplification in Molecular Diagnostics*," Biochip J. 10(4):262-271.
Haddad, H. et al. (2020) "*Mirna Target Prediction Might Explain the Reduced Transmission of SARS-CoV-2 in Jordan, Middle East*," Noncoding RNA Res. 5(3):135-143.
Han, S.X. et al. (2013) "*Molecular Beacons: A Novel Optical Diagnostic Tool*," Arch. Immunol. Ther. Exp. (Warsz). 61(2):139-148.
He, Y. et al. (2004) *Receptor-Binding Domain of SARS-CoV Spike Protein Induces Highly Potent Neutralizing Antibodies: Implication for Developing Subunit Vaccine*, Biochem. Biophys. Res. Commun. 324:773-781.
Holland, P.M. et al. (1991) "*Detection of Specific Polymerase Chain Reaction Product by Utilizing the 5'→3' Exonuclease Activity of Thermus Aquaticus DNA Polymerase*," Proc. Natl. Acad. Sci. (U.S.A.) 88(16):7276-7280.
Hu, Y. et al. (2009) "*Nested Real-Time PCR for Hepatitis A Detection*," Lett. Appl. Microbiol. 49(5):615-619.
Ieven, M. (2007) "*Currently Used Nucleic Acid Amplification Tests for the Detection of Viruses and Atypicals in Acute Respiratory Infections*," J. Clin. Virol. 40(4):259-276.
Isabel, S. et al. (2020) "*Evolutionary and Structural Analyses of SARS-Cov-2 D614G Spike Protein Mutation Now Documented Worldwide*," Sci. Rep. 10(1):14031:1-9.
Ji, W. et al. (2020) "*Cross-Species Transmission of the Newly Identified Coronavirus 2019-nCoV*," J Med. Virol. 92:433-440.
Jung, Y.J. et al. (2020) "*Comparative Analysis of Primer-Probe Sets for the Laboratory Confirmation of SARS-Cov-2*," bioRxiv 2020.02.25.964775:1-13.
Kitamura, Y. et al. (2020) "*Electrochemical Molecular Beacon for Nucleic Acid Sensing in a Homogeneous Solution*," Analyt. Sci. 36:959-964.
Kolpashchikov, D.M. (2012) "*An Elegant Biosensor Molecular Beacon Probe: Challenges and Recent Solutions*," Scientifica (Cairo). 2012:928783:1-17.
Kong, I. et al. (2020) "*Early Epidemiological and Clinical Characteristics of 28 Cases of Coronavirus Disease in South Korea*," Osong Public Health Res Perspect. 11(1):8-14.
Kralik, P. et al. (2017) "*A Basic Guide to Real-Time PCR in Microbial Diagnostics: Definitions, Parameters, and Everything*," Front. Microbiol. 8:108; pp. 1-9.
Laamarti, M et al. (2020) "*Genome Sequences of Six SARS-CoV-2 Strains Isolated in Morocco, Obtained Using Oxford Nanopore MinION Technology*," Microbiol. Resour. Announc. 9(32):e00767-20:1-4.
Lai, C.C. et al. (2020) "*Severe Acute Respiratory Syndrome Coronavirus 2 (SARS-CoV-2) and Coronavirus Disease—2019 (COVID-19): The Epidemic and The Challenges*," Int. J. Antimicrob. Agents. 55(3):105924; pp. 1-9.
Lam, W.Y. et al. (2007) "*Rapid Multiplex Nested PCR for Detection of Respiratory Viruses*," J. Clin. Microbiol. 45(11):3631-3640.
Li, C. et al. (2020) "*High Sensitivity Detection of SARS-CoV-2 using Multiplex PCR and a Multiplex-PCR-Based Metagenomic Method*," bioRxiv:1-24.
Li, F. (2016) "*Structure, Function, and Evolution of Coronavirus Spike Proteins*," Annu. Rev. Virol. 3:237-261.
Li, Q. et al. (2020) "*Early Transmission Dynamics in Wuhan, China, Of Novel Coronavirus-Infected Pneumonia*," New Engl. J. Med. DOI: 10.1056/NEJMoa2001316; pp. 1-9.
Li, Z. et al. (2020) "*Development and Clinical Application of a Rapid IgM-IgG Combined Antibody Test for SARS-CoV-2 Infection Diagnosis*," J. Med. Virol. doi: 10.1002/jmv.25727; pp. 1-16.
Lieberman, J.A. et al. (2020) "*Comparison of Commercially Available and Laboratory-Developed Assays for In Vitro Detection of SARS-CoV-2 in Clinical Laboratories*," J. Clin. Microbiol. 58(8):e00821-20:1-6.
Liotti, F.M. et al. (2020) "*Evaluation of Three Commercial Assays for SARS-CoV-2 Molecular Detection in Upper Respiratory Tract Samples*," Eur. J. Clin. Microbiol. Infect. Dis. 10.1007/s10096-020-04025-0:1-9.
Liu, R. et al. (2020) "*Positive Rate of RT-PCR Detection of SARS-CoV-2 Infection in 4880 Cases From One Hospital in Wuhan, China, From Jan. To Feb. 2020*," Clinica Chimica Acta 505:172-175.
Lorenz, T.C. (2012) "*Polymerase Chain Reaction: Basic Protocol Plus Troubleshooting and Optimization Strategies*," J. Vis. Exp. May 22, 2012;(63):e3998; pp. 1-15.
Lu, G. et al. (2015) "*Bat-To-Human: Spike Features Determining 'Host Jump' Of Coronaviruses SARS-CoV, MERS-CoV, and Beyond*," Trends Microbiol. 23:468-478.
Lu, R. et al. (2020) "*Genomic Characterisation and Epidemiology of 2019 Novel Coronavirus: Implications for Virus Origins and Receptor Binding*," Lancet 395(10224):565-574.
Lu, R. et al. (2020) "*SARS-Cov-2 Detection Using Digital PCR for COVID-19 Diagnosis, Treatment Monitoring and Criteria for Discharge*," medRxiv 2020.03.24.20042689:1-21.
Ma, M.Y.X. et al. (1993) "*Design and Synthesis of RNA Miniduplexes Via a Synthetic Linker Approach*," Biochemistry 32(7):1751-1758.
Ma, M.Y.X. et al. (1993) "*Design and Synthesis of RNA Miniduplexes Via a Synthetic Linker Approach. 2. Generation of Covalently Closed, Double-Stranded Cyclic HIV-1 TAR RNA Analogs With High Tat-Binding Affinity*," Nucleic Acids Res. 21(11):2585-2589.
Mackay, I.M. (2015) "*MERS Coronavirus: Diagnostics, Epidemiology and Transmission*," Virol. J. 12:222. doi: 10.1186/s12985-015-0439-5; pp. 1-21.
Mahony, J.B. et al. (2011) "*Molecular Diagnosis of Respiratory Virus Infections*," Crit. Rev. Clin. Lab. Sci. 48(5-6):217-249.
Marra, M.A. et al. (2003) "*The Genome Sequence of the SARS-Associated Coronavirus*," Science 300(5624):1399-1404.
Masters, P.S. (2006) "*The Molecular Biology of Coronaviruses*," Adv. Virus Res. 66:193-292.

(56) References Cited

OTHER PUBLICATIONS

Navarro, E. et al. (2015) "*Real-Time PCR Detection Chemistry*," Clin. Chim. Acta 439:231-250.
Northill, J. et al. (2020) *Severe Acute Respiratory Syndrome Coronavirus 2 (Sarscov-2) Real-Time RT-PCR ORF lab 2020 (Wuhan-ORF lab; 2019-Ncov-Related Test) V.3*, dx.doi.org/w10.17504/protocols.io.bchvit66, pp. 1-5.
Notomi, T. et al. (2000) "*Loop-Mediated Isothermal Amplification of DNA*," Nucl. Acids Res. 28(12):E63:1-7.
Ogawa, J. et al. (2020) "*The D614G Mutation in the SARS-Cov2 Spike Protein Increases Infectivity in an ACE2 Receptor Dependent Manner*," Preprint. bioRxiv. 2020;2020.07.21.214932:1-10.
Omotuyi, I.O. et al. (2020) "*Atomistic Simulation Reveals Structural Mechanisms Underlying D614G Spike Glycoprotein-Enhanced Fitness in SARS-CoV-2*," J. Comput. Chem. 41(24):2158-2161.
Pang, J. et al. (2020) "*Potential Rapid Diagnostics, Vaccine and Therapeutics for 2019 Novel Coronavirus (2019-nCoV): A Systematic Review*," J. Clin. Med. 26;9(3)E623; pp. 1-33.
Peake, I. (1989) "*The Polymerase Chain Reaction*," J. Clin. Pathol. ;42(7):673-676.
Peng, Q. et al. (2020) "*A Molecular-Beacon-Based Asymmetric PCR Assay for Detecting Polymorphisms Related to Folate Metabolism*," J. Clin. Lab. Anal. 34:e23337:1-7.
Persing, D.H. et al. (1989) "*In Vitro Amplification Techniques for the Detection of Nucleic Acids: New Tools for the Diagnostic Laboratory*," Yale J. Biol. Med. 62(2):159-171.
Pfefferle, S. et al. (2020) "*Evaluation of a Quantitative RT-PCR Assay for the Detection of the Emerging Coronavirus SARS-CoV-2 Using a High Throughput System*," Euro. Surveill. 25(9) doi: 10.2807/1560-7917.ES.2020.25.9.2000152; pp. 1-5.
Quenchers Design and Protocols (2020) Gene Link Web Brochure; 3 pages.
Reid, A. (2020) "*WHOinHouseAssays*," World Health Organization (WHO) Publication, https://www.who.int/docs/default-source/coronaviruse/whoinhouseassays.pdf?sfvrsn=de3a76aa_2 pp. 1-82.
Rhoads, D.D. et al. (2020) "*Comparison of Abbott ID Now™, DiaSorin Simplexa®, and CDC FDA Emergency Use Authorization Methods for the Detection of SARS-CoV-2 From Nasopharyngeal and Nasal Swabs From Individuals Diagnosed With COVID-19*," J. Clin. Microbiol. 58(8):e00760-20:1-2.
Sah, R. et al. (2020) "*Complete Genome Sequence of a 2019 Novel Coronavirus (SARS-CoV-2) Strain Isolated in Nepal*," Microbiol. Resource Announcements 9(11): e00169-20, pp. 1-3.
SantaLucia, J. (1998) *A Unified View of Polymer, Dumbbell, and Oligonucleotide DNA Nearest-Neighbor Thermodynamics*, Proc. Natl. Acad. Sci. (U.S.A.) 95:1460-1465.
Schwab, K.J. et al. (2001) "*Development of a Reverse Transcription-PCR-DNA Enzyme Immunoassay for Detection of "Norwalk-Like" Viruses and Hepatitis A Virus in Stool and Shellfish. Applied and Environmental Microbiology*," 67(2):742-749.
Sigma Aldrich (2014) "*Primers and Fluorescent Probes* for Real-Time PCR and Other Applications," Product Brochure; pp. 1-20.
Solinas, A. et al. (2001) "*Duplex Scorpion Primers in SNP Analysis and FRET Applications*," Nucl. Acids Res. 29(20):E96:1-9.
Spiteri, G. et al. (2020) "*First Cases of Coronavirus Disease 2019 (COVID-19) In the WHO European Region, Jan. 24 To Feb. 21, 2020*," Eurosurveill. 25(9) doi: 10.2807/1560-7917.ES.2020.25.9.2000178; pp. 1-11.
Su, S. et al. (2016) "*Epidemiology, Genetic Recombination, and Pathogenesis of Coronaviruses*," Trends Microbiol. 24:490-502.
Tang, A. et al. (2020) "*Detection of Novel Coronavirus by RT-PCR in Stool Specimen from Asymptomatic Child, China*," Emerg Infect Dis. 26(6):pp. 1-7.
Thelwell, N. et al. (2000) "*Mode of Action and Application of Scorpion Primers to Mutation Detection*," Nucleic Acids Res. 28(19):3752-3761.
Thorton, B. et al. (2011) "*Real-Time PCR (qPCR) Primer Design Using Free Online Software*," Biochem. Molec. Biol. Educat. 39(2):145-154.
Tsourkas, A. et al. (2003) "*Hybridization Kinetics and Thermodynamics of Molecular Beacons*," Nucleic Acids Research 31(4):1319-1330.
Von Ahsen, N. et al. (1999) "*Application of a Thermodynamic Nearest-Neighbor Model to Estimate Nucleic Acid Stability and Optimize Probe Design: Prediction of Melting Points of Multiple Mutations of Apolipoprotein B-3500 and Factor V With A Hybridization Probe Genotyping Assay on the Lightcycler*," Clin. Chem. 45(12):2094-2101.
Wang, C. et al. (2020) "*The Establishment of Reference Sequence for SARS-CoV-2 and Variation Analysis*," J. Med. Virol. doi: 10.1002/jmv.25762; pp. 1-8.
Wang, Q. et al. (2016) "*MERS-CoV Spike Protein: Targets for Vaccines and Therapeutics*," Antiviral. Res. 133:165-177.
Wang, W. et al. (2020) "*Detection of SARS-CoV-2 in Different Types of Clinical Specimens*," JAMA doi: 10.1001/jama.2020.3786; pp. 1-2.
Whitcombe, D. et al. (1999) "*Detection of PCR Products Using Self-Probing Amplicons and Fluorescence*," Nat. Biotechnol. 17(8):804-807.
Won, J. et al. (2020) "*Development of a Laboratory-Safe and Low-Cost Detection Protocol for SARS-CoV-2 of the Coronavirus Disease 2019 (COVID-19)*," Exp. Neurobiol. 29(2):pp. 1-13.
Wu, X. et al. (2020) "*Co-Infection with SARS-CoV-2 and Influenza A Virus in Patient with Pneumonia, China*," Emerg Infect Dis. 26(6 26(6); pp. 1-7.
Xie, C. et al. (2020) "*Comparison of Different Samples for 2019 Novel Coronavirus Detection by Nucleic Acid Amplification Tests*" Int. J. Infect. Dis. /doi.org/10.1016/j.ijid.2020.02.050; pp. 1-12.
Xu, K. et al. (2020) "*Management of Corona Virus Disease-19 (Covid-19): The Zhejiang Experience*," Zhejiang Da Xue Bao Yi Xue Ban. 49(1):0; Abstract Only; pp. 1-2.
Yin, Y. et al. (2018) "*MERS, SARS and Other Coronaviruses As Causes of Pneumonia*," Respirology 23(2):130-137.
Yuan, X. et al. (2019) "*LAMP Real-Time Turbidity Detection for Fowl Adenovirus*," BMC Vet. Res. 15: 256:1-4.
Zearfoss, N.R. et al. (2012) "*End-Labeling Oligonucleotides with Chemical Tags After Synthesis*," Meth. Mol. Biol. 941:181-193.
Zhang, H. et al. (2019) "*LAMP-On-A-Chip: Revising Microfluidic Platforms for Loop-Mediated DNA Amplification*," Trends Analyt. Chem. 113:44-53.
Zhang, W. et al. (2020) "*Molecular and Serological Investigation of 2019-nCoV Infected Patients: Implication of Multiple Shedding Routes*," Emerg. Microbes Infect. 9(1):386-389.
Zhao, W.M. et al. (2020) "*The 2019 Novel Coronavirus Resource*," Yi Chuan. 42(2):212-221; Abstract Only; pp. 1-2.
Zhen, W. et al. (2020) "*Comparison of Four Molecular In Vitro Diagnostic Assays for the Detection of SARS-CoV-2 in Nasopharyngeal Specimens*," J. Clin. Microbiol. 58(8):e00743-20:1-8.
Zheng, J. et al. (2015) "*Rationally Designed Molecular Beacons for Bioanalytical and Biomedical Applications*," Chem. Soc. Rev. 44(10):3036-3055.
Zhou, Y. et al. (2020) "*Network-Based Drug Repurposing for Novel Coronavirus 2019-nCoV/SARS-CoV-2*," Cell Discov. 6(14): doi.org/10.1038/s41421-020-0153-3; pp. 1-18.
Zhu, N. et al. (2020) "*A Novel Coronavirus from Patients with Pneumonia in China, 2019*," New Engl. J. Med. 382(8):727-733.

* cited by examiner

ASSAYS FOR THE DETECTION OF SARS-COV-2

CROSS-REFERENCE TO RELATED APPLICATIONS

This application is a continuation-in-part of, and claims priority to, U.S. patent application Ser. No. 16/837,364 (filed on Apr. 1, 2020; pending), which application claims priority to Italian Patent Application No. 102020000006754, filed on Mar. 31, 2020 (pending), each of which applications is herein incorporated by reference in its entirety.

REFERENCE TO SEQUENCE LISTING

This application includes one or more Sequence Listings pursuant to 37 C.F.R. 1.821 et seq., which are disclosed in computer-readable media (file name: SARS-CoV-2_0400_0020US2_ST25.txt, created on Oct. 18, 2020, and having a size of 156,199 bytes), which file is herein incorporated by reference in its entirety.

FIELD OF THE INVENTION

The present invention is directed to methods for assaying for the presence of SARS-CoV-2 in a sample, including a clinical sample, and to oligonucleotides, reagents, and kits useful in such assays. In particular, the present invention is directed to such assays that are rapid, accurate and specific for the detection of SARS-CoV-2.

BACKGROUND OF THE INVENTION

I. SARS-CoV-2

Severe Acute Respiratory Syndrome Coronavirus 2 (SARS-CoV-2) is a newly identified coronavirus species (the virus was previously provisionally named "2019 novel coronavirus" or "2019-nCoV"). SARS-CoV-2 infection is spread by human-to-human transmission via droplets or direct contact, and infection has been estimated to have a mean incubation period of 6.4 days and a Basic Reproduction Number of 2.24-3.58 (i.e., an epidemic doubling time of 6-8 days) (Fang, Y. et al. (2020) "*Transmission Dynamics Of The COVID-*19 *Outbreak And Effectiveness Of Government Interventions: A Data-Driven Analysis," J. Med. Virol*. doi: 10.1002/jmv.25750; Zhao, W. M. et al. (2020) "The 2019 Novel Coronavirus Resource," Yi Chuan. 42(2):212-221; Zhu, N. et al. (2020) "*A Novel Coronavirus from Patients with Pneumonia in China,* 2019," New Engl. J. Med. 382 (8):727-733).

Patients infected with SARS-CoV-2 exhibit COVID-19, a condition initially characterized by fever and cough (Kong, I. et al. (2020) "*Early Epidemiological and Clinical Characteristics of* 28 *Cases of Coronavirus Disease in South Korea*," Osong Public Health Res Perspect. 11(1):8-14). In approximately 20% of patients, COVID-19 progresses to a severe respiratory disease and pneumonia that has a mortality of 5-10% (1-2% overall mortality). Bilateral lung involvement with ground-glass opacity are the most common finding from computed tomography images of the chest (Lai, C C. et al. (2020) "*Severe Acute Respiratory Syndrome Coronavirus* 2 (*SARS-CoV-*2) *And Coronavirus Disease-*2019 (*COVID-*19): *The Epidemic And The Challenges*," Int. *J. Antimicrob*. Agents. 55(3):105924). Since a cure for COVID-19 has not yet been identified, treatment presently consists of a "Four-Anti and Two-Balance" strategy included antivirus, anti-shock, anti-hyoxemia, anti-secondary infection, and maintaining water, electrolyte and acid-base balance and microecological balance (Xu, K. et al. (2020) "*Management Of Corona Virus Disease-*19 (*COVID-*19): *The Zhejiang Experience*," Zhejiang Da Xue Bao Yi Xue Ban. 49(1):0).

Coronaviruses (CoVs) belong to the subfamily Orthocoronavirinae in the family Coronaviridae and the order Nidovirales. The Coronaviridae family of viruses are enveloped, single-stranded, RNA viruses that possess a positive-sense RNA genome of 26 to 32 kilobases in length. Four genera of coronaviruses have been identified, namely, Alphacoronavirus (αCoV), Betacoronavirus (βCoV), Deltacoronavirus (δCoV), and Gammacoronavirus (γCoV) (Chan, J. F. et al. (2013) "*Interspecies Transmission And Emergence Of Novel Viruses: Lessons From Bats And Birds," Trends Microbiol.* 21(10):544-555). Evolutionary analyses have shown that bats and rodents are the gene sources of most αCoVs and βCoVs, while avian species are the gene sources of most δCoVs and γCoVs.

Prior to 2019, only six coronavirus species were known to be pathogenic to humans. Four of these species were associated with mild clinical symptoms, but two coronaviruses, Severe Acute Respiratory Syndrome (SARS) coronavirus (SARS-CoV) (Marra, M. A. et al. (2003) "*The Genome Sequence of the SARS-Associated Coronavirus*," Science 300(5624):1399-1404) and Middle East Respiratory Syndrome (MERS) coronavirus (MERS-CoV) (Mackay, I. M. (2015) "*MERS Coronavirus: Diagnostics, Epidemiology And Transmission*," Virol. J. 12:222. doi: 10.1186/s12985-015-0439-5) were associated with human mortalities approaching 10% (Su, S. et al. (2016) "*Epidemiology, Genetic Recombination, And Pathogenesis Of Coronaviruses*," Trends Microbiol. 24:490-502; Al Johani, S. et al. (2016) "*MERS-CoV Diagnosis: An Update*," J. Infect. Public Health 9(3):216-219).

SARS-CoV-2 is closely related (88%) to two bat-derived Severe Acute Respiratory Syndrome-like coronaviruses, bat-SL-CoVZC45 and bat-SL-CoVZXC21, and is more distantly related to SARS-CoV (79%) and MERS-CoV (50%) (Xie, C. et al. (2020) "*Comparison Of Different Samples For* 2019 *Novel Coronavirus Detection By Nucleic Acid Amplification Tests*" Int. J. Infect. Dis. /doi.org/10.1016/j.ijid.2020.02.050; Mackay, I. M. (2015) "*MERS Coronavirus: Diagnostics, Epidemiology And Transmission," Virol. J.* 12:222. doi: 10.1186/s12985-015-0439-5; Gong, S. R. et al. (2018) "*The Battle Against SARS And MERS Coronaviruses: Reservoirs And Animal Models*," Animal Model Exp. Med. 1(2):125-133; Yin, Y. et al. (2018) "*MERS, SARS And Other Coronaviruses As Causes Of Pneumonia*," Respirology 23(2):130-137). Phylogenetic analysis revealed that SARS-CoV-2 fell within the subgenus Sarbecovirus of the genus Betacoronavirus, with a relatively long branch length to its closest relatives bat-SL-CoVZC45 and bat-SL-CoVZXC21, and was genetically distinct from SARS-CoV (Drosten et al. (2003) "Identification Of A Novel Coronavirus In Patients With Severe Acute Respiratory Syndrome," New Engl. J. Med. 348:1967-1976; Lai, C C. et al. (2020) "*Severe Acute Respiratory Syndrome Coronavirus* 2 (*SARS-CoV-*2) *And Coronavirus Disease-*2019 (*COVID-*19): *The Epidemic And The Challenges*," Int. J. Antimicrob. Agents. 55(3):105924; Lu, R. et al. (2020) "*Genomic Characterisation And Epidemiology Of* 2019 *Novel Coronavirus: Implications For Virus Origins And Receptor Binding*," The Lancet 395(10224):565-574; Zhou, Y. et al. (2020) "Network-Based Drug Repurposing For Novel Coronavirus 2019-nCoV/SARS-CoV-2," Cell Discov. 6(14): doi.org/10.1038/s41421-020-0153-3).

The SARS-CoV-2 genome has been sequenced from at least 170 isolates. The reference sequence is GenBank NC_045512 (Wang, C. et al. (2020) "*The Establishment Of Reference Sequence For SARS-CoV-*2 *And Variation Analysis*," J. Med. Virol. doi: 10.1002/jmv.25762; Chan, J. F. et al. (2020) "*Genomic Characterization Of The* 2019 *Novel Human-Pathogenic Coronavirus Isolated From A Patient With Atypical Pneumonia After Visiting Wuhan*," Emerg. Microbes. Infect. 9(1):221-236).

Comparisons of the sequences of multiple isolates of the virus (MN988668 and NC_045512, isolated from Wuhan, China, and MN938384.1, MN975262.1, MN985325.1, MN988713.1, MN994467.1, MN994468.1, and MN997409.1) reveal greater than 99.99% identity (Sah, R. et al. (2020) "*Complete Genome Sequence of a* 2019 *Novel Coronavirus* (*SARS-CoV-*2) *Strain Isolated in Nepal*," Microbiol. Resource Announcements 9(11): e00169-20, pages 1-3; Brussow, H. (2020) "*The Novel Coronavirus-A Snapshot of Current Knowledge*," Microbial Biotechnology 0:(0):1-6).

The SARS-CoV-2 genome is highly similar to that of human SARS-CoV, with an overall nucleotide identity of approximately 82% (Chan, J. F. et al. (2020) "*Genomic Characterization Of The* 2019 *Novel Human-Pathogenic Corona Virus Isolated From A Patient With Atypical Pneumonia After Visiting Wuhan*," Emerg Microbes Infect 9:221-236; Chan, J. F. et al. (2020) "*Improved Molecular Diagnosis Of COVID*-19 *By The Novel, Highly Sensitive And Specific COVID*-19-*RdRp/Hel Real-Time Reverse Transcription-Polymerase Chain Reaction Assay Validated In Vitro And With Clinical Specimens*," J Clin. Microbiol. JCM.00310-20. doi: 10.1128/JCM.00310-20). Based on its homology to related coronaviruses, SARS-CoV-2 is predicted to encode 12 open reading frame (ORFs) coding regions (ORF1ab, S (spike protein), 3, E (envelope protein), M (matrix), 7, 8, 9, 10b, N, 13 and 14. The arrangement of these coding regions is shown in FIG. 1. Two ORFs coding regions are of particular significance to the present invention: ORF1ab and the S gene (Lu, R. et al. (2020) "*Genomic Characterisation And Epidemiology Of* 2019 *Novel Coronavirus: Implications For Virus Origins And Receptor Binding*," Lancet 395(10224):565-574).

A. ORF1ab

ORF1ab is composed of 21290 nucleotides and encodes an open reading frame of 7096 amino acids in length. Via a −1 ribosomal frameshift, the encoded protein is a polyprotein (pp) composed of a first segment (pp1a) of 4401 amino acid residues, and a second segment (pp1ab) of 2695 amino acid residues (Chen, Y, et al. (2020) "*Emerging Coronaviruses: Genome Structure, Replication, And Pathogenesis*," J. Med. Virol. 92:418-423; Lu, R. et al. (2020) "*Genomic Characterisation And Epidemiology Of* 2019 *Novel Coronavirus: Implications For Virus Origins And Receptor Binding*," Lancet 395(10224):565-574). Both segments include the same 180 amino acid long leader sequence. The polyprotein includes multiple non-structural proteins (nsp): a 638 amino acid long nsp2 protein, a 1945 amino acid long nsp3 protein, a 500 amino acid long nsp4 protein, a 306 amino acid long nsp5 protein, a 290 amino acid long nsp6 protein, an 83 amino acid long nsp7 protein, a 198 amino acid long nsp8 protein, a 113 amino acid long nsp9 single-strand binding protein, a 139 amino acid long nsp10 protein, a 923 amino acid long nsp12 RNA-dependent RNA polymerase (RdRp), a 601 amino acid long nsp13 helicase, a 527 amino acid long nsp14a2 3→5' exonuclease, a 346 amino acid long nsp15 endoRNAse, and a 298 amino acid long nsp16 2'-O-ribose-methyltransferase (Chen, Y, et al. (2020) "*Emerging Coronaviruses: Genome Structure, Replication, And Pathogenesis*," J. Med. Virol. 92:418-423; Lu, R. et al. (2020) "*Genomic Characterisation And Epidemiology Of* 2019 *Novel Coronavirus: Implications For Virus Origins And Receptor Binding*," Lancet 395(10224):565-574).

The sequence of the positive sense ("sense") strand of the ORF1ab of SARS-CoV-2 of GenBank NC_045512 (SEQ ID NO:415) is shown in Table 1.

TABLE 1

| The ORF1ab of SARS-CoV-2 (SEQ ID NO: 415) | ORF 1ab | SARS-CoV-2 |
|---|---|---|
| atggagagcc ttgtccctgg tttcaacgag aaaacacacg tccaactcag | 50 | 316 |
| tttgcctgtt ttacaggttc gcgacgtgct cgtacgtggc tttggagact | 100 | 366 |
| ccgtggagga ggtcttatca gaggcacgtc aacatcttaa agatggcact | 150 | 416 |
| tgtggcttag tagaagttga aaaaggcgtt ttgcctcaac ttgaacagcc | 200 | 466 |
| ctatgtgttc atcaaacgtt cggatgctcg aactgcacct catggtcatg | 250 | 516 |
| ttatggttga gctggtagca gaactcgaag gcattcagta cggtcgtagt | 300 | 566 |
| ggtgagacac ttggtgtcct tgtccctcat gtgggcgaaa taccagtggc | 350 | 616 |
| ttaccgcaag gttcttcttc gtaagaacgg taataaagga gctggtggcc | 400 | 666 |
| atagttacgg cgccgatcta aagtcatttg acttaggcga cgagcttggc | 450 | 716 |
| actgatcctt atgaagattt tcaagaaaac tggaacacta aacatagcag | 500 | 766 |
| tggtgttacc cgtgaactca tgcgtgagct taacggaggg gcatacactc | 550 | 816 |
| gctatgtcga taacaacttc tgtggccctg atggctaccc tcttgagtgc | 600 | 866 |
| attaaagacc ttctagcacg tgctggtaaa gcttcatgca ctttgtccga | 650 | 916 |
| acaactggac tttattgaca ctaagagggg tgtatactgc tgccgtgaac | 700 | 966 |
| atgagcatga aattgcttgg tacacggaac gttctgaaaa gagctatgaa | 750 | 1,016 |

TABLE 1-continued

| The ORF1ab of SARS-CoV-2 (SEQ ID NO: 415) | ORF 1ab | SARS-CoV-2 |
|---|---|---|
| ttgcagacac cttttgaaat taaattggca aagaaatttg acaccttcaa | 800 | 1,066 |
| tggggaatgt ccaaattttg tatttccctt aaattccata atcaagacta | 850 | 1,116 |
| ttcaaccaag ggttgaaaag aaaaagcttg atggctttat gggtagaatt | 900 | 1,166 |
| cgatctgtct atccagttgc gtcaccaaat gaatgcaacc aaatgtgcct | 950 | 1,216 |
| ttcaactctc atgaagtgtg atcattgtgg tgaaacttca tggcagacgg | 1,000 | 1,266 |
| gcgattttgt taaagccact tgcgaatttt gtggcactga gaatttgact | 1,050 | 1,316 |
| aaagaaggtg ccactacttg tggttactta ccccaaaatg ctgttgttaa | 1,100 | 1,366 |
| aatttattgt ccagcatgtc acaattcaga agtaggacct gagcatagtc | 1,150 | 1,416 |
| ttgccgaata ccataatgaa tctggcttga aaaccattct tcgtaagggt | 1,200 | 1,466 |
| ggtcgcacta ttgcctttgg aggctgtgtg ttctcttatg ttggttgcca | 1,250 | 1,516 |
| taacaagtgt gcctattggg ttccacgtgc tagcgctaac ataggttgta | 1,300 | 1,566 |
| accatacagg tgttgttgga gaaggttccg aaggtcttaa tgacaacctt | 1,350 | 1,616 |
| cttgaaatac tccaaaaaga gaaagtcaac atcaatattg ttggtgactt | 1,400 | 1,666 |
| taaacttaat gaagagatcg ccattatttt ggcatctttt tctgcttcca | 1,450 | 1,716 |
| caagtgcttt tgtggaaact gtgaaaggtt tggattataa agcattcaaa | 1,500 | 1,766 |
| caaattgttg aatcctgtgg taattttaaa gttacaaaag gaaaagctaa | 1,550 | 1,816 |
| aaaaggtgcc tggaatattg gtgaacagaa atcaatactg agtcctcttt | 1,600 | 1,866 |
| atgcatttgc atcagaggct gctcgtgttg tacgatcaat ttctcccgc | 1,650 | 1,916 |
| actcttgaaa ctgctcaaaa ttctgtgcgt gttttacaga aggccgctat | 1,700 | 1,966 |
| aacaatacta gatggaattt cacagtattc actgagactc attgatgcta | 1,750 | 2,016 |
| tgatgttcac atctgatttg gctactaaca atctagttgt aatggcctac | 1,800 | 2,066 |
| attacaggtg gtgttgttca gttgacttcg cagtggctaa ctaacatctt | 1,850 | 2,116 |
| tggcactgtt tatgaaaaac tcaaacccgt ccttgattgg cttgaagaga | 1,900 | 2,166 |
| agtttaagga aggtgtagag tttcttagag acggttggga aattgttaaa | 1,950 | 2,216 |
| tttatctcaa cctgtgcttg tgaaattgtc ggtggacaaa ttgtcacctg | 2,000 | 2,266 |
| tgcaaaggaa attaaggaga gtgttcagac attctttaag cttgtaaata | 2,050 | 2,316 |
| aatttttggc tttgtgtgct gactctatca ttattggtgg agctaaactt | 2,100 | 2,366 |
| aaagccttga atttaggtga aacatttgtc acgcactcaa agggattgta | 2,150 | 2,416 |
| cagaaagtgt gttaaatcca gagaagaaac tggcctactc atgcctctaa | 2,200 | 2,466 |
| aagccccaaa agaaattatc ttcttagagg gagaaacact tcccacagaa | 2,250 | 2,516 |
| gtgttaacag aggaagttgt cttgaaaact ggtgatttac aaccattaga | 2,300 | 2,566 |
| acaacctact agtgaagctg ttgaagctcc attggttggt acaccagttt | 2,350 | 2,616 |
| gtattaacgg gcttatgttg ctcgaaatca aagacacaga aaagtactgt | 2,400 | 2,666 |
| gcccttgcac ctaatatgat ggtaacaaac aataccttca cactcaaagg | 2,450 | 2,716 |
| cggtgcacca acaaaggtta cttttggtga tgacactgtg atagaagtgc | 2,500 | 2,766 |
| aaggttacaa gagtgtgaat atcacttttg aacttgatga aaggattgat | 2,550 | 2,816 |
| aaagtactta atgagaagtg ctctgcctat acagttgaac tcggtacaga | 2,600 | 2,866 |
| agtaaatgag ttcgcctgtg ttgtggcaga tgctgtcata aaaactttgc | 2,650 | 2,916 |

TABLE 1-continued

| The ORF1ab of SARS-CoV-2 (SEQ ID NO: 415) | ORF 1ab | SARS-CoV-2 |
|---|---|---|
| aaccagtatc tgaattactt acaccactgg gcattgattt agatgagtgg | 2,700 | 2,966 |
| agtatggcta catactactt atttgatgag tctggtgagt ttaaattggc | 2,750 | 3,016 |
| ttcacatatg tattgttctt tctaccctcc agatgaggat gaagaagaag | 2,800 | 3,066 |
| gtgattgtga agaagaagag tttgagccat caactcaata tgagtatggt | 2,850 | 3,116 |
| actgaagatg attaccaagg taaacctttg gaatttggtg ccacttctgc | 2,900 | 3,166 |
| tgctcttcaa cctgaagaag agcaagaaga agattggtta gatgatgata | 2,950 | 3,216 |
| gtcaacaaac tgttggtcaa caagacggca gtgaggacaa tcagacaact | 3,000 | 3,266 |
| actattcaaa caattgttga ggttcaacct caattagaga tggaacttac | 3,050 | 3,316 |
| accagttgtt cagactattg aagtgaatag ttttagtggt tatttaaaac | 3,100 | 3,366 |
| ttactgacaa tgtatacatt aaaaatgcag acattgtgga agaagctaaa | 3,150 | 3,416 |
| aaggtaaaac caacagtggt tgttaatgca gccaatgttt accttaaaca | 3,200 | 3,466 |
| tggaggaggt gttgcaggag ccttaaataa ggctactaac aatgccatgc | 3,250 | 3,516 |
| aagttgaatc tgatgattac atagctacta atggaccact taaagtgggt | 3,300 | 3,566 |
| ggtagttgtg ttttaagcgg acacaatctt gctaaacact gtcttcatgt | 3,350 | 3,616 |
| tgtcggccca aatgttaaca aaggtgaaga cattcaactt cttaagagtg | 3,400 | 3,666 |
| cttatgaaaa ttttaatcag cacgaagttc tacttgcacc attattatca | 3,450 | 3,716 |
| gctggtattt ttggtgctga ccctatacat tctttaagag tttgtgtaga | 3,500 | 3,766 |
| tactgttcgc acaaatgtct acttagctgt ctttgataaa aatctctatg | 3,550 | 3,816 |
| acaaacttgt ttcaagcttt ttggaaatga agagtgaaaa gcaagttgaa | 3,600 | 3,866 |
| caaaagatcg ctgagattcc taaagaggaa gttaagccat ttataactga | 3,650 | 3,916 |
| aagtaaacct tcagttgaac agagaaaaca agatgataag aaaatcaaag | 3,700 | 3,966 |
| cttgtgttga agaagttaca acaactctgg aagaaactaa gttcctcaca | 3,750 | 4,016 |
| gaaaacttgt tactttatat tgacattaat ggcaatcttc atccagattc | 3,800 | 4,066 |
| tgccactctt gttagtgaca ttgacatcac tttcttaaag aaagatgctc | 3,850 | 4,116 |
| catatatagt gggtgatgtt gttcaagagg gtgttttaac tgctgtggtt | 3,900 | 4,166 |
| atacctacta aaaaggctgg tggcactact gaaatgctag cgaaagcttt | 3,950 | 4,216 |
| gagaaaagtg ccaacagaca attatataac cacttacccg ggtcagggtt | 4,000 | 4,266 |
| taaatggtta cactgtagag gaggcaaaga cagtgcttaa aaagtgtaaa | 4,050 | 4,316 |
| agtgcctttt acattctacc atctattatc tctaatgaga agcaagaaat | 4,100 | 4,366 |
| tcttggaact gtttcttgga atttgcgaga aatgcttgca catgcagaag | 4,150 | 4,416 |
| aaacacgcaa attaatgcct gtctgtgtgg aaactaaagc catagtttca | 4,200 | 4,466 |
| actatacagc gtaaatataa gggtattaaa atacaagagg gtgtggttga | 4,250 | 4,516 |
| ttatggtgct agattttact tttacaccag taaaacaact gtagcgtcac | 4,300 | 4,566 |
| ttatcaacac acttaacgat ctaaatgaaa ctcttgttac aatgccactt | 4,350 | 4,616 |
| ggctatgtaa cacatggctt aaatttggaa gaagctgctc ggtatatgag | 4,400 | 4,666 |
| atctctcaaa gtgccagcta cagtttctgt ttcttcacct gatgctgtta | 4,450 | 4,716 |
| cagcgtataa tggttatctt acttcttctt ctaaaacacc tgaagaacat | 4,500 | 4,766 |
| tttattgaaa ccatctcact tgctggttcc tataaagatt ggtcctattc | 4,550 | 4,816 |
| tggacaatct acacaactag gtatagaatt tcttaagaga ggtgataaaa | 4,600 | 4,866 |

TABLE 1-continued

| The ORF1ab of SARS-CoV-2 (SEQ ID NO: 415) | ORF 1ab | SARS-CoV-2 |
|---|---|---|
| gtgtatatta cactagtaat cctaccacat tccacctaga tggtgaagtt | 4,650 | 4,916 |
| atcacctttg acaatcttaa gacacttctt tctttgagag aagtgaggac | 4,700 | 4,966 |
| tattaaggtg tttacaacag tagacaacat taacctccac acgcaagttg | 4,750 | 5,016 |
| tggacatgtc aatgacatat ggacaacagt ttggtccaac ttatttggat | 4,800 | 5,066 |
| ggagctgatg ttactaaaat aaaacctcat aattcacatg aaggtaaaac | 4,850 | 5,116 |
| attttatgtt ttacctaatg atgacactct acgtgttgag gcttttgagt | 4,900 | 5,166 |
| actaccacac aactgatcct agttttctgg gtaggtacat gtcagcatta | 4,950 | 5,216 |
| aatcacacta aaaagtggaa atacccacaa gttaatggtt taacttctat | 5,000 | 5,266 |
| taaatgggca gataacaact gttatcttgc cactgcattg ttaacactcc | 5,050 | 5,316 |
| aacaaataga gttgaagttt aatccacctg ctctacaaga tgcttattac | 5,100 | 5,366 |
| agagcaaggg ctggtgaagc tgctaacttt tgtgcactta tcttagccta | 5,150 | 5,416 |
| ctgtaataag acagtaggtg agttaggtga tgttagagaa acaatgagtt | 5,200 | 5,466 |
| acttgtttca acatgccaat ttagattctt gcaaaagagt cttgaacgtg | 5,250 | 5,516 |
| gtgtgtaaaa cttgtggaca acagcagaca acccttaagg gtgtagaagc | 5,300 | 5,566 |
| tgttatgtac atgggcacac tttcttatga acaatttaag aaaggtgttc | 5,350 | 5,616 |
| agataccttg tacgtgtggt aaacaagcta caaaatatct agtacaacag | 5,400 | 5,666 |
| gagtcacctt ttgttatgat gtcagcacca cctgctcagt atgaacttaa | 5,450 | 5,716 |
| gcatggtaca tttacttgtg ctagtgagta cactggtaat taccagtgtg | 5,500 | 5,766 |
| gtcactataa acatataact tctaaagaaa ctttgtattg catagacggt | 5,550 | 5,816 |
| gctttactta caaagtcctc agaatacaaa ggtcctatta cggatgtttt | 5,600 | 5,866 |
| ctacaaagaa aacagttaca caacaaccat aaaaccagtt acttataaat | 5,650 | 5,916 |
| tggatggtgt tgtttgtaca gaaattgacc ctaagttgga caattattat | 5,700 | 5,966 |
| aagaaagaca attcttattt cacagagcaa ccaattgatc ttgtaccaaa | 5,750 | 6,016 |
| ccaaccatat ccaaacgcaa gcttcgataa ttttaagttt gtatgtgata | 5,800 | 6,066 |
| atatcaaatt tgctgatgat ttaaaccagt taactggtta taagaaacct | 5,850 | 6,116 |
| gcttcaagag agcttaaagt tacatttttc cctgacttaa atggtgatgt | 5,900 | 6,166 |
| ggtggctatt gattataaac actacacacc ctcttttaag aaaggagcta | 5,950 | 6,216 |
| aattgttaca taaacctatt gtttggcatg ttaacaatgc aactaataaa | 6,000 | 6,266 |
| gccacgtata aaccaaatac ctggtgtata cgttgtcttt ggagcacaaa | 6,050 | 6,316 |
| accagttgaa acatcaaatt cgtttgatgt actgaagtca gaggacgcgc | 6,100 | 6,366 |
| agggaatgga taatcttgcc tgcgaagatc taaaaccagt ctctgaagaa | 6,150 | 6,416 |
| gtagtggaaa atcctaccat acagaaagac gttcttgagt gtaatgtgaa | 6,200 | 6,466 |
| aactaccgaa gttgtaggag acattatact taaaccagca aataatagtt | 6,250 | 6,516 |
| taaaaattac agaagaggtt ggccacacag atctaatggc tgcttatgta | 6,300 | 6,566 |
| gacaattcta gtcttactat taagaaacct aatgaattat ctagagtatt | 6,350 | 6,616 |
| aggtttgaaa acccttgcta ctcatggttt agctgctgtt aatagtgtcc | 6,400 | 6,666 |
| cttgggatac tatagctaat tatgctaagc cttttcttaa caaagttgtt | 6,450 | 6,716 |
| agtacaacta ctaacatagt tacacggtgt ttaaaccgtg tttgtactaa | 6,500 | 6,766 |

TABLE 1-continued

| The ORF1ab of SARS-CoV-2 (SEQ ID NO: 415) | ORF 1ab | SARS-CoV-2 |
|---|---|---|
| ttatatgcct tatttcttta ctttattgct acaattgtgt acttttacta | 6,550 | 6,816 |
| gaagtacaaa ttctagaatt aaagcatcta tgccgactac tatagcaaag | 6,600 | 6,866 |
| aatactgtta agagtgtcgg taaattttgt ctagaggctt catttaatta | 6,650 | 6,916 |
| tttgaagtca cctaattttt ctaaactgat aaatattata atttggtttt | 6,700 | 6,966 |
| tactattaag tgtttgccta ggttctttaa tctactcaac cgctgcttta | 6,750 | 7,016 |
| ggtgttttaa tgtctaattt aggcatgcct tcttactgta ctggttacag | 6,800 | 7,066 |
| agaaggctat ttgaactcta ctaatgtcac tattgcaacc tactgtactg | 6,850 | 7,116 |
| gttctatacc ttgtagtgtt tgtcttagtg gtttagattc tttagacacc | 6,900 | 7,166 |
| tatccttctt tagaaactat acaaattacc atttcatctt ttaaatggga | 6,950 | 7,216 |
| tttaactgct tttggcttag ttgcagagtg gtttttggca tatattcttt | 7,000 | 7,266 |
| tcactaggtt tttctatgta cttggattgg ctgcaatcat gcaattgttt | 7,050 | 7,316 |
| ttcagctatt ttgcagtaca ttttattagt aattcttggc ttatgtggtt | 7,100 | 7,366 |
| aataattaat cttgtacaaa tggccccgat ttcagctatg gttagaatgt | 7,150 | 7,416 |
| acatcttctt tgcatcattt tattatgtat ggaaaagtta tgtgcatgtt | 7,200 | 7,466 |
| gtagacggtt gtaattcatc aacttgtatg atgtgttaca aacgtaatag | 7,250 | 7,516 |
| agcaacaaga gtcgaatgta caactattgt taatggtgtt agaaggtcct | 7,300 | 7,566 |
| tttatgtcta tgctaatgga ggtaaaggct tttgcaaact acacaattgg | 7,350 | 7,616 |
| aattgtgtta attgtgatac attctgtgct ggtagtacat ttattagtga | 7,400 | 7,666 |
| tgaagttgcg agagacttgt cactacagtt taaaagacca ataaatccta | 7,450 | 7,716 |
| ctgaccagtc ttcttacatc gttgatagtg ttacagtgaa gaatggttcc | 7,500 | 7,766 |
| atccatcttt actttgataa agctggtcaa aagacttatg aaagacattc | 7,550 | 7,816 |
| tctctctcat tttgttaact tagacaacct gagagctaat aacactaaag | 7,600 | 7,866 |
| gttcattgcc tattaatgtt atagtttttg atggtaaatc aaaatgtgaa | 7,650 | 7,916 |
| gaatcatctg caaaatcagc gtctgtttac tacagtcagc ttatgtgtca | 7,700 | 7,966 |
| acctatactg ttactagatc aggcattagt gtctgatgtt ggtgatagtg | 7,750 | 8,016 |
| cggaagttgc agttaaaatg tttgatgctt acgttaatac gttttcatca | 7,800 | 8,066 |
| acttttaacg taccaatgga aaaactcaaa acactagttg caactgcaga | 7,850 | 8,116 |
| agctgaactt gcaaagaatg tgtccttaga caatgtctta tctactttta | 7,900 | 8,166 |
| tttcagcagc tcggcaaggg tttgttgatt cagatgtaga aactaaagat | 7,950 | 8,216 |
| gttgttgaat gtcttaaatt gtcacatcaa tctgacatag aagttactgg | 8,000 | 8,266 |
| cgatagttgt aataactata tgctcaccta taacaaagtt gaaaacatga | 8,050 | 8,316 |
| caccccgtga ccttggtgct tgtattgact gtagtgcgcg tcatattaat | 8,100 | 8,366 |
| gcgcaggtag caaaaagtca caacattgct ttgatatgga acgttaaaga | 8,150 | 8,416 |
| tttcatgtca ttgtctgaac aactacgaaa acaaatacgt agtgctgcta | 8,200 | 8,466 |
| aaaagaataa cttacctttt aagttgacat gtgcaactac tagacaagtt | 8,250 | 8,516 |
| gttaatgttg taacaacaaa gatagcactt aagggtggta aaattgttaa | 8,300 | 8,566 |
| taattggttg aagcagttaa ttaaagttac acttgtgttc ctttttgttg | 8,350 | 8,616 |
| ctgctatttt ctatttaata acacctgttc atgtcatgtc taaacatact | 8,400 | 8,666 |
| gacttttcaa gtgaaatcat aggatacaag gctattgatg gtggtgtcac | 8,450 | 8,716 |

TABLE 1-continued

| The ORF1ab of SARS-CoV-2 (SEQ ID NO: 415) | ORF 1ab | SARS-CoV-2 |
|---|---|---|
| tcgtgacata gcatctacag atacttgttt tgctaacaaa catgctgatt | 8,500 | 8,766 |
| ttgacacatg gtttagccag cgtggtggta gttatactaa tgacaaagct | 8,550 | 8,816 |
| tgcccattga ttgctgcagt cataacaaga gaagtgggtt ttgtcgtgcc | 8,600 | 8,866 |
| tggtttgcct ggcacgatat tacgcacaac taatggtgac tttttgcatt | 8,650 | 8,916 |
| tcttacctag agtttttagt gcagttggta acatctgtta cacaccatca | 8,700 | 8,966 |
| aaacttatag agtacactga ctttgcaaca tcagcttgtg ttttggctgc | 8,750 | 9,016 |
| tgaatgtaca atttttaaag atgcttctgg taagccagta ccatattgtt | 8,800 | 9,066 |
| atgataccaa tgtactagaa ggttctgttg cttatgaaag tttacgccct | 8,850 | 9,116 |
| gacacacgtt atgtgctcat ggatggctct attattcaat ttcctaacac | 8,900 | 9,166 |
| ctaccttgaa ggttctgtta gagtggtaac aacttttgat tctgagtact | 8,950 | 9,216 |
| gtaggcacgg cacttgtgaa agatcagaag ctggtgtttg tgtatctact | 9,000 | 9,266 |
| agtggtagat gggtacttaa caatgattat tacagatctt taccaggagt | 9,050 | 9,316 |
| tttctgtggt gtagatgctg taaatttact tactaatatg tttacaccac | 9,100 | 9,366 |
| taattcaacc tattggtgct ttggacatat cagcatctat agtagctggt | 9,150 | 9,416 |
| ggtattgtag ctatcgtagt aacatgcctt gcctactatt ttatgaggtt | 9,200 | 9,466 |
| tagaagagct tttggtgaat acagtcatgt agttgccttt aatactttac | 9,250 | 9,516 |
| tattccttat gtcattcact gtactctgtt taacaccagt ttactcattc | 9,300 | 9,566 |
| ttacctggtg tttattctgt tatttacttg tacttgacat tttatcttac | 9,350 | 9,616 |
| taatgatgtt tctttttttag cacatattca gtggatggtt atgttcacac | 9,400 | 9,666 |
| ctttagtacc tttctggata acaattgctt atatcatttg tatttccaca | 9,450 | 9,716 |
| aagcatttct attggttctt tagtaattac ctaaagagac gtgtagtctt | 9,500 | 9,766 |
| taatggtgtt tcctttagta cttttgaaga agctgcgctg tgcacctttt | 9,550 | 9,816 |
| tgttaaataa agaaatgtat ctaaagttgc gtagtgatgt gctattacct | 9,600 | 9,866 |
| cttacgcaat ataatagata cttagctctt tataataagt acaagtattt | 9,650 | 9,916 |
| tagtggagca atggatacaa ctagctacag agaagctgct tgttgtcatc | 9,700 | 9,966 |
| tcgcaaaggc tctcaatgac ttcagtaact caggttctga tgttctttac | 9,750 | 10,016 |
| caaccaccac aaacctctat cacctcagct gttttgcaga gtggttttag | 9,800 | 10,066 |
| aaaaatggca ttcccatctg gtaaagttga gggttgtatg gtacaagtaa | 9,850 | 10,116 |
| cttgtggtac aactacactt aacggtcttt ggcttgatga cgtagtttac | 9,900 | 10,166 |
| tgtccaagac atgtgatctg cacctctgaa gacatgctta accctaatta | 9,950 | 10,216 |
| tgaagattta ctcattcgta agtctaatca taatttcttg gtacaggctg | 10,000 | 10,266 |
| gtaatgttca actcagggtt attggacatt ctatgcaaaa ttgtgtactt | 10,050 | 10,316 |
| aagcttaagg ttgatacagc caatcctaag acacctaagt ataagtttgt | 10,100 | 10,366 |
| tcgcattcaa ccaggacaga ctttttcagt gttagcttgt tacaatggtt | 10,150 | 10,416 |
| caccatctgg tgtttaccaa tgtgctatga ggcccaattt cactattaag | 10,200 | 10,466 |
| ggttcattcc ttaatggttc atgtggtagt gttggtttta acatagatta | 10,250 | 10,516 |
| tgactgtgtc tctttttgtt acatgcacca tatggaatta ccaactggag | 10,300 | 10,566 |
| ttcatgctgg cacagactta gaaggtaact tttatggacc ttttgttgac | 10,350 | 10,616 |

TABLE 1-continued

| The ORF1ab of SARS-CoV-2 (SEQ ID NO: 415) | ORF 1ab | SARS-CoV-2 |
|---|---|---|
| aggcaaacag cacaagcagc tggtacggac acaactatta cagttaatgt | 10,400 | 10,666 |
| tttagcttgg ttgtacgctg ctgttataaa tggagacagg tggtttctca | 10,450 | 10,716 |
| atcgatttac cacaactctt aatgacttta accttgtggc tatgaagtac | 10,500 | 10,766 |
| aattatgaac ctctaacaca agaccatgtt gacatactag gacctctttc | 10,550 | 10,816 |
| tgctcaaact ggaattgccg ttttagatat gtgtgcttca ttaaaagaat | 10,600 | 10,866 |
| tactgcaaaa tggtatgaat ggacgtacca tattgggtag tgctttatta | 10,650 | 10,916 |
| gaagatgaat ttacaccttt tgatgttgtt agacaatgct caggtgttac | 10,700 | 10,966 |
| tttccaaagt gcagtgaaaa gaacaatcaa gggtacacac cactggttgt | 10,750 | 11,016 |
| tactcacaat tttgacttca cttttagttt tagtccagag tactcaatgg | 10,800 | 11,066 |
| tctttgttct ttttttgta tgaaaatgcc tttttacctt ttgctatggg | 10,850 | 11,116 |
| tattattgct atgtctgctt ttgcaatgat gtttgtcaaa cataagcatg | 10,900 | 11,166 |
| catttctctg tttgtttttg ttaccttctc ttgccactgt agcttatttt | 10,950 | 11,216 |
| aatatggtct atatgcctgc tagttgggtg atgcgtatta tgacatggtt | 11,000 | 11,266 |
| ggatatggtt gatactagtt tgtctggttt taagctaaaa gactgtgtta | 11,050 | 11,316 |
| tgtatgcatc agctgtagtg ttactaatcc ttatgacagc aagaactgtg | 11,100 | 11,366 |
| tatgatgatg gtgctaggag agtgtggaca cttatgaatg tcttgacact | 11,150 | 11,416 |
| cgtttataaa gtttattatg gtaatgcttt agatcaagcc atttccatgt | 11,200 | 11,466 |
| gggctcttat aatctctgtt acttctaact actcaggtgt agttacaact | 11,250 | 11,516 |
| gtcatgtttt tggccagagg tattgttttt atgtgtgttg agtattgccc | 11,300 | 11,566 |
| tattttcttc ataactggta atacacttca gtgtataatg ctagtttatt | 11,350 | 11,616 |
| gtttcttagg ctatttttgt acttgttact ttggcctctt ttgtttactc | 11,400 | 11,666 |
| aaccgctact ttagactgac tcttggtgtt tatgattact tagtttctac | 11,450 | 11,716 |
| acaggagttt agatatatga attcacaggg actactccca cccaagaata | 11,500 | 11,766 |
| gcatagatgc cttcaaactc aacattaaat tgttgggtgt tggtggcaaa | 11,550 | 11,816 |
| ccttgtatca aagtagccac tgtacagtct aaaatgtcag atgtaaagtg | 11,600 | 11,866 |
| cacatcagta gtcttactct cagttttgca acaactcaga gtagaatcat | 11,650 | 11,916 |
| catctaaatt gtgggctcaa tgtgtccagt tacacaatga cattctctta | 11,700 | 11,966 |
| gctaaagata ctactgaagc ctttgaaaaa atggtttcac tactttctgt | 11,750 | 12,016 |
| tttgctttcc atgcagggtg ctgtagacat aaacaagctt tgtgaagaaa | 11,800 | 12,066 |
| tgctggacaa cagggcaacc ttacaagcta tagcctcaga gtttagttcc | 11,850 | 12,116 |
| cttccatcat atgcagcttt tgctactgct caagaagctt atgagcaggc | 11,900 | 12,166 |
| tgttgctaat ggtgattctg aagttgttct taaaaagttg aagaagtctt | 11,950 | 12,216 |
| tgaatgtggc taaatctgaa tttgaccgtg atgcagccat gcaacgtaag | 12,000 | 12,266 |
| ttggaaaaga tggctgatca agctatgacc caaatgtata aacaggctag | 12,050 | 12,316 |
| atctgaggac aagagggcaa aagttactag tgctatgcag acaatgcttt | 12,100 | 12,366 |
| tcactatgct tagaaagttg gataatgatg cactcaacaa cattatcaac | 12,150 | 12,416 |
| aatgcaagag atggttgtgt tcccttgaac ataatacctc ttacaacagc | 12,200 | 12,466 |
| agccaaacta atggttgtca taccagacta taacacatat aaaaatacgt | 12,250 | 12,516 |
| gtgatggtac aacatttact tatgcatcag cattgtggga aatccaacag | 12,300 | 12,566 |

TABLE 1-continued

| The ORF1ab of SARS-CoV-2 (SEQ ID NO: 415) | ORF 1ab | SARS-CoV-2 |
|---|---|---|
| gttgtagatg cagatagtaa aattgttcaa cttagtgaaa ttagtatgga | 12,350 | 12,616 |
| caattcacct aatttagcat ggcctcttat tgtaacagct ttaagggcca | 12,400 | 12,666 |
| attctgctgt caaattacag aataatgagc ttagtcctgt tgcactacga | 12,450 | 12,716 |
| cagatgtctt gtgctgccgg tactacacaa actgcttgca ctgatgacaa | 12,500 | 12,766 |
| tgcgttagct tactacaaca caacaaaggg aggtaggttt gtacttgcac | 12,550 | 12,816 |
| tgttatccga tttacaggat ttgaaatggg ctagattccc taagagtgat | 12,600 | 12,866 |
| ggaactggta ctatctatac agaactggaa ccaccttgta ggtttgttac | 12,650 | 12,916 |
| agacacacct aaaggtccta aagtgaagta tttatacttt attaaaggat | 12,700 | 12,966 |
| taaacaacct aaatagaggt atggtacttg gtagtttagc tgccacagta | 12,750 | 13,016 |
| cgtctacaag ctggtaatgc aacagaagtg cctgccaatt caactgtatt | 12,800 | 13,066 |
| atctttctgt gcttttgctg tagatgctgc taaagcttac aaagattatc | 12,850 | 13,116 |
| tagctagtgg gggacaacca atcactaatt gtgttaagat gttgtgtaca | 12,900 | 13,166 |
| cacactggta ctggtcaggc aataacagtt acaccggaag ccaatatgga | 12,950 | 13,216 |
| tcaagaatcc tttggtggtg catcgtgttg tctgtactgc cgttgccaca | 13,000 | 13,266 |
| tagatcatcc aaatcctaaa ggattttgtg acttaaaagg taagtatgta | 13,050 | 13,316 |
| caaataccta caacttgtgc taatgaccct gtgggtttta cacttaaaaa | 13,100 | 13,366 |
| cacagtctgt accgtctgcg gtatgtggaa aggttatggc tgtagttgtg | 13,150 | 13,416 |
| atcaactccg cgaacccatg cttcagtcag ctgatgcaca atcgttttta | 13,200 | 13,466 |
| aacgggtttg cggtgtaagt gcagcccgtc ttacaccgtg cggcacaggc | 13,250 | 13,516 |
| actagtactg atgtcgtata cagggctttt gacatctaca atgataaagt | 13,300 | 13,566 |
| agctggtttt gctaaattcc taaaaactaa ttgttgtcgc ttccaagaaa | 13,350 | 13,616 |
| aggacgaaga tgacaattta attgattctt actttgtagt taagagacac | 13,400 | 13,666 |
| actttctcta actaccaaca tgaagaaaca atttataatt tacttaagga | 13,450 | 13,716 |
| ttgtccagct gttgctaaac atgacttctt taagtttaga atagacggtg | 13,500 | 13,766 |
| acatggtacc acatatatca cgtcaacgtc ttactaaata cacaatggca | 13,550 | 13,816 |
| gacctcgtct atgctttaag gcattttgat gaaggtaatt gtgacacatt | 13,600 | 13,866 |
| aaaagaaata cttgtcacat acaattgttg tgatgatgat tatttcaata | 13,650 | 13,916 |
| aaaaggactg gtatgatttt gtagaaaacc cagatatatt acgcgtatac | 13,700 | 13,966 |
| gccaacttag gtgaacgtgt acgccaagct ttgttaaaaa cagtacaatt | 13,750 | 14,016 |
| ctgtgatgcc atgcgaaatg ctggtattgt tggtgtactg acattagata | 13,800 | 14,066 |
| atcaagatct caatggtaac tggtatgatt tcggtgattt catacaaacc | 13,850 | 14,116 |
| acgccaggta gtggagttcc tgttgtagat tcttattatt cattgttaat | 13,900 | 14,166 |
| gcctatatta accttgacca gggctttaac tgcagagtca catgttgaca | 13,950 | 14,216 |
| ctgacttaac aaagccttac attaagtggg atttgttaaa atatgacttc | 14,000 | 14,266 |
| acggaagaga ggttaaaact ctttgaccgt tattttaaat attgggatca | 14,050 | 14,316 |
| gacataccac ccaaattgtg ttaactgttt ggatgacaga tgcattctgc | 14,100 | 14,366 |
| attgtgcaaa ctttaatgtt ttattctcta cagtgttccc acctacaagt | 14,150 | 14,416 |
| tttggaccac tagtgagaaa aatatttgtt gatggtgttc catttgtagt | 14,200 | 14,466 |

TABLE 1-continued

| The ORF1ab of SARS-CoV-2 (SEQ ID NO: 415) | ORF 1ab | SARS-CoV-2 |
|---|---|---|
| ttcaactgga taccacttca gagagctagg tgttgtacat aatcaggatg | 14,250 | 14,516 |
| taaacttaca tagctctaga cttagtttta aggaattact tgtgtatgct | 14,300 | 14,566 |
| gctgaccctg ctatgcacgc tgcttctggt aatctattac tagataaacg | 14,350 | 14,616 |
| cactacgtgc ttttcagtag ctgcacttac taacaatgtt gcttttcaaa | 14,400 | 14,666 |
| ctgtcaaacc cggtaatttt aacaaagact tctatgactt tgctgtgtct | 14,450 | 14,716 |
| aagggtttct ttaaggaagg aagttctgtt gaattaaaac acttcttctt | 14,500 | 14,766 |
| tgctcaggat ggtaatgctg ctatcagcga ttatgactac tatcgttata | 14,550 | 14,816 |
| atctaccaac aatgtgtgat atcagacaac tactatttgt agttgaagtt | 14,600 | 14,866 |
| gttgataagt actttgattg ttacgatggt ggctgtatta atgctaacca | 14,650 | 14,916 |
| agtcatcgtc aacaacctag acaaatcagc tggttttcca tttaataaat | 14,700 | 14,966 |
| ggggtaaggc tagactttat tatgattcaa tgagttatga ggatcaagat | 14,750 | 15,016 |
| gcacttttcg catatacaaa acgtaatgtc atocctacta taactcaaat | 14,800 | 15,066 |
| gaatcttaag tatgccatta gtgcaaagaa tagagctcgc accgtagctg | 14,850 | 15,116 |
| gtgtctctat ctgtagtact atgaccaata gacagtttca tcaaaaatta | 14,900 | 15,166 |
| ttgaaatcaa tagccgccac tagaggagct actgtagtaa ttggaacaag | 14,950 | 15,216 |
| caaattctat ggtggttggc acaacatgtt aaaaactgtt tatagtgatg | 15,000 | 15,266 |
| tagaaaaccc tcaccttatg ggttgggatt atcctaaatg tgatagagcc | 15,050 | 15,316 |
| atgcctaaca tgcttagaat tatggcctca cttgttottg ctcgcaaaca | 15,100 | 15,366 |
| tacaacgtgt tgtagcttgt cacaccgttt ctatagatta gctaatgagt | 15,150 | 15,416 |
| gtgctcaagt attgagtgaa atggtcatgt gtggcggttc actatatgtt | 15,200 | 15,466 |
| aaaccaggtg gaacctcatc aggagatgcc acaactgctt atgctaatag | 15,250 | 15,516 |
| tgtttttaac atttgtcaag ctgtcacggc caatgttaat gcacttttat | 15,300 | 15,566 |
| ctactgatgg taacaaaatt gccgataagt atgtccgcaa tttacaacac | 15,350 | 15,616 |
| agactttatg agtgtctcta tagaaataga gatgttgaca cagactttgt | 15,400 | 15,666 |
| gaatgagttt tacgcatatt tgcgtaaaca tttctcaatg atgatactct | 15,450 | 15,716 |
| ctgacgatgc tgttgtgtgt ttcaatagca cttatgcatc tcaaggtcta | 15,500 | 15,766 |
| gtggctagca taaagaactt taagtcagtt ctttattatc aaaacaatgt | 15,550 | 15,816 |
| ttttatgtct gaagcaaaat gttggactga gactgacctt actaaaggac | 15,600 | 15,866 |
| ctcatgaatt ttgctctcaa catacaatgc tagttaaaca gggtgatgat | 15,650 | 15,916 |
| tatgtgtacc ttccttaccc agatccatca agaatcctag gggccggctg | 15,700 | 15,966 |
| ttttgtagat gatatcgtaa aaacagatgg tacacttatg attgaacggt | 15,750 | 16,016 |
| tcgtgtcttt agctatagat gcttacccac ttactaaaca tcctaatcag | 15,800 | 16,066 |
| gagtatgctg atgtctttca tttgtactta caatacataa gaaagctaca | 15,850 | 16,116 |
| tgatgagtta acaggacaca tgttagacat gtattctgtt atgcttacta | 15,900 | 16,166 |
| atgataacac ttcaaggtat tgggaacctg agttttatga ggctatgtac | 15,950 | 16,216 |
| acaccgcata cagtcttaca ggctgttggg gottgtgttc tttgcaattc | 16,000 | 16,266 |
| acagacttca ttaagatgtg gtgcttgcat acgtagacca ttcttatgtt | 16,050 | 16,316 |
| gtaaatgctg ttacgaccat gtcatatcaa catcacataa attagtcttg | 16,100 | 16,366 |
| tctgttaatc cgtatgtttg caatgctcca ggttgtgatg tcacagatgt | 16,150 | 16,416 |

TABLE 1-continued

| The ORF1ab of SARS-CoV-2 (SEQ ID NO: 415) | ORF 1ab | SARS-CoV-2 |
|---|---|---|
| gactcaactt tacttaggag gtatgagcta ttattgtaaa tcacataaac | 16,200 | 16,466 |
| cacccattag ttttccattg tgtgctaatg gacaagtttt tggtttatat | 16,250 | 16,516 |
| aaaaatacat gtgttggtag cgataatgtt actgacttta atgcaattgc | 16,300 | 16,566 |
| aacatgtgac tggacaaatg ctggtgatta cattttagct aacacctgta | 16,350 | 16,616 |
| ctgaaagact caagcttttt gcagcagaaa cgctcaaagc tactgaggag | 16,400 | 16,666 |
| acatttaaac tgtcttatgg tattgctact gtacgtgaag tgctgtctga | 16,450 | 16,716 |
| cagagaatta catctttcat gggaagttgg taaacctaga ccaccactta | 16,500 | 16,766 |
| accgaaatta tgtctttact ggttatcgtg taactaaaaa cagtaaagta | 16,550 | 16,816 |
| caaataggag agtacacctt tgaaaaaggt gactatggtg atgctgttgt | 16,600 | 16,866 |
| ttaccgaggt acaacaactt acaaattaaa tgttggtgat tattttgtgc | 16,650 | 16,916 |
| tgacatcaca tacagtaatg ccattaagtg cacctacact agtgccacaa | 16,700 | 16,966 |
| gagcactatg ttagaattac tggcttatac ccaacactca atatctcaga | 16,750 | 17,016 |
| tgagttttct agcaatgttg caaattatca aaaggttggt atgcaaaagt | 16,800 | 17,066 |
| attctacact ccagggacca cctggtactg gtaagagtca ttttgctatt | 16,850 | 17,116 |
| ggcctagctc tctactaccc ttctgctcgc atagtgtata cagcttgctc | 16,900 | 17,166 |
| tcatgccgct gttgatgcac tatgtgagaa ggcattaaaa tatttgccta | 16,950 | 17,216 |
| tagataaatg tagtagaatt atacctgcac gtgctcgtgt agagtgtttt | 17,000 | 17,266 |
| gataaattca aagtgaattc aacattagaa cagtatgtct tttgtactgt | 17,050 | 17,316 |
| aaatgcattg cctgagacga cagcagatat agttgtcttt gatgaaattt | 17,100 | 17,366 |
| caatggccac aaattatgat ttgagtgttg tcaatgccag attacgtgct | 17,150 | 17,416 |
| aagcactatg tgtacattgg cgaccctgct caattacctg caccacgcac | 17,200 | 17,466 |
| attgctaact aagggcacac tagaaccaga atatttcaat tcagtgtgta | 17,250 | 17,516 |
| gacttatgaa aactataggt ccagacatgt tcctcggaac ttgtcggcgt | 17,300 | 17,566 |
| tgtcctgctg aaattgttga cactgtgagt gctttggttt atgataataa | 17,350 | 17,616 |
| gcttaaagca cataaagaca aatcagctca atgctttaaa atgttttata | 17,400 | 17,666 |
| agggtgttat cacgcatgat gtttcatctg caattaacag gccacaaata | 17,450 | 17,716 |
| ggcgtggtaa gagaattcct tacacgtaac cctgcttgga gaaaagctgt | 17,500 | 17,766 |
| ctttatttca ccttataatt cacagaatgc tgtagcctca aagattttgg | 17,550 | 17,816 |
| gactaccaac tcaaactgtt gattcatcac agggctcaga atatgactat | 17,600 | 17,866 |
| gtcatattca ctcaaaccac tgaaacagct cactcttgta atgtaaacag | 17,650 | 17,916 |
| atttaatgtt gctattacca gagcaaaagt aggcatactt tgcataatgt | 17,700 | 17,966 |
| ctgatagaga cctttatgac aagttgcaat ttacaagtct tgaaattcca | 17,750 | 18,016 |
| cgtaggaatg tggcaacttt acaagctgaa aatgtaacag gactctttaa | 17,800 | 18,066 |
| agattgtagt aaggtaatca ctgggttaca tcctacacag gcacctacac | 17,850 | 18,116 |
| acctcagtgt tgacactaaa ttcaaaactg aaggtttatg tgttgacata | 17,900 | 18,166 |
| cctggcatac ctaaggacat gacctataga agactcatct ctatgatggg | 17,950 | 18,216 |
| ttttaaaatg aattatcaag ttaatggtta ccctaacatg tttatcaccc | 18,000 | 18,266 |
| gcgaagaagc tataagacat gtacgtgcat ggattggctt cgatgtcgag | 18,050 | 18,316 |

TABLE 1-continued

| The ORF1ab of SARS-CoV-2 (SEQ ID NO: 415) | ORF 1ab | SARS-CoV-2 |
|---|---|---|
| gggtgtcatg ctactagaga agctgttggt accaatttac ctttacagct | 18,100 | 18,366 |
| aggtttttct acaggtgtta acctagttgc tgtacctaca ggttatgttg | 18,150 | 18,416 |
| atacacctaa taatacagat tttccagag ttagtgctaa accaccgcct | 18,200 | 18,466 |
| ggagatcaat ttaaacacct cataccactt atgtacaaag gacttccttg | 18,250 | 18,516 |
| gaatgtagtg cgtataaaga ttgtacaaat gttaagtgac acacttaaaa | 18,300 | 18,566 |
| atctctctga cagagtcgta tttgtcttat gggcacatgg ctttgagttg | 18,350 | 18,616 |
| acatctatga agtattttgt gaaaatagga cctgagcgca cctgttgtct | 18,400 | 18,666 |
| atgtgataga cgtgccacat gcttttccac tgcttcagac acttatgcct | 18,450 | 18,716 |
| gttggcatca ttctattgga tttgattacg tctataatcc gtttatgatt | 18,500 | 18,766 |
| gatgttcaac aatggggttt tacaggtaac ctacaaagca accatgatct | 18,550 | 18,816 |
| gtattgtcaa gtccatggta atgcacatgt agctagttgt gatgcaatca | 18,600 | 18,866 |
| tgactaggtg tctagctgtc cacgagtgct ttgttaagcg tgttgactgg | 18,650 | 18,916 |
| actattgaat atcctataat tggtgatgaa ctgaagatta atgcggcttg | 18,700 | 18,966 |
| tagaaaggtt caacacatgg ttgttaaagc tgcattatta gcagacaaat | 18,750 | 19,016 |
| tcccagttct tcacgacatt ggtaacccta aagctattaa gtgtgtacct | 18,800 | 19,066 |
| caagctgatg tagaatggaa gttctatgat gcacagcctt gtagtgacaa | 18,850 | 19,116 |
| agcttataaa atagaagaat tattctattc ttatgccaca cattctgaca | 18,900 | 19,166 |
| aattcacaga tggtgtatgc ctattttgga attgcaatgt cgatagatat | 18,950 | 19,216 |
| cctgctaatt ccattgtttg tagatttgac actagagtgc tatctaacct | 19,000 | 19,266 |
| taacttgcct ggttgtgatg gtggcagttt gtatgtaaat aaacatgcat | 19,050 | 19,316 |
| tccacacacc agcttttgat aaaagtgctt ttgttaattt aaaacaatta | 19,100 | 19,366 |
| ccatttttct attactctga cagtccatgt gagtctcatg gaaaacaagt | 19,150 | 19,416 |
| agtgtcagat atagattatg taccactaaa gtctgctacg tgtataacac | 19,200 | 19,466 |
| gttgcaattt aggtggtgct gtctgtagac atcatgctaa tgagtacaga | 19,250 | 19,516 |
| ttgtatctcg atgcttataa catgatgatc tcagctggct ttagcttgtg | 19,300 | 19,566 |
| ggtttacaaa caatttgata cttataacct ctggaacact tttacaagac | 19,350 | 19,616 |
| ttcagagttt agaaaatgtg gcttttaatg ttgtaaataa gggacacttt | 19,400 | 19,666 |
| gatggacaac agggtgaagt accagtttct atcattaata acactgttta | 19,450 | 19,716 |
| cacaaaagtt gatggtgttg atgtagaatt gtttgaaaat aaaacaacat | 19,500 | 19,766 |
| tacctgttaa tgtagcattt gagctttggg ctaagcgcaa cattaaacca | 19,550 | 19,816 |
| gtaccagagg tgaaaatact caataatttg ggtgtggaca ttgctgctaa | 19,600 | 19,866 |
| tactgtgatc tgggactaca aaagagatgc tccagcacat atatctacta | 19,650 | 19,916 |
| ttggtgtttg ttctatgact gacatagcca agaaaccaac tgaaacgatt | 19,700 | 19,966 |
| tgtgcaccac tcactgtctt ttttgatggt agagttgatg gtcaagtaga | 19,750 | 20,016 |
| cttatttaga aatgcccgta atggtgttct tattacagaa ggtagtgtta | 19,800 | 20,066 |
| aaggtttaca accatctgta ggtcccaaac aagctagtct taatggagtc | 19,850 | 20,116 |
| acattaattg gagaagccgt aaaaacacag ttcaattatt ataagaaagt | 19,900 | 20,166 |
| tgatggtgtt gtccaacaat tacctgaaac ttactttact cagagtagaa | 19,950 | 20,216 |
| atttacaaga atttaaaccc aggagtcaaa tggaaattga tttcttagaa | 20,000 | 20,266 |

TABLE 1-continued

| The ORF1ab of SARS-CoV-2 (SEQ ID NO: 415) | ORF 1ab | SARS-CoV-2 |
|---|---|---|
| ttagctatgg atgaattcat tgaacggtat aaattagaag gctatgcctt | 20,050 | 20,316 |
| cgaacatatc gtttatggag attttagtca tagtcagtta ggtggtttac | 20,100 | 20,366 |
| atctactgat tggactagct aaacgtttta aggaatcacc ttttgaatta | 20,150 | 20,416 |
| gaagatttta ttcctatgga cagtacagtt aaaaactatt tcataacaga | 20,200 | 20,466 |
| tgcgcaaaca ggttcatcta agtgtgtgtg ttctgttatt gatttattac | 20,250 | 20,516 |
| ttgatgattt tgttgaaata ataaaatccc aagatttatc tgtagtttct | 20,300 | 20,566 |
| aaggttgtca aagtgactat tgactataca gaaatttcat ttatgctttg | 20,350 | 20,616 |
| gtgtaaagat ggccatgtag aaacatttta cccaaaatta caatctagtc | 20,400 | 20,666 |
| aagcgtggca accgggtgtt gctatgccta atctttacaa aatgcaaaga | 20,450 | 20,716 |
| atgctattag aaaagtgtga ccttcaaaat tatggtgata gtgcaacatt | 20,500 | 20,766 |
| acctaaaggc ataatgatga atgtcgcaaa atatactcaa ctgtgtcaat | 20,550 | 20,816 |
| atttaaacac attaacatta gctgtaccct ataatatgag agttatacat | 20,600 | 20,866 |
| tttggtgctg gttctgataa aggagttgca ccaggtacag ctgttttaag | 20,650 | 20,916 |
| acagtggttg cctacgggta cgctgcttgt cgattcagat cttaatgact | 20,700 | 20,966 |
| ttgtctctga tgcagattca actttgattg gtgattgtgc aactgtacat | 20,750 | 21,016 |
| acagctaata aatgggatct cattattagt gatatgtacg accctaagac | 20,800 | 21,066 |
| taaaaatgtt acaaaagaaa atgactctaa agagggtttt ttcacttaca | 20,850 | 21,116 |
| tttgtgggtt tatacaacaa aagctagctc ttggaggttc cgtggctata | 20,900 | 21,166 |
| aagataacag aacattcttg gaatgctgat ctttataagc tcatgggaca | 20,950 | 21,216 |
| cttcgcatgg tggacagcct ttgttactaa tgtgaatgcg tcatcatctg | 21,000 | 21,266 |
| aagcattttt aattggatgt aattatcttg gcaaaccacg cgaacaaata | 21,050 | 21,316 |
| gatggttatg tcatgcatgc aaattacata ttttggagga atacaaatcc | 21,100 | 21,366 |
| aattcagttg tcttcctatt ctttatttga catgagtaaa tttcccctta | 21,150 | 21,416 |
| aattaagggg tactgctgtt atgtctttaa aagaaggtca aatcaatgat | 21,200 | 21,466 |
| atgattttat ctcttcttag taaaggtaga cttataatta gagaaaacaa | 21,250 | 21,516 |
| cagagttgtt atttctagtg atgttcttgt taacaactaa | 21,290 | 21,556 |

B. The S Gene

The S gene encodes the SARS-CoV-2 spike protein. The S protein of SARS-CoV is functionally cleaved into two subunits: the S1 domain and the S2 domain (He, Y. et al. (2004) "*Receptor-Binding Domain Of SARS-CoV Spike Protein Induces Highly Potent Neutralizing Antibodies: Implication For Developing Subunit Vaccine*," Biochem. Biophys. Res. Commun. 324:773-781). The SARS-CoV S1 domain mediates receptor binding, while the SARS-CoV S2 domain mediates membrane fusion (Li, F. (2016) "*Structure, Function, And Evolution Of Coronavirus Spike Proteins*," Annu. Rev. Virol. 3:237-261; He, Y. et al. (2004) "*Receptor-Binding Domain Of SARS-CoV Spike Protein Induces Highly Potent Neutralizing Antibodies: Implication For Developing Subunit Vaccine*, Biochem. Biophys. Res. Commun. 324:773-781). The S gene of SARS-CoV-2 may have a similar function. Thus, the spike protein of coronaviruses is considered crucial for determining host tropism and transmission capacity (Lu, G. et al. (2015) "*Bat-To-Human: Spike Features Determining 'Host Jump' Of Coronaviruses SARS-CoV, MERS-CoV, And Beyond*," Trends Microbiol. 23:468-478; Wang, Q. et al. (2016) "*MERS-CoV Spike Protein: Targets For Vaccines And Therapeutics*," Antiviral. Res. 133:165-177). In this regard, the S2 domain of the SARS-CoV-2 spike protein shows high sequence identity (93%) with bat-SL-CoVZC45 and bat-SL-CoVZXC21, but the SARS-CoV-2 S1 domain shows a much lower degree of identity (68%) with these bat-derived viruses (Lu, R. et al. (2020) "*Genomic Characterisation And Epidemiology Of* 2019 *Novel Coronavirus: Implications For Virus Origins And Receptor Binding*," Lancet 395(10224):565-574). Thus, SARS-CoV-2 may bind to a different receptor than that bound by its related bat-derived viruses. It has been proposed that SARS-CoV-2 may bind to the angiotensin-converting enzyme 2 (ACE2) as a cell receptor (Lu, R. et al. (2020) "*Genomic Characterisation And Epidemiology Of* 2019 *Novel Coronavirus: Implications For Virus Origins And Receptor Binding*," Lancet 395(10224):565-574).

The sequence of the positive sense ("sense") strand of the S Gene of SARS-CoV-2 of GenBank NC_045512 (SEQ ID NO: 16) is shown in Table 2.

TABLE 2

| The S Gene of SARS-CoV-2 (SEQ ID NO: 16) | S Gene | SAS-CoV-2 |
|---|---|---|
| atgtttgttt ttcttgtttt attgccacta gtctctagtc agtgtgttaa | 50 | 21,612 |
| tcttacaacc agaactcaat taccccctgc atacactaat tctttcacac | 100 | 21,662 |
| gtggtgttta ttaccctgac aaagttttca gatcctcagt tttacattca | 150 | 21,712 |
| actcaggact tgttcttacc tttcttttcc aatgttactt ggttccatgc | 200 | 21,762 |
| tatacatgtc tctgggacca atggtactaa gaggtttgat aaccctgtcc | 250 | 21,812 |
| taccatttaa tgatggtgtt tattttgctt ccactgagaa gtctaacata | 300 | 21,862 |
| ataagaggct ggatttttgg tactacttta gattcgaaga cccagtccct | 350 | 21,912 |
| acttattgtt aataacgcta ctaatgttgt tattaaagtc tgtgaatttc | 400 | 21,962 |
| aattttgtaa tgatccattt ttgggtgttt attaccacaa aaacaacaaa | 450 | 22,012 |
| agttggatgg aaagtgagtt cagagtttat tctagtgcga ataattgcac | 500 | 22,062 |
| ttttgaatat gtctctcagc cttttcttat ggaccttgaa ggaaaacagg | 550 | 22,112 |
| gtaatttcaa aaatcttagg gaatttgtgt ttaagaatat tgatggttat | 600 | 22,162 |
| tttaaaatat attctaagca cacgcctatt aatttagtgc gtgatctccc | 650 | 22,212 |
| tcagggtttt tcggctttag aaccattggt agatttgcca ataggtatta | 700 | 22,262 |
| acatcactag gtttcaaact ttacttgctt tacatagaag ttatttgact | 750 | 22,312 |
| cctggtgatt cttcttcagg ttggacagct ggtgctgcag cttattatgt | 800 | 22,362 |
| gggttatctt caacctagga cttttctatt aaaatataat gaaaatggaa | 850 | 22,412 |
| ccattacaga tgctgtagac tgtgcacttg accctctctc agaaacaaag | 900 | 22,462 |
| tgtacgttga aatccttcac tgtagaaaaa ggaatctatc aaacttctaa | 950 | 22,512 |
| ctttagagtc caaccaacag aatctattgt tagatttcct aatattacaa | 1,000 | 22,562 |
| acttgtgccc ttttggtgaa gtttttaacg ccaccagatt tgcatctgtt | 1,050 | 22,612 |
| tatgcttgga acaggaagag aatcagcaac tgtgttgctg attattctgt | 1,100 | 22,662 |
| cctatataat tccgcatcat tttccacttt taagtgttat ggagtgtctc | 1,150 | 22,712 |
| ctactaaatt aaatgatctc tgctttacta atgtctatgc agattcattt | 1,200 | 22,762 |
| gtaattagag gtgatgaagt cagacaaatc gctccagggc aaactggaaa | 1,250 | 22,812 |
| gattgctgat tataattata aattaccaga tgattttaca ggctgcgtta | 1,300 | 22,862 |
| tagcttggaa ttctaacaat cttgattcta aggttggtgg taattataat | 1,350 | 22,912 |
| tacctgtata gattgtttag gaagtctaat ctcaaacctt ttgagagaga | 1,400 | 22,962 |
| tatttcaact gaaatctatc aggccggtag cacaccttgt aatggtgttg | 1,450 | 23,012 |
| aaggttttaa ttgttacttt cctttacaat catatggttt ccaacccact | 1,500 | 23,062 |
| aatggtgttg gttaccaacc atacagagta gtagtacttt cttttgaact | 1,550 | 23,112 |
| tctacatgca ccagcaactg tttgtggacc taaaaagtct actaatttgg | 1,600 | 23,162 |
| ttaaaaacaa atgtgtcaat ttcaacttca atggtttaac aggcacaggt | 1,650 | 23,212 |
| gttcttactg agtctaacaa aaagtttctg cctttccaac aatttggcag | 1,700 | 23,262 |
| agacattgct gacactactg atgctgtccg tgatccacag acacttgaga | 1,750 | 23,312 |
| ttcttgacat tacaccatgt tcttttggtg gtgtcagtgt tataacacca | 1,800 | 23,362 |

TABLE 2-continued

| The S Gene of SARS-CoV-2 (SEQ ID NO: 16) | S Gene | SAS-CoV-2 |
|---|---|---|
| ggaacaaata cttctaacca ggttgctgtt ctttatcagg atgttaactg | 1,850 | 23,412 |
| cacagaagtc cctgttgcta ttcatgcaga tcaacttact cctacttggc | 1,900 | 23,462 |
| gtgtttattc tacaggttct aatgtttttc aaacacgtgc aggctgttta | 1,950 | 23,512 |
| atagggggctg aacatgtcaa caactcatat gagtgtgaca tacccattgg | 2,000 | 23,562 |
| tgcaggtata tgcgctagtt atcagactca gactaattct cctcggcggg | 2,050 | 23,612 |
| cacgtagtgt agctagtcaa tccatcattg cctacactat gtcacttggt | 2,100 | 23,662 |
| gcagaaaatt cagttgctta ctctaataac tctattgcca tacccacaaa | 2,150 | 23,712 |
| ttttactatt agtgttacca cagaaattct accagtgtct atgaccaaga | 2,200 | 23,762 |
| catcagtaga ttgtacaatg tacatttgtg gtgattcaac tgaatgcagc | 2,250 | 23,812 |
| aatcttttgt tgcaatatgg cagtttttgt acacaattaa accgtgcttt | 2,300 | 23,862 |
| aactggaata gctgttgaac aagacaaaaa cacccaagaa gtttttgcac | 2,350 | 23,912 |
| aagtcaaaca aatttacaaa acaccaccaa ttaaagattt tggtggtttt | 2,400 | 23,962 |
| aatttttcac aaatattacc agatccatca aaaccaagca agaggtcatt | 2,450 | 24,012 |
| tattgaagat ctacttttca acaaagtgac acttgcagat gctggcttca | 2,500 | 24,062 |
| tcaaacaata tggtgattgc cttggtgata ttgctgctag agacctcatt | 2,550 | 24,112 |
| tgtgcacaaa agtttaacgg ccttactgtt ttgccacctt tgctcacaga | 2,600 | 24,162 |
| tgaaatgatt gctcaataca cttctgcact gttagcgggt acaatcactt | 2,650 | 24,212 |
| ctggttggac ctttggtgca ggtgctgcat tacaaatacc atttgctatg | 2,700 | 24,262 |
| caaatggctt ataggtttaa tggtattgga gttacacaga atgttctcta | 2,750 | 24,312 |
| tgagaaccaa aaattgattg ccaaccaatt taatagtgct attggcaaaa | 2,800 | 24,362 |
| ttcaagactc actttcttcc acagcaagtg cacttggaaa acttcaagat | 2,850 | 24,412 |
| gtggtcaacc aaaatgcaca agctttaaac acgcttgtta aacaacttag | 2,900 | 24,462 |
| ctccaatttt ggtgcaattt caagtgtttt aaatgatatc ctttcacgtc | 2,950 | 24,512 |
| ttgacaaagt tgaggctgaa gtgcaaattg ataggttgat cacaggcaga | 3,000 | 24,562 |
| cttcaaagtt tgcagacata tgtgactcaa caattaatta gagctgcaga | 3,050 | 24,612 |
| aatcagagct tctgctaatc ttgctgctac taaaatgtca gagtgtgtac | 3,100 | 24,662 |
| ttggacaatc aaaaagagtt gatttttgtg gaaagggcta tcatcttatg | 3,150 | 24,712 |
| tccttccctc agtcagcacc tcatggtgta gtcttcttgc atgtgactta | 3,200 | 24,762 |
| tgtccctgca caagaaaaga acttcacaac tgctcctgcc atttgtcatg | 3,250 | 24,812 |
| atggaaaagc acactttcct cgtgaaggtg tctttgtttc aaatggcaca | 3,300 | 24,862 |
| cactggtttg taacacaaag gaatttttat gaaccacaaa tcattactac | 3,350 | 24,912 |
| agacaacaca tttgtgtctg gtaactgtga tgttgtaata ggaattgtca | 3,400 | 24,962 |
| acaacacagt ttatgatcct ttgcaacctg aattagactc attcaaggag | 3,450 | 25,012 |
| gagttagata aatattttaa gaatcataca tcaccagatg ttgatttagg | 3,500 | 25,062 |
| tgacatctct ggcattaatg cttcagttgt aaacattcaa aaagaaattg | 3,550 | 25,112 |
| accgcctcaa tgaggttgcc aagaatttaa atgaatctct catcgatctc | 3,600 | 25,162 |
| caagaacttg gaaagtatga gcagtatata aaatggccat ggtacatttg | 3,650 | 25,212 |
| gctaggtttt atagctggct tgattgccat agtaatggtg acaattatgc | 3,700 | 25,262 |
| tttgctgtat gaccagttgc tgtagttgtc tcaagggctg ttgttcttgt | 3,750 | 25,312 |

TABLE 2-continued

| The S Gene of SARS-CoV-2 (SEQ ID NO: 16) | S Gene | SAS-CoV-2 |
|---|---|---|
| ggatcctgct gcaaatttga tgaagacgac tctgagccag tgctcaaagg | 3,800 | 25,362 |
| agtcaaatta cattacaca | 3,819 | 25,381 |

II. Assays for the Detection of SARS-CoV-2

SARS-CoV-2 was first identified in late 2019, and is believed to be a unique virus that had not previously existed. The first diagnostic test for SARS-CoV-2 used a real-time reverse transcription-PCR (rRT-PCR) assay that employed probes and primers of the SARS-CoV-2E, N and nsp2 (RNA-dependent RNA polymerase; RdRp) genes (the "SARS-CoV-2-RdRp-P2" assay) (Corman, V. M. et al. (2020) "*Detection Of* 2019 *Novel Coronavirus* (209-*nCoV*) *By Real-Time RT-PCR*," Eurosurveill. 25(3):2000045; Spiteri, G. et al. (2020) "*First Cases Of Coronavirus Disease* 2019 (*COVID*-19) *In The WHO European Region,* 24 *Jan. To* 21 *Feb.* 2020," Eurosurveill. 25(9) doi: 10.2807/1560-7917.ES.2020.25.9.2000178).

The probes employed in such assays were "TaqMan" oligonucleotide probes that were labeled with a fluorophore on the oligonucleotide's 5' terminus and complexed to a quencher on the oligonucleotide's 3' terminus. The "TaqMan" probe principle relies on the 5→3' exonuclease activity of Taq polymerase (Peake, I. (1989) "*The Polymerase Chain Reaction*," J. Clin. Pathol.; 42(7):673-676) to cleave the dual-labeled probe when it has hybridized to a complementary target sequence. The cleavage of the molecule separates the fluorophore from the quencher and thus leads to the production of a detectable fluorescent signal.

In the SARS-CoV-2-RdRp-P2 assay of Corman, V. M. et al. (2020), the RdRp Probe 2 and the probes of the E and N genes are described as being specific for SARS-CoV-2, whereas the RdRp Probe 2 is described as being a "PanSarbeco-Probe" that detects SARS-CoV and bat-SARS-related coronaviruses in addition to SARS-CoV-2. The assay is stated to have provided its best results using the E gene and nsp12 (RdRp) gene primers and probes (5.2 and 3.8 copies per 25 μL reaction at 95% detection probability, respectively). The resulting limit of detection (LoD) from replicate tests was 3.9 copies per 25 μL reaction (156 copies/mL) for the E gene assay and 3.6 copies per 25 μL reaction (144 copies/mL) for the nsp12 (RdRp) assay. The assay was reported to be specific for SARS-CoV-2 and to require less than 60 minutes to complete.

The US Center for Disease Control and Prevention (CDC) developed an rRT-PCR based assay protocol that targeted the SARS-CoV-2 N gene (Won, J. et al. (2020) "*Development Of A Laboratory-Safe And Low-Cost Detection Protocol For SARS-CoV-*2 *Of The Coronavirus Disease* 2019 (*COVID*-19)," Exp. Neurobiol. 29(2) doi: 10.5607/en20009).

Pfefferle, S. et al. (2020) ("*Evaluation Of A Quantitative RT-PCR Assay For The Detection Of The Emerging Coronavirus SARS-CoV-*2 *Using A High Throughput System*," Eurosurveill. 25(9) doi: 10.2807/1560-7917.ES.2020.25.9.2000152) discloses the use of a custom-made primer/probe set targeting the E gene. The employed primers were modified with 2'-O-methyl bases in their penultimate base to prevent formation of primer dimers. ZEN double-quenched probe (IDT) were used to lower background fluorescence. The LoD was 689.3 copies/mL with 275.72 copies per reaction at 95% detection probability. The assay was reported to be specific for SARS-CoV-2 and to require less than 60 minutes.

Chan, J. F. et al. (2020) ("*Improved Molecular Diagnosis Of COVID*-19 *By The Novel, Highly Sensitive And Specific COVID*-19-*RdRp/Hel Real-Time Reverse Transcription-Polymerase Chain Reaction Assay Validated In Vitro And With Clinical Specimens*," J. Clin. Microbiol. JCM.00310-20. doi: 10.1128/JCM.00310-20) explored the use of conserved and/or abundantly expressed SARS-CoV-2 genes as preferred targets of coronavirus RT-PCR assays. Such genes include the structural S and N genes, and the non-structural RdRp gene and ORF1ab. Chan, J. F. et al. (2020) describes the development of three real-time reverse transcriptase PCR (rRT-PCR) assays targeting the RNA-dependent RNA polymerase (RdRp)/helicase (Hel), spike (S), and nucleocapsid (N) genes of SARS-CoV-2 and compares such assays to the RdRp-P2 assay of Corman, V. M. et al. The LoD of the SARS-CoV-2-RdRp/Hel assay, the SARS-CoV-2-S assay, and the SARS-CoV-2-N assay was 1.8 $TCID_{50}$/ml, while the LoD of the SARS-CoV-2-RdRp-P2 assay was 18 $TCID_{50}$/ml. The $TCID_{50}$ is the median tissue culture infectious dose.

An rt-PCR-based assay protocol targeting the E, N, S and RdRp genes was designed for specimen self-collection from a subject via pharyngeal swab. The assay required Trizol-based RNA purification, and detection was accomplished via an RT-PCR assay using SYBR Green as a detection fluor. The assay was reported to require approximately 4 hours to complete (Won, J. et al. (2020) ("*Development Of A Laboratory-Safe And Low-Cost Detection Protocol For SARS-CoV-*2 *Of The Coronavirus Disease* 2019 (*COVID*-19)," Exp. Neurobiol. 29(2) doi: 10.5607/en20009).

Although prior rRT-PCR assays, such as the SARS-CoV-2-RdRp-P2 assay of Corman V. M. et al., are capable of detecting SARS-CoV-2, researchers have found them to suffer from major deficiencies. In use, such prior assays have been found to require laborious batch-wise manual processing and to not permit random access to individual samples (Cordes, A. K. et al. (2020) "*Rapid Random Access Detection Of The Novel SARS-Coronavirus-*2 (*SARS-CoV-*2, *Previously* 2019-*nCoV*) *Using An Open Access Protocol For The Panther Fusion*," J. Clin. Virol. 125:104305 doi: 10.1016/j.jcv.2020.104305). Additionally, long turnaround times and complicated operations are required. These factors cause such assays to generally take more than 2-3 hours to generate results. Due to such factors, certified laboratories are required to process such assays. The need for expensive equipment and trained technicians to perform such prior rRT-PCR assays encumbers the use of such assays in the field or at mobile locations. Thus, researchers have found such prior assays to have limited suitability for use in the rapid and simple diagnosis and screening of patients required to contain an outbreak (Li, Z. et al. (2020) "*Development and Clinical Application of A Rapid IgM-IgG Combined Antibody Test for SARS-CoV-*2 *Infection Diagnosis*," J. Med. Virol. doi: 10.1002/jmv.25727).

More significantly, prior rRT-PCR assays, such as the SARS-CoV-2-RdRp-P2 assay of Corman V. M. et al., have been found to lack specificity for SARS-CoV-2 (cross-reacting with SARS-CoV or other pathogens) (Chan, J. F. et al. (2020) "*Improved Molecular Diagnosis Of COVID-19 By The Novel, Highly Sensitive And Specific COVID-19-RdRp/Hel Real-Time Reverse Transcription-Polymerase Chain Reaction Assay Validated In Vitro And With Clinical Specimens*," J. Clin. Microbiol. JCM.00310-20) and to provide a significant number of false negative results (Li, Z. et al. (2020) "*Development and Clinical Application of A Rapid IgM-IgG Combined Antibody Test for SARS-CoV-2 Infection Diagnosis*," J. Med. Virol. doi: 10.1002/jmv.25727).

For example, in a retrospective analysis of 4880 clinically-identified COVID-19 patients, samples obtained from the respiratory tracts of the patients were subjected to rRT-PCR amplification of the SARS-CoV-2 open reading frame 1ab (ORF1ab) and nucleocapsid protein (N) genes. Nasal and pharyngeal swabs of patients were evaluated for COVID-19 using a quantitative rRT-PCR (qRT-PCR) test. Only 38.42% (1875 of 4880) of actual COVID-19 patients were identified as positive using the rRT-PCR test. Of those testing positive, 39.80% were positive as determined by probes of the SARS-CoV-2 N gene and 40.98% were positive as determined by probes of the SARS-CoV-2 ORF1ab (Liu, R. et al. (2020) "*Positive Rate Of RT-PCR Detection Of SARS-CoV-2 Infection In 4880 Cases From One Hospital In Wuhan, China, From January To February 2020*," Clinica Chimica Acta 505:172-175).

The study of Chan, J. F. et al. (2020) ("*Improved Molecular Diagnosis Of COVID-19 By The Novel, Highly Sensitive And Specific COVID-19-RdRp/Hel Real-Time Reverse Transcription-Polymerase Chain Reaction Assay Validated In Vitro And With Clinical Specimens*," J. Clin. Microbiol. JCM.00310-20. doi: 10.1128/JCM.00310-20) found that of 273 specimens from 15 patients with laboratory-confirmed COVID-19, only 28% were SARS-CoV-2 positive by both the SARS-CoV-2-RdRp/Hel and RdRp-P2 assays. The SARS-CoV-2-RdRp/Hel assay was more sensitive, but still confirmed only 43.6% of the patients as having SARS-CoV-2 infection.

In a different study, RNA was extracted from 1070 clinical samples of 205 patients suffering from COVID-19. Real-time reverse transcription-PCR (rRT-PCR) was then used to amplify SARS-CoV-2 ORF1ab in order to confirm the COVID-19 diagnosis (Wang, W. et al. (2020) ("*Detection of SARS-CoV-2 in Different Types of Clinical Specimens*," JAMA doi: 10.1001/jama.2020.3786). Bronchoalveolar lavage fluid specimens were reported to exhibit the highest positive rates (14 of 15; 93%), followed by sputum (72 of 104; 72%), nasal swabs (5 of 8; 63%), fibrobronchoscope brush biopsy (6 of 13; 46%), pharyngeal swabs (126 of 398; 32%), feces (44 of 153; 29%), and blood (3 of 307; 1%). None of the 72 urine specimens tested indicated a positive result. Thus, for example, pharyngeal swabs from such actual COVID-19 patients failed to accurately diagnose SARS-CoV-2 infection in 68% of those tested. Zhang, W. et al. (2020) ("*Molecular And Serological Investigation Of 2019-nCoV Infected Patients: Implication Of Multiple Shedding Routes*," Emerg. Microbes Infect. 9(1):386-389) also discloses the presence of SARS-CoV-2 in feces of COVID-19 patients, however, its rRT-PCR assay results showed more anal swab positives than oral swab positives in a later stage of infection, suggesting viral shedding and the capacity of the infection to be transmitted through an oral-fecal route. A similar teaching is provided by Tang, A. et al. (2020) ("*Detection of Novel Coronavirus by RT-PCR in Stool Specimen from Asymptomatic Child, China*," Emerg Infect Dis. 26(6). doi: 10.3201/eid2606.200301), which discloses that RT-PCR assays targeting ORF1ab and nucleoprotein N gene failed to detect SARS-CoV-2 in nasopharyngeal swab and sputum samples, but were able to detect virus in stool samples.

In a further study of individuals suffering from COVID-19, repeated assays for SARS-CoV-2 were also found to report negative results (Wu, X. et al. (2020) ("*Co-infection with SARS-CoV-2 and Influenza A Virus in Patient with Pneumonia, China,*" 26(6):pages 1-7. The publication teaches that existing assays for SARS-CoV-2 lack sufficient sensitivity, and thus lead to false negative diagnoses.

In light of the deficiencies encountered in using prior rRT-PCR assays, such as the SARS-CoV-2-RdRp-P2 assay of Corman V. M. et al., other approaches to assaying for SARS-CoV-2 have been explored. Li, Z. et al. (2020) ("*Development and Clinical Application of A Rapid IgM-IgG Combined Antibody Test for SARS-CoV-2 Infection Diagnosis*," J. Med. Virol. doi: 10.1002/jmv.25727) teaches that a point-of-care lateral flow immunoassay could be used to simultaneously detect anti-SARS-CoV-2 IgM and IgG antibodies in human blood and thus avoid the problems of the RdRp-P2 assay of Corman, V. M. et al. Immunoassays, however, may fail to discriminate between individuals suffering from COVID-19 and individuals who were previously infected with SARS-CoV-2, but have since recovered.

In sum, despite all prior efforts a need remains for a method of rapidly and accurately assaying for the presence of SARS-CoV-2. The present invention is directed to this and other goals.

SUMMARY OF THE INVENTION

The present invention is directed to methods for assaying for the presence of SARS-CoV-2 in a sample, including a clinical sample, and to oligonucleotides, reagents, and kits useful in such assays. In particular, the present invention is directed to such assays that are rapid, accurate and specific for the detection of SARS-CoV-2.

In detail, the invention provides a detectably labeled oligonucleotide that is capable of specifically hybridizing to a SARS-CoV-2 polynucleotide, wherein the detectably labeled oligonucleotide has a nucleotide sequence that is able to specifically hybridize to an oligonucleotide having a nucleotide sequence that consists of the nucleotide sequence of SEQ ID NO:3, SEQ ID NO:4, SEQ ID NO:7 or SEQ ID NO:8.

The invention additionally provides a kit for detecting the presence of SARS-CoV-2 in a clinical sample, wherein the kit comprises a detectably labeled oligonucleotide that is capable of specifically hybridizing to a SARS-CoV-2 polynucleotide, wherein the detectably labeled oligonucleotide has a nucleotide sequence that is able to specifically hybridize to an oligonucleotide having the nucleotide sequence of SEQ ID NO:3, SEQ ID NO:4, SEQ ID NO:7 or SEQ ID NO:8.

The invention additionally provides the embodiment of such kit, wherein the detectably labeled oligonucleotide has a nucleotide sequence that is able to specifically hybridize to an oligonucleotide having the nucleotide sequence of SEQ ID NO:3 or SEQ ID NO:4, and wherein the kit permits a determination of the presence or absence of the SARS-CoV-2 ORF1ab in a clinical sample.

The invention additionally provides the embodiment of such kit, wherein the detectably labeled oligonucleotide has a nucleotide sequence that is able to specifically hybridize to an oligonucleotide having the nucleotide sequence of SEQ ID NO:7 or SEQ ID NO:8, and wherein the kit permits a determination of the presence or absence of the SARS-CoV-2 S gene in a clinical sample.

The invention additionally provides the embodiment of such kits, wherein the kit comprises two detectably labeled oligonucleotides, wherein the detectable labels of the oligonucleotides are distinguishable, and wherein one of the two detectably labeled oligonucleotides has a nucleotide sequence that is able to specifically hybridize to an oligonucleotide having the nucleotide sequence of SEQ ID NO:3 or SEQ ID NO:4, and the second of the two detectably labeled oligonucleotides has a nucleotide sequence that is able to specifically hybridize to an oligonucleotide having the nucleotide sequence of SEQ ID NO:7 or SEQ ID NO:8.

The invention additionally provides the embodiment of such kits, wherein the detectably labeled oligonucleotide is a TaqMan probe, a molecular beacon probe, a scorpion primer-probe, or a HyBeacon probe.

The invention additionally provides the embodiment of such kits, wherein the detectably labeled oligonucleotide is fluorescently labeled.

The invention additionally provides the embodiment of such kits, wherein the kit permits the detection of the D614G polymorphism of the S gene of SARS-CoV-2.

The invention additionally provides the embodiment of such kits, wherein the kit is a multi-chambered, fluidic device.

The invention additionally provides a method for detecting the presence of SARS-CoV-2 in a clinical sample, wherein the method comprises incubating the clinical sample in vitro in the presence of a detectably labeled oligonucleotide that is capable of specifically hybridizing to a SARS-CoV-2 polynucleotide, wherein the detectably labeled oligonucleotide has a nucleotide sequence that is able to specifically hybridize to an oligonucleotide having the nucleotide sequence of SEQ ID NO:3, SEQ ID NO:4, SEQ ID NO:7 or SEQ ID NO:8; wherein the method detects the presence of SARS-CoV-2 in the clinical sample by detecting the presence of SARS-CoV-2 ORF1ab and/or SARS-CoV-2 S gene.

The invention additionally provides the embodiment of such method, wherein the detectably labeled oligonucleotide has a nucleotide sequence that is able to specifically hybridize to an oligonucleotide having the nucleotide sequence of SEQ ID NO:3 or SEQ ID NO:4, and wherein the method detects the presence of SARS-CoV-2 in the clinical sample by detecting the presence of SARS-CoV-2 ORF1ab.

The invention additionally provides the embodiment of such method, wherein the detectably labeled oligonucleotide has a nucleotide sequence that is able to specifically hybridize to an oligonucleotide having the nucleotide sequence of SEQ ID NO:7 or SEQ ID NO:8, and wherein the method detects the presence of SARS-CoV-2 in the clinical sample by detecting the presence of SARS-CoV-2 S gene.

The invention additionally provides the embodiment of such methods, wherein the detectably labeled oligonucleotide is fluorescently labeled.

The invention additionally provides the embodiment of such methods, wherein the method comprises incubating the clinical sample in the presence of two detectably labeled oligonucleotides, wherein the detectable labels of the oligonucleotides are distinguishable, and wherein one of the two detectably labeled oligonucleotides has a nucleotide sequence that is able to specifically hybridize to an oligonucleotide having the nucleotide sequence of SEQ ID NO:3 or SEQ ID NO:4, and the second of the two detectably labeled oligonucleotides has a nucleotide sequence that is able to specifically hybridize to an oligonucleotide having the nucleotide sequence of SEQ ID NO:7 or SEQ ID NO:8; wherein the method detects the presence of SARS-CoV-2 in the clinical sample by detecting the presence of both SARS-CoV-2 ORF1ab and SARS-CoV-2 S gene.

The invention additionally provides the embodiment of such method, wherein the detectably labeled oligonucleotide is fluorescently labeled.

The invention additionally provides the embodiment of such methods, wherein the method detects the presence or absence of the D614G polymorphism of the S gene of SARS-CoV-2.

The invention additionally provides the embodiment of such methods, wherein the method comprises a PCR amplification of the SARS-CoV-2 polynucleotide.

The invention additionally provides the embodiment of such methods, wherein the detectably labeled oligonucleotide is a TaqMan probe, a molecular beacon probe, a scorpion primer-probe, or a HyBeacon probe.

The invention additionally provides the embodiment of such methods, wherein the method comprises a LAMP amplification of the SARS-CoV-2 polynucleotide.

The invention additionally provides an oligonucleotide that comprises a 5' terminus and a 3' terminus, wherein the oligonucleotide has a SARS-CoV-2 oligonucleotide domain that has a nucleotide sequence that consists of, consists essentially of, comprises, or is a variant of, the nucleotide sequence of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, any of SEQ ID NOs:17-42, any of SEQ ID NOs:43-70, any of SEQ ID NOs:71-84, any of SEQ ID NOs:85-112, any of SEQ ID NOs:113-126, any of SEQ ID NOs:127-146, any of SEQ ID NOs:147-166, any of SEQ ID NOs:167-252, any of SEQ ID NOs:253-272, any of SEQ ID NOs:273-363, any of SEQ ID NOs:364-381, any of SEQ ID NOs:398-402, any of SEQ ID NOs:403-406, SEQ ID NO:411, or SEQ ID NO:412.

The invention additionally provides such an oligonucleotide wherein the oligonucleotide is detectably labeled and comprises a 5' terminus and a 3' terminus, wherein the oligonucleotide has a SARS-CoV-2 oligonucleotide domain that has a nucleotide sequence that consists of, consists essentially of, or comprises, or is a variant of, the nucleotide sequence of: SEQ ID NO:9, SEQ ID NO:10, SEQ ID NO:11, SEQ ID NO:12, any of SEQ ID NOs:43-70, any of SEQ ID NOs:85-112, any of SEQ ID NOs:127-146, any of SEQ ID NOs:147-166, any of SEQ ID NOs:167-252, any of SEQ ID NOs:253-272, any of SEQ ID NOs:273-363, any of SEQ ID NOs:364-381, any of SEQ ID NOs:403-406, SEQ ID NO:411, or SEQ ID NO:412.

The invention additionally provides such an oligonucleotide wherein the oligonucleotide is detectably labeled and comprises a 5' terminus and a 3' terminus, wherein the oligonucleotide has a SARS-CoV-2 oligonucleotide domain that consists essentially of the nucleotide sequence of: SEQ ID NO:9, or SEQ ID NO:10.

The invention additionally provides such an oligonucleotide wherein the oligonucleotide is detectably labeled and comprises a 5' terminus and a 3' terminus, wherein the oligonucleotide has a SARS-CoV-2 oligonucleotide domain that consists essentially of the nucleotide sequence of: SEQ ID NO:11, or SEQ ID NO:12.

The invention additionally provides a TaqMan probe capable of detecting the presence of SARS-CoV-2, wherein the probe comprises an oligonucleotide, having a 5' terminus and a 3' terminus, that comprises a SARS-CoV-2 oligonucleotide domain whose nucleotide sequence consists of, consists essentially of, comprises, or is a variant of the nucleotide sequence of: SEQ ID NO:9, SEQ ID NO:10, SEQ ID NO:11, SEQ ID NO:12, any of SEQ ID NOs:127-146, any of SEQ ID NOs:147-166, any of SEQ ID NOs:167-252, any of SEQ ID NOs:253-272, any of SEQ ID NOs:273-363, any of SEQ ID NOs:364-381, wherein the 5' terminus of the oligonucleotide is labeled with a fluorophore and the 3' terminus of the oligonucleotide is complexed to a quencher of such fluorophore.

The invention additionally provides such a TaqMan probe, wherein the probe is capable of detecting the SARS-CoV-2 ORF1ab, and wherein the SARS-CoV-2 oligonucleotide domain of the probe has a nucleotide sequence that consists of, consists essentially of, comprises, or is a variant of, the nucleotide sequence of: SEQ ID NO:9, SEQ ID NO:10, any of SEQ ID NOs:127-146, or any of SEQ ID NOs:147-166.

The invention additionally provides such a TaqMan probe, wherein the probe is capable of detecting the SARS-CoV-2 S gene, and wherein the SARS-CoV-2 oligonucleotide domain of the probe has a nucleotide sequence that consists of, consists essentially of, comprises, or is a variant of, the nucleotide sequence of: SEQ ID NO:11, SEQ ID NO:12, any of SEQ ID NOs:167-252, any of SEQ ID NOs:253-272, any of SEQ ID NOs:273-363, or any of SEQ ID NOs:364-381.

The invention additionally provides such a TaqMan probe, wherein the probe is capable of detecting a polymorphism in the SARS-CoV-2 S gene, and wherein the SARS-CoV-2 oligonucleotide domain of the probe has a nucleotide sequence that consists of, consists essentially of, comprises, or is a variant of, the nucleotide sequence of: any of SEQ ID NOs:167-252, or any of SEQ ID NOs:273-363.

The invention additionally provides a molecular beacon probe capable of detecting the presence of SARS-CoV-2, wherein the probe comprises an oligonucleotide, having a 5' terminus and a 3' terminus, that comprises a SARS-CoV-2 oligonucleotide domain whose nucleotide sequence consists of, consists essentially of, comprises, or is a variant of, the nucleotide sequence of: SEQ ID NO:9, SEQ ID NO:10, SEQ ID NO:11, SEQ ID NO:12, any of SEQ ID NOs:127-146, any of SEQ ID NOs:147-166, any of SEQ ID NOs:167-252, any of SEQ ID NOs:253-272, any of SEQ ID NOs:273-363, any of SEQ ID NOs:364-381, wherein such a SARS-CoV-2 oligonucleotide domain is flanked by a 5' oligonucleotide and a 3' oligonucleotide, wherein such 5' oligonucleotide and such 3' oligonucleotide are at least substantially complementary to one another, and wherein at least one of such 5' oligonucleotide and such 3' oligonucleotide is detectably labeled and another of such 5' oligonucleotide and such 3' oligonucleotide is complexed to a quencher or an acceptor of such detectable label.

The invention additionally provides such a molecular beacon probe, wherein the probe is capable of detecting the SARS-CoV-2 ORF1ab, and wherein the SARS-CoV-2 oligonucleotide domain of the probe has a nucleotide sequence that consists of, consists essentially of, comprises, or is a variant of, the nucleotide sequence of: SEQ ID NO:9, SEQ ID NO:10, any of SEQ ID NOs:127-146, or any of SEQ ID NOs:147-166.

The invention additionally provides such a molecular beacon probe, wherein the probe is capable of detecting the SARS-CoV-2 S gene, and wherein the SARS-CoV-2 oligonucleotide domain of the probe has a nucleotide sequence that consists of, consists essentially of, comprises, or is a variant of, the nucleotide sequence of: SEQ ID NO:11, SEQ ID NO:12, any of SEQ ID NOs:167-252, any of SEQ ID NOs:253-272, any of SEQ ID NOs:273-363, or any of SEQ ID NOs:364-381.

The invention additionally provides such a molecular beacon probe, wherein the probe is capable of detecting a polymorphism in the SARS-CoV-2 S gene, and wherein the SARS-CoV-2 oligonucleotide domain of the probe has a nucleotide sequence that consists of, consists essentially of, comprises, or is a variant of, the nucleotide sequence of: any of SEQ ID NOs:167-252, or any of SEQ ID NOs:273-363.

The invention additionally provides a scorpion primer-probe capable of detecting the presence of SARS-CoV-2, wherein the probe comprises an oligonucleotide, having a 5' terminus and a 3' terminus, that comprises a SARS-CoV-2 oligonucleotide domain whose nucleotide sequence consists of, consists essentially of, comprises, or is a variant of, the nucleotide sequence of: SEQ ID NO:9, SEQ ID NO:10, SEQ ID NO:11, SEQ ID NO:12, any of SEQ ID NOs:127-146, any of SEQ ID NOs:147-166, any of SEQ ID NOs:167-252, any of SEQ ID NOs:253-272, any of SEQ ID NOs:273-363, any of SEQ ID NOs:364-381, wherein such a SARS-CoV-2 oligonucleotide domain is flanked by a 5' oligonucleotide and a 3' oligonucleotide, wherein such 5' oligonucleotide and such 3' oligonucleotide are at least substantially complementary to one another, and wherein at least one of such 5' oligonucleotide and such 3' oligonucleotide is detectably labeled and the other of such 5' oligonucleotide and such 3' oligonucleotide is complexed to a quencher or an acceptor of such detectably label, and wherein such 3' oligonucleotide further comprises a polymerization blocking moiety, and a PCR primer oligonucleotide positioned 3' from said blocking moiety.

The invention additionally provides such a scorpion primer-probe, wherein the probe is capable of detecting the SARS-CoV-2 ORF1ab, and wherein the SARS-CoV-2 oligonucleotide domain of the probe has a nucleotide sequence that consists of, consists essentially of, comprises, or is a variant of, the nucleotide sequence of: SEQ ID NO:9, SEQ ID NO:10, any of SEQ ID NOs:127-146, or any of SEQ ID NOs:147-166.

The invention additionally provides such a scorpion primer-probe, wherein the probe is capable of detecting the SARS-CoV-2 S gene, and wherein the SARS-CoV-2 oligonucleotide domain of the probe has a nucleotide sequence that consists of, consists essentially of, comprises, or is a variant of, the nucleotide sequence of: SEQ ID NO:11, SEQ ID NO:12, any of SEQ ID NOs:167-252, any of SEQ ID NOs:253-272, any of SEQ ID NOs:273-363, or any of SEQ ID NOs:364-381.

The invention additionally provides such a scorpion primer-probe, wherein the probe is capable of detecting a polymorphism in the SARS-CoV-2 S gene, and wherein the SARS-CoV-2 oligonucleotide domain of the probe has a nucleotide sequence that consists of, consists essentially of, comprises, or is a variant of, the nucleotide sequence of: any of SEQ ID NOs:167-252, or any of SEQ ID NOs:273-363.

The invention additionally provides such a scorpion primer-probe, wherein the probe is capable of detecting a polymorphism in the SARS-CoV-2 S gene, and wherein the PCR primer oligonucleotide has a nucleotide sequence that consists of, consists essentially of, comprises, or is a variant of, the nucleotide sequence of: any of SEQ ID NOs:43-70, or any of SEQ ID NOs:85-112.

The invention additionally provides a HyBeacon™ probe capable of detecting the presence of SARS-CoV-2, wherein the probe comprises an oligonucleotide, having a 5' terminus and a 3' terminus, that comprises a SARS-CoV-2 oligonucleotide domain whose nucleotide sequence consists of, consists essentially of, comprises, or is a variant of, the nucleotide sequence of: SEQ ID NO:9, SEQ ID NO:10, SEQ ID NO:11, SEQ ID NO:12, any of SEQ ID NOs:127-146, any of SEQ ID NOs:147-166, any of SEQ ID NOs:167-252, any of SEQ ID NOs:253-272, any of SEQ ID NOs:273-363, any of SEQ ID NOs:364-381, wherein at least one nucleotide residue of such SARS-CoV-2 oligonucleotide domain is detectably labeled.

The invention additionally provides such a HyBeacon™ probe, wherein the probe is capable of detecting a polymorphism in the SARS-CoV-2 S gene, and wherein the SARS-CoV-2 oligonucleotide domain of the probe has a nucleotide sequence that consists of, consists essentially of, comprises, or is a variant of, the nucleotide sequence of: any of SEQ ID NOs:43-70, any of SEQ ID NOs:85-112, any of SEQ ID NOs:167-252, or any of SEQ ID NOs:273-363.

The invention additionally provides the embodiment of the above-described oligonucleotides, TaqMan probes, molecular beacon probes, scorpion primer-probes, or HyBeacon™ probes, wherein the detectable label is a fluorophore that has an excitation wavelength within the range of about 352-690 nm and an emission wavelength that is within the range of about 447-705 nm. The invention additionally provides the embodiment of such oligonucleotides, wherein the fluorophore is JOE or FAM.

The invention additionally provides an oligonucleotide primer capable of amplifying an oligonucleotide portion of a SARS-CoV-2 polynucleotide present in a sample, wherein such oligonucleotide primer has a nucleotide sequence that consists of, consists essentially of, comprises, or is a variant of, the nucleotide sequence of: any of: SEQ ID NO:1, SEQ ID NO:2, SEQ ID NO:5, SEQ ID NO:6, any of SEQ ID NOs:17-28, any of SEQ ID NOs:29-42, any of SEQ ID NOs:43-70, any of SEQ ID NOs:71-84, any of SEQ ID NOs:85-112, any of SEQ ID NOs:113-126, or any of SEQ ID NOs:398-410.

The invention additionally provides an oligonucleotide that has a nucleotide sequence that consists of, consists essentially of, comprises, or is a variant of, the nucleotide sequence of: SEQ ID NO:3 or SEQ ID NO:4.

The invention additionally provides an oligonucleotide that has a nucleotide sequence that consists of, consists essentially of, comprises, or is a variant of, the nucleotide sequence of: SEQ ID NO:7 or SEQ ID NO:8.

DETAILED DESCRIPTION OF THE INVENTION

Figure 1:
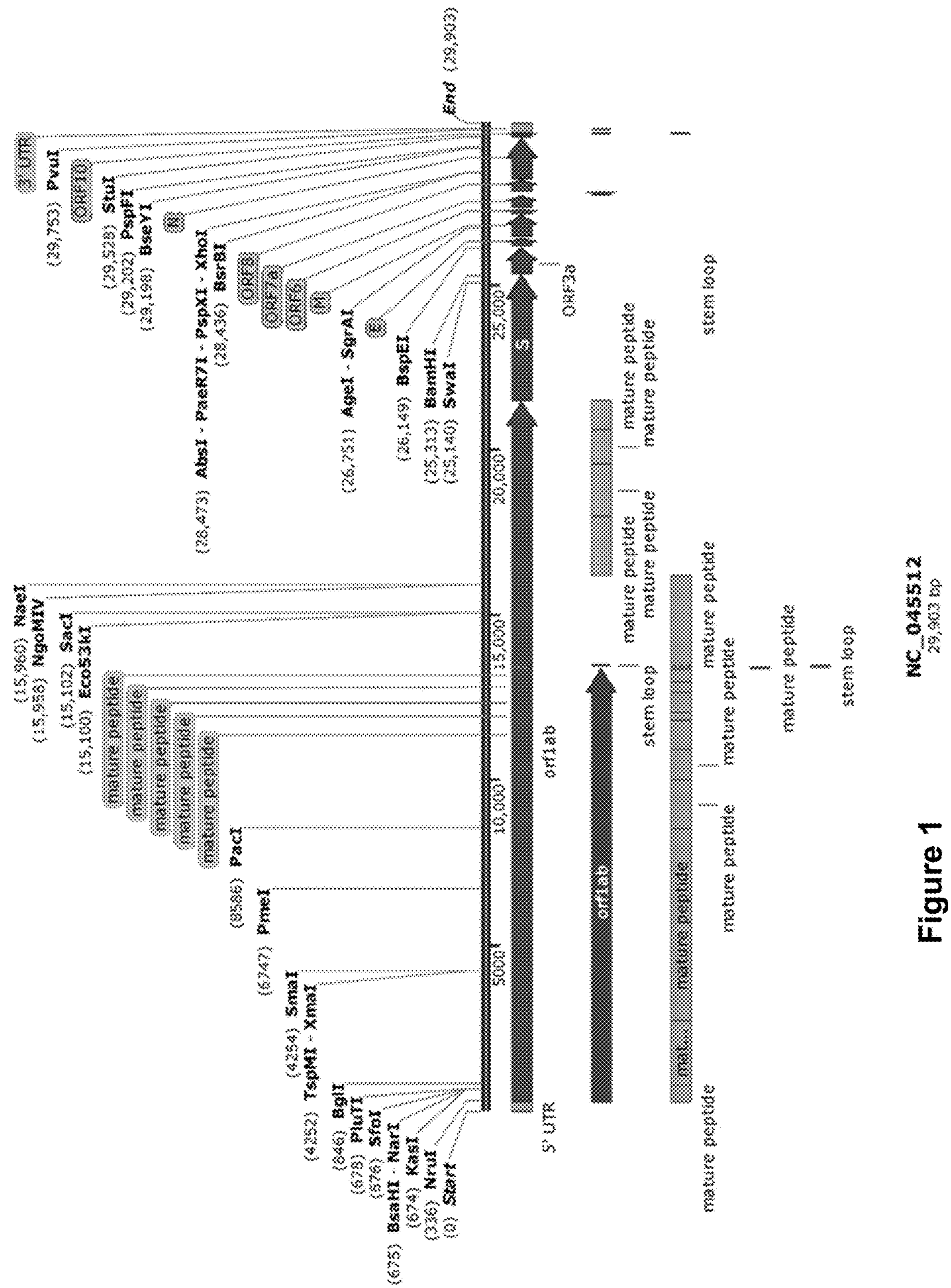
FIG. 1 provides an illustration of the structure of SARS-CoV-2 and its open reading frames (ORFs). The sequence presented is that of the reference SARS-CoV-2 sequence (GenBank NC_045512).

The present invention is directed to methods for assaying for the presence of SARS-CoV-2 in a sample, including a clinical sample, and to oligonucleotides, reagents, and kits useful in such assays. In particular, the present invention is directed to such assays that are rapid, accurate and specific for the detection of SARS-CoV-2.

As used herein, an assay for the detection of SARS-CoV-2 is said to be "specific" for SARS-CoV-2 if it can be conducted under conditions that permit it to detect SARS-CoV-2 without exhibiting cross-reactivity to human DNA, or to DNA (or cDNA) of other pathogens, especially other coronavirus pathogens. The assays of the present invention detect SARS-CoV-2 by detecting the presence of a "SARS-CoV-2 polynucleotide" nucleic acid molecule in a clinical sample. As used herein, a SARS-CoV-2 polynucleotide nucleic acid molecule is an RNA or DNA molecule that comprises the genome of SARS-CoV-2 or a portion of a gene or open reading frame (ORF) thereof (i.e., at least 1,000 nucleotides, at least 2,000 nucleotides, at least 5,000 nucleotides, at least 10,000 nucleotides, or at least 20,000 nucleotides of the SARS-CoV-2 genome, or more preferably, the entire SARS-CoV-2 genome of 29,903 nucleotides).

In particular, an assay for the detection of SARS-CoV-2 is said to be specific for SARS-CoV-2 if it can be conducted under conditions that permit it to detect SARS-CoV-2 without exhibiting cross-reactivity to DNA (or cDNA) of Influenza A, Influenza B, Respiratory Syncytial Virus, Group A *Streptococcus* (*Streptococcus pyogenes*), Parainfluenza I, Parainfluenza III, *Haemophilus parainfluenzae*, Enterovirus or Adenovirus, or to SARS-CoV, MERS-CoV, or bat-derived Severe Acute Respiratory Syndrome-like coronaviruses, such as bat-SL-CoVZC45 or bat-SL-CoVZXC21. More preferably, an assay for the detection of SARS-CoV-2 is said to be specific for SARS-CoV-2 if it can be conducted under conditions that permit it to detect SARS-CoV-2 without exhibiting cross-reactivity to DNA (or cDNA) of Adenovirus 1, *Bordetella pertussis, Chlamydophila pneumoniae*, Coronavirus 229E, Coronavirus NL63, Coronavirus OC43, Enterovirus 68, *Haemophilus influenzae*, Human metapneumovirus (hMPV-9), Influenza A H3N2 (Hong Kong 8/68), Influenza B (Phuket 3073/2013), *Legionella* pneumophilia, MERS Coronavirus, *Mycobacterium tuberculosis*, Parainfluenza Type 1, Parainfluenza Type 2, Parainfluenza Type 3, Parainfluenza Type 4A, Rhinovirus B14, RSV A Long, RSV B Washington, SARS-Coronavirus, SARS-Coronavirus HKU39849, *Streptococcus pneumoniae, Streptococcus pyogenes*, human leukocytes, or pooled human nasal fluid.

As used herein, an assay for the detection of SARS-CoV-2 is said to be "accurate" for SARS-CoV-2 if it is capable of detecting a viral dose of 400 copies/ml of SARS-CoV-2 with an LoD of at least 80%, and of detecting a viral dose of 500 copies/ml of SARS-CoV-2 with an LoD of at least 90%.

As used herein, an assay for the detection of SARS-CoV-2 is said to be "rapid" for SARS-CoV-2 if it is capable of providing a determination of the presence or absence of SARS-CoV-2 within 2 hours, and more preferably within 90 minutes and most preferably, within 1 hour after the commencement of the assay.

III. Preferred Assays for the Detection of SARS-CoV-2

The present invention provides an assay for detecting the presence of SARS-CoV-2 in a "clinical sample". Such detection may be accomplished in situ or in vitro, but is preferably conducted in vitro. The clinical samples that may be evaluated in accordance with the present invention include any that may contain SARS-CoV-2, and include blood samples, bronchoalveolar lavage fluid specimens, fecal samples, fibrobronchoscope brush biopsy samples, nasal swab samples, nasopharyngeal swab samples, pharyngeal swab sample, oral samples (including saliva samples, sputum samples, etc.) and urine samples. Preferably, however, the employed clinical sample will be a nasal swab sample, a nasopharyngeal swab sample, a pharyngeal swab sample, or a sputum sample, and most preferably, the employed clinical sample will be a nasopharyngeal swab sample. In one embodiment, the sample will be pre-treated to extract RNA that may be present in the sample. Alternatively, and more preferably, the sample will be evaluated without prior RNA extraction.

A. Real-Time Reverse Transcriptase Polymerase Chain Reaction (rRT-PCR) Assay Formats In one embodiment, the present invention preferably uses a real-time reverse transcriptase polymerase chain reaction (rRT-PCR) assay to detect the presence of SARS-CoV-2 in clinical samples. rRT-PCR assays are well known and widely deployed in diagnostic virology (see, e.g., Pang, J. et al. (2020) "*Potential Rapid Diagnostics, Vaccine and Therapeutics for* 2019 *Novel Coronavirus* (2019-*nCoV*): *A Systematic Review*," J. Clin. Med. 26; 9(3)E623 doi: 10.3390/jcm9030623; Kralik, P. et al. (2017) "*A Basic Guide to Real-Time PCR in Microbial Diagnostics: Definitions, Parameters, and Everything*," Front. Microbiol. 8:108. doi: 10.3389/fmicb.2017.00108).

To more easily describe the rRT-PCR assays of the present invention, such assays may be envisioned as involving multiple reaction steps:

(1) the reverse transcription of SARS-CoV-2 RNA that may be present in the clinical sample that is to be evaluated for SARS-CoV-2 presence;
(2) the PCR-mediated amplification of the SARS-CoV-2 cDNA produced from such reverse transcription;
(3) the hybridization of SARS-CoV-2-specific probes to such amplification products;
(4) the double-strand-dependent 5→3' exonuclease cleavage of the hybridized SARS-CoV-2-specific probes; and
(5) the detection of the unquenched probe fluorophores signifying that the evaluated clinical sample contained SARS-CoV-2.

It will be understood that such steps may be conducted separately (for example, in two or more reaction chambers, or with reagents for the different steps being added at differing times, etc.). However, it is preferred that such steps are to be conducted within the same reaction chamber, and that all reagents needed for the rRT-PCR assays of the present invention are to be provided to the reaction chamber at the start of the assay. It will also be understood that although the polymerase chain reaction (PCR) (see, e.g. Ghannam, M, G, et al. (2020) "*Biochemistry, Polymerase Chain Reaction* (*PCR*)," StatPearls Publishing, Treasure Is.; pp. 1-4; Lorenz, T. C. (2012) "*Polymerase Chain Reaction: Basic Protocol Plus Troubleshooting And Optimization Strategies*," J. Vis. Exp. 2012 May 22; (63):e3998; pp. 1-15) is the preferred method of amplifying SARS-CoV-2 cDNA produced via reverse transcription, other DNA amplification technologies could alternatively be employed.

Accordingly, in a preferred embodiment, the rRT-PCR assays of the present invention comprise incubating a clinical sample in the presence of a DNA polymerase, a reverse transcriptase, one or more pairs of SARS-CoV-2-specific primers, one or more SARS-CoV-2-specific probes (typically, at least one probe for each region being amplified by an employed pair of primers), deoxynucleotide triphosphates (dNTPs) and buffers. The conditions of the incubation are cycled to permit the reverse transcription of SARS-CoV-2 RNA, the amplification of SARS-CoV-2 cDNA, the hybridization of SARS-CoV-2-specific probes to such cDNA, the cleavage of the hybridized SARS-CoV-2-specific probes and the detection of unquenched probe fluorophores. The reverse transcriptase is needed only to produce a cDNA version of SARS-CoV-2 RNA.

The rRT-PCR assays of the present invention employ at least one set of at least one "Forward" primer that hybridizes to a polynucleotide domain of a first strand of a DNA molecule, and at least one "Reverse" primer that hybridizes to a polynucleotide domain of a second (and complementary) strand of such DNA molecule.

Preferably, such Forward and Reverse primers will permit the amplification of a region of ORF1ab, which encodes a non-structural polyprotein of SARS-CoV-2 and/or a region of the S gene, which encodes the virus spike surface glycoprotein and is required for host cell targeting. The SARS-CoV-2 spike surface glycoprotein is a key protein for specifically characterizing a coronavirus as being SARS-CoV-2 (Chen, Y. et al. (2020) "*Structure Analysis Of The Receptor Binding Of* 2019-*Ncov*," Biochem. Biophys. Res. Commun. 525:135-140; Masters, P. S. (2006) "*The Molecular Biology Of Coronaviruses*," Adv. Virus Res. 66:193-292). The amplification of either of such targets alone is sufficient for the specific determination of SARS-CoV-2 presence in clinical samples. It is, however, preferred to assay for SARS-CoV-2 by incubating nucleic acid molecules of a clinical sample under conditions sufficient to amplify both such targets, if present therein, and then determining whether both such amplified products are detectable.

The present invention encompasses methods, kits and oligonucleotides sufficient to amplify any portion of the SARS-CoV-2 ORF1ab. The nucleotide sequence of an exemplary ORF1ab region is provided as SEQ ID NO:415. The primers of the present invention thus include any two or more oligonucleotide SARS-CoV-2 ORF1ab primers, each being of 15, 16, 17, 18, 19, 20 or more than 20 nucleotide residues in length, that is capable of specifically hybridizing to SEQ ID NO:415, or its complement, and of mediating the amplification of an oligonucleotide region (for example, via PCR, Loop-Mediated Isothermal Amplification (LAMP), rolling circle amplification, ligase chain reaction amplification, strand-displacement amplification, bind-wash PCR, singing wire PCR, NASBA, etc.) thereof that is capable of specifically hybridizing to SEQ ID NO:415. Preferably, such amplified region of SEQ ID NO:415 will be greater than about 20 nucleotide residues in length, and preferably less than about 50 nucleotide residues in length, more preferably less than about 100 nucleotide residues in length, more preferably less than about 150 nucleotide residues in length, more preferably less than about 200 nucleotide residues in length, more preferably less than about 300 nucleotide residues in length, more preferably less than about 400 nucleotide residues in length, and most preferably less than about 500 nucleotide residues in length. The present invention further encompasses one or more detectably-labeled SARS-CoV-2 ORF1ab probe oligonucleotide(s) (and especially fluorophore labeled oligonucleotides, as discussed in detail below), that is capable of specifically hybridizing to such amplified region of SEQ ID NO:415, and of detecting the presence of such amplified region, for example, by comprising a molecular beacon probe, HyBeacon® probe, scorpion primer-probe, TaqMan probe, biotinylated oligo-probe, etc.

The present invention additionally encompasses methods, kits and oligonucleotides sufficient to amplify any portion of the SARS-CoV-2 S gene. The nucleotide sequence of an exemplary S gene is provided as SEQ ID NO:16. The primers of the present invention thus include any two or more oligonucleotide SARS-CoV-2 S gene primers, each being of 15, 16, 17, 18, 19, 20 or more than 20 nucleotide residues in length, that is capable of specifically hybridizing to SEQ ID NO:16, or its complement, and of mediating the amplification of an oligonucleotide region (for example, via PCR, Loop-Mediated Isothermal Amplification (LAMP), rolling circle amplification, ligase chain reaction amplification, strand-displacement amplification, bind-wash PCR, singing wire PCR, NASBA, etc.) thereof that is capable of specifically hybridizing to SEQ ID NO:16. Preferably, such amplified region of SEQ ID NO:16 will be greater than about 20 nucleotide residues in length, and preferably less than about 50 nucleotide residues in length, more preferably less than about 100 nucleotide residues in length, more preferably less than about 150 nucleotide residues in length, more preferably less than about 200 nucleotide residues in length, more preferably less than about 300 nucleotide residues in length, more preferably less than about 400 nucleotide residues in length, and most preferably less than about 500 nucleotide residues in length. The present invention further encompasses one or more detectably-labeled SARS-CoV-2 S gene probe oligonucleotide(s) (and especially fluorophore labeled oligonucleotides, as discussed in detail below), that is capable of specifically hybridizing to such amplified region of SEQ ID NO:16, and of detecting the presence of such amplified region, for example, by comprising a molecular beacon probe, HyBeacon® probe, scorpion primer-probe, TaqMan probe, biotinylated oligo-probe, etc.

1. Preferred ORF1ab Primers

The amplification of SARS-CoV-2 ORF1ab is preferably mediated using a "Forward ORF1ab Primer" and a "Reverse ORF1ab Primer," whose sequences are suitable for amplifying a region of the SARS-CoV-2 ORF1ab. Although any Forward and Reverse ORF1ab Primers capable of mediating such amplification may be employed in accordance with the present invention, it is preferred to employ Forward and Reverse ORF1ab Primers that possess distinctive advantages. The preferred Forward ORF1ab Primer of the present invention comprises, consists essentially of, or consists of, the sequence (SEQ ID NO:1) atggtagagttgatggtcaa, which corresponds to the nucleotide sequence of nucleotides 19991-20010 of the sense-strand of the SARS-CoV-2 ORF1ab, or is a variant thereof. The preferred Reverse ORF1ab Primer of the present invention comprises, consists essentially of, or consists of, the sequence (SEQ ID NO:2) taagactagcttgtttggga, which corresponds to the nucleotide sequence of nucleotides 20088-20107 of the anti-sense-strand of SARS-CoV-2 ORF1ab, or is a variant thereof. Primers that consist essentially of the sequences of SEQ ID NO:1 and SEQ ID NO:2 amplify a double-stranded oligonucleotide having the sequence of nucleotides 19991-20107 of SARS-CoV-2 ORF1ab. Such preferred "Forward ORF1ab Primer" and preferred "Reverse ORF1ab Primer" have distinctive attributes for use in the detection of SARS-CoV-2.

The sequence of the "sense" strand of nucleotides 19991-20107 of the SARS-CoV-2 ORF1ab is SEQ ID NO:3; the sequence of the complement ("anti-sense") strand is SEQ ID NO:4:

```
                                           SEQ ID NO: 3
atggtagagt tgatggtcaa gtagacttat ttagaaatgc

ccgtaatggt gttcttatta cagaaggtag tgttaaaggt

ttacaaccat ctgtaggtcc caaacaagct agtctta

                                           SEQ ID NO: 4
taagactagc ttgtttggga cctacagatg gttgtaaacc

tttaacacta ccttctgtaa taagaacacc attacgggca

tttctaaata agtctacttg accatcaact ctaccat
```

Such oligonucleotides illustrate the SARS-CoV-2 oligonucleotides that may be amplified using the ORF1ab primers of the present invention.

While it is preferred to detect the presence of the ORF1ab using primers that consist of the sequences of SEQ ID NO:1 and SEQ ID NO:2, the invention contemplates that other primers that consist essentially of the sequence of SEQ ID NO:1 or that consist essentially of the sequence of SEQ ID NO:2 (in that they possess 1, 2, 3, 4, 5, 6, 7, 8, 9, or 10 additional nucleotide residues, but retain the ability to specifically hybridize to DNA molecules having the nucleotide sequence of SEQ ID NO:3 or SEQ ID NO:4, and more preferably retain the ability to specifically hybridize to DNA molecules having the nucleotide sequence of complement of the nucleotide sequence of SEQ ID NO:1 or the nucleotide sequence of complement of the nucleotide sequence of SEQ ID NO:2), or "variants" of such primers that retain the ability to specifically hybridize to DNA molecules having the nucleotide sequence of SEQ ID NO:3 or SEQ ID NO:4, and more preferably retain the ability to specifically hybridize to DNA molecules having the nucleotide sequence of complement of the nucleotide sequence of SEQ ID NO:1 or the nucleotide sequence of complement of the nucleotide sequence of SEQ ID NO:2, could be employed in accordance with the principles and goals of the present invention. Such "Variant ORF1ab Primers" may, for example:

(1) lack 1, 2, 3, 4, 5, 6, 7, 8, 9, or 10 nucleotides of SEQ ID NO:1 or of SEQ ID NO:2, or (2) lack 1, 2, 3, 4, 5, 6, 7, 8, 9, or 10 of the 10 3' terminal nucleotides of the sequence of SEQ ID NO:1 or of SEQ ID NO:2, or (3) lack 1, 2, 3, 4, 5, 6, 7, 8, 9, or 10 of the 10 5' terminal nucleotides of the sequence of SEQ ID NO:1 or of SEQ ID NO:2, or (4) have a sequence that differs from that of SEQ ID NO:1 or of SEQ ID NO:2 in having 1, 2, 3, 4, 5, 6, 7, 8, 9, 10 or more than 10 additional nucleotides, or (5) have a sequence that differs from that of SEQ ID NO:1 or of SEQ ID NO:2 in having 1, 2, 3, 4, 5, 6, 7, 8, 9, 10 or more than 10 substitution nucleotides in lieu of the nucleotides present in SEQ ID NO:1 or of SEQ ID NO:2, or (6) combinations of such (1)-(5).

Non-limiting examples of such primers are shown in Table 3 and Table 4.

TABLE 3

| Illustrative Variants of the Preferred Forward ORF1ab Primer | |
|---|---|
| SEQ ID NO | Sequence |
| 17 | atggtagagttgatggtca |
| 18 | atggtagagttgatggtc |
| 19 | atggtagagttgatggt |
| 20 | atggtagagttgatgg |
| 21 | atggtagagttgatg |
| 22 | tggtagagttgatggtcaa |
| 23 | ggtagagttgatggtcaa |
| 24 | gtagagttgatggtcaa |
| 25 | tagagttgatggtcaa |
| 26 | agagttgatggtcaa |
| 27 | tggtagagttgatggtca |
| 28 | ggtagagttgatggtc |

TABLE 4

| Illustrative Variants of the Preferred Reverse ORF1ab Primer | |
|---|---|
| SEQ ID NO | Sequence |
| 29 | taagactagcttgtttggg |
| 30 | taagactagcttgtttgg |
| 31 | taagactagcttgtttg |
| 32 | taagactagcttgttt |
| 33 | taagactagcttgtt |
| 34 | aagactagcttgtttggga |
| 35 | agactagcttgtttggga |
| 36 | gactagcttgtttggga |
| 37 | actagcttgtttggga |
| 38 | ctagcttgtttggga |
| 39 | aagactagcttgtttggg |
| 40 | agactagcttgtttggg |
| 41 | agactagcttgtttgg |
| 42 | gactagcttgtttgg |

Figure 2:
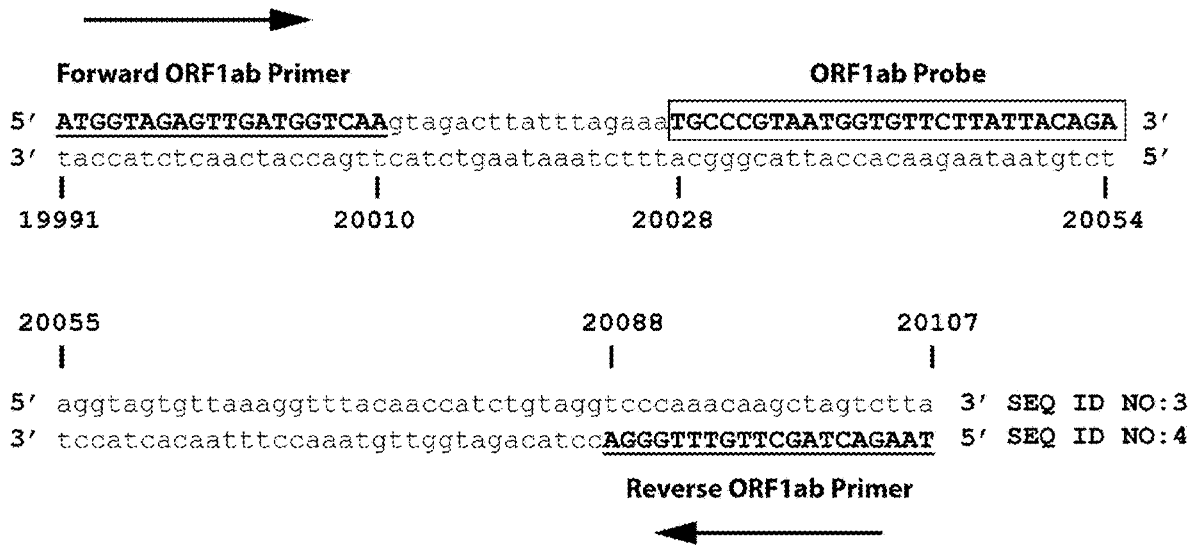
FIG. 2 shows the alignment and orientation of a Forward ORF1ab Primer and Reverse ORF1ab Primer of the present invention and the region of ORF1ab that these primers amplify in an rRT-PCR assay of SARS-CoV-2. Primer sequences are shown in underlined upper case letters; probe sequences are shown in boxed uppercase letters.

The alignment and relative orientation of the preferred Forward ORF1ab Primer (SEQ ID NO: 1) and Reverse ORF1ab Primer (SEQ ID NO:2) of the present invention and the region of SARS-CoV-2 ORF1ab that these primers amplify in a rRT-PCR assay of SARS-CoV-2 are shown in FIG. 2.

2. Preferred S Gene Primers

The amplification of SARS-CoV-2 S gene is preferably mediated using a "Forward S Gene Primer" and a "Reverse S Gene Primer," whose sequences are suitable for amplifying a region of the SARS-CoV-2 S gene. Although any Forward and Reverse S Gene Primers capable of mediating such amplification may be employed in accordance with the present invention, it is preferred to employ Forward and Reverse S Gene Primers that possess distinctive advantages. The preferred Forward S Gene Primer of the present invention comprises, consists essentially of, or consists of, the sequence (SEQ ID NO:5) ctaaccaggttgctgttctt, which corresponds to the nucleotide sequence of nucleotides 23376-23395 of the sense-strand of the SARS-CoV-2 S gene, or is a variant thereof. The preferred Reverse S Gene Primer comprises, consists essentially of, or consists of, the sequence (SEQ ID NO:6) cctgtagaataaacacgcca, which corresponds to the nucleotide sequence of nucleotides 23459-23478 of the anti-sense-strand of the SARS-CoV-2 S gene, or is a variant thereof. Primers that consist essentially of the sequences of SEQ ID NO:5 and SEQ ID NO:6 amplify a double-stranded oligonucleotide having the sequence of nucleotides 23376-23478 of the SARS-CoV-2 S gene. Such preferred "Forward S Gene Primer" and preferred "Reverse S Gene Primer" have distinctive attributes for use in the detection of SARS-CoV-2.

The sequence of the "sense" strand of nucleotides 23376-23478 of the SARS-CoV-2 S gene is SEQ ID NO:7; the sequence of the complement ("anti-sense") strand is SEQ ID NO:8:

```
SEQ ID NO:7:
ctaaccaggt tgctgttctt tatcaggatg ttaactgcac

agaagtccct gttgctattc atgcagatca acttactcct

acttggcgtg tttattctac agg

SEQ ID NO:8:
cctgtagaat aaacacgcca agtaggagta agttgatctg

catgaatagc aacagggact tctgtgcagt taacatcctg

ataaagaaca gcaacctggt tag
```

Such oligonucleotides illustrate the SARS-CoV-2 oligonucleotides that may be amplified using the S Gene Primers of the present invention.

The nucleotide residue that is responsible for the D614G single nucleotide polymorphism of the SARS-CoV-2 S gene is underlined. SARS-CoV-2 possessing the D614G mutation (in which the adenine residue present at position 28 of SEQ ID NO:7 (position 1841 of SEQ ID NO:16) is replaced with a guanine residue, and the thymine residue present at position 76 of SEQ ID NO:8 is replaced with a cytosine residue) has emerged as a predominant clade in Europe and is spreading worldwide and is associated with enhanced fitness and higher transmissibility (Haddad, H. et al. (2020) "*Mirna Target Prediction Might Explain The Reduced Transmission Of SARS-CoV-2 In Jordan, Middle East*," Noncoding RNA Res. 5(3):135-143; Isabel, S. et al. (2020) "*Evolutionary And Structural Analyses Of SARS-Cov-2 D614G Spike Protein Mutation Now Documented Worldwide*," Sci. Rep. 10(1): 14031:1-9; Laamarti, M. et al. (2020) "*Genome Sequences of Six SARS-CoV-2* Strains *Isolated in Morocco, Obtained Using Oxford Nanopore MinION Technology*," Microbiol. Resour. Announc. 9(32):e00767-20:1-4; Omotuyi, I. O. et al. (2020) "*Atomistic Simulation Reveals Structural Mecha-*

*nisms Underlying D614G Spike Glycoprotein-Enhanced Fitness In SARS-CoV-2*," J. Comput. Chem. 41(24):2158-2161; Ogawa, J. et al. (2020) "*The D614G Mutation In The SARS-Cov2 Spike Protein Increases Infectivity In An ACE2 Receptor Dependent Manner*," Preprint. bioRxiv. 2020; 2020.07.21.214932:1-10).

While it is preferred to detect the presence of the S gene using primers that consist of the sequences of SEQ ID NO:5 and SEQ ID NO:6, the invention contemplates that other primers that consist essentially of the sequence of SEQ ID NO:5 or that consist essentially of the sequence of SEQ ID NO:6 (in that they possess 1, 2, 3, 4, 5, 6, 7, 8, 9, or 10 additional nucleotide residues, but retain the ability to specifically hybridize to DNA molecules having the nucleotide sequence of SEQ ID NO:7 or SEQ ID NO:8, and more preferably retain the ability to specifically hybridize to DNA molecules having the nucleotide sequence of complement of the nucleotide sequence of SEQ ID NO:5 or the nucleotide sequence of complement of the nucleotide sequence of SEQ ID NO:6), or "variants" of such primers that retain the ability to specifically hybridize to DNA molecules having the nucleotide sequence of SEQ ID NO:7 or SEQ ID NO:8, and more preferably retain the ability to specifically hybridize to DNA molecules having the nucleotide sequence of complement of the nucleotide sequence of SEQ ID NO:5 or the nucleotide sequence of complement of the nucleotide sequence of SEQ ID NO:6, could be employed in accordance with the principles and goals of the present invention. Such "Variant S Gene Primers" may, for example:

(1) lack 1, 2, 3, 4, 5, 6, 7, 8, 9, or 10 nucleotides of SEQ ID NO:5 or of SEQ ID NO:6, or
(2) lack 1, 2, 3, 4, 5, 6, 7, 8, 9, or 10 of the 10 3' terminal nucleotides of the sequence of SEQ ID NO:5 or of SEQ ID NO:6, or
(3) lack 1, 2, 3, 4, 5, 6, 7, 8, 9, or 10 of the 10 5' terminal nucleotides of the sequence of SEQ ID NO:5 or of SEQ ID NO:6, or
(4) have a sequence that differs from that of SEQ ID NO:5 or of SEQ ID NO:6 in having 1, 2, 3, 4, 5, 6, 7, 8, 9, 10 or more than 10 additional nucleotides, or
(5) have a sequence that differs from that of SEQ ID NO:5 or of SEQ ID NO:6 in having 1, 2, 3, 4, 5, 6, 7, 8, 9, 10 or more than 10 substitution nucleotides in lieu of the nucleotides present in SEQ ID NO:5 or of SEQ ID NO:6, or
(6) combinations of such (1)-(5).

Non-limiting examples of such primers are shown in Table 5 and Table 6 (the nucleotide residue that is responsible for the D614G single nucleotide polymorphism of the SARS-CoV-2 S gene is underlined).

TABLE 5

Illustrative Variants of the Preferred Forward S Gene Primer

| SEQ ID NO | Sequence |
|---|---|
| 43 | ctaaccaggttgctgttctttatcagg**a** |
| 44 | ctaaccaggttgctgttctttatcagg**g** |
| 45 | taaccaggttgctgttctttatcagg**a** |
| 46 | taaccaggttgctgttctttatcagg**g** |
| 47 | aaccaggttgctgttctttatcagg**a** |

TABLE 5-continued

Illustrative Variants of the Preferred Forward S Gene Primer

| SEQ ID NO | Sequence |
|---|---|
| 48 | aaccaggttgctgttctttatcagg**g** |
| 49 | accaggttgctgttctttatcagg**a** |
| 50 | accaggttgctgttctttatcagg**g** |
| 51 | ccaggttgctgttctttatcagg**a** |
| 52 | ccaggttgctgttctttatcagg**g** |
| 53 | caggttgctgttctttatcagg**a** |
| 54 | caggttgctgttctttatcagg**g** |
| 55 | aggttgctgttctttatcagg**a** |
| 56 | aggttgctgttctttatcagg**g** |
| 57 | ggttgctgttctttatcagg**a** |
| 58 | ggttgctgttctttatcagg**g** |
| 59 | gttgctgttctttatcagg**a** |
| 60 | gttgctgttctttatcagg**g** |
| 61 | ttgctgttctttatcagg**a** |
| 62 | ttgctgttctttatcagg**g** |
| 63 | tgctgttctttatcagg**a** |
| 64 | tgctgttctttatcagg**g** |
| 65 | gctgttctttatcagg**a** |
| 66 | gctgttctttatcagg**g** |
| 67 | ctgttctttatcagg**a** |
| 68 | ctgttctttatcagg**g** |
| 69 | tgttctttatcagg**a** |
| 70 | tgttctttatcagg**g** |
| 71 | ctaaccaggttgctgttct |
| 72 | ctaaccaggttgctgttc |
| 73 | ctaaccaggttgctgtt |
| 74 | ctaaccaggttgctgt |
| 75 | ctaaccaggttgctg |
| 76 | taaccaggttgctgttctt |
| 77 | aaccaggttgctgttctt |
| 78 | accaggttgctgttctt |
| 79 | ccaggttgctgttctt |
| 80 | caggttgctgttctt |
| 81 | taaccaggttgctgttct |
| 82 | aaccaggttgctgttct |
| 83 | aaccaggttgctgttc |
| 84 | accaggttgctgttc |

TABLE 6

| Illustrative Variants of the Preferred Reverse S Gene Primer | |
|---|---|
| SEQ ID NO | Sequence |
| 85 | gcaacagggacttctgtgcagttaaca**t** |
| 86 | gcaacagggacttctgtgcagttaaca**c** |
| 87 | caacagggacttctgtgcagttaaca**t** |
| 88 | caacagggacttctgtgcagttaaca**c** |
| 89 | aacagggacttctgtgcagttaaca**t** |
| 90 | aacagggacttctgtgcagttaaca**c** |
| 91 | acagggacttctgtgcagttaaca**t** |
| 92 | acagggacttctgtgcagttaaca**c** |
| 93 | cagggacttctgtgcagttaaca**t** |
| 94 | cagggacttctgtgcagttaaca**c** |
| 95 | agggacttctgtgcagttaaca**t** |
| 96 | agggacttctgtgcagttaaca**c** |
| 97 | gggacttctgtgcagttaaca**t** |
| 98 | gggacttctgtgcagttaaca**c** |
| 99 | ggacttctgtgcagttaaca**t** |
| 100 | ggacttctgtgcagttaaca**c** |
| 101 | gacttctgtgcagttaaca**t** |
| 102 | gacttctgtgcagttaaca**c** |
| 103 | acttctgtgcagttaaca**t** |
| 104 | acttctgtgcagttaaca**c** |
| 105 | cttctgtgcagttaaca**t** |
| 106 | cttctgtgcagttaaca**c** |
| 107 | ttctgtgcagttaaca**t** |
| 108 | ttctgtgcagttaaca**c** |
| 109 | tctgtgcagttaaca**t** |
| 110 | tctgtgcagttaaca**c** |
| 111 | ctgtgcagttaaca**t** |
| 112 | ctgtgcagttaaca**c** |
| 113 | cctgtagaataaacacgcc |
| 114 | cctgtagaataaacacgc |
| 115 | cctgtagaataaacacg |
| 116 | cctgtagaataaacac |
| 117 | cctgtagaataaaca |
| 118 | ctgtagaataaacacgcca |
| 119 | tgtagaataaacacgcca |
| 120 | gtagaataaacacgcca |
| 121 | tagaataaacacgcca |
| 122 | agaataaacacgcca |
| 123 | ctgtagaataaacacgcc |
| 124 | tgtagaataaacacgcc |
| 125 | tgtagaataaacacgc |
| 126 | gtagaataaacacgc |

Figure 3:
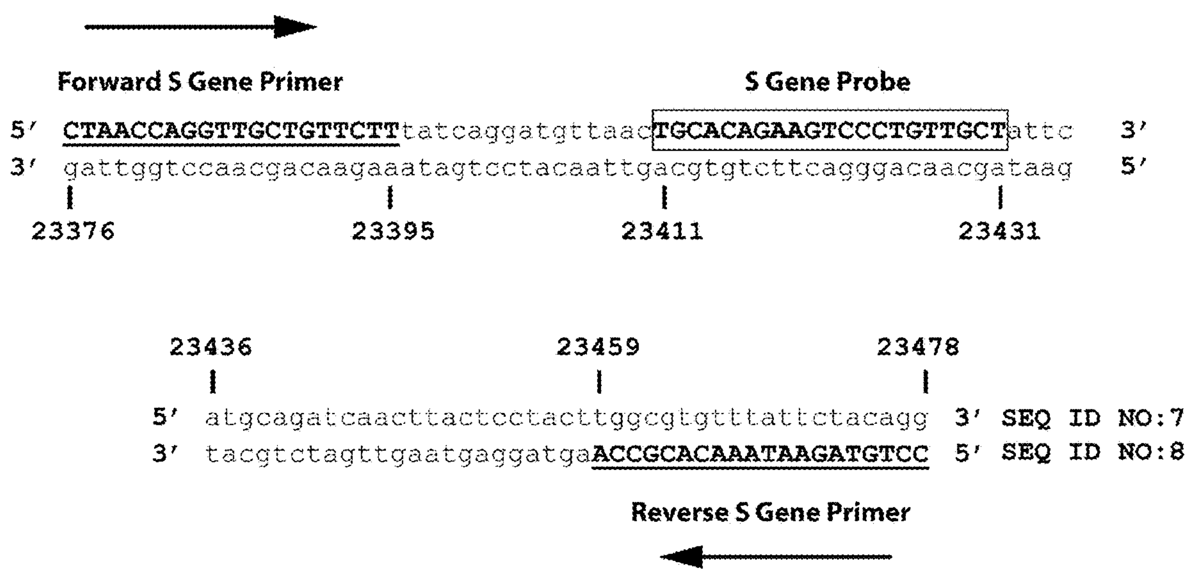
FIG. 3 shows the alignment and orientation of a Forward S Gene Primer and Reverse S Gene Primer of the present invention and the region of the S gene that these primers amplify in an rRT-PCR assay of SARS-CoV-2. Primer sequences are shown in underlined upper case letters; probe sequences are shown in boxed uppercase letters.

The alignment and relative orientation of the Forward S Gene Primer (SEQ ID NO:5) and Reverse S Gene Primer (SEQ ID NO:6) of the present invention and the region of the SARS-CoV-2 S gene that these primers amplify in a rRT-PCR assay of SARS-CoV-2 are shown in FIG. 3.

B. Detection of SARS-CoV-2

In accordance with the present invention, the presence or absence of SARS-CoV-2 in a sample, such as a clinical sample, is preferably accomplished using one or more detectably labeled oligonucleotides as probe(s). As used herein, the term "detectably labeled oligonucleotide" denotes a nucleic acid molecule that comprises at least 10 nucleotide residues and not more than 500 nucleotide residues, more preferably, not more than 200 nucleotide residues, still more preferably, not more than 100 nucleotide residues, and still more preferably, not more than 50 nucleotide residues, and that is capable of specifically hybridizing to the RNA or CDNA of SARS-CoV-2. As used herein, the term "specifically hybridizing" denotes the capability of a nucleic acid molecule to detectably anneal to another nucleic acid molecule under conditions in which such nucleic acid molecule does not detectably anneal to a non-complementary nucleic acid molecule. The probes of the present invention permit the detection of SARS-CoV-2-specific polynucleotides, and thus permit a diagnosis of COVID-19. Additionally, the variant probes of the present invention permit the detection of polymorphisms (such as single nucleotide polymorphisms (SNPs), e.g., the SNPs that cause the D614G, V515F, V622I, P631S polymorphisms in the SARS-CoV-2 S gene), that may be present in the SARS-CoV-2 polynucleotides of a clinical sample. SNPs may be advantageously detected using two probes having distinguishable labels.

Detection can be accomplished using any suitable method, e.g., molecular beacon probes, HyBeacon® probes, scorpion primer-probes, TaqMan probes, biotinylated oligoprobes in an enzyme-linked immunosorbent assay-based format, turbidity, radioisotopic-labeled oligoprobes, chemiluminescent detectors, amplification of the probe sequences using Q beta replicase, PNA-based detectors, LAMP, etc. (Bustin, S. A. et al. (2020) "*RT-qPCR Testing of SARS-CoV-2: A Primer*," Intl. J. Molec. Sci. 21:3004:1-9; Chang, G.-J. J. et al. (1994) "*An Integrated Target Sequence and Signal Amplification Assay, Reverse Transcriptase-PCR-Enzyme-Linked Immunosorbent Assay, To Detect and Characterize Flaviviruses*," J. Clin. Microbiol. 32(2):477-483; Navarro, E. et al. (2015) "*Real-Time PCR Detection Chemistry*," Clin. Chim. Acta 439:231-250; Persing, D. H. et al. (1989) "*In Vitro Amplification Techniques For The Detection Of*

*Nucleic Acids: New Tools For The Diagnostic Laboratory*," Yale J. Biol. Med. 62(2):159-171; Schwab, K. J. et al. (2001) "*Development Of A Reverse Transcription-PCR-DNA Enzyme Immunoassay For Detection Of "Norwalk-Like" Viruses And Hepatitis A Virus In Stool And Shellfish. Applied And Environmental Microbiology*," 67(2):742-749; Yuan, X. et al. (2019) "*LAMP Real-Time Turbidity Detection For Fowl Adenovirus*," BMC Vet. Res. 15: 256:1-4; French, D. J. et al. (2001) "*HyBeacon Probes: A New Tool For DNA Sequence Detection And Allele Discrimination*," Mol. Cell. Probes 15(6):363-374; French, D. J. et al. (2006) "*HyBeacons®: A Novel DNA Probe Chemistry For Rapid Genetic Analysis*," Intl. Cong. Series 1288:707-709; French, D. J. et al. (2008) "*HyBeacon Probes For Rapid DNA Sequence Detection And Allele Discrimination*," Methods Mol. Biol. 429:171-85; Notomi, T. et al. (2000) "*Loop-Mediated Isothermal Amplification Of DNA*," Nucl. Acids Res. 28(12): E63:1-7; Zhang, H. et al. (2019) "*LAMP-On-A-Chip: Revising Microfluidic Platforms For Loop-Mediated DNA Amplification*," Trends Analyt. Chem. 113:44-53; Eiken Chemical Co., Ltd. (2020) "*Eiken Chemical Launches the Loopamp* 2019 *nCoV Detection Kit*," Press Release; pages 1-2; Zhang, H. et al. (2019) "*LAMP-On-A-Chip: Revising Microfluidic Platforms For Loop-Mediated DNA Amplification*," Trends Analyt. Chem. 113:44-53; Yuan, X. et al. (2019) "*LAMP Real-Time Turbidity Detection For Fowl Adenovirus*," BMC Vet. Res. 15: 256:1-4; U.S. Pat. Nos. 6,974,670; 7,175,985; 7,348,141; 7,399,588; 7,494,790; 7,998,673; and 9,909,168).

Preferably, the detection of the amplified SARS-CoV-2 polynucleotides of the present invention employs an oligonucleotide that is labeled with a fluorophore and complexed to a quencher of the fluorescence of that fluorophore (Navarro, E. et al. (2015) "*Real-Time PCR Detection Chemistry*," Clin. Chim. Acta 439:231-250).

A wide variety of fluorophores and quenchers are known and are commercially available (e.g., Biosearch Technologies, Gene Link), and may be used in accordance with the methods of the present invention. Preferred fluorophores include the fluorophores Biosearch Blue, Alexa488, FAM, Oregon Green, Rhodamine Green-X, NBD-X, TET, Alexa430, BODIPY R6G-X, CAL Fluor Gold 540, JOE, Yakima Yellow, Alexa 532, VIC, HEX, and CAL Fluor Orange 560 (which have an excitation wavelength in the range of about 352-538 nm and an emission wavelength in the range of about 447-559 nm, and whose fluorescence can be quenched with the quencher BHQ1), or the fluorophores RBG, Alexa555, BODIPY 564/570, BODIPY TMR-X, Quasar 570, Cy3, Alexa 546, NED, TAMRA, Rhodamine Red-X, BODIPY 581/591, Redmond Red, CAL Fluor Red 590, Cy3.5, ROX, Alexa 568, CAL Fluor Red 610, BODIPY TR-X, Texas Red, CAL Fluor Red 635, Pulsar 650, Cy5, Quasar 670, CY5.5, Alexa 594, BODIPY 630/650-X, or Quasar 705 (which have an excitation wavelength in the range of about 524-690 nm and an emission wavelength in the range of about 557-705 nm, and whose fluorescence can be quenched with the quencher BHQ2). The preferred SARS-CoV-2-specific probes of the present invention are labeled with either the fluorophore 2',7'-dimethoxy-4',5'-dichloro-6-carboxyfluorescein ("JOE") or the fluorophore 5(6)-carboxyfluorescein ("FAM") on their 5' termini. JOE is a xanthene fluorophore with an emission in yellow range (absorption wavelength of 520 nm; emission wavelength of 548 nm). FAM is a carboxyfluorescein molecule with an absorption wavelength of 495 nm and an emission wavelength of 517 nm; it is typically provided as a mixture of two isomers (5-FAM and 6-FAM). Quasar 670 is similar to cyanine dyes, and has an absorption wavelength of 647 nm and an emission wavelength of 670 nm.

The black hole quencher 1 ("BHQ1") is a preferred quencher for FAM and JOE fluorophores. BHQ1 quenches fluorescent signals of 480-580 nm and has an absorption maximum at 534 nm.

The black hole quencher 2 ("BHQ2") is a preferred quencher for Quasar 670. BHQ2 quenches fluorescent signals of 560-670 nm and has an absorption maximum at 579 nm.

JOE, FAM, Quasar 670, BHQ1 and BHQ2 are widely available commercially (e.g., Sigma Aldrich; Biosearch Technologies, etc.) and are coupled to oligonucleotides using methods that are well known (see, e.g., Zearfoss, N. R. et al. (2012) "*End-Labeling Oligonucleotides with Chemical Tags After Synthesis*," Meth. Mol. Biol. 941:181-193). Oligonucleotide probes of any desired sequence labeled may be obtained commercially (e.g., ThermoFisher Scientific) already labeled with a desired fluorophore and complexed to a desired quencher.

As discussed above, the proximity of the quencher of a probe to the fluorophore of that probe results in a quenching of the fluorescent signal. Incubation of the probe in the presence of a double-strand-dependent 5→3' exonuclease (such as the 5→3' exonuclease activity of Taq polymerase) cleaves the probe when it has hybridized to a complementary target sequence, thus separating the fluorophore from the quencher and permitting the production of a detectable fluorescent signal.

In a preferred embodiment, such oligonucleotides are modified to be TaqMan probes by being detectably complexed to a fluorophore and a quencher, with the fluorophore being preferably complexed to a nucleotide residue within 5 nucleotides, within 4 nucleotides, within 3 nucleotides, or within 2 nucleotides of the 5' terminus of the probe, and the quencher being preferably complexed to a nucleotide residue within 5 nucleotides, within 4 nucleotides, within 3 nucleotides, or within 2 nucleotides of the 3' terminus of the probe. In one embodiment, the fluorophore is complexed to the 5' terminal nucleotide residue of the probe and the quencher is complexed to the 3' terminal nucleotide of the probe. Labeling for molecular beacon and scorpion primer-probes is similar, but the positions of the fluorophore and quencher are modified in order to account for the presence of stem oligonucleotides and/or a PCR primer oligonucleotide.

1. Preferred Probes for Detecting SARS-CoV-2

(a) Preferred Probes for Detecting SARS-CoV-2 ORF1ab

The preferred probe for detecting the region of ORF1ab that is amplified by the above-described preferred ORF1ab Primers (SEQ ID NO:1 and SEQ ID NO:2) comprises, consists essentially of, or consists of, the nucleotide sequence (SEQ ID NO:9) tgcccgtaatggtgttcttattacaga (the preferred "ORF1ab Probe"). Alternatively, an oligonucleotide that comprises, consists essentially of, or consists of, the complementary nucleotide sequence (SEQ ID NO:10) tctgtaataagaacaccattacgggca could be employed. The alignment and relative position of the preferred ORF1ab Probe of the present invention is shown in FIG. 2.

While the preferred rRT-PCR assays of the present invention detect the presence of the ORF1ab using a probe that consists of the nucleotide sequence of SEQ ID NO:9 or a probe that consists of the nucleotide sequence of SEQ ID NO:10, the invention contemplates that other probes that comprise an oligonucleotide domain that consists essentially of the nucleotide sequence of SEQ ID NO:9 or SEQ ID NO:10 (in that they possess 1, 2, 3, 4, 5, 6, 7, 8, 9, or 10 additional nucleotide residues, but retain the ability to specifically hybridize to DNA molecules having the nucleotide sequence of SEQ ID NO:3 or SEQ ID NO:4, and more that preferably retain the ability to specifically hybridize to DNA molecules having the nucleotide sequence of SEQ ID NO:9 or SEQ ID NO:10), or "variants" of such probes that comprise an oligonucleotide domain that exhibits the ability to specifically hybridize to DNA molecules having the nucleotide sequence of SEQ ID NO:3 or SEQ ID NO:4, and more that preferably exhibits the ability to specifically hybridize to DNA molecules having the nucleotide sequence of SEQ ID NO:9 or SEQ ID NO:10 could be employed in accordance with the principles and goals of the present invention. Such "Variant ORF1ab Probes" may, for example:

(1) lack 1, 2, 3, 4, 5, 6, 7, 8, 9, or 10 nucleotides of SEQ ID NO:9 or of SEQ ID NO:10, or
(2) lack 1, 2, 3, 4, 5, 6, 7, 8, 9, or 10 of the 10 3' terminal nucleotides of the sequence of SEQ ID NO:9 or of SEQ ID NO:10, or
(3) lack 1, 2, 3, 4, 5, 6, 7, 8, 9, or 10 of the 10 5' terminal nucleotides of the sequence of SEQ ID NO:9 or of SEQ ID NO:10, or
(4) have a sequence that differs from that of SEQ ID NO:9 or of SEQ ID NO:10 in having 1, 2, 3, 4, 5, 6, 7, 8, 9, 10 or more than 10 additional nucleotides, or
(5) have a sequence that differs from that of SEQ ID NO:9 or of SEQ ID NO:10 in having 1, 2, 3, 4, 5, 6, 7, 8, 9, 10 or more than 10 substitution nucleotides in lieu of the nucleotides present in SEQ ID NO:9 or of SEQ ID NO:10, or
(6) combinations of such (1)-(5).

Non-limiting examples of such probes are shown in Table 7 and Table 8.

TABLE 7

Illustrative SARS-CoV-2 Oligonucleotide Domains of Sense-Strand Probes for Detecting the Presence of the SARS-CoV-2 ORF1ab

| SEQ ID NO | Sequence |
|---|---|
| 127 | tgcccgtaatggtgttcttattacag |
| 128 | tgcccgtaatggtgttcttattaca |
| 129 | tgcccgtaatggtgttcttattac |
| 130 | tgcccgtaatggtgttcttatta |
| 131 | tgcccgtaatggtgttcttatt |
| 132 | tgcccgtaatggtgttcttat |
| 133 | tgcccgtaatggtgttctta |
| 134 | gcccgtaatggtgttcttattacaga |
| 135 | cccgtaatggtgttcttattacaga |
| 136 | ccgtaatggtgttcttattacaga |
| 137 | cgtaatggtgttcttattacaga |
| 138 | gtaatggtgttcttattacaga |

TABLE 7-continued

Illustrative SARS-CoV-2 Oligonucleotide Domains of Sense-Strand Probes for Detecting the Presence of the SARS-CoV-2 ORF1ab

| SEQ ID NO | Sequence |
|---|---|
| 139 | taatggtgttcttattacaga |
| 140 | aatggtgttcttattacaga |
| 141 | ttcttattacagaaggtagt |
| 142 | gcccgtaatggtgttcttattaca |
| 143 | gcccgtaatggtgttcttattac |
| 144 | cccgtaatggtgttcttattac |
| 145 | cccgtaatggtgttcttatta |
| 146 | ccgtaatggtgttcttatta |

TABLE 8

Illustrative SARS-CoV-2 Oligonucleotide Domains of Antisense-Strand Probes for Detecting the Presence of the SARS-CoV-2 ORF1ab

| SEQ ID NO | Sequence |
|---|---|
| 147 | tctgtaataagaacaccattacgggc |
| 148 | tctgtaataagaacaccattacggg |
| 149 | tctgtaataagaacaccattacgg |
| 150 | tctgtaataagaacaccattacg |
| 151 | tctgtaataagaacaccattac |
| 152 | tctgtaataagaacaccatta |
| 153 | tctgtaataagaacaccatt |
| 154 | ctgtaataagaacaccattacgggca |
| 155 | tgtaataagaacaccattacgggca |
| 156 | gtaataagaacaccattacgggca |

TABLE 8

Illustrative SARS-CoV-2 Oligonucleotide Domains of Antisense-Strand Probes for Detecting the Presence of the SARS-CoV-2 ORF1ab

| SEQ ID NO | Sequence |
|---|---|
| 157 | taataagaacaccattacgggca |
| 158 | aataagaacaccattacgggca |
| 159 | ataagaacaccattacgggca |
| 160 | taagaacaccattacgggca |
| 161 | ctgtaataagaacaccattacgggc |
| 162 | tgtaataagaacaccattacgggc |

TABLE 8-continued

Illustrative SARS-CoV-2 Oligonucleotide Domains of Antisense-Strand Probes for Detecting the Presence of the SARS-CoV-2 ORF1ab

| SEQ ID NO | Sequence |
|---|---|
| 163 | gtaataagaacaccattacgggc |
| 164 | gtaataagaacaccattacggg |
| 165 | taataagaacaccattacggg |
| 166 | taataagaacaccattacgg |

(b) Preferred Probes for Detecting SARS-CoV-2 S Gene

The preferred probe for detecting the region of the S gene that is amplified by the above-described preferred S Gene Primers (SEQ ID NO:5 and SEQ ID NO:6) comprises, consists essentially of, or consists of, the sequence (SEQ ID NO:11) tgcacagaagtccctgttgct (the preferred "S Gene Probe"). Alternatively, an oligonucleotide that comprises, consists essentially of, or consists of, the complementary nucleotide sequence (SEQ ID NO:12) agcaacagggacttctgtgca could be employed. The alignment and relative position of the S Gene Probe of the present invention is shown in FIG. 3.

While the preferred rRT-PCR assays of the present invention detect the presence of the S gene using a probe that consists of the nucleotide sequence of SEQ ID NO:11 or a probe that consists of the nucleotide sequence of SEQ ID NO:12, the invention contemplates that other probes that comprise an oligonucleotide domain that consists essentially of the nucleotide sequence of SEQ ID NO:11 or SEQ ID NO:12 (in that they possess 1, 2, 3, 4, 5, 6, 7, 8, 9, or 10 additional nucleotide residues, but retain the ability to specifically hybridize to DNA molecules having the nucleotide sequence of SEQ ID NO:7 or SEQ ID NO:8, and that more preferably retain the ability to specifically hybridize to DNA molecules having the nucleotide sequence of SEQ ID NO:11 or SEQ ID NO:12), or "variants" of such probes that comprise an oligonucleotide domain that exhibits the ability to specifically hybridize to DNA molecules having the nucleotide sequence of SEQ ID NO:7 or SEQ ID NO:8, and more that preferably exhibits the ability to specifically hybridize to DNA molecules having the nucleotide sequence of SEQ ID NO:11 or SEQ ID NO:12 could be employed in accordance with the principles and goals of the present invention. Such "Variant S Gene Probes" may, for example:

(1) lack 1, 2, 3, 4, 5, 6, 7, 8, 9, or 10 nucleotides of SEQ ID NO:11 or of SEQ ID NO:12, or (2) lack 1, 2, 3, 4, 5, 6, 7, 8, 9, or 10 of the 10 3' terminal nucleotides of the sequence of SEQ ID NO:11 or of SEQ ID NO:12, or (3) lack 1, 2, 3, 4, 5, 6, 7, 8, 9, or 10 of the 10 5' terminal nucleotides of the sequence of SEQ ID NO:11 or of SEQ ID NO:12, or (4) have a sequence that differs from that of SEQ ID NO:11 or of SEQ ID NO:12 in having 1, 2, 3, 4, 5, 6, 7, 8, 9, 10 or more than 10 additional nucleotides, or (5) have a sequence that differs from that of SEQ ID NO:11 or of SEQ ID NO:12 in having 1, 2, 3, 4, 5, 6, 7, 8, 9, 10 or more than 10 substitution nucleotides in lieu of the nucleotides present in SEQ ID NO:11 or of SEQ ID NO:12, or (6) combinations of such (1)-(5).

Non-limiting examples of such probes are shown in Table 9 and Table 10 (the nucleotide residue that is responsible for the D614G single nucleotide polymorphism of the SARS-CoV-2 S gene is underlined).

TABLE 9

Illustrative SARS-CoV-2 Oligonucleotide Domains of Sense Strand Probes for Detecting the Presence of the SARS-CoV-2 S Gene

| SEQ ID NO | Sequence |
|---|---|
| 11 | tgcacagaagtccctgttgct |
| 167 | ctgttctttatcagg**a**tgttaactgcacaga |
| 168 | ctgttctttatcagg**g**tgttaactgcacaga |
| 169 | tgttctttatcagg**a**tgttaactgcacaga |
| 170 | tgttctttatcagg**g**tgttaactgcacaga |
| 171 | gttctttatcagg**a**tgttaactgcacaga |
| 172 | gttctttatcagg**g**tgttaactgcacaga |
| 173 | ttctttatcagg**a**tgttaactgcacaga |
| 174 | ttctttatcagg**g**tgttaactgcacaga |
| 175 | tctttatcagg**a**tgttaactgcacaga |
| 176 | tctttatcagg**g**tgttaactgcacaga |
| 177 | ctttatcagg**a**tgttaactgcacaga |
| 178 | ctttatcagg**g**tgttaactgcacaga |
| 179 | tttatcagg**a**tgttaactgcacaga |
| 180 | tttatcagg**g**tgttaactgcacaga |
| 181 | ttatcagg**a**tgttaactgcacaga |
| 182 | ttatcagg**g**tgttaactgcacaga |
| 183 | tatcagg**a**tgttaactgcacaga |
| 184 | tatcagg**g**tgttaactgcacaga |
| 185 | atcagg**a**tgttaactgcacaga |
| 186 | atcagg**g**tgttaactgcacaga |
| 187 | tcagg**a**tgttaactgcacaga |
| 188 | tcagg**g**tgttaactgcacaga |
| 11 | tgcacagaagtccctgttgct |
| 189 | cagg**a**tgttaactgcacaga |
| 190 | cagg**g**tgttaactgcacaga |
| 191 | ctgttctttatcagg**a**tgttaactgcacag |
| 192 | ctgttctttatcagg**g**tgttaactgcacag |
| 193 | ctgttctttatcagg**a**tgttaactgcaca |

TABLE 9-continued

Illustrative SARS-CoV-2 Oligonucleotide Domains of Sense Strand Probes for Detecting the Presence of the SARS-CoV-2 S Gene

| SEQ ID NO | Sequence |
|---|---|
| 194 | ctgttctttatcagg**g**tgttaactgcaca |
| 195 | ctgttctttatcagg**a**tgttaactgcac |
| 196 | ctgttctttatcagg**g**tgttaactgcac |
| 197 | ctgttctttatcagg**a**tgttaactgca |
| 198 | ctgttctttatcagg**g**tgttaactgca |
| 199 | ctgttctttatcagg**a**tgttaactgc |
| 200 | ctgttctttatcagg**g**tgttaactgc |
| 201 | ctgttctttatcagg**a**tgttaactg |
| 202 | ctgttctttatcagg**g**tgttaactg |
| 203 | ctgttctttatcagg**a**tgttaact |
| 204 | ctgttctttatcagg**g**tgttaact |
| 205 | ctgttctttatcagg**a**tgttaac |
| 206 | ctgttctttatcagg**g**tgttaac |
| 207 | ctgttctttatcagg**a**tgttaa |
| 208 | ctgttctttatcagg**g**tgttaa |
| 209 | ctgttctttatcagg**a**tgtta |
| 210 | ctgttctttatcagg**g**tgtta |
| 211 | ctgttctttatcagg**a**tgtt |
| 212 | ctgttctttatcagg**g**tgtt |
| 213 | tgttctttatcagg**a**tgttaactgcacaga |
| 214 | tgttctttatcagg**g**tgttaactgcacaga |
| 11 | tgcacagaagtccctgttgct |
| 215 | tgttctttatcagg**a**tgttaactgcacag |
| 216 | tgttctttatcagg**g**tgttaactgcacag |
| 217 | gttctttatcagg**a**tgttaactgcacag |
| 218 | gttctttatcagg**g**tgttaactgcacag |
| 219 | gttctttatcagg**a**tgttaactgcaca |
| 220 | gttctttatcagg**g**tgttaactgcaca |
| 221 | ttctttatcagg**a**tgttaactgcaca |
| 222 | ttctttatcagg**g**tgttaactgcaca |
| 223 | ttctttatcagg**a**tgttaactgcac |
| 224 | ttctttatcagg**g**tgttaactgcac |
| 225 | tctttatcagg**a**tgttaactgcac |
| 226 | tctttatcagg**g**tgttaactgcac |
| 227 | tctttatcagg**a**tgttaactgca |
| 228 | tctttatcagg**g**tgttaactgca |
| 229 | ctttatcagg**a**tgttaactgca |
| 230 | ctttatcagg**g**tgttaactgca |
| 231 | ctttatcagg**a**tgttaactgc |
| 232 | ctttatcagg**g**tgttaactgc |
| 233 | tttatcagg**a**tgttaactgc |
| 234 | tttatcagg**g**tgttaactgc |
| 235 | tttatcagg**a**tgttaactg |
| 236 | tttatcagg**g**tgttaactg |
| 237 | ttatcagg**a**tgttaactg |
| 238 | ttatcagg**g**tgttaactg |
| 239 | tatcagg**a**tgttaactg |
| 240 | tatcagg**g**tgttaactg |
| 11 | tgcacagaagtccctgttgct |
| 241 | tatcagg**a**tgttaact |
| 242 | tatcagg**g**tgttaact |
| 243 | atcagg**a**tgttaact |
| 244 | atcagg**g**tgttaact |
| 245 | tcagg**a**tgttaact |
| 246 | tcagg**g**tgttaact |
| 247 | tcagg**a**tgttaac |
| 248 | tcagg**g**tgttaac |
| 249 | tcagg**a**tgttaa |
| 250 | tcagg**g**tgttaa |
| 251 | tcagg**a**tgtta |
| 252 | tcagg**g**tgtta |
| 253 | gcacagaagtccctgttgct |
| 254 | cacagaagtccctgttgct |
| 255 | acagaagtccctgttgct |
| 256 | cagaagtccctgttgct |
| 257 | cagaagtccctgttgctatt |
| 258 | agaagtccctgttgct |
| 259 | gaagtccctgttgct |
| 260 | tgcacagaagtccctgttgc |
| 261 | tgcacagaagtccctgttg |
| 262 | tgcacagaagtccctgtt |
| 263 | tgcacagaagtccctgt |

TABLE 9-continued

Illustrative SARS-CoV-2 Oligonucleotide Domains of Sense Strand Probes for Detecting the Presence of the SARS-CoV-2 S Gene

| SEQ ID NO | Sequence |
|---|---|
| 264 | tgcacagaagtccctg |
| 265 | tgcacagaagtccct |
| 266 | gcacagaagtccctgttgc |
| 11 | tgcacagaagtccctgttgct |
| 267 | cacagaagtccctgttgc |
| 268 | cacagaagtccctgttg |
| 269 | acagaagtccctgttgc |
| 270 | acagaagtccctgttg |
| 271 | cagaagtccctgttgc |
| 272 | cagaagtccctgttg |

TABLE 10

Illustrative SARS-CoV-2 Oligonucleotide Domains of Antisense-Strand Probes for Detecting the Presence of the SARS-CoV-2 S Gene

| SEQ ID NO | Sequence |
|---|---|
| 12 | agcaacagggacttctgtgca |
| 273 | tctgtgcagttaaca**t**cctgataaagaacag |
| 274 | tctgtgcagttaaca**t**cctgataaagaacag |
| 275 | tctgtgcagttaaca**c**cctgataaagaacag |
| 276 | ctgtgcagttaaca**t**cctgataaagaacag |
| 277 | ctgtgcagttaaca**c**cctgataaagaacag |
| 278 | tgtgcagttaaca**t**cctgataaagaacag |
| 279 | tgtgcagttaaca**c**cctgataaagaacag |
| 280 | gtgcagttaaca**t**cctgataaagaacag |
| 281 | gtgcagttaaca**c**cctgataaagaacag |
| 282 | tgcagttaaca**t**cctgataaagaacag |
| 283 | tgcagttaaca**c**cctgataaagaacag |
| 284 | gcagttaaca**t**cctgataaagaacag |
| 285 | gcagttaaca**c**cctgataaagaacag |
| 12 | agcaacagggacttctgtgca |
| 286 | cagttaaca**t**cctgataaagaacag |
| 287 | cagttaaca**c**cctgataaagaacag |
| 288 | agttaaca**t**cctgataaagaacag |
| 289 | agttaaca**c**cctgataaagaacag |
| 290 | gttaaca**t**cctgataaagaacag |

TABLE 10-continued

Illustrative SARS-CoV-2 Oligonucleotide Domains of Antisense-Strand Probes for Detecting the Presence of the SARS-CoV-2 S Gene

| SEQ ID NO | Sequence |
|---|---|
| 291 | gttaaca**c**cctgataaagaacag |
| 292 | ttaaca**t**cctgataaagaacag |
| 293 | ttaaca**c**cctgataaagaacag |
| 294 | taaca**t**cctgataaagaacag |
| 295 | taaca**c**cctgataaagaacag |
| 296 | aaca**t**cctgataaagaacag |
| 297 | aaca**c**cctgataaagaacag |
| 298 | tctgtgcagttaaca**t**cctgataaagaaca |
| 299 | tctgtgcagttaaca**c**cctgataaagaaca |
| 300 | tctgtgcagttaaca**t**cctgataaagaac |
| 301 | tctgtgcagttaaca**c**cctgataaagaac |
| 302 | tctgtgcagttaaca**t**cctgataaagaa |
| 303 | tctgtgcagttaaca**c**cctgataaagaa |
| 304 | tctgtgcagttaaca**t**cctgataaaga |
| 305 | tctgtgcagttaaca**c**cctgataaaga |
| 306 | tctgtgcagttaaca**t**cctgataaag |
| 307 | tctgtgcagttaaca**c**cctgataaag |
| 308 | tctgtgcagttaaca**t**cctgataaa |
| 309 | tctgtgcagttaaca**c**cctgataaa |
| 310 | tctgtgcagttaaca**t**cctgataa |
| 311 | tctgtgcagttaaca**c**cctgataa |
| 312 | tctgtgcagttaaca**t**cctgata |
| 12 | agcaacagggacttctgtgca |
| 313 | tctgtgcagttaaca**c**cctgata |
| 314 | tctgtgcagttaaca**t**cctgat |
| 315 | tctgtgcagttaaca**c**cctgat |
| 316 | tctgtgcagttaaca**t**cctga |
| 317 | tctgtgcagttaaca**c**cctga |
| 318 | tctgtgcagttaaca**t**cctg |
| 319 | tctgtgcagttaaca**c**cctg |
| 320 | ctgtgcagttaaca**t**cctgataaagaacag |
| 321 | ctgtgcagttaaca**c**cctgataaagaacag |
| 322 | ctgtgcagttaaca**t**cctgataaagaaca |
| 323 | ctgtgcagttaaca**c**cctgataaagaaca |
| 324 | tgtgcagttaaca**t**cctgataaagaaca |
| 325 | tgtgcagttaaca**c**cctgataaagaaca |
| 326 | tgtgcagttaaca**t**cctgataaagaac |

TABLE 10-continued

Illustrative SARS-CoV-2 Oligonucleotide Domains of Antisense-Strand Probes for Detecting the Presence of the SARS-CoV-2 S Gene

| SEQ ID NO | Sequence |
|---|---|
| 327 | tgtgcagttaaca**c**cctgataaagaac |
| 328 | gtgcagttaaca**t**cctgataaagaac |
| 329 | gtgcagttaaca**c**cctgataaagaac |
| 330 | gtgcagttaaca**t**cctgataaagaa |
| 331 | gtgcagttaaca**c**cctgataaagaa |
| 332 | tgcagttaaca**t**cctgataaagaa |
| 333 | tgcagttaaca**c**cctgataaagaa |
| 334 | tgcagttaaca**t**cctgataaaga |
| 335 | tgcagttaaca**c**cctgataaaga |
| 336 | gcagttaaca**t**cctgataaaga |
| 337 | gcagttaaca**c**cctgataaaga |
| 338 | cagttaaca**t**cctgataaaga |
| 339 | cagttaaca**c**cctgataaaga |
| 12 | agcaacagggacttctgtgca |
| 340 | agttaaca**t**cctgataaaga |
| 341 | agttaaca**c**cctgataaaga |
| 342 | agttaaca**t**cctgataaag |
| 343 | agttaaca**c**cctgataaag |
| 344 | gttaaca**t**cctgataaag |
| 345 | gttaaca**c**cctgataaag |
| 346 | gttaaca**t**cctgataaa |
| 347 | gttaaca**c**cctgataaa |
| 348 | ttaaca**t**cctgataaa |
| 349 | ttaaca**c**cctgataaa |
| 350 | ttaaca**t**cctgataa |
| 351 | ttaaca**c**cctgataa |
| 352 | taaca**t**cctgataa |
| 353 | taaca**c**cctgataa |
| 354 | taaca**t**cctgata |
| 355 | taaca**c**cctgata |
| 356 | taaca**t**cctgat |
| 357 | taaca**c**cctgat |
| 358 | taaca**t**cctg |
| 359 | taaca**c**cctg |
| 360 | aaca**t**cctgat |
| 361 | aaca**c**cctgat |
| 362 | aaca**t**cctga |
| 363 | aaca**c**cctga |
| 364 | gcaacagggacttctgtgca |
| 365 | caacagggacttctgtgca |
| 366 | aacagggacttctgtgca |
| 12 | agcaacagggacttctgtgca |
| 367 | acagggacttctgtgca |
| 368 | cagggacttctgtgca |
| 369 | agggacttctgtgca |
| 370 | agcaacagggacttctgtgc |
| 371 | agcaacagggacttctgtg |
| 372 | agcaacagggacttctgt |
| 373 | agcaacagggacttctg |
| 374 | agcaacagggacttct |
| 375 | agcaacagggacttc |
| 376 | gcaacagggacttctgtgca |
| 377 | gcaacagggacttctgtgc |
| 378 | caacagggacttctgtgc |
| 379 | caacagggacttctgtg |
| 380 | aacagggacttctgtg |
| 381 | aacagggacttctgt |

2. Preferred Types of Probes

(a) TaqMan Probes

In a preferred embodiment, TaqMan probes are employed to detect amplified SARS-CoV-2 oligonucleotides in accordance with the present invention. As described above, such probes are labeled on their 5' termini with a fluorophore, and are complexed on their 3' termini with a quencher of the fluorescence of that fluorophore. In order to simultaneously detect the amplification of two polynucleotide domains of SARS-CoV-2, two TaqMan probes are employed that have different fluorophores (with differing and distinguishable emission wavelengths); the employed quenchers may be the same or different. The chemistry and design of "TaMan" probes is reviewed by Holland, P. M. et al. (1991) ("*Detection Of Specific Polymerase Chain Reaction Product By Utilizing The 5'-3' Exonuclease Activity Of Thermus Aquaticus DNA Polymerase*," Proc. Natl. Acad. Sci. (U.S.A.) 88(16):7276-7280), by Navarro, E. et al. (2015) ("*Real-Time PCR Detection Chemistry*," Clin. Chim. Acta 439:231-250), and by Gasparic, B. M. et al. (2010) ("*Comparison Of Nine Different Real-Time PCR Chemistries For Qualitative And Quantitative Applications In GMO Detection*," Anal. Bioanal. Chem. 396(6):2023-2029).

Suitable fluorophores and quenchers are as described above. In one embodiment of the invention, the 5' terminus of the ORF1ab Probe is labeled with the fluorophore JOE, and the 3' terminus of such probe is complexed to the quencher BHQ1 and the 5' terminus of the S Gene Probe is labeled with the fluorophore FAM, and the 3' terminus of such probe is complexed to the quencher BHQ1. In an alternative embodiment, the 5' terminus of the ORF1ab Probe is labeled with the fluorophore FAM, and the 5' terminus of the S Gene Probe is labeled with the fluorophore JOE. The use of such two fluorophores permits both probes to be used in the same assay.

Any of the SARS-CoV-2 oligonucleotide domains of the above-described ORF1ab probes may be employed to form TaqMan probes suitable for detecting the region of ORF1ab that is amplified by the above-described preferred ORF1ab Primers (e.g., SEQ ID NO:1, SEQ ID NO:2, any of SEQ ID NOs:17-28, any of SEQ ID NOs:29-42, any of SEQ ID NOs:398-399, any of SEQ ID NOs:403-406, and their respective variants).

Illustrative TaqMan ORF1ab probes may thus comprise any of the SARS-CoV-2 oligonucleotide domains of the above-described ORF1ab probes (e.g., SEQ ID NO:9, SEQ ID NO:10, any of SEQ ID NOs:127-146, or any of SEQ ID NOs:147-166, etc.)). As discussed above, the 5' terminus of the TaqMan ORF1ab probe is labeled with a fluorophore, and the 3' terminus of the probe is complexed to a quencher.

Similarly, any of the SARS-CoV-2 oligonucleotide domains of the above-described S gene probes may be employed to form TaqMan probes suitable for detecting the region of the S gene that is amplified by the above-described preferred S Gene Primers (e.g., SEQ ID NO:5, SEQ ID NO:6, any of SEQ ID NOs:43-70, any of SEQ ID NOs:71-84, any of SEQ ID NOs:85-112, any of SEQ ID NOs:113-126, or any of SEQ ID NOs:400-402, or any of SEQ ID NOs:407-410, and their respective variants).

Illustrative TaqMan S Gene probes may comprise any of the SARS-CoV-2 oligonucleotide domains of the above-described S gene probes (e.g., SEQ ID NO:11, SEQ ID NO:12, any of SEQ ID NOs:167-252, any of SEQ ID NOs:253-272, any of SEQ ID NOs:273-363, or any of SEQ ID NOs:364-381, etc.)). As discussed above, the 5' terminus of the TaqMan S Gene probe is labeled with a fluorophore, and the 3' terminus of the probe is complexed to a quencher.

(b) Molecular Beacon Probes

Molecular beacon probes can alternatively be employed to detect amplified SARS-CoV-2 oligonucleotides in accordance with the present invention. Molecular beacon probes are also labeled with a fluorophore and complexed to a quencher. However, in such probes, the quenching of the fluorescence of the fluorophore only occurs when the quencher is directly adjacent to the fluorophore. Molecular beacon probes are thus designed to adopt a hairpin structure while free in solution (thus bringing the fluorescent dye and quencher into close proximity with one another). When a molecular beacon probe hybridizes to a target, the fluorophore is separated from the quencher, and the fluorescence of the fluorophore becomes detectable. Unlike TaqMan probes, molecular beacon probes are designed to remain intact during the amplification reaction, and must re-anneal to the target nucleic acid molecule in every cycle for signal measurement. The chemistry and design of molecular beacon probes is reviewed by Han, S. X. et al. (2013) ("*Molecular Beacons: A Novel Optical Diagnostic Tool*," Arch. Immunol. Ther. Exp. (Warsz). 61(2):139-148), by Navarro, E. et al. (2015) ("*Real-Time PCR Detection Chemistry*," Clin. Chim. Acta 439:231-250), by Goel, G. et al. (2005) ("*Molecular Beacon: A Multitask Probe*," J. Appl. Microbiol. 99(3):435-442), by Kitamura, Y. et al. (2020) ("*Electrochemical Molecular Beacon for Nucleic Acid Sensing in a Homogeneous Solution*," Analyt. Sci. 36:959-964), and by Zheng, J. et al. (2015) ("*Rationally Designed Molecular Beacons For Bioanalytical And Biomedical Applications*," Chem. Soc. Rev. 44(10):3036-3055). The use of molecular beacon probes to detect polymorphisms is reviewed by Peng, Q. et al. (2020) ("*A Molecular-Beacon-Based Asymmetric PCR Assay For Detecting Polymorphisms Related To Folate Metabolism*," J. Clin. Lab. Anal. 34:e23337:1-7).

Additional nucleotides and/or linkers (e.g., oligo ethylene glycol linkers) may be interposed between the stem oligonucleotides and the loop oligonucleotide of the hairpin structure in order to provide improve the detection of single nucleotide polymorphisms (Farzan, V. M. et al. (2017) "*Specificity Of SNP Detection With Molecular Beacons Is Improved By Stem And Loop Separation With Spacers,*" *Analyst* 142:945-950). "Dumbbell" molecular beacon probes may be used to detect single nucleotide polymorphisms using a single label (Bengston, H. N. et al. (2014) "*A Differential Fluorescent Receptor for Nucleic Acid Analysis*," Chembiochem. 15(2):228-231).

The design of molecular beacon probes can be assisted using software, such as Beacon Designer (Premier Biosoft) (Thorton, B. et al. (2011) "*Real-Time PCR (qPCR) Primer Design Using Free Online Software*," Biochem. Molec. Biol. Educat. 39(2):145-154). However, common considerations are typically sufficient for acceptable results (Kolpashchikov, D. M. (2012) "*An Elegant Biosensor Molecular Beacon Probe: Challenges And Recent Solutions*," Scientifica (Cairo). 2012:928783:1-17). Overall, to favor the formation of the probe-target complex, the melting temperature of the loop domain should be higher than that of the stem. The loop is typically 15-20 nucleotides long and fully complementary to the analyte. The stem should be C/G rich and contain 4-7 base pairs to ensure high stability and acceptable hybridization rates. Longer and more stable stems will reduce hybridization rates but may improve assay selectivity (Tsourkas, A. et al. (2003) "*Hybridization Kinetics And Thermodynamics Of Molecular Beacons*," Nucleic Acids Research 31(4):1319-1330). The melting temperature of the stem should be at least 7° C. higher than the assay temperature to ensure efficient fluorescent quenching in the free MB probe. If the assay is SNP specific, the interrogated position should be complementary to a nucleotide close to the middle position of the loop sequence for better allele differentiation (Kolpashchikov, D. M. (2012) "*An Elegant Biosensor Molecular Beacon Probe: Challenges And Recent Solutions*," Scientifica (Cairo). 2012:928783:1-17; Finetti-Sialer, M M. et al. (2005) "*Isolate-Specific Detection of Grapevine fanleaf virus from Xiphinema index Through DNA-Based Molecular Probes*," Phytopathology 95(3):262-268).

Such probes thus comprise two small (e.g., 5-7 nucleotide long) complementary oligonucleotides positioned so as to flank the SARS-CoV-2 oligonucleotide and cause the probe to adopt a stem and loop-containing hairpin structure that positions a quencher adjacent to a fluorophore unless the probe's secondary structure is disrupted by hybridization to an oligonucleotide sequence that is complementary to the probe's loop sequence. The 5' terminal potion of the complementary oligonucleotide that is positioned 5' to the SARS-CoV-2 oligonucleotide is preferably labeled with a fluorophore, and the 3' terminal domain of the complementary oligonucleotide that is positioned 3' to the SARS-CoV-2 oligonucleotide is preferably complexed to a quencher of such fluorophore. Although it is preferred that such fluorophore be complexed to the 5' terminal residue of the complementary oligonucleotide that is positioned 5' to the SARS-CoV-2 oligonucleotide, it may be complexed within 5 nucleotides, within 4 nucleotides, within 3 nucleotides, or within 2 nucleotides of such 5' terminal residue. Similarly, although it is preferred that such quencher be complexed to the 3' terminal residue of the complementary oligonucleotide that is positioned 3' to the SARS-CoV-2 oligonucleotide, it may be complexed within 5 nucleotides, within 4 nucleotides, within 3 nucleotides, or within 2 nucleotides of such 3' terminal residue.

Examples of complementary oligonucleotides that may be added to the 3' or 5' termini of a SARS-CoV-2 oligonucleotide to form a molecular beacon probe include cggcgcc (SEQ ID NO:382) and its complement gcgccgg (SEQ ID NO:383); cggcgc (SEQ ID NO:384) and its complement gcgccg (SEQ ID NO:385); ccccccc (SEQ ID NO:386) and its complement ggggggg (SEQ ID NO:387); cccccc (SEQ ID NO:388) and its complement gggggg (SEQ ID NO:389); ccccc (SEQ ID NO:390) and its complement ggggg (SEQ ID NO:391); cgacc (SEQ ID NO:392) and its complement ggtcg (SEQ ID NO:393); ggcgc (SEQ ID NO:394) and its complement gcgcc (SEQ ID NO:395); gcgag (SEQ ID NO:396) and its complement ctcgc (SEQ ID NO:397).

Any of the SARS-CoV-2 oligonucleotide domains of the above-described ORF1ab probes may be employed as the loop domain of a molecular beacon probe suitable for detecting the region of ORF1ab that is amplified by the above-described preferred ORF1ab Primers (e.g., SEQ ID NO:1, SEQ ID NO:2, any of SEQ ID NOs:17-28, any of SEQ ID NOs:29-42, any of SEQ ID NOs:398-399, any of SEQ ID NOs:403-406, and their respective variants). Additional molecular beacon probes for the SARS-CoV-2 ORF1ab having shorter or longer loop regions can be readily constructed, for example by reducing or increasing the size of employed SARS-CoV-2 ORF1ab loop oligonucleotide, as desired.

Illustrative ORF1ab molecular beacon probes may comprise, from 5' to 3', a 5' stem oligonucleotide (e.g., any of SEQ ID NOs:382-397, etc.), an ORF1ab oligonucleotide (e.g., any of the SARS-CoV-2 oligonucleotide domains of the above-described ORF1ab probes (e.g., SEQ ID NO:9, SEQ ID NO:10, any of SEQ ID NOs:127-146, or any of SEQ ID NOs:147-166, etc.)), which forms the loop domain of the molecular beacon probe, and a 3' stem oligonucleotide whose sequence is complementary to that of the probe's 5' stem oligonucleotide. As discussed above, the 5' terminus of the ORF1ab molecular beacon probe is labeled with a fluorophore, and the 3' terminus of the ORF1ab molecular beacon probe is complexed to a quencher. Additional molecular beacon probes for the SARS-CoV-2 ORF1ab having shorter or longer loop regions can be readily constructed, for example by reducing or increasing the size of employed SARS-CoV-2 ORF1ab loop oligonucleotide, as desired.

Similarly, any of the SARS-CoV-2 oligonucleotide domains of the above-described S gene probes may be employed as the loop domain of a molecular beacon probe suitable for detecting the region of the S gene that is amplified by the above-described preferred S Gene Primers (e.g., SEQ ID NO:5, SEQ ID NO:6, any of SEQ ID NOs:43-70, any of SEQ ID NOs:71-84, any of SEQ ID NOs:85-112, any of SEQ ID NOs:113-126, or any of SEQ ID NOs:400-402, or any of SEQ ID NOs:407-410, and their respective variants). Additional molecular beacon probes for the SARS-CoV-2 ORF1ab having shorter or longer loop regions can be readily constructed, for example by reducing or increasing the size of employed SARS-CoV-2 ORF1ab loop oligonucleotide, as desired.

Illustrative S Gene molecular beacon probes may comprise, from 5' to 3', a 5' stem oligonucleotide (e.g., any of SEQ ID NOs:382-397, etc.), an S Gene oligonucleotide (e.g., any of the SARS-CoV-2 oligonucleotide domains of the above-described S gene probes (e.g., SEQ ID NO:11, SEQ ID NO:12, any of SEQ ID NOs:167-252, any of SEQ ID NOs:253-272, any of SEQ ID NOs:273-363, or any of SEQ ID NOs:364-381, etc.)) which forms the loop domain of the molecular beacon probe, and a 3' stem oligonucleotide whose sequence is complementary to that of the probe's 5' stem oligonucleotide. As discussed above, the 5' terminus of the S Gene molecular beacon probe is labeled with a fluorophore, and the 3' terminus of the ORF1ab molecular beacon probe is complexed to a quencher. Additional molecular beacon probes for the SARS-CoV-2 S gene having shorter or longer loop regions can be readily constructed, for example by reducing or increasing the size of employed SARS-CoV-2 S gene loop oligonucleotide, as desired. Suitable fluorophores and quenchers are as described above.

(c) Scorpion Primer-Probes

Scorpion primer-probes (Whitcombe, D. et al. (1999) "*Detection Of PCR Products Using Self-Probing Amplicons And Fluorescence*," Nat. Biotechnol. 17(8):804-807; Thelwell, N. et al. (2000) "*Mode Of Action And Application Of Scorpion Primers To Mutation Detection*," Nucleic Acids Res. 28(19):3752-3761; Finetti-Sialer, M. M. et al. (2005) "*Isolate-Specific Detection of Grapevine fanleaf virus from Xiphinema index Through DNA-Based Molecular Probes*," Phytopathology 95(3):262-268; Solinas, A. et al. (2001) "*Duplex Scorpion Primers In SNP Analysis And FRET Applications*," Nucl. Acids Res. 29(20):E96:1-9) can alternatively be employed to detect amplified SARS-CoV-2 oligonucleotides in accordance with the present invention. Scorpion primer-probes comprise 3' and 5' complementary oligonucleotides that are separated by an intervening loop oligonucleotide so as to adopt a stem and loop hairpin structure while free in solution. The 5' terminus of the 5' stem oligonucleotide is labeled with a fluorophore. The 3' terminus of the 3' stem oligonucleotide is complexed to a quencher, so that upon formation of a hairpin structure with the 5' stem oligonucleotide, fluorescence is quenched. Scorpion primer-probes differ from molecular beacon probes in that the 3' terminus of the 3' stem oligonucleotide is additionally complexed to a blocker of polymerase-mediated primer extension (e.g., a hexaethylene glycol (HEG) blocker (Ma, M. Y. X. et al. (1993) "*Design And Synthesis Of RNA Miniduplexes Via A Synthetic Linker Approach*," Biochemistry 32(7):1751-1758; Ma, M. Y. X. et al. (1993) "*Design And Synthesis Of RNA Miniduplexes Via A Synthetic Linker Approach. 2. Generation Of Covalently Closed, Double-Stranded Cyclic HIV-1 TAR RNA Analogs With High Tat-Binding Affinity*," Nucleic Acids Res. 21(11):2585-2589)), and additionally comprises a 3' PCR primer oligonucleotide that is complementary to a sequence of a target oligonucleotide. Thus, scorpion primer-probes have the overall structure (5' to 3'): [fluorophore]-[5' stem oligonucleotide]-[loop oligonucleotide]-[complementary 3' stem oligonucleotide]-[quencher]-[blocker]-PCR primer oligonucleotide.

Upon hybridizing to a target oligonucleotide, the 3' terminus of the PCR primer oligonucleotide is extended;

however, the presence of the blocker prevents the polymerase-mediated extension of the 3' terminus of the target hybridized target oligonucleotide. The sequences of the PCR primer oligonucleotide and the loop oligonucleotide are selected such that the sequence of the loop oligonucleotide is the same as a sequence of the target molecule approximately 11 bases or less downstream from the base of the target molecule that is hybridized to the 3' terminus of the PCR primer oligonucleotide. Thus, extension of the PCR primer forms a oligonucleotide domain of the scorpion primer-probe that is complementary to the sequence of the loop oligonucleotide. In the next denaturation step of the PCR process, the loop sequence of the scorpion primer-probe hybridizes to the extended PCR product, thus opening the probe's hairpin structure. This separates the scorpion primer-probe's fluorophore from its quencher and permits fluorescence to be detected.

Any of the SARS-CoV-2 oligonucleotide domains of the above-described ORF1ab probes may be employed as the loop domain of a scorpion primer-probe suitable for detecting the region of ORF1ab that is amplified by the above-described preferred ORF1ab Primers (e.g., SEQ ID NO:1, SEQ ID NO:2, any of SEQ ID NOs:17-28, any of SEQ ID NOs:29-42, any of SEQ ID NOs:398-399, any of SEQ ID NOs:403-406, and their respective variants). As discussed above, such probes are similar to molecular beacon probes, but comprise a blocker moiety, typically positioned 3' to the probe's quencher moiety, and a 3' PCR primer oligonucleotide.

Illustrative ORF1ab scorpion primer-probes would comprise, from 5' to 3', a 5' stem oligonucleotide (e.g., any of SEQ ID NOs:382-398, etc.), an ORF1ab oligonucleotide (e.g., any of the SARS-CoV-2 oligonucleotide domains of the above-described ORF1ab probes (e.g., SEQ ID NO:9, SEQ ID NO:10, any of SEQ ID NOs:127-146, or any of SEQ ID NOs:147-166, etc.), a 3' stem oligonucleotide whose sequence is complementary to that of the probe's 5' stem oligonucleotide, and a PCR primer oligonucleotide domain whose sequence is selected so that it is capable of hybridizing to a region of ORF1ab that is approximately 7 bases, 8 bases, 9 bases, 10 bases, or more preferably 11 bases upstream of an ORF1ab sequence that is the same as the sequence of the probe's ORF1ab oligonucleotide domain (or differs from such sequence by 5, 4, 3, 2 or 1 nucleotide residues), such that extension of the PCR primer oligonucleotide domain forms an extension product whose sequence is complementary to the probe's ORF1ab oligonucleotide domain.

To illustrate the structure of such ORF1ab scorpion primer-probes, the nucleotide sequences of an ORF1ab scorpion primer-probe whose loop polypeptide domain has the sequence of the preferred ORF1ab Probe tgcccgtaatggtgttcttattacaga (SEQ ID NO:9) could have the sequence, from 5' to 3', of a 5' stem oligonucleotide (e.g., any of SEQ ID NOs:382-397, etc.), the preferred ORF1ab Probe (SEQ ID NO:9), a 3' stem oligonucleotide whose sequence is complementary to that of the probe's 5' stem oligonucleotide, and a PCR primer oligonucleotide having the sequence gagttgatggtcaagtagac (SEQ ID NO:398, corresponding to residues 12-26 of SEQ ID NO:3). After extension of the primer by 38 bases, the primer extension product contains a domain complementary to the sequence of the preferred ORF1ab Probe. Denaturation occurring in a subsequent step of the PCR process denatures the hybridized, complementary stem oligonucleotides, thereby permitting such oligonucleotides to separate from one another. Such separation attenuates the quenching of the fluorophore and thereby causes the fluorescent signal to become detectable. During the subsequent annealing stage of the PCR process, hybridization occurs between the loop domain of the probe and the complementary primer extension product of the probe. Such hybridization prevents the complementary stem oligonucleotides of the scorpion probe from re-hybridizing to one another, and thus causes the detectable fluorescent signal to be maintained.

Similarly, an ORF1ab scorpion primer-probe whose loop polypeptide domain has the sequence ttcttattacagaaggtagt (SEQ ID NO:141, corresponding to residues 52-73 of SEQ ID NO:3) could have the sequence, from 5' to 3', of a 5' stem oligonucleotide (e.g., any of SEQ ID NOs:382-397, etc.), the ORF1ab oligonucleotide (SEQ ID NO:141), a 3' stem oligonucleotide whose sequence is complementary to that of the probe's 5' stem oligonucleotide, and a PCR primer oligonucleotide having the sequence gtagacttatttagaaatgc (SEQ ID NO:399, corresponding to residues 21-40 of SEQ ID NO:3).

Similarly, illustrative S Gene Scorpion Primer-Probes would comprise, from 5' to 3', a 5' stem oligonucleotide (e.g., any of SEQ ID NOs:382-397, etc.), an S Gene oligonucleotide (e.g., any of the SARS-CoV-2 oligonucleotide domains of the above-described ORF1ab probes (e.g., SEQ ID NO:11, SEQ ID NO:12, any of SEQ ID NOs:167-252, any of SEQ ID NOs:253-272, any of SEQ ID NOs:273-363, or any of SEQ ID NOs:364-381, etc.)), a 3' stem oligonucleotide whose sequence is complementary to that of the probe's 5' stem oligonucleotide, and a PCR primer oligonucleotide domain whose sequence is selected so that it is capable of hybridizing to a region of the S gene that is approximately 7 bases, 8 bases, 9 bases, 10 bases, or more preferably 11 bases upstream of an S gene sequence that is the same as the sequence of the probe's S gene oligonucleotide domain (or differs from such sequence by 5, 4, 3, 2 or 1 nucleotide residues), such that extension of the PCR primer oligonucleotide domain forms an extension product whose sequence is complementary to the probe's S gene oligonucleotide domain.

To illustrate the structure of such S gene scorpion primer-probes, the nucleotide sequences of an S gene scorpion primer-probe whose loop polypeptide domain has the sequence of the preferred S gene probe tgcacagaagtccctgttgct (SEQ ID NO:11) could have the sequence, from 5' to 3', of a 5' stem oligonucleotide (e.g., any of SEQ ID NOs:382-397, etc.), the preferred S gene probe (SEQ ID NO:11), a 3' stem oligonucleotide whose sequence is complementary to that of the probe's 5' stem oligonucleotide, and a PCR primer oligonucleotide having the sequence ccaggttgctgttctttatc (SEQ ID NO:400, corresponding to residues 5-24 of SEQ ID NO:7). After extension of the primer by 32 bases, the primer extension product contains a domain complementary to the sequence of the preferred S gene probe. Denaturation occurring in a subsequent step of the PCR process denatures the hybridized, complementary stem oligonucleotides, thereby permitting such oligonucleotides to separate from one another. Such separation attenuates the quenching of the fluorophore and thereby causes the fluorescent signal to become detectable. During the subsequent annealing stage of the PCR process, hybridization occurs between the loop domain of the probe and the complementary primer extension product of the probe. Such hybridization prevents the complementary stem oligonucleotides of the scorpion probe from re-hybridizing to one another, and thus causes the detectable fluorescent signal to be maintained.

Similarly, an S gene scorpion primer-probe whose loop polypeptide domain has the sequence cagaagtccctgttgctatt (SEQ ID NO:257, corresponding to residues 40-59 of SEQ ID NO:7) could have the sequence, from 5' to 3', of a 5' stem oligonucleotide (e.g., any of SEQ ID NOs:382-297, etc.), the S gene oligonucleotide (SEQ ID NO:257), a 3' stem oligonucleotide whose sequence is complementary to that of the probe's 5' stem oligonucleotide, and a PCR primer oligonucleotide having either the sequence gttgctgttctttatcagga (SEQ ID NO:401, corresponding to residues 9-28 of SEQ ID NO:7) or the sequence gttgctgttctttatcaggg (SEQ ID NO:402). The nucleotide residue that is responsible for the D614G single nucleotide polymorphism of the SARS-CoV-2 S gene is underlined. The use of S gene scorpion primer-probes having such PCR primer oligonucleotides would distinguish SARS-CoV-2 genomes having the single nucleotide polymorphism responsible for the D614G variation from SARS-CoV-2 S genomes lacking such polymorphism.

As discussed above, the 5' terminus of the 5' stem oligonucleotide of such scorpion primer-probes is labeled with a fluorophore, and the 3' terminus of the 3' stem oligonucleotide of such scorpion primer-probes is complexed to a quencher, which is separated from the 5' terminus of the probe's PCR primer oligonucleotide by a blocker moiety. Suitable fluorophores and quenchers are as described above.

(d) HyBeacon™ Probes

As discussed above, the invention additionally contemplates rRT-PCR assays in which detection is mediated through the use of HyBeacon™ probes (LGC Limited). HyBeacon™ probes comprise oligonucleotides that lack significant secondary structure and possess a fluorophore moiety attached to an internal nucleotide, and are typically modified at their 3' terminus to prevent polymerase-mediated extension (U.S. Pat. Nos. 7,348,141 and 7,998,673; French, D. J. et al. (2001) "*HyBeacon Probes: A New Tool For DNA Sequence Detection And Allele Discrimination*," Mol. Cell. Probes 15(6):363-374; French, D. J. et al. (2006) "*HyBeacons: A Novel DNA Probe Chemistry For Rapid Genetic Analysis*," Intl. Cong. Series 1288:707-709; French, D. J. et al. (2008) "*HyBeacon Probes For Rapid DNA Sequence Detection And Allele Discrimination*," Methods Mol Biol. 429:171-85). Such probes do not rely on probe secondary structures, enzymatic digestion or interaction with additional oligonucleotides for target detection and sequence discrimination, but instead emit greater amounts of fluorescence when hybridized to complementary target oligonucleotides than when present in a non-hybridized single-stranded conformation. This shift in the quantity of fluorescence emission occurs as a direct result of target hybridization and, therefore, permits the detection and discrimination of DNA sequences by real-time PCR and melting curve analysis methodologies. Sequences differing by as little as a single nucleotide may be distinguished by measuring and exploiting the variation in $T_m$ that occurs between different probe/target duplexes. HyBeacon™ Probes do not rely on probe secondary structures, enzymatic digestion or interaction with additional oligonucleotides for target detection and sequence discrimination. Typically, the HyBeacon™ probes of the present invention comprise 20 nucleotides or more in length. Suitable fluorophores and quenchers are as described above. Exemplary fluorophores that may be employed as the fluorophore of such probes include FAM, HEX, and TET.

Any of the SARS-CoV-2 oligonucleotide domains of the above-described ORF1ab probes (e.g., SEQ ID NO:9, SEQ ID NO:10, any of SEQ ID NOs:127-146, or any of SEQ ID NOs:147-166, etc.) may be employed to form a HyBeacon™ probe suitable for detecting the region of ORF1ab that is amplified by the above-described preferred ORF1ab Primers (e.g., SEQ ID NO:1, SEQ ID NO:2, any of SEQ ID NOs:17-28, any of SEQ ID NOs:29-42, any of SEQ ID NOs:398-399, any of SEQ ID NOs:403-406, and their respective variants). Additional HyBeacon™ probes for the SARS-CoV-2 ORF1ab having shorter or longer ORF1ab regions can be readily constructed, for example by reducing or increasing the size of employed SARS-CoV-2 ORF1ab oligonucleotide, as desired.

Illustrative ORF1ab HyBeacon™ probes thus comprise, from 5' to 3', an oligonucleotide capable of hybridizing to a domain of the SARS-CoV-2 ORF1ab (e.g., any of the SARS-CoV-2 oligonucleotide domains of the above-described ORF1ab probes (e.g., SEQ ID NO:9, SEQ ID NO:10, any of SEQ ID NOs:127-146, or any of SEQ ID NOs:147-166, etc.). As discussed above, an internal residue of the ORF1ab HyBeacon™ probe is labeled, preferably with a fluorophore, and the 3' terminus of the probe is preferably modified terminus to prevent its polymerase-mediated extension when annealed to a complementary target molecule.

Similarly, any of the SARS-CoV-2 oligonucleotide domains of the above-described S Gene probes (e.g., SEQ ID NO:11, SEQ ID NO:12, any of SEQ ID NOs:167-252, any of SEQ ID NOs:253-272, any of SEQ ID NOs:273-363, or any of SEQ ID NOs:364-381, etc.) may be employed to form a HyBeacon™ probe suitable for detecting the region of the S gene that is amplified by the above-described preferred S Gene Primers (e.g., SEQ ID NO:5, SEQ ID NO:6, any of SEQ ID NOs:43-70, any of SEQ ID NOs:71-84, any of SEQ ID NOs:85-112, any of SEQ ID NOs:113-126, or any of SEQ ID NOs:400-402, or any of SEQ ID NOs:407-410, and their respective variants). Additional HyBeacon™ probes for the SARS-CoV-2 S Gene having shorter or longer S Gene regions can be readily constructed, for example by reducing or increasing the size of employed SARS-CoV-2 S Gene oligonucleotide, as desired.

Illustrative S Gene HyBeacon™ probes thus comprise, from 5' to 3', an oligonucleotide capable of hybridizing to a domain of the SARS-CoV-2 S Gene (e.g., any of the SARS-CoV-2 oligonucleotide domains of the above-described S gene probes (e.g., SEQ ID NO:11, SEQ ID NO:12, any of SEQ ID NOs:167-252, any of SEQ ID NOs:253-272, any of SEQ ID NOs:273-363, or any of SEQ ID NOs:364-381, etc.). As discussed above, an internal residue of the S Gene HyBeacon™ probe is labeled with a fluorophore, and the 3' terminus of the probe is preferably modified terminus to prevent its polymerase-mediated extension when annealed to a complementary target molecule. HyBeacon™ probes are particularly suitable for detecting single nucleotide polymorphisms (SNPs) in the S gene of SARS-CoV-2 viruses of a clinical sample (such as SNPs that cause the D614G, V515F, V622I, or P631S S gene polymorphisms). Particularly preferred are HyBeacon™ probes that are capable of detecting the A1841G single nucleotide polymorphism that causes the S gene D614G polymorphism. Examples of such probes include oligonucleotides that have the sequence of: any of SEQ ID NOs:43-70, any of SEQ ID NOs:85-112, any of SEQ ID NOs:167-252, or any of SEQ ID NOs:273-363, etc.

3. Distinctive Attributes of the Preferred rRT-PCR Primers and Probes of the Present Invention The assays of the present invention possess particular distinctive attributes that distinguish such assays from the assays of the prior art. One characteristic of the present invention relates to the use of at least two SARS-CoV-2 target regions as a basis for detection in an rRT-PCR assay. Thus, the rRT-PCR assays of the present invention preferably employ at least two sets of Forward and Reverse primers so as to be capable of specifically and simultaneously amplifying two oligonucleotide regions of SARS-CoV-2 RNA. In preferred embodiments, the primers of one of such two sets of primers have sequences that are capable of specifically amplifying a region of ORF1ab, and the primers of the second of such two sets of primers have sequences that are capable of specifically amplifying a region of the S gene.

The use of two amplification targets increases the accuracy of the assays of the present invention since they help ensure that such assays will continue to detect SARS-CoV-2 even if one target becomes eliminated from clinical isolates (for example by spontaneous mutation). The use of two amplification targets also increases the sensitivity of the assay because it is possible that the amplification of a particular target might not provide a detectable concentration of amplified product, for example due to processing or handling issues. By having two targets, the assays of the present invention are more likely to avoid such "false negative" results.

The selection of ORF1ab and the S genes as targets is a further characteristic of the assays of the present invention. These genes are particularly characteristic of SARS-CoV-2, and indeed the targeted region of the SARS-CoV-2 S gene (i.e., its S1 domain) exhibits relatively low homology (only 68%) to the S genes of other coronaviruses (by comparison the ORF1a of SARS-CoV-2 exhibits about 90% homology to the ORF1a of SARS-CoV; the ORF1b of SARS-CoV-2 exhibits about 86% homology to the ORF1b of SARS-CoV (Lu, R. et al. (2020) "*Genomic Characterisation And Epidemiology Of* 2019 *Novel Coronavirus: Implications For Virus Origins And Receptor Binding*," The Lancet 395 (10224):565-574). Thus, it is more likely that the assays of the present invention will not inaccurately amplify sequences of non-SARS-CoV-2 pathogens. Thus, the assays of the present invention are more likely to avoid "false positive" results.

The assays of the present invention employ probes that are unique to SARS-CoV-2 and detect SARS-CoV-2 under conditions in which non-SARS-CoV-2 pathogens are not detected. In a further attribute, the assays of the present invention employ very fast system primers that are designed to mediate the same degree of amplification under the same reaction parameters and temperatures.

The melting temperatures ($T_m$) of PCR primers determine their kinetics of denaturation from complementary oligonucleotides and their kinetics of annealing to complementary oligonucleotides (see, SantaLucia, J. (1998) *A Unified View Of Polymer, Dumbbell, And Oligonucleotide DNA Nearest-Neighbor Thermodynamics*," Proc. Natl. Acad. Sci. (U.S.A.) 95:1460-1465; von Ahsen, N. et al. (1999) "*Application Of A Thermodynamic Nearest-Neighbor Model To Estimate Nucleic Acid Stability And Optimize Probe Design: Prediction Of Melting Points Of Multiple Mutations Of Apolipoprotein B*-3500 *And Factor V With A Hybridization Probe Genotyping Assay On The Lightcycler*," Clin. Chem. 45(12):2094-2101). Primer pairs that exhibit "substantially identical melting temperatures" (i.e., ±2° C., more preferably, ±1° C., still more preferably ±0.5° C., and most preferably ±0.1° C., as calculated using the method of SantaLucia, J. (1998)) maximize the overall yield of the products that they amplify, and the rate at which such products are produced.

Significantly, the preferred Forward and Reverse ORF1ab Primers of the present invention exhibit such substantially identical melting temperatures, which is a further distinction of the present invention. The preferred Forward ORF1ab Primer has a base-stacking $T_m$ of 58.2° C., whereas the preferred Reverse ORF1ab Primer has a base-stacking $T_m$ of 58.1° C. Thus, the use of the preferred Forward and Reverse ORF1ab Primers of the present invention serves to maximize the overall yield of the amplified ORF1ab product, and the rate at which such product is produced.

The preferred Forward and Reverse S Gene Primers of the present invention also exhibit substantially identical melting temperatures, which is a further distinction of the present invention. The preferred Forward S Gene Primer has a base-stacking $T_m$ of 60° C., whereas the preferred Reverse S Gene Primer has a base-stacking $T_m$ of 59.9° C. Thus, the use of the preferred Forward and Reverse S Gene Primers of the present invention serves to maximize the overall yield of the amplified S Gene product, and the rate at which such product is produced.

Significantly, the melting temperatures of the Forward and Reverse ORF1ab Primers of the present invention are substantially similar to the melting temperature of the preferred Forward and Reverse S Gene Primers of the present invention. Thus, these two sets of preferred primers are extremely well-matched, which is a further distinction of the present invention. Their combined use serves to equalize the overall yield of the amplified ORF1ab and S gene products, which are of similar length (117 nucleotides vs. 103 nucleotides). The substantially similar melting temperatures of the employed sets of primers and the similar lengths of the two amplified products are further distinctions of the present invention.

In designing an rRT-PCR assay, it is desirable for the employed probe to have a $T_m$ that is 5-10° C. higher than the employed amplification primers. The employed ORF1ab Probe has a base-stacking $T_m$ of 66.2° C., an 8° C. difference from the $T_m$ of the preferred ORF1ab Primers of the present invention. The employed S Gene Probe has a matching base-stacking $T_m$ of 66.6° C., a 6.6° C. difference from the $T_m$ of the preferred S Gene Primers of the present invention. Thus, each of the preferred probes of the present invention exhibit a desired $T_m$ and the two preferred probes of the present invention exhibit substantially identical $T_m$s. These are further distinctions of the present invention.

C. Other Amplification Assay Formats

Although the invention's assays for the detection of SARS-CoV-2 have been described in terms of rRT-PCR assays, the invention additionally contemplates the use of other assay formats, such as Loop-Mediated Isothermal Amplification (LAMP), rolling circle amplification, ligase chain reaction amplification, strand-displacement amplification, bind-wash PCR, singing wire PCR, NASBA (Fakruddin, M. et al. (2013) "*Nucleic Acid Amplification: Alternative Methods Of Polymerase Chain Reaction," J.* Pharm. Bioallied Sci. 5(4):245-252; Zhang, H. et al. (2019) "*LAMP-On-A-Chip: Revising Microfluidic Platforms For Loop-Mediated DNA Amplification*," Trends Analyt. Chem. 113:44-53; Bodulev, O. L. et al. (2020) "*Isothermal Nucleic Acid Amplification Techniques and Their Use in Bioanalysis*," Biochemistry (Mosc) 85(2):147-166; Dunbar, S. et al.

(2019) "*Amplification Chemistries In Clinical Virology*," J. Clin. Virol. 115:18-31; Daher, R. K. et al. (2016) "*Recombinase Polymerase Amplification for Diagnostic Applications*," Clin. Chem. 62(7):947-958; Goo, N. I. et al. (2016) "*Rolling Circle Amplification As Isothermal Gene Amplification In Molecular Diagnostics*," Biochip J. 10(4):262-271; PCT Publication No. WO 2018/073435; U.S. Pat. No. 10,619,151; US Patent Publication No. US 2020/0063173; US 2019/0249168; US 2018/0237842), etc.).

For example, loop-mediated isothermal amplification (LAMP) may be used to detect SARS-CoV-2 in accordance with the present invention. The LAMP process amplifies DNA using four primers to amplify a target DNA oligonucleotide that is present in a double-stranded DNA molecule whose strands comprise the following domains: 3' F3c-F2c-F1c-target oligonucleotide-B1-B2-B3 5' and 5' F3-F2-F1-complement of target oligonucleotide-B1c-B2c-B3c 3', wherein F3 and F3c, F2 and F2c, F1 and F1c, B3 and B3c, B2 and B2c, and B and B1c have complementary sequences. The four LAMP primers are:

(1) a forward internal primer (FIP) composed of a 5' F1c domain, whose sequence is complementary to the sequence of the F1 domain, and a 3' F2 domain whose sequence is complementary to the sequence of the F2c domain;
(2) a forward external primer (F3) whose sequence is complementary to the sequence of the F3c domain;
(3) a backward internal primer (BIP) composed of a 5' B1c domain, whose sequence is complementary to the sequence of the B1 domain, and a 3' B2 domain whose sequence is complementary to the sequence of the B2c domain;
(4) a backward external primer (B3) whose sequence is complementary to the sequence of the B3c domain;

(see, Notomi, T. et al. (2000) "*Loop-Mediated Isothermal Amplification Of DNA*," Nucl. Acids Res. 28(12):E63:1-7; U.S. Pat. Nos. 6,974,670; 7,175,985; 7,494,790; 7,638,280; 9,909,168; US Patent Publication Nos. 2018/0371534; 2007/0099178; PCT Publication No. WO 2017/108663A1; EP Publication Nos. EP 1642978 and EP 1020534).

The selection of appropriate primers may be facilitated through the use of primer selection software (e.g., PrimerExplorerV5, NEB LAMP Primer Design Tool, etc.). Illustrative sets of LAMP primers for amplifying domains of the SARS-CoV-2 ORF1ab and S gene are shown in Table 11.

TABLE 11

| Illustrative LAMP Primer | Sequence | SEQ ID NO: |
|---|---|---|
| ORF1ab FIP | gaacaccattacgggcattt-ctatctttttttgatggtaga-gttga | 403 |
| ORF1ab F3 | tttgtgcaccactcactg | 404 |
| ORF1ab BIP | aggtagtgttaaaggtttac-aaccacaattaatgtgactc-cattaagact | 405 |
| ORF1ab B3 | ctgtgtttttacggcttctc | 406 |
| S Gene FIP | ctgtgcagttaacatcctga-taaagagtgttataacacca-ggaacaa | 407 |
| S Gene F3 | tgttcttttggtggtgtca | 408 |

TABLE 11-continued

| Illustrative LAMP Primer | Sequence | SEQ ID NO: |
|---|---|---|
| S Gene BIP | gaagtccctgttgctattca-tgcgtgtttgaaaaacatta-gaacct | 409 |
| S Gene B3 | gcccctattaaacagcct | 410 |

The illustrative ORF1ab LAMP primers mediate the amplification of a domain of ORF1ab between the F2/F2c domains and the B2/B2c domains (SEQ ID NO:411) (residues 10-126 of which correspond to SEQ ID NO:3):

```
tctttttga tggtagagtt gatggtcaag tagacttatt
tagaaatgcc cgtaatggtg ttcttattac agaaggtagt
gttaaaggtt tacaaccatc tgtaggtccc aaacaagcta
gtcttaatgg agtcacatta attg
```

and its complement (SEQ ID NO:412) (residues 19-135 of which correspond to SEQ ID NO:4):

```
caattaatgt gactccatta agactagctt gtttgggacc
tacagatggt tgtaaacctt taacactacc ttctgtaata
agaacaccat tacgggcatt tctaaataag tctacttgac
catcaactct accatcaaaa aaga
```

The illustrative S Gene LAMP primers mediate the amplification of a domain of the S gene between the F2/F2c domains and the B2/B2c domains (SEQ ID NO:413) (residues 28-130 of which correspond to SEQ ID NO:7) (the nucleotide residue that is responsible for the D614G single nucleotide polymorphism of the SARS-CoV-2 S gene is underlined):

```
gtgttataac accaggaaca aatacttcta accaggttgc
tgttctttat caggatgtta actgcacaga agtccctgtt
gctattcatg cagatcaact tactcctact tggcgtgttt
attctacagg ttctaatgtt tttcaaacac gtgc
```

and its complement (SEQ ID NO:414) (residues 25-127 of which correspond to SEQ ID NO:8):

```
gcacgtgttt gaaaaacatt agaacctgta gaataaacac
gccaagtagg agtaagttga tctgcatgaa tagcaacagg
gacttctgtg cagttaacat cctgataaag aacagcaacc
tggttagaag tatttgttcc tggtgttata acac
```

In a preferred embodiment, detection of LAMP amplification is accomplished using one or two loop-primers, i.e., a Loop Primer B and/or a Loop Primer F (which contain sequences complementary to the single-stranded domain located between the above-described B1 and B2 domains or between the above-described F1 and F2 domains (PCT Publication No. WO 2017/108663). Either the Loop Primer F or the Loop Primer B, if present, is labeled at its 5'-end with at least one acceptor fluorophore. A further oligonucleotide probe, which is labeled at its 3'-end with at least one donor fluorophore is also employed. Especially preferred is the donor/acceptor pair BODIPY FL/ATTO647N. The further oligonucleotide probe has a sequence that is capable of hybridizing to the target nucleic acid sequence at a position which is 5' to the labeled Loop Primer F or Loop Primer B so that, when hybridized to the target nucleic acid sequence, the 3'-end of the oligonucleotide probe is brought into close proximity to the 5'-end of the labeled Loop Primer F or Loop Primer B.

D. Nested and Multiplexed Amplification Reactions

In one embodiment, the specificity and efficiency of the SARS-CoV-2 detection assays of the present invention are increased through the use of pairs of nested primers (see, e.g., U.S. Pat. Nos. 4,683,202 and 8,906,622; Basiri, A. et al. (2020) "*Microfluidic Devices For Detection Of RNA Viruses*," Rev Med Virol. e2154:1-11; Ratcliff, R. M. et al. (2007) "*Molecular diagnosis of medical viruses*," Curr. Issues Mol. Biol. 9(2):87-102; Hu, Y. et al. (2009) "*Nested Real-Time PCR For Hepatitis A Detection*," Lett. Appl. Microbiol. 49(5):615-619).

In one embodiment, the SARS-CoV-2 detection assays of the present invention are multiplexed reactions (Elnifro, E. M. et al. (2000) "*Multiplex PCR: Optimization And Application In Diagnostic Virology*," Clin. Microbiol. Rev. 13(4): 559-570; Lam, W. Y. et al. (2007) "*Rapid Multiplex Nested PCR For Detection Of Respiratory Viruses*," J. Clin. Microbiol. 45(11):3631-3640; Ratcliff, R. M. et al. (2007) "*Molecular diagnosis of medical viruses*," Curr. Issues Mol. Biol. 9(2):87-102).

In one such embodiment the amplification of SARS-CoV-2 ORF1ab and S gene sequences is concurrently achieved in the same reaction chamber. The invention also pertains to multiplexed amplification reactions, in which the amplification and/or detection of two or more different SARS-CoV-2 target sequences of the same gene (e.g., one or more different SARS-CoV-2 ORF1ab target sequences in addition to the SARS-CoV-2 ORF1ab target sequences described above, one or more different SARS-CoV-2 S gene target sequences in addition to the SARS-CoV-2 S gene target sequences described above, etc.) is concurrently achieved through the use of additional sets of primer and probe molecules specific for such other target sequences. In one embodiment, such additional SARS-CoV-2 target sequences encompass polymorphisms that distinguish different SARS-CoV-2 clades. Exemplary polymorphisms of the SARS-CoV-2 S gene that may be detected in such embodiments of the invention are shown in Table 12.

TABLE 12

| GenBank | GenBank | Polymorphism | | GenBank | GenBank | Polymorphism | |
|---|---|---|---|---|---|---|---|
| Ref. No. Protein | Ref. No. Genomic | S Protein | S Gene | Ref. No. Protein | Ref. No. Genomic | S Protein | S Gene |
| QHR84449.1 | MT007544.1 | S247R | T741G | QIZ16509.1 | MT327745.1 | V772I | G2314A |
| QHU79173.2 | MT020781.2 | H49Y | C145T | QIZ16559.1 | MT328034.1 | I197V | A589G |
| QHZ00379.1 | MT039890.1 | S221W | C662G | QIZ64470.1 | MT334539.1 | D614G<br>A1078S | A1841G<br>G3232T |
| QIA20044.1 | MT049951.1 | Y28N | T82A | QIZ64530.1 | MT334544.1 | D614G<br>S939F | A1841R<br>G3371K |
| QIA98583.1 | MT050493.1 | A930V | C2789T | QIZ64578.1 | MT334548.1 | H146Y<br>D614G | C436T<br>A1841G |
| QI053204.1 | MT093571.1 | F797C | T2390G | QIZ64624.1 | MT334552.1 | S98F | C293T |
| QI157278.1 | MT159716.2 | F157L | C471A | QIZ97039.1 | MT339039.1 | N148S | A443G |
| QI187830.1 | MT163720.1 | H655Y | C1963T | QIZ97051.1 | MT339040.1 | Y279X<br>D614G | A836N<br>T837N<br>A1841G |
| QI196493.1 | MT184910.1 | G181V | G542T | QJA17276.1 | MT345871.1 | D614G<br>I818V | A1841G<br>A2452G |
| QIK50427.1 | MT192765.1 | D614G | A1841G | QJA17468.1 | MT345887.1 | L5F<br>D614G | C13T<br>A1841G |
| QI004367.1 | MT226610.1 | N74K | T222A | QJA17524.1 | MT344944.1 | D614X<br>G1124X | A1841G<br>C2816T |
| QIQ08810.1 | MT233521.1 | K528X | A1582N | QJA17596.1 | MT344950.1 | D614G<br>L1203F | A1841G<br>C3607T |
| QIQ49882.1 | MT246461.1 | L5F<br>G476S | C13T<br>G1426A | QJA42177.1 | MT350252.1 | D614G<br>V1065L | A1841G<br>G3193T |
| QIQ50092.1 | MT246482.1 | K814X | A2440N<br>A2441N<br>G2442N | QJC19491.1 | MT358637.1 | Q271R<br>D614G | A812G<br>A1841G |
| QIS30105.1 | MT258381.1 | D614X | A1841R | QJC20043.1 | MT358689.1 | K529E<br>D614G | A1585G<br>A1841G |
| QIS30115.1 | MT258382.1 | P427X<br>D614G | T1281W<br>A1841G | QJC20367.1 | MT358716.1 | D614G<br>S929I | A1841G<br>G2786T |
| QIS30165.1 | MT259236.1 | V483A | T1448C | QJC20391.1 | MT358718.1 | D614G<br>T768I | A1841G<br>C2303T |
| QIS30295.1 | MT259249.1 | L54F<br>D614G | G162C<br>A1841G | QJC20993.1 | MT230904.1 | V367F | G1099T |
| QIS30335.1 | MT259253.1 | A348T | G1042A | QJD20632.1 | MT370516.1 | T791I | C2372T |
| QIS30425.1 | MT259262.1 | G476S | C84T<br>G1426A | QJD23273.1 | MT370831.1 | V90F<br>D614G | G268T<br>G906T<br>A1841G |
| QIS60489.1 | MT262915.1 | A520S | G1558T | QJD23524.1 | MT370852.1 | P217X | C650N |
| QIS60546.1 | MT263384.1 | T29I | C86T<br>C2472T | QJD24377.1 | MT370923.1 | A522S<br>D614G | G1564T<br>A1841G |
| QIS60582.1 | MT263387.1 | D1259H | G3775C | QJD25085.1 | MT370982.1 | F220X<br>D614G | 1659N<br>A1841G |

TABLE 12-continued

| GenBank | GenBank | Polymorphism | | GenBank | GenBank | Polymorphism | |
|---|---|---|---|---|---|---|---|
| Ref. No. Protein | Ref. No. Genomic | S Protein | S Gene | Ref. No. Protein | Ref. No. Genomic | S Protein | S Gene |
| QIS60906.1 | MT263414.1 | L5F | C13T | QJD25529.1 | MT371019.1 | D614G | A1841G |
| | | | | | | P631S | C1891T |
| QIS60930.1 | MT263416.1 | E96D | G288T | QJD47202.1 | MT375441.1 | M731I | G21931 |
| QIS60978.1 | MT263420.1 | D1168H | G3502C | QJD47358.1 | MT375454.1 | Y423X | A1268N |
| | | | | | | D614G | A1841G |
| QIS61254.1 | MT263443.1 | A1078V | C3233T | QJD47442.1 | MT375461.1 | Y200X | A599N |
| | | | | | | D614G | A1841G |
| QIS61338.1 | MT263450.1 | D111N | G331A | QJD47718.1 | MT374101.1 | H49Y | C1451 |
| | | | | | | S884F | C2651T |
| QIS61422.1 | MT263457.1 | H519Q | T1557A | QJD48279.1 | MT252707.1 | M1237I | A3711C |
| QIS61468.1 | MT263461.1 | A942X | A2823N | QJE38426.1 | MT385432.1 | A845S | G8533T |
| | | | G2824N | | | | |
| QIT07011.1 | MT276600.1 | L8V | T22G | QJE38606.1 | MT385447.1 | Y145H | T433C |
| | | | | | | D614G | A1841G |
| QIU78825.1 | MT292579.1 | G910X | G2728N | QJE38822.1 | MT385465.1 | S704X | T2110 Y |
| QIU80913.1 | MT281577.1 | S50L | C249T | QJF11959.1 | MT394529.1 | L752X | C2254Y |
| QIU80973.1 | MT293160.1 | A27V | C80T | QJF11971.1 | MT394530.1 | H655X | C1963Y |
| QIU81585.1 | MT293211.1 | T240I | C719T | QJF75467.1 | MT412183.1 | N354B | A441R |
| | | | | | | | A1060R |
| | | | | | | | C2472T |
| QIU81873.2 | MT291835.2 | A653V | C1958T | QJF75779.1 | MT412209.1 | V503X | G1507K |
| | | | | | | D614G | A1841G |
| QIU81885.1 | MT291836.1 | A570V | C1709T | QJF76007.1 | MT412228.1 | S704L | C2111T |
| | | | C2461T | | | | C2820T |
| QIV15164.1 | MT304489.1 | Q644X | T771Y | QJF76438.1 | MT412264.1 | L118F | C352T |
| | | | C1930Y | | | D614G | A1841G |
| QIV65033.1 | MT308695.1 | Y265X | A794W | QJF77194.1 | MT412327.1 | A27S | G79T |
| | | | | | | D614G | A1841G |
| QIZ13143.1 | MT326038.1 | L1152X | T3454N | QJF77846.1 | MT415320.1 | Y28H | 182C |
| | | | T3455N | | | | C2568T |
| QIZ13179.1 | MT326041.1 | S71F | C212T | QJG65949.1 | MT415368.1 | G485R | G1453A |
| | | | | | | | T1455G |
| QIZ13299.1 | MT326051.1 | D80Y | G238T | QJG65951.1 | MT415370.1 | A67S | G199T |
| | | | | | | F1103L | T3307C |
| | | | | | | | A3312G |
| QIZ13765.1 | MT326090.1 | D614G | A1841G | QJG65954.1 | MT415373.1 | S750R | C2250A |
| | | V615F | G1843T | | | L752R | C2254A |
| | | | | | | | T2255G |
| | | | | | | | T2256G |
| | | | | | | | C2461T |
| QIZ13789.1 | MT326092.1 | D614G | A1841G | QJG65956.1 | MT415375.1 | G838S | G2512A |
| | | V622I | G1864A | | | | |
| | | | C2013T | | | | |
| QIZ13861.1 | MT326098.1 | V70F | G208T | QJG65957.1 | MT415376.1 | W152R | T454C |
| QIZ14569.1 | MT326157.1 | C1250Y | G3749A | QJI53955.1 | MT419818.1 | Q239R | A716G |
| | | | | | | D614G | A1841G |
| QIZ15585.1 | MT325564.1 | D614G | A1841G | QJQ04352.1 | MT429191.1 | D614G | A1841G |
| | | V1228X | T3683Y | | | T676S | A2026T |
| QIZ15717.1 | MT325575.1 | P9L | C26T | QJQ27878.1 | MT434760.1 | K557X | A1669N |
| | | | C2472T | | | | C2367T |
| QIZ15969.1 | MT325596.1 | F238X | T708Y | QJQ28105.1 | MT434799.1 | T95I | C284T |
| | | D614G | T712W | | | D614G | A1841G |
| | | | T713K | | | | |
| | | | A1841G | | | | |
| QIZ16197.1 | MT325615.1 | W258L | G7731 | | | | |
| | | D614G | A1841G | | | | |

In one embodiment, the SARS-CoV-2 detection assays of the present invention are multiplexed reactions in which the amplification and/or detection of one or more SARS-CoV-2 target sequences other than ORF1a or the S gene is concurrently achieved through the use of additional sets of primer and probe molecules specific for such other target sequences. Such sequences could be sequences of the 3, E (envelope protein), M (matrix), 7, 8, 9, 10b, N, 13 and 14 genes, or sequences that encode the nsp2, nsp3, nsp4, nsp5, nsp6, nsp7, nsp8, nsp9, nsp10, nsp12, nsp13, nsp14a2, nsp15, and/or nsp16 proteins, etc.

In one embodiment, the SARS-CoV-2 detection assays of the present invention are multiplexed reactions in which the amplification and/or detection of one or more SARS-CoV-2 target sequences and the amplification and/or detection of one or more target sequences of a pathogen other than SARS-CoV-2 (and especially a respiratory pathogen other than SARS-CoV-2) is concurrently achieved through the use of additional sets of primer and probe molecules specific for such other target sequences. Examples of such other pathogens include *Streptococcus pneumoniae, Mycoplasma pneumoniae, Legionella pneumophila, Haemophilus influenzae, Neisseria meningitidis*, influenza virus (e.g., influenza A, influenza B, etc.), rhinovirus, non-SARS-CoV-2 pathogenic coronavirus, parainfluenza virus, human metapneumovirus (hMPV), respiratory syncytial virus (RSV), adenovirus, etc. (see, e.g., Basile, K. et al. (2018) "*Point-Of-Care Diagnostics For Respiratory Viral Infections*," Exp. Rev. Molec.

Diagnos. 18(1):75-83; Mahony, J. B. et al. (2011) "*Molecular Diagnosis Of Respiratory Virus Infections*," Crit. Rev. Clin. Lab. Sci. 48(5-6):217-249; Ieven, M. (2007) "*Currently Used Nucleic Acid Amplification Tests For The Detection Of Viruses And Atypicals In Acute Respiratory Infections*," J. Clin. Virol. 40(4):259-276).

IV. Preferred Methods for Conducting the Assays of the Present Invention

A. Detection of the SARS-CoV-2 ORF1ab

In accordance with the methods of the present invention, the detection of the presence of SARS-CoV-2 ORF1ab oligonucleotides in a clinical sample may be achieved using a TaqMan ORF1ab Probe by:

(I) incubating the clinical sample in vitro in the presence of:
  (1) a reverse transcriptase and a DNA polymerase that has a 5'-3' exonuclease activity;
  (2) a Forward (or sense strand) ORF1ab Primer;
  (3) a Reverse (or antisense strand) ORF1ab Primer; and
  (4) a TaqMan ORF1ab Probe capable of detecting the presence of a SARS-CoV-2 ORF1ab oligonucleotide that is amplified by conducting PCR in the presence of such Forward and Reverse ORF1ab Primers, wherein the TaqMan ORF1ab Probe comprises a 5' terminus and a 3' terminus, and has a SARS-CoV-2 oligonucleotide domain whose nucleotide sequence consists of, consists essentially of, comprises, or is a variant of the nucleotide sequence of: SEQ ID NO:9, SEQ ID NO:10, any of SEQ ID NOs:127-146, or any of SEQ ID NOs:147-166, wherein the 5' terminus of the oligonucleotide is labeled with a fluorophore and the 3' terminus of the oligonucleotide is complexed to a quencher of such fluorophore.

wherein the incubation is in a reaction under conditions sufficient to permit:
  (a) the Forward and Reverse ORF1ab Primers to mediate a polymerase chain reaction amplification of a region of the ORF1ab of SARS-CoV-2 to thereby produce amplified ORF1ab oligonucleotide molecules, if the SARS-CoV-2 is present in the clinical sample;
  (b) the TaqMan ORF1ab Probe to hybridize to amplified ORF1ab oligonucleotide molecules; and
  (c) the 5→3' exonuclease activity to hydrolyze hybridized TaqMan ORF1ab Probe, to thereby separate the fluorophore thereof from the quencher thereof and cause a fluorescent signal to become detectable; and (II) determining whether the SARS-CoV-2 is present in the clinical sample by determining whether a fluorescent signal of the fluorophore has become detectable.

In accordance with the methods of the present invention, the detection of the presence of SARS-CoV-2 ORF1ab oligonucleotides in a clinical sample may alternatively be achieved using a Molecular Beacon ORF1ab Probe by:

(I) incubating the clinical sample in vitro in the presence of:
  (1) a reverse transcriptase and a DNA polymerase;
  (2) a Forward (or sense strand) ORF1ab Primer;
  (3) a Reverse (or antisense strand) ORF1ab Primer; and
  (4) a Molecular Beacon ORF1ab Probe capable of detecting the presence of a SARS-CoV-2 ORF1ab oligonucleotide that is amplified by conducting PCR in the presence of such Forward and Reverse ORF1ab Primers, wherein the Molecular Beacon ORF1ab Probe comprises a SARS-CoV-2 ORF1ab oligonucleotide domain that is flanked by a 5' oligonucleotide and a 3' oligonucleotide, wherein such 5' oligonucleotide and such 3' oligonucleotide are at least substantially complementary to one another, and wherein at least one of such 5' oligonucleotide and such 3' oligonucleotide is detectably labeled and another of such 5' oligonucleotide and such 3' oligonucleotide is complexed to a quencher or an acceptor of such detectable label, wherein the SARS-CoV-2 ORF1ab oligonucleotide domain of the Molecular Beacon ORF1ab Probe has a nucleotide sequence that consists of, consists essentially of, comprises, or is a variant of the nucleotide sequence of: SEQ ID NO:9, SEQ ID NO:10, any of SEQ ID NOs:127-146, or any of SEQ ID NOs:147-166;

wherein the incubation is in a reaction under conditions sufficient to permit:
  (a) the Forward and Reverse ORF1ab Primers to mediate a polymerase chain reaction amplification of a region of the ORF1ab of SARS-CoV-2 to thereby produce amplified ORF1ab oligonucleotide molecules, if the SARS-CoV-2 is present in the clinical sample;
  (b) the Molecular Beacon ORF1ab Probe to hybridize to amplified ORF1ab oligonucleotide molecules, thereby separating the fluorophore thereof from the quencher thereof and causing a fluorescent signal to become detectable; and (II) determining whether the SARS-CoV-2 is present in the clinical sample by determining whether a fluorescent signal of the fluorophore has become detectable.

In accordance with the methods of the present invention, the detection of the presence of SARS-CoV-2 ORF1ab oligonucleotides in a clinical sample may alternatively be achieved using an ORF1ab Scorpion Primer-Probe by:

(I) incubating the clinical sample in vitro in the presence of:
  (1) a reverse transcriptase and a DNA polymerase;
  (2) a Forward (or sense strand) ORF1ab Primer;
  (3) a Reverse (or antisense strand) ORF1ab Primer; and
  (4) an ORF1ab Scorpion Primer-Probe capable of detecting the presence of a SARS-CoV-2 ORF1ab oligonucleotide that is amplified by conducting PCR in the presence of such Forward and Reverse ORF1ab Primers, wherein the ORF1ab Scorpion Primer-Probe comprises a SARS-CoV-2 oligonucleotide domain that is flanked by a 5' oligonucleotide and a 3' oligonucleotide, wherein such 5' oligonucleotide and such 3' oligonucleotide are at least substantially complementary to one another, and wherein at least one of such 5' oligonucleotide and such 3' oligonucleotide is detectably labeled and the other of such 5' oligonucleotide and such 3' oligonucleotide is complexed to a quencher or an acceptor of such detectably label, and wherein such 3' oligonucleotide further comprises a polymerization blocking moiety, and a PCR primer oligonucleotide positioned 3' from the blocking moiety, wherein the SARS-CoV-2 oligonucleotide domain of the ORF1ab Scorpion Primer-Probe has a nucleotide sequence that consists of, consists essentially of, comprises, or is a variant of the nucleotide sequence of: SEQ ID NO:9, SEQ ID NO:10, any of SEQ ID NOs:127-146, or any of SEQ ID NOs:147-166; and wherein the PCR primer oligonucleotide is selected so that it is capable of hybridizing to a region of ORF1ab that is approximately 7 bases, 8 bases, 9 bases, 10 bases, or more preferably 11 bases upstream of an ORF1ab sequence that is the same as the sequence of the probe's ORF1ab oligonucleotide domain (or differs from such sequence by 5, 4, 3, 2 or 1 nucleotide residues), such that extension of the PCR primer oligonucleotide domain of the ORF1ab Scorpion Primer-Probe forms an extension product whose sequence is complementary to the probe's ORF1ab oligonucleotide domain;

wherein the incubation is in a reaction under conditions sufficient to permit:

(a) the Forward and Reverse ORF1ab Primers to mediate a polymerase chain reaction amplification of a region of the ORF1ab of SARS-CoV-2 to thereby produce amplified ORF1ab oligonucleotide molecules, if the SARS-CoV-2 is present in the clinical sample;

(b) the ORF1ab Scorpion Primer-Probe to hybridize to amplified ORF1ab oligonucleotide molecules and be extended to form a domain that is complementary to the sequence of the SARS-CoV-2 oligonucleotide domain of the ORF1ab Scorpion Primer-Probe, such that, upon denaturation, the SARS-CoV-2 oligonucleotide domain of the ORF1ab Scorpion Primer-Probe hybridizes to the extended domain of the ORF1ab Scorpion Primer-Probe, and thereby prevents the complementary 5' oligonucleotide and 3' oligonucleotide domains of the probe from re-hybridizing to one another and attenuating the quenching of the detectable label;

(II) determining whether the SARS-CoV-2 is present in the clinical sample by determining whether a fluorescent signal of the fluorophore has become detectable.

Suitable Forward (or sense strand) ORF1ab Primers for such assays include oligonucleotides having a nucleotide sequence that consists of, consists essentially of, comprises, or is a variant of, the nucleotide sequence of: SEQ ID NO:1 or any of SEQ ID NOs:17-28. Suitable Reverse (or antisense strand) ORF1ab Primers for such assays include oligonucleotides having a nucleotide sequence that consists of, consists essentially of, comprises, or is a variant of, the nucleotide sequence of: SEQ ID NO:2 or any of SEQ ID NOs:29-42.

B. Detection of the SARS-CoV-2 S Gene

In accordance with the methods of the present invention, the detection of the presence of SARS-CoV-2 S Gene oligonucleotides in a clinical sample may be achieved using a TaqMan S Gene Probe by:

(I) incubating the clinical sample in vitro in the presence of:

(1) a reverse transcriptase and a DNA polymerase that has a 5'-3' exonuclease activity;

(2) a Forward (or sense strand) S Gene Primer;

(3) a Reverse (or antisense strand) S Gene Primer; and (4) the TaqMan S Gene Probe, wherein such probe is capable of detecting the presence of a SARS-CoV-2 S Gene oligonucleotide that is amplified by conducting PCR in the presence of such Forward and Reverse S Gene Primers, wherein the TaqMan S Gene Probe comprises a 5' terminus and a 3' terminus, and has a SARS-CoV-2 oligonucleotide portion whose nucleotide sequence consists of, consists essentially of, comprises, or is a variant of the nucleotide sequence of: SEQ ID NO:11, SEQ ID NO:12, any of SEQ ID NOs:167-252, any of SEQ ID NOs:253-272, any of SEQ ID NOs:273-363, or any of SEQ ID NOs:364-381, wherein the 5' terminus of the oligonucleotide is labeled with a fluorophore and the 3' terminus of the oligonucleotide is complexed to a quencher of such fluorophore.

wherein the incubation is in a reaction under conditions sufficient to permit:

(a) the Forward and Reverse S Gene Primers to mediate a polymerase chain reaction amplification of a region of the S gene of SARS-CoV-2 to thereby produce amplified S gene oligonucleotide molecules, if the SARS-CoV-2 is present in the clinical sample;

(b) the TaqMan S Gene Probe to hybridize to amplified S gene oligonucleotide molecules; and (c) the 5→3' exonuclease activity to hydrolyze hybridized TaqMan S Gene Probe, to thereby separate the fluorophore thereof from the quencher thereof and cause a fluorescent signal to become detectable; and (II) determining whether the SARS-CoV-2 is present in the clinical sample by determining whether a fluorescent signal of the fluorophore has become detectable.

In accordance with the methods of the present invention, the detection of the presence of SARS-CoV-2 S gene oligonucleotides in a clinical sample may be achieved using a Molecular Beacon S Gene Probe by:

(I) incubating the clinical sample in vitro in the presence of:

(1) a reverse transcriptase and a DNA polymerase;

(2) a Forward (or sense strand) S Gene Primer;

(3) a Reverse (or antisense strand) S Gene Primer; and (4) the Molecular Beacon S Gene Probe, wherein such probe is capable of detecting the presence of a SARS-CoV-2 S gene oligonucleotide that is amplified by conducting PCR in the presence of such Forward and Reverse S Gene Primers, wherein the Molecular Beacon S Gene Probe comprises a SARS-CoV-2 S gene oligonucleotide portion that is flanked by a 5' oligonucleotide and a 3' oligonucleotide, wherein such 5' oligonucleotide and such 3' oligonucleotide are at least substantially complementary to one another, and wherein at least one of such 5' oligonucleotide and such 3' oligonucleotide is detectably labeled and another of such 5' oligonucleotide and such 3' oligonucleotide is complexed to a quencher or an acceptor of such detectable label, wherein the SARS-CoV-2 S gene oligonucleotide portion of the Molecular Beacon S Gene Probe has a nucleotide sequence that consists of, consists essentially of, comprises, or is a variant of the nucleotide sequence of: SEQ ID NO:11, SEQ ID NO:12, any of SEQ ID NOs:167-252, any of SEQ ID NOs:253-272, any of SEQ ID NOs:273-363, or any of SEQ ID NOs:364-381;

wherein the incubation is in a reaction under conditions sufficient to permit:

(a) the Forward and Reverse S Gene Primers to mediate a polymerase chain reaction amplification of a region of the S Gene of SARS-CoV-2 to thereby produce amplified S gene oligonucleotide molecules, if the SARS-CoV-2 is present in the clinical sample;

(b) the Molecular Beacon S Gene Probe to hybridize to amplified S gene oligonucleotide molecules, thereby separating the fluorophore thereof from the quencher thereof and causing a fluorescent signal to become detectable; and (II) determining whether the SARS-CoV-2 is present in the clinical sample by determining whether a fluorescent signal of the fluorophore has become detectable.

In accordance with the methods of the present invention, the detection of the presence of SARS-CoV-2 S gene oligonucleotides in a clinical sample may alternatively be achieved using an S Gene Scorpion Primer-Probe by:

(I) incubating the clinical sample in vitro in the presence of:

(1) a reverse transcriptase and a DNA polymerase;

(2) a Forward (or sense strand) S Gene Primer;

(3) a Reverse (or antisense strand) S Gene Primer; and (4) the S Gene Scorpion Primer-Probe, wherein such probe is capable of detecting the presence of a SARS-CoV-2 S gene oligonucleotide that is amplified by conducting PCR in the presence of such Forward and Reverse S Gene Primers, wherein the S Gene Scorpion Primer-Probe comprises a SARS-CoV-2 oligonucleotide domain that is flanked by a 5' oligonucleotide and a 3' oligonucleotide, wherein such 5' oligonucleotide and such 3' oligonucleotide are at least substantially complementary to one another, and wherein at least one of such 5' oligonucleotide and such 3' oligonucleotide is detectably labeled and the other of such 5' oligonucleotide and such 3' oligonucleotide is complexed to a quencher or an acceptor of such detectably label, and wherein such 3' oligonucleotide further comprises a polymerization blocking moiety, and a PCR primer oligonucleotide positioned 3' from the blocking moiety, wherein the SARS-CoV-2 oligonucleotide domain of the S Gene Scorpion Primer-Probe has a nucleotide sequence that consists of, consists essentially of, comprises, or is a variant of the nucleotide sequence of: SEQ ID NO:11, SEQ ID NO:12, any of SEQ ID NOs:167-252, any of SEQ ID NOs:253-272, any of SEQ ID NOs:273-363, or any of SEQ ID NOs:364-381; and wherein the PCR primer oligonucleotide is selected so that it is capable of hybridizing to a region of S gene that is approximately 7 bases, 8 bases, 9 bases, 10 bases, or more preferably 11 bases upstream of an S gene sequence that is the same as the sequence of the probe's S gene oligonucleotide domain (or differs from such sequence by 5, 4, 3, 2 or 1 nucleotide residues), such that extension of the PCR primer oligonucleotide domain of the S Gene Scorpion Primer-Probe forms an extension product whose sequence is complementary to the probe's S Gene oligonucleotide domain;

wherein the incubation is in a reaction under conditions sufficient to permit:

(a) the Forward and Reverse S Gene Primers to mediate a polymerase chain reaction amplification of a region of the S gene of SARS-CoV-2 to thereby produce amplified S gene oligonucleotide molecules, if the SARS-CoV-2 is present in the clinical sample;

(b) the S Gene Scorpion Primer-Probe to hybridize to amplified S gene oligonucleotide molecules and be extended to form a domain that is complementary to the sequence of the SARS-CoV-2 oligonucleotide domain of the S Gene Scorpion Primer-Probe, such that, upon denaturation, the SARS-CoV-2 oligonucleotide domain of the S Gene Scorpion Primer-Probe hybridizes to the extended domain of the S Gene Scorpion Primer-Probe, and thereby prevents the complementary 5' oligonucleotide and 3' oligonucleotide domains of the probe from re-hybridizing to one another and attenuating the quenching of the detectable label;

(II) determining whether the SARS-CoV-2 is present in the clinical sample by determining whether a fluorescent signal of the fluorophore has become detectable.

Suitable Forward (or sense strand) S Gene Primers include oligonucleotides having a nucleotide sequence that consists of, consists essentially of, comprises, or is a variant of, the nucleotide sequence of: SEQ ID NO:5 or any of SEQ ID NOs:43-70, or any of SEQ ID NOs:71-84. Suitable Reverse (or antisense strand) S Gene Primers include oligonucleotides having a nucleotide sequence that consists of, consists essentially of, comprises, or is a variant of, the nucleotide sequence of: SEQ ID NO:6, or any of SEQ ID NOs:85-112, or any of SEQ ID NOs:113-126.

As discussed above, the region of the SARS-CoV-2 S gene amplified by the primers of the present invention comprises the nucleotide residue (position 1841 of SEQ ID NO:16) that is responsible for the D614G polymorphism of the SARS-CoV-2 S gene. In accordance with the methods of the present invention, the detection of the presence of the D614G polymorphism may be achieved using primers whose 3' termini distinguish the nucleotide residue present at such position. Exemplary primers having this characteristic include primers having the nucleotide sequence of any of SEQ ID NOs:43-70 or any of SEQ ID NOs:85-112.

In accordance with the methods of the present invention, the detection of the presence of the D614G polymorphism may alternatively be achieved using molecular beacon probes, HyBeacon™ probes or scorpion primer-probes whose sequences comprise the position 1841 nucleotide. Exemplary oligonucleotides having this characteristic include: any of SEQ ID NOs:43-70, any of SEQ ID NOs: 85-112, any of SEQ ID NOs:167-252, or any of SEQ ID NOs:273-363

V. Preferred Platform for Conducting the Assays of the Present Invention

In a preferred embodiment, the above-described preferred primers and probes assay the presence of SARS-CoV-2 using a Direct Amplification Disc (DiaSorin Molecular LLC) and SIMPLEXA® Direct Chemistry (DiaSorin Molecular LLC), as processed by a LIAISON® MDX (DiaSorin Molecular LLC) rRt-PCR platform. The operating principles of DiaSorin Molecular LLC's LIAISON® MDX rRt-PCR platform, SIMPLEXA® Direct Chemistry and Direct Amplification Disc are disclosed in U.S. Pat. No. 9,067,205, US Patent Publn. No. 2012/0291565 A1, EP 2499498 B1, EP 2709760 B1, all herein incorporated by reference in their entireties.

In brief, the LIAISON® MDX (DiaSorin) rRt-PCR platform is a compact and portable thermocycler that additionally provides centrifugation and reaction processing capabilities. The device is capable of mediating sample heating (>5° C./sec) and cooling (>4° C./sec), and of regulating temperature to 0.5° C. (in the range from room temperature to 99° C.). The LIAISON® MDX rRt-PCR platform has the ability to excite fluorescent labels at 475 nm, 475 nm, 520 nm, 580 nm, and 640 nm, and to measure fluorescence at 520 nm, 560 nm, 610 nm, and 682 nm, respectively.

The Direct Amplification Disc is radially oriented, multi-chambered, fluidic device that is capable of processing the amplification of target sequences (if present) in up to 8 (50 μL) clinical samples at a time. The samples may be provided directly to the Direct Amplification Disc, as cellular material or lysates, without any prior DNA or RNA extraction.

In brief, an aliquot of the clinical sample and reaction reagents (i.e., a DNA polymerase, a reverse transcriptase, one or more pairs of SARS-CoV-2-specific primers (preferably, the above-discussed preferred Forward and Reverse ORF1ab Primers and the above-discussed preferred Forward and Reverse S Gene Primers, two or more SARS-CoV-2-specific probes (preferably, the above-discussed preferred ORF1ab Probe and the above-discussed preferred S Gene Probe), and deoxynucleotide triphosphates (dNTPs) and buffers) are separately provided to a provision area of the Direct Amplification Disc (see, U.S. Pat. No. 9,067,205, US Patent Publn No. 2012/0291565 A1, EP 2709760 B1). Preferably, the reaction reagents required for rRT-PCR are provided using "master mixes," which are widely available commercially (Applied Biosystems; ThermoFisher Scientific, etc.). Primers may be provided at a concentration of between 0.1 and 0.5 μM (5-25 pmol/per 50 μl reaction).

Probe molecules may be provided at a concentration of between 0.05 and 0.25 μM (2.5-12.5 pmol/per 50 μl reaction).

The LIAISON® MDX device centrifuges the Direct Amplification Disc to thereby force a domain of the sample and reagents to be separately moved into reservoirs for a reaction chamber. The centrifugation moves any excess sample or reagents to a holding chamber. A laser within the LIAISON® MDX device then opens a first valve permitting the sample to flow into the reaction chamber. The chamber is then heated (for example to 95° C.); the high temperature and centrifugation serves to lyse cells that may be present in the sample. The laser within the LIAISON® MDX device then opens a second valve permitting reagents sample to flow into the reaction chamber and mix with the sample. The LIAISON® MDX device then commences to subject the reaction to PCR thermocycling. An internal control may be used to monitor successful instrument and sample processing and to detect RT-PCR failure and/or inhibition.

An internal control may be employed in order to confirm that the reaction conditions are suitable for target amplification and detection. A suitable internal control, for example, is one that amplifies MS2 phage sequences. A suitable Forward MS2 Phage Internal Control Primer has the sequence (SEQ ID NO:13 tgctcgcggatacccg); a suitable Reverse MS2 Phage Internal Control Primer has the sequence (SEQ ID NO:14 aacttgcgttctcgagcgat). Amplification mediated by such internal control primers may be detected using a TaqMan probe (MS2 Phage Internal Control Probe) having the sequence (SEQ ID NO:15 acctcgggtttccgtcttgctcgt. Alternatively, other MS2 internal control primers may be employed (Dreier, J. et al. (2005) "*Use of Bacteriophage MS2 as an Internal Control in Viral Reverse Transcription-PCR Assays*," J. Clin. Microbiol. 43(9):4551-4557). The probe may be labeled with the Quasar 670 fluorophore and complexed to the BHQ2 quencher, or with any other fluorophore and any quencher capable of quenching the fluorescence of such fluorophore.

The LIAISON MDX Software runs a pre-heating cycle to denature the SARS-CoV-2 viral coat protein and thereby release the SARS-CoV-2 RNA. This step is followed by reverse transcription and subsequent amplification. During the extension phase of the PCR cycle, the 5' nuclease activity of DNA polymerase degrades any probe that has hybridized to amplified product in the reaction, thereby causing the fluorescent label of the probe to separate from the quencher of the probe. Such separation permits a fluorescent signal to be detected. With each cycle, additional fluorescent label molecules are cleaved from their respective probes, increasing the fluorescence intensity.

Reaction results are monitored and presented to users via LIAISON® MDX's software. Such software provides easy to understand results with the ability to check amplification curves after a run. The software also plots QC Charts and can be bi-directionally interfaced with LIS for easy integration into lab workflow. The LIAISON® MDX permit random access to individual samples, and thus allows users to start the analysis of new samples without waiting for previously-started analyses to complete. Assay results can be obtained in one hour or less. Table 13 shows the Diagnostic Algorithm of the assay.

TABLE 13

| SARS-CoV-2 $C_T$ value (ORF1ab Target) | SARS-CoV-2 $C_T$ value (S Gene Target) | RNA IC $C_T$ value | Interpretation |
|---|---|---|---|
| ≤40, ≠0 | ≤40, ≠0 | N/A | SARS-CoV-2 RNA: Detected |
| ≤40, ≠0 | N/A | N/A | SARS-CoV-2 RNA: Detected |
| N/A | ≤40, ≠0 | N/A | SARS-CoV-2 RNA: Detected |
| 0 | 0 | ≤40, ≠0 | SARS-CoV-2 RNA: Not Detected |
| 0 | 0 | 0 | Results Invalid Repeat Assay: If RNA IC is still 0 on repeat, test with a new sample if clinically warranted |

Accordingly, if the ORF1ab and the S gene CT values are both ≤40 for a patient specimen, the result is reported as "Detected" for the SARS-CoV-2 RNA. The internal control is not applicable. If the ORF1ab CT value is ≤40 and the S gene CT value is 0 for a patient specimen, the result is reported as "Detected" for the SARS-CoV-2 RNA. The internal control is not applicable. If the ORF1ab CT value is 0 and the S gene CT value is ≤40 for a patient specimen, the result is reported as "Detected" for the SARS-CoV-2 RNA. The internal control is not applicable. If the ORF1ab and the S gene CT values are both 0 for a patient specimen and the internal control CT is non-zero and ≤45, the result is reported as "Not Detected" for the SARS-CoV-2 RNA. If the ORF1ab and the S gene CT values are both 0 for a patient specimen and the internal control CT is also 0, the result is reported as "Invalid." This specimen should be re-assayed. If the internal control is still 0 for the repeated assay, the test should be repeated with a new sample, if clinically warranted.

VI. Kits

The invention additionally includes kits for conducting the above-described assays. In one embodiment, such kits will include one or more containers containing reagents for specifically detecting the SARS-CoV-2 ORF1ab (e.g., a Forward ORF1ab Primer, a Reverse ORF1ab Primer, and an ORF1ab Probe, that is preferably detectably labelled) and instructions for the use of such reagents to detect SARS-CoV-2. Such kits may comprise a Variant Forward ORF1ab Primer, a Variant Reverse ORF1ab Primer, and/or a Variant ORF1ab Probe. Most preferably, such kits will comprise the above-described preferred ORF1ab Forward Primer, the above-described preferred ORF1ab Reverse Primer and the above-described preferred ORF1ab Probe.

In a second embodiment, such kits will include one or more containers containing reagents for specifically detecting the SARS-CoV-2 S gene (e.g., a Forward S Gene Primer, a Reverse S Gene Primer, and an S Gene Probe, that is preferably detectably labelled) and instructions for the use of such reagents to detect SARS-CoV-2. Such kits may comprise a Variant Forward S Gene Primer, a Variant Reverse S Gene Primer, and/or a Variant S Gene Probe. Most preferably, such kits will comprise the above-described preferred S Gene Forward Primer, the above-described preferred S Gene Reverse Primer, and the above-described preferred S Gene Probe.

In a third embodiment, such kits will include one or more containers containing reagents for specifically detecting both the SARS-CoV-2 ORF1ab and the SARS-CoV-2 S gene (e.g., a Forward ORF1ab Primer, a Reverse ORF1ab Primer, an ORF1ab Probe, a Forward S Gene Primer, a Reverse S Gene Primer, and an S Gene Probe) and instructions for the use of such reagents to detect SARS-CoV-2, and will most preferably comprise the above-described preferred ORF1ab Forward Primer, the above-described preferred ORF1ab Reverse Primer, the above-described preferred ORF1ab Probe, the above-described preferred S Gene Forward Primer, the above-described preferred S Gene Reverse Primer and the above-described preferred S Gene Probe.

The containers of such kits will be vials, tubes, etc. and the reagents may be in liquid form or may be lyophilized. Alternatively, such containers will be a multi-chambered, fluidic device that is capable of processing the amplification of such primers. For example, the kits of the present invention may be a Direct Amplification Disc (U.S. Pat. No. 9,067,205) that has been preloaded with reagents for amplifying the above-described SARS-CoV-2 gene sequences.

VII. Embodiments of the Invention

Having now generally described the invention, the same will be more readily understood through reference to the following numbered Embodiments ("E"), which are provided by way of illustration and are not intended to be limiting of the present invention unless specified:

E1. A detectably labeled oligonucleotide that is capable of specifically hybridizing to a SARS-CoV-2 polynucleotide, wherein the detectably labeled oligonucleotide has a nucleotide sequence that is able to specifically hybridize to an oligonucleotide having a nucleotide sequence that consists of the nucleotide sequence of SEQ ID NO:3, SEQ ID NO:4, SEQ ID NO:7 or SEQ ID NO:8.

E2. The detectably labeled oligonucleotide of E1, wherein the oligonucleotide has a nucleotide sequence that is able to specifically hybridize to an oligonucleotide having a nucleotide sequence that consists of the nucleotide sequence of SEQ ID NO:3 or SEQ ID NO:4.

E3. The detectably labeled oligonucleotide of E1, wherein the oligonucleotide has a nucleotide sequence that is able to specifically hybridize to an oligonucleotide having a nucleotide sequence that consists of the nucleotide sequence of SEQ ID NO:7 or SEQ ID NO:8.

E4. A kit for detecting the presence of SARS-CoV-2 in a clinical sample, wherein the kit comprises a detectably labeled oligonucleotide that is capable of specifically hybridizing to a SARS-CoV-2 polynucleotide, wherein the detectably labeled oligonucleotide has a nucleotide sequence that is able to specifically hybridize to an oligonucleotide having the nucleotide sequence of SEQ ID NO:3, SEQ ID NO:4, SEQ ID NO:7 or SEQ ID NO:8.

E5. The kit of E4, wherein the detectably labeled oligonucleotide has a nucleotide sequence that is able to specifically hybridize to an oligonucleotide having the nucleotide sequence of SEQ ID NO:3 or SEQ ID NO:4, and wherein the kit permits a determination of the presence or absence of the SARS-CoV-2 ORF1ab in a clinical sample.

E6. The kit of E4, wherein the detectably labeled oligonucleotide has a nucleotide sequence that is able to specifically hybridize to an oligonucleotide having the nucleotide sequence of SEQ ID NO:7 or SEQ ID NO:8, and wherein the kit permits a determination of the presence or absence of the SARS-CoV-2 S gene in a clinical sample.

E7. The kit of E4, wherein the kit comprises two detectably labeled oligonucleotides, wherein the detectable labels of the oligonucleotides are distinguishable, and wherein one of the two detectably labeled oligonucleotides has a nucleotide sequence that is able to specifically hybridize to an oligonucleotide having the nucleotide sequence of SEQ ID NO:3 or SEQ ID NO:4, and the second of the two detectably labeled oligonucleotides has a nucleotide sequence that is able to specifically hybridize to an oligonucleotide having the nucleotide sequence of SEQ ID NO:7 or SEQ ID NO:8.

E8. The kit of any one of E7, wherein the distinguishable detectable labels of the oligonucleotides are fluorescent labels.

E9. The kit of any one E4-E8, wherein at least one of the detectably labeled oligonucleotides is a TaqMan probe, a molecular beacon probe, a scorpion primer-probe probe or a HyBeacon™ probe.

E10. The kit of any one of E4 or E6-E9, wherein the kit permits the detection of the D614G polymorphism of the S gene of SARS-CoV-2.

E11. The kit of any one of E4-E10, wherein the kit is a multi-chambered, fluidic device.

E12. The kit of any one of E4-E11, wherein the detectably labeled oligonucleotide is fluorescently labeled.

E13. A method for detecting the presence of SARS-CoV-2 in a clinical sample, wherein the method comprises incubating the clinical sample in vitro in the presence of a detectably labeled oligonucleotide that is capable of specifically hybridizing to a SARS-CoV-2 polynucleotide, wherein the detectably labeled oligonucleotide has a nucleotide sequence that is able to specifically hybridize to an oligonucleotide having the nucleotide sequence of SEQ ID NO:3, SEQ ID NO:4, SEQ ID NO:7 or SEQ ID NO:8; wherein the method detects the presence of SARS-CoV-2 in the clinical sample by detecting the presence of SARS-CoV-2 ORF1ab and/or SARS-CoV-2 S gene.

E14. The method of E13, wherein the detectably labeled oligonucleotide has a nucleotide sequence that is able to specifically hybridize to an oligonucleotide having the nucleotide sequence of SEQ ID NO:3 or SEQ ID NO:4, and wherein the method detects the presence of SARS-CoV-2 in the clinical sample by detecting the presence of SARS-CoV-2 ORF1ab.

E15. The method of E14, wherein the method comprises a PCR amplification of the SARS-CoV-2 polynucleotide.

E16. The method of any one of E14, wherein the detectably labeled oligonucleotide is a TaqMan probe.

E17. The method of E16, wherein the detectably labeled oligonucleotide is a TaqMan ORF1ab Probe, and wherein the method comprises:

(I) incubating the clinical sample in vitro in the presence of:

(1) a reverse transcriptase and a DNA polymerase that has a 5→3' exonuclease activity;

(2) a Forward (or sense strand) ORF1ab Primer;

(3) a Reverse (or antisense strand) ORF1ab Primer; and (4) the TaqMan ORF1ab Probe, wherein such probe is capable of detecting the presence of a SARS-CoV-2 ORF1ab oligonucleotide that is amplified by conducting PCR in the presence of such Forward and Reverse ORf1ab Primers, wherein the TaqMan ORF1ab Probe comprises a 5' terminus and a 3' terminus, and has a SARS-CoV-2 oligonucleotide domain whose nucleotide sequence consists of, consists essentially of, comprises, or is a variant of the nucleotide sequence of. SEQ ID NO:9, SEQ ID NO:10, any of SEQ ID NOs:127-146, or any of SEQ ID NOs:147-166, wherein the 5' terminus of the oligonucleotide is labeled with a fluorophore and the 3' terminus of the oligonucleotide is complexed to a quencher of such fluorophore.

wherein the incubation is in a reaction under conditions sufficient to permit:

(a) the Forward and Reverse ORF1ab Primers to mediate a polymerase chain reaction amplification of a region of the ORF1ab of SARS-CoV-2 to thereby produce amplified ORF1ab oligonucleotide molecules, if the SARS-CoV-2 is present in the clinical sample;

(b) the TaqMan ORF1ab Probe to hybridize to amplified ORF1ab oligonucleotide molecules; and (c) the 5→3' exonuclease activity to hydrolyze hybridized TaqMan ORF1ab Probe, to thereby separate the fluorophore thereof from the quencher thereof and cause a fluorescent signal to become detectable; and (II) determining whether the SARS-CoV-2 is present in the clinical sample by determining whether a fluorescent signal of the fluorophore has become detectable.

E18. The method of any one of claims E14-E15, wherein the detectably labeled oligonucleotide is a molecular beacon probe.

E19. The method of E18, wherein the detectably labeled oligonucleotide is a Molecular Beacon ORF1ab Probe, and wherein the method comprises:

(I) incubating the clinical sample in vitro in the presence of:

(1) a reverse transcriptase and a DNA polymerase;

(2) a Forward (or sense strand) ORF1ab Primer;

(3) a Reverse (or antisense strand) ORF1ab Primer; and (4) the Molecular Beacon ORF1ab Probe, wherein such probe is capable of detecting the presence of a SARS-CoV-2 ORF1ab oligonucleotide that is amplified by conducting PCR in the presence of such Forward and Reverse ORF1ab Primers, wherein the Molecular Beacon ORF1ab Probe comprises a SARS-CoV-2 ORF1ab oligonucleotide domain that is flanked by a 5' oligonucleotide and a 3' oligonucleotide, wherein such 5' oligonucleotide and such 3' oligonucleotide are at least substantially complementary to one another, and wherein at least one of such 5' oligonucleotide and such 3' oligonucleotide is detectably labeled and another of such 5' oligonucleotide and such 3' oligonucleotide is complexed to a quencher or an acceptor of such detectable label, wherein the SARS-CoV-2 ORF1ab oligonucleotide domain of the Molecular Beacon ORF1ab Probe has a nucleotide sequence that consists of, consists essentially of, comprises, or is a variant of the nucleotide sequence of: SEQ ID NO:9, SEQ ID NO:10, any of SEQ ID NOs:127-146, or any of SEQ ID NOs:147-166;

wherein the incubation is in a reaction under conditions sufficient to permit:

(a) the Forward and Reverse ORF1ab Primers to mediate a polymerase chain reaction amplification of a region of the ORF1ab of SARS-CoV-2 to thereby produce amplified ORF1ab oligonucleotide molecules, if the SARS-CoV-2 is present in the clinical sample;

(b) the Molecular Beacon ORF1ab Probe to hybridize to amplified ORF1ab oligonucleotide molecules, thereby separating the fluorophore thereof from the quencher thereof and causing a fluorescent signal to become detectable; and (II) determining whether the SARS-CoV-2 is present in the clinical sample by determining whether a fluorescent signal of the fluorophore has become detectable.

E20. The method of any of E14-E15, wherein the detectably labeled oligonucleotide is a scorpion primer-probe.

E21. The method of E20, wherein the detectably labeled oligonucleotide is an ORF1ab Scorpion Primer-Probe, and wherein the method comprises:

(I) incubating the clinical sample in vitro in the presence of:

(1) a reverse transcriptase and a DNA polymerase;

(2) a Forward (or sense strand) ORF1ab Primer;

(3) a Reverse (or antisense strand) ORF1ab Primer; and (4) the ORF1ab Scorpion Primer-Probe, wherein such probe is capable of detecting the presence of a SARS-CoV-2 ORF1ab oligonucleotide that is amplified by conducting PCR in the presence of such Forward and Reverse ORF1ab Primers, wherein the ORF1ab Scorpion Primer-Probe comprises a SARS-CoV-2 oligonucleotide domain that is flanked by a 5' oligonucleotide and a 3' oligonucleotide, wherein such 5' oligonucleotide and such 3' oligonucleotide are at least substantially complementary to one another, and wherein at least one of such 5' oligonucleotide and such 3' oligonucleotide is detectably labeled and the other of such 5' oligonucleotide and such 3' oligonucleotide is complexed to a quencher or an acceptor of such detectably label, and wherein such 3' oligonucleotide further comprises a polymerization blocking moiety, and a PCR primer oligonucleotide positioned 3' from the blocking moiety, wherein the SARS-CoV-2 oligonucleotide domain of the ORF1ab Scorpion Primer-Probe has a nucleotide sequence that consists of, consists essentially of, comprises, or is a variant of the nucleotide sequence of. SEQ ID NO:9, SEQ ID NO:10, any of SEQ ID NOs:127-146, or any of SEQ ID NOs:147-166; and wherein the PCR primer polynucleotide is selected so that it is capable of hybridizing to a region of ORF1ab that is approximately 7 bases, 8 bases, 9 bases, 10 bases, or more preferably 11 bases upstream of an ORF1ab sequence that is the same as the sequence of the probe's ORF1ab polynucleotide domain (or differs from such sequence by 5, 4, 3, 2 or 1 nucleotide residues), such that extension of the PCR primer polynucleotide domain of the ORF1ab Scorpion Primer-Probe forms an extension product whose sequence is complementary to the probe's ORF1ab polynucleotide domain;

wherein the incubation is in a reaction under conditions sufficient to permit:

(a) the Forward and Reverse ORF1ab Primers to mediate a polymerase chain reaction amplification of a region of the ORF1ab of SARS-CoV-2 to thereby produce amplified ORF1ab oligonucleotide molecules, if the SARS-CoV-2 is present in the clinical sample;

(b) the ORF1ab Scorpion Primer-Probe to hybridize to amplified ORF1ab oligonucleotide molecules and be extended to form a domain that is complementary to the sequence of the SARS-CoV-2 oligonucleotide domain of the ORF1ab Scorpion Primer-Probe, such that, upon denaturation, the SARS-CoV-2 oligonucleotide domain of the ORF1ab Scorpion Primer-Probe hybridizes to the extended domain of the ORF1ab Scorpion Primer-Probe, and thereby prevents the complementary 5' oligonucleotide and 3' oligonucleotide domains of the probe from re-hybridizing to one another and attenuating the quenching of the detectable label;

(II) determining whether the SARS-CoV-2 is present in the clinical sample by determining whether a fluorescent signal of the fluorophore has become detectable.

E22. The method of any of E17, E19, or E21, wherein the Forward (or sense strand) ORF1ab Primer is an oligonucleotide having a nucleotide sequence that consists of, consists essentially of, comprises, or is a variant of, the nucleotide sequence of: SEQ ID NO:1 or any of SEQ ID NOs:17-28.

E23. The method of any of E17, E19, or E22, wherein the Reverse (or antisense strand) ORF1ab Primer is an oligonucleotide having a nucleotide sequence that consists of, consists essentially of, comprises, or is a variant of, the nucleotide sequence of. SEQ ID NO:2 or any of SEQ ID NOs:29-42.

E24. The method of E13, wherein the detectably labeled oligonucleotide has a nucleotide sequence that is able to specifically hybridize to an oligonucleotide having the nucleotide sequence of SEQ ID NO:7 or SEQ ID NO:8, and wherein the method detects the presence of SARS-CoV-2 in the clinical sample by detecting the presence of SARS-CoV-2 S gene.

E25. The method of E24, wherein the method comprises a PCR amplification of the SARS-CoV-2 polynucleotide.

E26. The method of E25, wherein the detectably labeled oligonucleotide is a TaqMan probe.

E27. The method of E26, wherein the detectably labeled oligonucleotide is a TaqMan S Gene Probe, and wherein the method comprises:

(I) incubating the clinical sample in vitro in the presence of:

(1) a reverse transcriptase and a DNA polymerase that has a 5→3' exonuclease activity;

(2) a Forward (or sense strand) S Gene Primer;

(3) a Reverse (or antisense strand) S Gene Primer; and (4) a TaqMan S Gene Probe capable of detecting the presence of a SARS-CoV-2 S Gene oligonucleotide that is amplified by conducting PCR in the presence of such Forward and Reverse S Gene Primers, wherein the TaqMan S Gene Probe comprises a 5' terminus and a 3' terminus, and has a SARS-CoV-2 oligonucleotide portion whose nucleotide sequence consists of, consists essentially of, comprises, or is a variant of the nucleotide sequence of: SEQ ID NO:11, SEQ ID NO:12, any of SEQ ID NOs:167-252, any of SEQ ID NOs:253-272, any of SEQ ID NOs:273-363, or any of SEQ ID NOs:364-381, wherein the 5' terminus of the oligonucleotide is labeled with a fluorophore and the 3' terminus of the oligonucleotide is complexed to a quencher of such fluorophore.

wherein the incubation is in a reaction under conditions sufficient to permit:

(a) the Forward and Reverse S Gene Primers to mediate a polymerase chain reaction amplification of a region of the S gene of SARS-CoV-2 to thereby produce amplified S gene oligonucleotide molecules, if the SARS-CoV-2 is present in the clinical sample;

(b) the TaqMan S Gene Probe to hybridize to amplified S gene oligonucleotide molecules; and (c) the 5→3' exonuclease activity to hydrolyze hybridized TaqMan S Gene Probe, to thereby separate the fluorophore thereof from the quencher thereof and cause a fluorescent signal to become detectable; and (II) determining whether the SARS-CoV-2 is present in the clinical sample by determining whether a fluorescent signal of the fluorophore has become detectable.

E28. The method of any one of E24-E25, wherein the detectably labeled oligonucleotide is a molecular beacon probe.

E29. The method of E28, wherein the detectably labeled oligonucleotide is a Molecular Beacon S Gene Probe, and wherein the method comprises:

(I) incubating the clinical sample in vitro in the presence of:

(1) a reverse transcriptase and a DNA polymerase;

(2) a Forward (or sense strand) S Gene Primer;

(3) a Reverse (or antisense strand) S Gene Primer; and (4) the Molecular Beacon S Gene Probe, wherein such probe is capable of detecting the presence of a SARS-CoV-2 S gene oligonucleotide that is amplified by conducting PCR in the presence of such Forward and Reverse S Gene Primers, wherein the Molecular Beacon S Gene Probe comprises a SARS-CoV-2 S gene oligonucleotide portion that is flanked by a 5' oligonucleotide and a 3' oligonucleotide, wherein such 5' oligonucleotide and such 3' oligonucleotide are at least substantially complementary to one another, and wherein at least one of such 5' oligonucleotide and such 3' oligonucleotide is detectably labeled and another of such 5' oligonucleotide and such 3' oligonucleotide is complexed to a quencher or an acceptor of such detectable label, wherein the SARS-CoV-2 S gene oligonucleotide portion of the Molecular Beacon S Gene Probe has a nucleotide sequence that consists of, consists essentially of, comprises, or is a variant of the nucleotide sequence of: SEQ ID NO:11, SEQ ID NO:12, any of SEQ ID NOs:167-252, any of SEQ ID NOs:253-272, any of SEQ ID NOs:273-363, or any of SEQ ID NOs:364-381;

wherein the incubation is in a reaction under conditions sufficient to permit:

(a) the Forward and Reverse S Gene Primers to mediate a polymerase chain reaction amplification of a region of the S Gene of SARS-CoV-2 to thereby produce amplified S gene oligonucleotide molecules, if the SARS-CoV-2 is present in the clinical sample;

(b) the Molecular Beacon S Gene Probe to hybridize to amplified S gene oligonucleotide molecules, thereby separating the fluorophore thereof from the quencher thereof and causing a fluorescent signal to become detectable; and (II) determining whether the SARS-CoV-2 is present in the clinical sample by determining whether a fluorescent signal of the fluorophore has become detectable.

E30. The method of any one of E24-E25, wherein the detectably labeled oligonucleotide is a scorpion primer-probe.

E31. The method of E30, wherein the detectably labeled oligonucleotide is an S Gene Scorpion Primer-Probe, and wherein the method comprises:

(I) incubating the clinical sample in vitro in the presence of:

(1) a reverse transcriptase and a DNA polymerase;

(2) a Forward (or sense strand) S Gene Primer;

(3) a Reverse (or antisense strand) S Gene Primer; and (4) the S Gene Scorpion Primer-Probe, wherein such probe is capable of detecting the presence of a SARS-CoV-2 S gene oligonucleotide that is amplified by conducting PCR in the presence of such Forward and Reverse S Gene Primers, wherein the S Gene Scorpion Primer-Probe comprises a SARS-CoV-2 oligonucleotide domain that is flanked by a 5' oligonucleotide and a 3' oligonucleotide, wherein such 5' oligonucleotide and such 3' oligonucleotide are at least substantially complementary to one another, and wherein at least one of such 5' oligonucleotide and such 3' oligonucleotide is detectably labeled and the other of such 5' oligonucleotide and such 3' oligonucleotide is complexed to a quencher or an acceptor of such detectably label, and wherein such 3' oligonucleotide further comprises a polymerization blocking moiety, and a PCR primer oligonucleotide positioned 3' from the blocking moiety, wherein the SARS-CoV-2 oligonucleotide domain of the S Gene Scorpion Primer-Probe has a nucleotide sequence that consists of, consists essentially of, comprises, or is a variant of the nucleotide sequence of. SEQ ID NO:11, SEQ ID NO:12, any of SEQ ID NOs:167-252, any of SEQ ID NOs:253-272, any of SEQ ID NOs:273-363, or any of SEQ ID NOs:364-381; and wherein the PCR primer polynucleotide is selected so that it is capable of hybridizing to a region of S gene that is approximately 7 bases, 8 bases, 9 bases, 10 bases, or more preferably 11 bases upstream of an S gene sequence that is the same as the sequence of the probe's S gene oligonucleotide domain (or differs from such sequence by 5, 4, 3, 2 or 1 nucleotide residues), such that extension of the PCR primer polynucleotide domain of the S Gene Scorpion Primer-Probe forms an extension product whose sequence is complementary to the probe's S Gene polynucleotide domain;

wherein the incubation is in a reaction under conditions sufficient to permit:

(a) the Forward and Reverse S Gene Primers to mediate a polymerase chain reaction amplification of a region of the S gene of SARS-CoV-2 to thereby produce amplified S gene oligonucleotide molecules, if the SARS-CoV-2 is present in the clinical sample;

(b) the S Gene Scorpion Primer-Probe to hybridize to amplified S gene oligonucleotide molecules and be extended to form a domain that is complementary to the sequence of the SARS-CoV-2 oligonucleotide domain of the S Gene Scorpion Primer-Probe, such that, upon denaturation, the SARS-CoV-2 oligonucleotide domain of the S Gene Scorpion Primer-Probe hybridizes to the extended domain of the S Gene Scorpion Primer-Probe, and thereby prevents the complementary 5' oligonucleotide and 3' oligonucleotide domains of the probe from re-hybridizing to one another and attenuating the quenching of the detectable label;

(II) determining whether the SARS-CoV-2 is present in the clinical sample by determining whether a fluorescent signal of the fluorophore has become detectable.

E32. The method of any of E27, E29, or E31, wherein the Forward (or sense strand) S Gene Primer is an oligonucleotide having a nucleotide sequence that consists of, consists essentially of, comprises, or is a variant of, the nucleotide sequence of: SEQ ID NO:5 or any of SEQ ID NOs:43-70, or any of SEQ ID NOs:71-84.

E33. The method of any of E27, E29, E31, or E32, wherein the Reverse (or antisense strand) S Gene Primer is an oligonucleotide having a nucleotide sequence that consists of, consists essentially of, comprises, or is a variant of, the nucleotide sequence of: SEQ ID NO:6, or any of SEQ ID NOs:85-112, or any of SEQ ID NOs:113-126.

E34. The method of any one of E24-E33, wherein the method detects the presence or absence of the D614G polymorphism of the S gene of SARS-CoV-2.

E35. The method of any one of E34, wherein the method employs a TaqMan probe, a molecular beacon probe, a scorpion primer-probe or a HyBeacon™ probe that comprises a SARS-CoV-2 oligonucleotide portion whose nucleotide sequence consists of, consists essentially of, comprises, or is a variant of the nucleotide sequence of: any of SEQ ID NOs:167-252, or any of SEQ ID NOs: 273-363.

E36. The method of E13, wherein the method comprises a LAMP amplification of the SARS-CoV-2 polynucleotide.

E37. The method of E13-E36, wherein the method employs a fluorescently labeled oligonucleotide.

E38. An oligonucleotide that comprises a 5' terminus and a 3' terminus, wherein the oligonucleotide has a SARS-CoV-2 oligonucleotide domain that has a nucleotide sequence that consists of, consists essentially of, comprises, or is a variant of, the nucleotide sequence of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, any of SEQ ID NOs:17-42, any of SEQ ID NOs:43-70, any of SEQ ID NOs:71-84, any of SEQ ID NOs:85-112, any of SEQ ID NOs:113-126, any of SEQ ID NOs:127-146, any of SEQ ID NOs:147-166, any of SEQ ID NOs:167-252, any of SEQ ID NOs:253-272, any of SEQ ID NOs:273-363, any of SEQ ID NOs:364-381, any of SEQ ID NOs:398-402, any of SEQ ID NOs:403-406, SEQ ID NO:411, or SEQ ID NO:412.

E39. An oligonucleotide, wherein the oligonucleotide is detectably labeled and comprises a 5' terminus and a 3' terminus, wherein the oligonucleotide has a SARS-CoV-2 oligonucleotide domain that consists essentially of the nucleotide sequence of: SEQ ID NO:9, SEQ ID NO:10, SEQ ID NO:11, SEQ ID NO:12, any of SEQ ID NOs: 43-70, any of SEQ ID NOs:85-112, any of SEQ ID NOs:127-146, any of SEQ ID NOs:147-166, any of SEQ ID NOs:167-252, any of SEQ ID NOs:253-272, any of SEQ ID NOs:273-363, any of SEQ ID NOs:364-381, any of SEQ ID NOs:403-406, SEQ ID NO:411, or SEQ ID NO:412.

E40. An oligonucleotide, wherein the oligonucleotide is detectably labeled and comprises a 5' terminus and a 3' terminus, wherein the oligonucleotide has a SARS-CoV-2 oligonucleotide domain that consists essentially of the nucleotide sequence of: SEQ ID NO:9, or SEQ ID NO:10.

E41 An oligonucleotide, wherein the oligonucleotide is detectably labeled and comprises a 5' terminus and a 3' terminus, wherein the oligonucleotide has a SARS-CoV-2 oligonucleotide domain that consists essentially of the nucleotide sequence of: SEQ ID NO:11, or SEQ ID NO:12.

E42. A TaqMan probe capable of detecting the presence of SARS-CoV-2, wherein the probe comprises an oligonucleotide, having a 5' terminus and a 3' terminus, that comprises a SARS-CoV-2 oligonucleotide domain whose nucleotide sequence consists of, consists essentially of, comprises, or is a variant of the nucleotide sequence of: SEQ ID NO:9, SEQ ID NO:10, SEQ ID NO:11, SEQ ID NO:12, any of SEQ ID NOs:127-146, any of SEQ ID NOs:147-166, any of SEQ ID NOs:167-252, any of SEQ ID NOs:253-272, any of SEQ ID NOs:273-363, any of SEQ ID NOs:364-381, wherein the 5' terminus of the oligonucleotide is labeled with a fluorophore and the 3' terminus of the oligonucleotide is complexed to a quencher of such fluorophore.

E43. A TaqMan probe, wherein the probe is capable of detecting the SARS-CoV-2 ORF1ab, and wherein the SARS-CoV-2 oligonucleotide domain of the probe has a nucleotide sequence that consists of, consists essentially of, comprises, or is a variant of, the nucleotide sequence of: SEQ ID NO:9, SEQ ID NO:10, any of SEQ ID NOs:127-146, or any of SEQ ID NOs:147-166.

E44. A TaqMan probe, wherein the probe is capable of detecting the SARS-CoV-2 S gene, and wherein the SARS-CoV-2 oligonucleotide domain of the probe has a nucleotide sequence that consists of, consists essentially of, comprises, or is a variant of, the nucleotide sequence of: SEQ ID NO:11, SEQ ID NO:12, any of SEQ ID NOs:167-252, any of SEQ ID NOs:253-272, any of SEQ ID NOs:273-363, or any of SEQ ID NOs:364-381.

E45. A TaqMan probe, wherein the probe is capable of detecting a polymorphism in the SARS-CoV-2 S gene, and wherein the SARS-CoV-2 oligonucleotide domain of the probe has a nucleotide sequence that consists of, consists essentially of, comprises, or is a variant of, the nucleotide sequence of: any of SEQ ID NOs:167-252, or any of SEQ ID NOs:273-363.

E46. A molecular beacon probe capable of detecting the presence of SARS-CoV-2, wherein the probe comprises an oligonucleotide, having a 5' terminus and a 3' terminus, that comprises a SARS-CoV-2 oligonucleotide domain whose nucleotide sequence consists of, consists essentially of, comprises, or is a variant of, the nucleotide sequence of: SEQ ID NO:9, SEQ ID NO:10, SEQ ID NO:11, SEQ ID NO:12, any of SEQ ID NOs:127-146, any of SEQ ID NOs:147-166, any of SEQ ID NOs:167-252, any of SEQ ID NOs:253-272, any of SEQ ID NOs:273-363, any of SEQ ID NOs:364-381, wherein such a SARS-CoV-2 oligonucleotide domain is flanked by a 5' oligonucleotide and a 3' oligonucleotide, wherein such 5' oligonucleotide and such 3' oligonucleotide are at least substantially complementary to one another, and wherein at least one of such 5' oligonucleotide and such 3' oligonucleotide is detectably labeled and another of such 5' oligonucleotide and such 3' oligonucleotide is complexed to a quencher or an acceptor of such detectable label.

E47. A molecular beacon probe, wherein the probe is capable of detecting the SARS-CoV-2 ORF1ab, and wherein the SARS-CoV-2 oligonucleotide domain of the probe has a nucleotide sequence that consists of, consists essentially of, comprises, or is a variant of, the nucleotide sequence of: SEQ ID NO:9, SEQ ID NO:10, any of SEQ ID NOs:127-146, or any of SEQ ID NOs:147-166.

E48. A molecular beacon probe, wherein the probe is capable of detecting the SARS-CoV-2 S gene, and wherein the SARS-CoV-2 oligonucleotide domain of the probe has a nucleotide sequence that consists of, consists essentially of, comprises, or is a variant of, the nucleotide sequence of: SEQ ID NO:11, SEQ ID NO:12, any of SEQ ID NOs:167-252, any of SEQ ID NOs:253-272, any of SEQ ID NOs:273-363, or any of SEQ ID NOs:364-381.

E49. A molecular beacon probe, wherein the probe is capable of detecting a polymorphism in the SARS-CoV-2 S gene, and wherein the SARS-CoV-2 oligonucleotide domain of the probe has a nucleotide sequence that consists of, consists essentially of, comprises, or is a variant of, the nucleotide sequence of: any of SEQ ID NOs:167-252, or any of SEQ ID NOs:273-363.

E50. A scorpion primer-probe capable of detecting the presence of SARS-CoV-2, wherein the probe comprises an oligonucleotide, having a 5' terminus and a 3' terminus, that comprises a SARS-CoV-2 oligonucleotide domain whose nucleotide sequence consists of, consists essentially of, comprises, or is a variant of, the nucleotide sequence of: SEQ ID NO:9, SEQ ID NO:10, SEQ ID NO:11, SEQ ID NO:12, any of SEQ ID NOs:127-146, any of SEQ ID NOs:147-166, any of SEQ ID NOs:167-252, any of SEQ ID NOs:253-272, any of SEQ ID NOs:273-363, any of SEQ ID NOs:364-381, wherein such a SARS-CoV-2 oligonucleotide domain is flanked by a 5' oligonucleotide and a 3' oligonucleotide, wherein such 5' oligonucleotide and such 3' oligonucleotide are at least substantially complementary to one another, and wherein at least one of such 5' oligonucleotide and such 3' oligonucleotide is detectably labeled and the other of such 5' oligonucleotide and such 3' oligonucleotide is complexed to a quencher or an acceptor of such detectably label, and wherein such 3' oligonucleotide further comprises a polymerization blocking moiety, and a PCR primer oligonucleotide positioned 3' from the blocking moiety.

E51. A scorpion primer-probe, wherein the probe is capable of detecting the SARS-CoV-2 ORF1ab, and wherein the SARS-CoV-2 oligonucleotide domain of the probe has a nucleotide sequence that consists of, consists essentially of, comprises, or is a variant of, the nucleotide sequence of: SEQ ID NO:9, SEQ ID NO:10, any of SEQ ID NOs:127-146, or any of SEQ ID NOs:147-166.

E52. A scorpion primer-probe, wherein the probe is capable of detecting the SARS-CoV-2 S gene, and wherein the SARS-CoV-2 oligonucleotide domain of the probe has a nucleotide sequence that consists of, consists essentially of, comprises, or is a variant of, the nucleotide sequence of: SEQ ID NO:11, SEQ ID NO:12, any of SEQ ID NOs:167-252, any of SEQ ID NOs:253-272, any of SEQ ID NOs:273-363, or any of SEQ ID NOs:364-381.

E53. A scorpion primer-probe, wherein the probe is capable of detecting a polymorphism in the SARS-CoV-2 S gene, and wherein the SARS-CoV-2 oligonucleotide domain of the probe has a nucleotide sequence that consists of, consists essentially of, comprises, or is a variant of, the nucleotide sequence of: any of SEQ ID NOs:167-252, or any of SEQ ID NOs:273-363.

E54. A scorpion primer-probe, wherein the probe is capable of detecting a polymorphism in the SARS-CoV-2 S gene, and wherein the PCR primer oligonucleotide has a nucleotide sequence that consists of, consists essentially of, comprises, or is a variant of, the nucleotide sequence of: any of SEQ ID NOs:43-70, or any of SEQ ID NOs:85-112.

E55. A HyBeacon™ probe capable of detecting the presence of SARS-CoV-2, wherein such probe comprises an oligonucleotide, having a 5' terminus and a 3' terminus, that comprises a SARS-CoV-2 oligonucleotide domain whose nucleotide sequence consists of, consists essentially of, comprises, or is a variant of, the nucleotide sequence of: SEQ ID NO:9, SEQ ID NO:10, SEQ ID NO:11, SEQ ID NO:12, any of SEQ ID NOs:127-146, any of SEQ ID NOs:147-166, any of SEQ ID NOs:167-252, any of SEQ ID NOs:253-272, any of SEQ ID NOs:273-363, any of SEQ ID NOs:364-381, wherein at least one nucleotide residue of such SARS-CoV-2 oligonucleotide domain is detectably labeled.

E56. A HyBeacon™ probe, wherein the probe is capable of detecting a polymorphism in the SARS-CoV-2 S gene, and wherein the SARS-CoV-2 oligonucleotide domain of the probe has a nucleotide sequence that consists of, consists essentially of, comprises, or is a variant of, the nucleotide sequence of: any of SEQ ID NOs:43-70, any of SEQ ID NOs:85-112, any of SEQ ID NOs:167-252, or any of SEQ ID NOs:273-363.

E57. The oligonucleotide of any of E39-E41, the TaqMan probe of any of E42-E45, the molecular beacon probe of any of E46-E49, the scorpion primer-probe of any of E50-E54, or the HyBeacon™ probe of any of E55-E56, wherein the detectable label is a fluorophore that has an excitation wavelength within the range of about 352-690 nm and an emission wavelength that is within the range of about 447-705 nm.

E58. The oligonucleotide, TaqMan probe, molecular beacon probe, scorpion primer-probe, or HyBeacon™ probe of E57, wherein the fluorophore is JOE or FAM.

E59. An oligonucleotide primer capable of amplifying an oligonucleotide portion of a SARS-CoV-2 polynucleotide present in a sample, wherein such oligonucleotide primer has a nucleotide sequence that consists of, consists essentially of, comprises, or is a variant of, the nucleotide sequence of: any of: SEQ ID NO:1, SEQ ID NO:2, SEQ ID NO:5, SEQ ID NO:6, any of SEQ ID NOs:17-28, any of SEQ ID NOs:29-42, any of SEQ ID NOs:43-70, any of SEQ ID NOs:71-84, any of SEQ ID NOs:85-112, any of SEQ ID NOs:113-126, or any of SEQ ID NOs:398-410.

E60. An oligonucleotide that has a nucleotide sequence that consists of, consists essentially of, comprises, or is a variant of, the nucleotide sequence of: SEQ ID NO:3 or SEQ ID NO:4.

E61. An oligonucleotide that has a nucleotide sequence that consists of, consists essentially of, comprises, or is a variant of, the nucleotide sequence of: SEQ ID NO:7 or SEQ ID NO:8.

EXAMPLES

Having now generally described the invention, the same will be more readily understood through reference to the following examples, which are provided by way of illustration and are not intended to be limiting of the present invention unless specified.

Example 1

Design of the Preferred Primers and Probes

Two sets of primers and probes were designed for the specific detection of SARS-CoV-2. Each primer/probe set on its own has been shown to provide sensitive and specific detection of SARS-CoV-2 with no detection or cross-reactivity to other coronaviruses. The SARS-CoV-2 Reference Sequence (NC_045512.2; Wuhan seafood market pneumonia virus isolate Wuhan-Hu-1, complete genome) was used to design such primers and probes.

The genome alignment of CoVs shows 58% identity of non-structural protein-coding region and 43% identity of structural proteins-coding region among different coronaviruses, with 54% identity at the whole genome level. This suggests that the non-structural proteins are more conserved and that the structural proteins exhibit greater diversity to fit their different environments (Chen, Y, et al. (2020) "*Emerging Coronaviruses: Genome Structure, Replication, And Pathogenesis*," J. Med. Virol. 92:418-423).

An analysis was conducted comparing the sequence of SARS-CoV-2 to the sequences of six other CoVs that can infect humans and cause respiratory diseases, in order to select a region that would be able to detect and specifically discriminate SARS-CoV-2 from such other CoVs. The analysis focused on genomic regions coding for structural proteins that are unique to this virus (Ji, W. et al. (2020) "*Cross-*Species *Transmission Of The Newly Identified Coronavirus* 2019-*nCoV*," J Med. Virol. 92:433-440). However, since it is possible that such regions might frequently recombine, in parallel, primers were designed against genomic regions coding for non-structural proteins.

Regarding the selection of the S gene, the SARS-CoV-2 may be generated by a homologous recombination within a region spanning between position 21500 and 24000 (2500 bp), which covers most of the S gene sequence (Chen, Y, et al. (2020) "*Emerging Coronaviruses: Genome Structure, Replication, And Pathogenesis*," J. Med. Virol. 92:418-423). In particular, inside the 2500 bp region, Chen, Y, et al. (2020) identified a unique sequence corresponding to the first 783 nucleotides at the 5' end of the S gene. BLAST analysis of a 783 nucleotide fragment provided no match with any sequence present in NCBI database, apart from the Wuhan seafood market pneumonia virus isolate Wuhan-Hu-14.

Regarding the selection of the ORF1ab sequence, the SARS-CoV-2 has a characteristic non-structural protein-coding region, covering about two-thirds of its genome length, and encoding 16 non-structural proteins (nsp1-16); the sequence shows 58% identity to the sequences of other CoVs (Chen, Y, et al. (2020) "*Emerging Coronaviruses: Genome Structure, Replication, And Pathogenesis,*" *J. Med. Virol.* 92:418-423). This approximately 20 kb region was chosen for the design of different primer sets specific for SARS-CoV-2.

All primer sets designed to target ORF1ab and the S gene have been tested on the SARS-CoV2 complete genome sequences available in the Global Initiative on Sharing All Influenza Data (GISAID) database, using Geneious Prime software. Sequences were mapped to the Reference Sequence of SARS-CoV-2 (NC_045512.2), and the identified primers and probes were tested against the consensus. The analysis showed that all regions recognized by the identified primers and probes have a homology of 100% with all available SARS-CoV-2 sequences.

In addition to verifying the specificity of the design, the sequences of the six CoVs that can infect humans causing respiratory diseases (i.e., HCoV-229E, HCoV-OC43, HCoV-NL63, HKU1, SARS-CoV and MERS-CoV) were examined. The accession numbers for such sequences are: NC_002645.1 (Human coronavirus 229E); NC_006213.1 (Human coronavirus OC43 strain ATCC VR-759); NC_005831.2 (Human Coronavirus NL63), NC_006577.2 (Human coronavirus HKU1), NC_004718.3 (SARS-coronavirus), and NC_019843.3 (Middle East Respiratory Syndrome coronavirus).

The sequences of the above-described preferred Forward and Reverse ORF1ab Primers (SEQ ID NO:1 and SEQ ID NO:2, respectively), the above-described preferred Forward and Reverse S Gene Primers (SEQ ID NO:5 and SEQ ID NO:6, respectively), the above-described preferred ORF1ab Probe (SEQ ID NO:9) and the above-described preferred S Gene Probe (SEQ ID NO:11) were identified through such an analysis.

Example 2

Specificity of the SARS-CoV-2 Assay

Upon in silico analysis, a SIMPLEXA® SARS-CoV-2 Direct assay using the above-described preferred Forward and Reverse ORF1ab and S Gene Primers and the above-described preferred ORF1ab and S Gene Probes were found to detect all SARS-CoV-2 virus strains and to exhibit no cross-reactivity with non-SARS-CoV-2 species.

In addition to the in silico analysis, an in vitro analysis of specificity was performed. The results of the in vitro specimen testing are presented in Table 14.

TABLE 14

| | | Qualitative % Detection (# Detected/# Tested) | | |
|---|---|---|---|---|
| Organism | Tested Concentration | S Gene (FAM) | ORF1ab (JOE) | Internal Control (Q670) |
| Adenovirus 1 | 1 × $10^5$ U/mL | 0% (0/3) | 0% (0/3) | 100% (3/3) |
| *Bordetella pertussis* | 1 × $10^6$ CFU/mL | 0% (0/3) | 0% (0/3) | 100% (3/3) |
| *Chlamydophila pneumoniae* | 1 × $10^6$ IFU/mL | 0% (0/3) | 0% (0/3) | 100% (3/3) |
| Coronavirus 229E | 1 × $10^5$ $TCID_{50}$/mL | 0% (0/3) | 0% (0/3) | 100% (3/3) |
| Coronavirus NL63 | 1 × $10^5$ U/mL | 0% (0/3) | 0% (0/3) | 100% (3/3) |
| Coronavirus OC43 | 1 × $10^5$ $TCID_{50}$/mL | 0% (0/3) | 0% (0/3) | 100% (3/3) |
| Enterovirus 68 | 1 × $10^5$ $TCID_{50}$/mL | 0% (0/3) | 0% (0/3) | 100% (3/3) |
| *Haemophilus influenzae* | 1 × $10^6$ CFU/mL | 0% (0/3) | 0% (0/3) | 100% (3/3) |
| Human metapneumovirus (hMPV-9) | 1 × $10^5$ $TCID_{50}$/mL | 0% (0/3) | 0% (0/3) | 100% (3/3) |
| Influenza A H3N2 Hong Kong 8/68 | 1 × $10^5$ $TCID_{50}$/mL | 0% (0/3) | 0% (0/3) | 100% (3/3) |
| Influenza B Phuket 3073/2013 | 1 × $10^5$ $TCID_{50}$/mL | 0% (0/3) | 0% (0/3) | 100% (3/3) |
| *Legionella pneumophilia* | 1 × $10^6$ CFU/mL | 0% (0/3) | 0% (0/3) | 100% (3/3) |
| MERS-Coronavirus (Extracted RNA) | 1:3 dilution | 0% (0/3) | 0% (0/3) | 100% (3/3) |
| *Mycobacterium tuberculosis* (Genomic DNA) | 1 × $10^6$ copies/mL | 0% (0/3) | 0% (0/3) | 100% (3/3) |
| Parainfluenza Type 1 | 1 × $10^5$ U/mL | 0% (0/3) | 0% (0/3) | 100% (3/3) |
| Parainfluenza Type 2 | 1 × $10^5$ U/mL | 0% (0/3) | 0% (0/3) | 100% (3/3) |
| Parainfluenza Type 3 | 1 × $10^5$ $TCID_{50}$/mL | 0% (0/3) | 0% (0/3) | 100% (3/3) |
| Parainfluenza Type 4A | 1 × $10^5$ U/mL | 0% (0/3) | 0% (0/3) | 100% (3/3) |
| Rhinovirus B14 | 1 × $10^5$ U/mL | 0% (0/3) | 0% (0/3) | 100% (3/3) |
| RSV A Long | 1 × $10^5$ $TCID_{50}$/mL | 0% (0/3) | 0% (0/3) | 100% (3/3) |
| RSV B Washington | 1 × $10^5$ $TCID_{50}$/mL | 0% (0/3) | 0% (0/3) | 100% (3/3) |
| SARS-Coronavirus (Purified RNA) | 1 × $10^5$ copies/mL | 0% (0/3) | 0% (0/3) | 100% (3/3) |

TABLE 14-continued

| | | Qualitative % Detection (# Detected/# Tested) | | |
|---|---|---|---|---|
| Organism | Tested Concentration | S Gene (FAM) | ORF1ab (JOE) | Internal Control (Q670) |
| SARS-Coronavirus HKU39849 (Extracted RNA) | 1:10 dilution | 0% (0/3) | 0% (0/3) | 100% (3/3) |
| *Streptococcus pneumoniae* | 1 × $10^6$ CFU/mL | 0% (0/3) | 0% (0/3) | 100% (3/3) |
| *Streptococcus pyogenes* | 1 × $10^6$ CFU/mL | 0% (0/3) | 0% (0/3) | 100% (3/3) |
| Human leukocytes (human genomic DNA) | 1 × $10^6$ cells/mL | 0% (0/3) | 0% (0/3) | 100% (3/3) |
| Pooled Human Nasal Fluid | 1:5 dilution | 0% (0/3) | 0% (0/3) | 100% (3/3) |

The assay was also found to demonstrate 100% specificity on a negative matrix (Universal Transport Medium (UTM); Copan Diagnostics). No not-specific signals were observed.

In conclusion, the above-described preferred Forward and Reverse ORF1ab Primers and the above-described preferred ORF1ab Probe were found to be capable of detecting SARS-CoV-2 without exhibiting cross-reactivity to human DNA, or to DNA (or cDNA) of other pathogens. Additionally, the above-described preferred Forward and Reverse S Gene Primers and the above-described preferred S Gene Probe were found to be capable of detecting SARS-CoV-2 without exhibiting cross-reactivity to human DNA, or to DNA (or cDNA) of other pathogens. The assay is thus specific for SARS-CoV-2.

The observation that the assay of the present invention reports the detection of SARS-CoV-2 when only one of such sets of primers and probes is employed (i.e., either a probe and primer set that targets ORF1ab or a probe and primer set that targets the S gene) indicates that by using both such sets of probes and primers, one can increase assay sensitivity in cases of low viral loads and that the accuracy of the assay will not be jeopardized by any point mutation which may occur during COVID-19 spread across the population.

To demonstrate the improvement in assay sensitivity obtained using both sets of preferred primers and probes, a preparation of SARS-CoV2 viral particles (from isolate 2019nCoV/italy-INMI1) in an oral swab-UTM matrix was tested at doses ranging from $10^{-5}$ to $10^{-8}$ $TCID_{50}$/mL. As reported in Table 15 and Table 16, relative to the detection of either ORF1ab sequences or S gene sequences, the use of both sets of preferred primers and probes was found to increase the sensitivity of the assay, achieving the detection of the $10^{-8}$ $TCID_{50}$/mL dose instead of $10^{-7}$ $TCID_{50}$/mL.

TABLE 15

| Samples | | | ORF1ab | S Gene | |
|---|---|---|---|---|---|
| Reps | $TCID_{50}$/mL | Copies/mL | Target | Target | Result |
| 1-40 | $10^{-7}$ | 4000 | Detected | Detected | Positive |
| 1-3 | $10^{-8}$ | 400 | Detected | Detected | Positive |
| 4 | | | Detected | Not Detected | Positive |
| 5 | | | Not Detected | Detected | Positive |
| 6 | | | Not Detected | Not Detected | Negative |
| 7 | | | Detected | Detected | Positive |
| 8 | | | Not Detected | Detected | Positive |
| 9 | | | Detected | Detected | Positive |
| 10 | | | Not Detected | Not Detected | Negative |
| 11 | | | Detected | Not Detected | Positive |
| 12-13 | | | Detected | Detected | Positive |

TABLE 15-continued

| Samples | | | ORF1ab | S Gene | |
|---|---|---|---|---|---|
| Reps | $TCID_{50}$/mL | Copies/mL | Target | Target | Result |
| 14 | | | Not Detected | Detected | Positive |
| 15-18 | | | Detected | Detected | Positive |
| 19 | | | Not Detected | Not Detected | Negative |

The results obtained at $10^{-8}$$TCID_{50}$/mL (400 copies/mL) are summarized in Table 16.

TABLE 16

| (Assay Detection Capability at 400 viral RNA copies/mL) | | | |
|---|---|---|---|
| | ORF1ab | S Gene | ORF1ab and S Gene |
| Number of Replicates Detected | 13/19 | 14/19 | 16/19 |
| Percentage of Detection | 68% | 73.7% | 84.2% |

The data used in Table 16 was based on a viral dose of $10^{-8}$ $TCID_{50}$/mL (400 copies/mL). When the samples contained 500 viral RNA copies/mL, the assays of the present invention exhibited a 100% ability to detect SARS-CoV-2 (Table 17).

TABLE 17

| (Assay Detection Capability at 500 viral RNA copies/mL) | | | |
|---|---|---|---|
| | ORF1ab | S Gene | ORF1ab and S Gene |
| Number of Replicates Detected | 34/47 | 46/48 | 48/48 |
| Percentage of Detection | 72.3% | 95.8% | 100% |

This level of sensitivity (determined with genomic viral RNA) reflects the type of results one would obtain using clinical samples containing SARS-CoV-2. The assays of the present invention thus will provide healthcare workers with analytical indications that will enable them to better interpret the results of the assay in clinical practice.

Example 3

Diagnostic Accuracy of the SARS-CoV-2 Assay

In a comparison between the methods of the present invention and the reference method of Corman, V. M. et al. (2020) ("*Detection Of* 2019 *Novel Coronavirus* (2019-*nCoV*) *By Real-Time RT-PCR*," Eurosurveill. 25(3): 2000045), the lower limit of detection (LoD) for both target genes was found to be the same: 3.2 (CI: 2.9-3.8) log 10 cp/mL and 0.40 (CI: 0.2-1.5) $TCID_{50}$/mL for S gene while 3.2 log 10 (CI: 2.9-3.7) log 10 cp/mL and 0.4 (CI: 0.2-1.3) $TCID_{50}$/mL for ORF1ab. The LoD obtained with extracted viral RNA for both S gene or ORF1ab was 2.7 log 10 cp/mL. Crossreactive analysis performed in 20 nasopharyngeal swabs confirmed a 100% of clinical specificity of the assay. Clinical performances of the SIMPLEXA® COVID-19 Direct assay were assessed in 278 nasopharyngeal swabs tested in parallel with Corman's method. Concordance analysis showed an "almost perfect" agreement in SARS-CoV-2 RNA detection between the two assays, being x=0.938; SE=0.021; 95% CI=0.896-0.980, with the SIMPLEXA® COVID-19 Direct assay showing a slightly higher sensitivity relative to the reference Corman's method, identifying nearly 3% additional positive samples, and detecting SARS-CoV-2 in BAL samples that had been found to give invalid results with the reference method (Bordi, L. et al. (2020) "*Rapid And Sensitive Detection Of SARS-Cov-*2 *RNA Using The SIMPLEXA® COVID-*19 *Direct Assay*," J. Clin. Virol. 128:104416:1-5).

The methods of the present invention were found to have the lowest LoD (39±23 copies/ml) in a comparative study of different SARS-CoV-2 assays (Zhen, W. et al. (2020) "*Comparison of Four Molecular In Vitro Diagnostic Assays for the Detection of SARS-CoV-*2 *in Nasopharyngeal Specimens*," J. Clin. Microbiol. 58(8):e00743-20:1-8).

Similar findings that the methods of the present invention were more sensitive than other laboratory tests for SARS-CoV-2 have been reported by other research groups (Lieberman, J. A. et al. (2020) "*Comparison of Commercially Available and Laboratory-Developed Assays for In Vitro Detection of SARS-CoV-*2 *in Clinical Laboratories*," J. Clin. Microbiol. 58(8):e00821-20:1-6; Rhoads, D. D. et al. (2020) "*Comparison Of Abbott ID NOW™, DiaSorin SIMPLEXA®, And CDC FDA Emergency Use Authorization Methods For The Detection Of SARS-CoV-*2 *From Nasopharyngeal And Nasal Swabs From Individuals Diagnosed With COVID-*19," J. Clin. Microbiol. 58(8):e00760-20:1-2).

Cradic, K. et al. (2020) ("*Clinical Evaluation and Utilization of Multiple Molecular In Vitro Diagnostic Assays for the Detection of SARS-CoV-*2," Am. J. Clin. *Pathol.* 154(2): 201-207) found that the methods of the present invention were more sensitive than the Abbott ID NOW™ test, and as sensitive as the Roche COBAS® SARS-CoV-2 assay, despite not requiring sample processing steps of the Roche COBAS® assay or the Roche COBAS® assay's larger sample volume.

Fung, B. et. al. (2020) ("*Direct Comparison of SARS-CoV-*2 *Analytical Limits of Detection across Seven Molecular Assays*," J. Clin. Microbiol. 58(9):e01535-20:) found that the Roche COBAS® assay was more sensitive than the assays of the present invention, but required more time to produce diagnostic results; the study did not evaluate the impact of specimen matrix on the ability to detect virus or compatibility with different media types.

Liotti, F. M. et al. (2020) ("*Evaluation Of Three Commercial Assays For SARS-CoV-*2 *Molecular Detection In Upper Respiratory Tract Samples*," Eur. J. Clin. *Microbiol.* Infect. Dis. 10.1007/s10096-020-04025-0:1-9), likewise found that the methods of the present invention provided an accurate diagnostic test for SARS-CoV-2.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A detectably labeled oligonucleotide that is capable of specifically hybridizing to a SARS-CoV-2 polynucleotide, wherein the nucleotide sequence of said detectably labeled oligonucleotide that is capable of specifically hybridizing to said SARS-CoV-2 polynucleotide is able to specifically hybridize to an oligonucleotide having a nucleotide sequence that consists essentially of the nucleotide sequence of SEQ ID NO:3, SEQ ID NO:4, SEQ ID NO:7 or SEQ ID NO:8.

2. The detectably labeled oligonucleotide of claim 1, wherein the nucleotide sequence of said oligonucleotide that is capable of specifically hybridizing to said SARS-CoV-2 polynucleotide is able to specifically hybridize to an oligonucleotide having a nucleotide sequence that consists essentially of the nucleotide sequence of SEQ ID NO:3 or SEQ ID NO:4.

3. The detectably labeled oligonucleotide of claim 1, wherein the nucleotide sequence of said oligonucleotide that is capable of specifically hybridizing to said SARS-CoV-2 polynucleotide is able to specifically hybridize to an oligonucleotide having a nucleotide sequence that consists essentially of the nucleotide sequence of SEQ ID NO:7 or SEQ ID NO:8.

4. A kit for detecting the presence of SARS-CoV-2 in a clinical sample, wherein said kit comprises (A) an oligonucleotide primer capable of amplifying a portion of a SARS-CoV-2 polynucleotide; and (B) a detectably labeled oligonucleotide that is capable of specifically hybridizing to said amplified portion of said SARS-CoV-2 polynucleotide, wherein the nucleotide sequence of said detectably labeled oligonucleotide that is capable of specifically hybridizing to said SARS-CoV-2 polynucleotide is able to specifically hybridize to an oligonucleotide having a nucleotide sequence that consists essentially of the nucleotide sequence of SEQ ID NO:3, SEQ ID NO:4, SEQ ID NO:7 or SEQ ID NO:8.

5. The kit of claim 4, wherein the nucleotide sequence of said detectably labeled oligonucleotide that is capable of specifically hybridizing to said SARS-CoV-2 polynucleotide is able to specifically hybridize to an oligonucleotide having a nucleotide sequence that consists essentially of the nucleotide sequence of SEQ ID NO:3 or SEQ ID NO:4, and wherein said kit permits a determination of the presence or absence of the SARS-CoV-2 ORF1ab in a clinical sample.

6. The kit of claim 4, wherein the nucleotide sequence of said detectably labeled oligonucleotide that is capable of specifically hybridizing to said SARS-CoV-2 polynucleotide is able to specifically hybridize to an oligonucleotide having a nucleotide sequence that consists essentially of the nucleotide sequence of SEQ ID NO:7 or SEQ ID NO:8, and wherein said kit permits a determination of the presence or absence of the SARS-CoV-2 S gene in a clinical sample.

7. The kit of claim 4, wherein said kit permits the detection of the D614G polymorphism of the S gene of SARS-CoV-2.

8. The kit of claim 4, wherein said kit is a multi-chambered, fluidic device.

9. The kit of claim 4, wherein said detectably labeled oligonucleotide is a TaqMan probe, a molecular beacon probe, a scorpion primer-probe, or a HyBeacon probe.

10. The kit of claim 4, wherein said detectably labeled oligonucleotide is fluorescently labeled.

11. The kit of claim 4, wherein said kit comprises two detectably labeled oligonucleotides, wherein the detectable labels of said oligonucleotides are distinguishable, and wherein the nucleotide sequence of one of said two detectably labeled oligonucleotides that is capable of specifically hybridizing to said SARS-CoV-2 polynucleotide is able to specifically hybridize to an oligonucleotide having a nucleotide sequence that consists essentially of the nucleotide sequence of SEQ ID NO:3 or SEQ ID NO:4, and the nucleotide sequence of the second of said two detectably labeled oligonucleotides that is capable of specifically hybridizing to said SARS-CoV-2 polynucleotide is able to specifically hybridize to an oligonucleotide having a nucleotide sequence that consists essentially of the nucleotide sequence of SEQ ID NO:7 or SEQ ID NO:8.

12. The kit of claim 11, wherein at least one of said detectably labeled oligonucleotides is a TaqMan probe, a molecular beacon probe, a scorpion primer-probe or a HyBeacon™ probe.

13. The kit of claim 11, wherein the distinguishable detectable labels of said oligonucleotides are fluorescent labels.

14. The kit of claim 11, wherein said kit permits the detection of the D614G polymorphism of the S gene of SARS-CoV-2.

15. The kit of claim 11, wherein said kit is a multi-chambered, fluidic device.

16. The kit of claim 11, wherein said detectably labeled oligonucleotide is fluorescently labeled.

17. A method for detecting the presence of SARS-CoV-2 in a clinical sample, wherein said method comprises incubating said clinical sample in vitro in the presence of a detectably labeled oligonucleotide that is capable of specifically hybridizing to a SARS-CoV-2 ORF1ab or SARS-CoV-2 S gene polynucleotide, wherein the nucleotide sequence of said detectably labeled oligonucleotide that is capable of specifically hybridizing to said SARS-CoV-2 polynucleotide is able to specifically hybridize to an oligonucleotide having a nucleotide sequence that consists essentially of the nucleotide sequence of SEQ ID NO:3, SEQ ID NO:4, SEQ ID NO:7 or SEQ ID NO:8; wherein said method detects the presence of SARS-CoV-2 in said clinical sample by detecting the presence of SARS-CoV-2 ORF1ab and/or SARS-CoV-2 S gene.

18. The method of claim 17, wherein the nucleotide sequence of said detectably labeled oligonucleotide that is capable of specifically hybridizing to said SARS-CoV-2 polynucleotide is able to specifically hybridize to an oligonucleotide having a nucleotide sequence that consists essentially of the nucleotide sequence of SEQ ID NO:3 or SEQ ID NO:4, and wherein said method detects the presence of SARS-CoV-2 in said clinical sample by detecting the presence of SARS-CoV-2 ORF1ab.

19. The method of claim 17, wherein the nucleotide sequence of said detectably labeled oligonucleotide that is capable of specifically hybridizing to said SARS-CoV-2 polynucleotide is able to specifically hybridize to an oligonucleotide having a nucleotide sequence that consists essentially of the nucleotide sequence of SEQ ID NO:7 or SEQ ID NO:8, and wherein said method detects the presence of SARS-CoV-2 in said clinical sample by detecting the presence of SARS-CoV-2 S gene.

20. The method of claim 19, wherein said method detects the presence or absence of the D614G polymorphism of the S gene of SARS-CoV-2.

21. The method of claim 17, wherein said method comprises a PCR amplification of said SARS-CoV-2 polynucleotide.

22. The method of claim 17, wherein said detectably labeled oligonucleotide is a TaqMan probe, a molecular beacon probe, a scorpion primer-probe, or a HyBeacon probe.

23. The method of claim 17, wherein said method comprises a LAMP amplification of said SARS-CoV-2 polynucleotide.

24. The method of claim 17, wherein said detectably labeled oligonucleotide is fluorescently labeled.

25. The method of claim 17, wherein said method comprises incubating said clinical sample in the presence of two detectably labeled oligonucleotides, wherein the detectable labels of said oligonucleotides are distinguishable, and wherein the nucleotide sequence of one of said two detectably labeled oligonucleotides that is capable of specifically hybridizing to said SARS-CoV-2 polynucleotide is able to specifically hybridize to an oligonucleotide having a nucleotide sequence that consists essentially of the nucleotide sequence of SEQ ID NO:3 or SEQ ID NO:4, and the nucleotide sequence of the second of said two detectably labeled oligonucleotides that is capable of specifically hybridizing to said SARS-CoV-2 polynucleotide is able to specifically hybridize to an oligonucleotide having a nucleotide sequence that consists essentially of the nucleotide sequence of SEQ ID NO:7 or SEQ ID NO:8; wherein said method detects the presence of SARS-CoV-2 in said clinical sample by detecting the presence of both SARS-CoV-2 ORF1ab and SARS-CoV-2 S gene.

26. The method of claim 25, wherein said method detects the presence or absence of the D614G polymorphism of the S gene of SARS-CoV-2.

27. The method of claim 25, wherein said method comprises a PCR amplification of said SARS-CoV-2 polynucleotide.

28. The method of claim 25, wherein said detectably labeled oligonucleotide is a TaqMan probe, a molecular beacon probe, a scorpion primer-probe, or a HyBeacon probe.

29. The method of claim 25, wherein said method comprises a LAMP amplification of said SARS-CoV-2 polynucleotide.

30. The method of claim 25, wherein said detectably labeled oligonucleotide is fluorescently labeled.

* * * * *

SEQUENCE LISTING

```
<160> NUMBER OF SEQ ID NOS: 415

<210> SEQ ID NO 1
<211> LENGTH: 20
<212> TYPE: DNA
<213> ORGANISM: SARS-CoV-2 Coronavirus
<220> FEATURE:
<221> NAME/KEY: misc_feature
<222> LOCATION: (1)..(20)
<223> OTHER INFORMATION: Preferred Forward ORF1ab Gene Primer

<400> SEQUENCE: 1

atggtagagt tgatggtcaa                                                  20


<210> SEQ ID NO 2
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: Preferred Reverse ORF1ab Gene Primer

<400> SEQUENCE: 2

taagactagc ttgtttggga                                                  20


<210> SEQ ID NO 3
<211> LENGTH: 117
<212> TYPE: DNA
<213> ORGANISM: SARS-CoV2 Coronavirus
<220> FEATURE:
<221> NAME/KEY: misc_feature
<222> LOCATION: (1)..(117)
<223> OTHER INFORMATION: Amplified Region of ORF1ab Gene ("Sense"
      Strand)

<400> SEQUENCE: 3

atggtagagt tgatggtcaa gtagacttat ttagaaatgc ccgtaatggt gttcttatta      60

cagaaggtag tgttaaaggt ttacaaccat ctgtaggtcc caaacaagct agtctta        117


<210> SEQ ID NO 4
<211> LENGTH: 117
<212> TYPE: DNA
<213> ORGANISM: SARS-CoV2 Coronavirus
<220> FEATURE:
<221> NAME/KEY: misc_feature
<222> LOCATION: (1)..(117)
<223> OTHER INFORMATION: Amplified Region of ORF1ab Gene ("Anti-Sense"
      Strand)

<400> SEQUENCE: 4

taagactagc ttgtttggga cctacagatg gttgtaaacc tttaacacta ccttctgtaa      60

taagaacacc attacgggca tttctaaata agtctacttg accatcaact ctaccat        117


<210> SEQ ID NO 5
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: Preferred Forward S Gene Primer

<400> SEQUENCE: 5

ctaaccaggt tgctgttctt                                                  20
```

<210> SEQ ID NO 6
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: Preferred Reverse S Gene Primer

<400> SEQUENCE: 6
cctgtagaat aaacacgcca 20

<210> SEQ ID NO 7
<211> LENGTH: 103
<212> TYPE: DNA
<213> ORGANISM: SARS-CoV2 Coronavirus
<220> FEATURE:
<221> NAME/KEY: misc_feature
<222> LOCATION: (1)..(103)
<223> OTHER INFORMATION: Amplified Region of S Gene ("Sense" Strand)

<400> SEQUENCE: 7
ctaaccaggt tgctgttctt tatcaggatg ttaactgcac agaagtccct gttgctattc 60
atgcagatca acttactcct acttggcgtg tttattctac agg 103

<210> SEQ ID NO 8
<211> LENGTH: 103
<212> TYPE: DNA
<213> ORGANISM: SARS-CoV2 Coronavirus
<220> FEATURE:
<221> NAME/KEY: misc_feature
<222> LOCATION: (1)..(103)
<223> OTHER INFORMATION: Amplified Region of S Gene ("Anti-Sernse"
Strand)

<400> SEQUENCE: 8
cctgtagaat aaacacgcca agtaggagta agttgatctg catgaatagc aacagggact 60
tctgtgcagt taacatcctg ataaagaaca gcaacctggt tag 103

<210> SEQ ID NO 9
<211> LENGTH: 27
<212> TYPE: DNA
<213> ORGANISM: SARS-CoV2 Coronavirus
<220> FEATURE:
<221> NAME/KEY: misc_feature
<222> LOCATION: (1)..(27)
<223> OTHER INFORMATION: Preferred ORF1ab Gene Probe

<400> SEQUENCE: 9
tgcccgtaat ggtgttctta ttacaga 27

<210> SEQ ID NO 10
<211> LENGTH: 27
<212> TYPE: DNA
<213> ORGANISM: SARS-CoV2 Coronavirus
<220> FEATURE:
<221> NAME/KEY: misc_feature
<222> LOCATION: (1)..(27)
<223> OTHER INFORMATION: Preferred Complement ORF1ab Probe

<400> SEQUENCE: 10
tctgtaataa gaacaccatt acgggca 27

<210> SEQ ID NO 11
<211> LENGTH: 21
<212> TYPE: DNA
<213> ORGANISM: SARS-CoV2 Coronavirus
<220> FEATURE:
<221> NAME/KEY: misc_feature
<222> LOCATION: (1)..(21)
<223> OTHER INFORMATION: Preferred S Gene Probe

<400> SEQUENCE: 11
tgcacagaag tccctgttgc t 21

<210> SEQ ID NO 12
<211> LENGTH: 21
<212> TYPE: DNA
<213> ORGANISM: SARS-CoV2 Coronavirus
<220> FEATURE:
<221> NAME/KEY: misc_feature
<222> LOCATION: (1)..(21)
<223> OTHER INFORMATION: Preferred Complement S Gene Probe

<400> SEQUENCE: 12
agcaacaggg acttctgtgc a 21

<210> SEQ ID NO 13
<211> LENGTH: 16
<212> TYPE: DNA
<213> ORGANISM: Bacteriophage MS2
<220> FEATURE:
<221> NAME/KEY: misc_feature
<222> LOCATION: (1)..(16)
<223> OTHER INFORMATION: Forward MS2 Phage Internal Control Primer

<400> SEQUENCE: 13
tgctcgcgga tacccg 16

<210> SEQ ID NO 14
<211> LENGTH: 20
<212> TYPE: DNA
<213> ORGANISM: Bacteriophage MS2
<220> FEATURE:
<221> NAME/KEY: misc_feature
<222> LOCATION: (1)..(20)
<223> OTHER INFORMATION: Reverse MS2 Phage Internal Control Primer

<400> SEQUENCE: 14
aacttgcgtt ctcgagcgat 20

<210> SEQ ID NO 15
<211> LENGTH: 24
<212> TYPE: DNA
<213> ORGANISM: Bacteriophage MS2
<220> FEATURE:
<221> NAME/KEY: misc_feature
<222> LOCATION: (1)..(24)
<223> OTHER INFORMATION: MS2 Phage Internal Control Probe

<400> SEQUENCE: 15
acctcgggtt tccgtcttgc tcgt 24

<210> SEQ ID NO 16
<211> LENGTH: 3819
<212> TYPE: DNA
<213> ORGANISM: SARS-CoV2 Coronavirus
<220> FEATURE:
<221> NAME/KEY: misc_feature
<222> LOCATION: (1)..(3819)
<223> OTHER INFORMATION: S Gene of SARS-CoV-2 of GenBank NC_045512

<400> SEQUENCE: 16
atgtttgttt ttcttgtttt attgccacta gtctctagtc agtgtgttaa tcttacaacc 60

-continued

```
agaactcaat taccccctgc atacactaat tctttcacac gtggtgttta ttaccctgac    120
aaagttttca gatcctcagt tttacattca actcaggact tgttcttacc tttcttttcc    180
aatgttactt ggttccatgc tatacatgtc tctgggacca atggtactaa gaggtttgat    240
aaccctgtcc taccatttaa tgatggtgtt tattttgctt ccactgagaa gtctaacata    300
ataagaggct ggatttttgg tactacttta gattcgaaga cccagtccct acttattgtt    360
aataacgcta ctaatgttgt tattaaagtc tgtgaatttc aattttgtaa tgatccattt    420
ttgggtgttt attaccacaa aaacaacaaa agttggatgg aaagtgagtt cagagtttat    480
tctagtgcga ataattgcac ttttgaatat gtctctcagc cttttcttat ggaccttgaa    540
ggaaaacagg gtaatttcaa aaatcttagg gaatttgtgt ttaagaatat tgatggttat    600
tttaaaatat attctaagca cacgcctatt aatttagtgc gtgatctccc tcagggtttt    660
tcggctttag aaccattggt agatttgcca ataggtatta acatcactag gtttcaaact    720
ttacttgctt tacatagaag ttatttgact cctggtgatt cttcttcagg ttggacagct    780
ggtgctgcag cttattatgt gggttatctt caacctagga cttttctatt aaaatataat    840
gaaaatggaa ccattacaga tgctgtagac tgtgcacttg accctctctc agaaacaaag    900
tgtacgttga aatccttcac tgtagaaaaa ggaatctatc aaacttctaa ctttagagtc    960
caaccaacag aatctattgt tagatttcct aatattacaa acttgtgccc ttttggtgaa   1020
gtttttaacg ccaccagatt tgcatctgtt tatgcttgga acaggaagag aatcagcaac   1080
tgtgttgctg attattctgt cctatataat tccgcatcat tttccacttt taagtgttat   1140
ggagtgtctc ctactaaatt aaatgatctc tgctttacta atgtctatgc agattcattt   1200
gtaattagag gtgatgaagt cagacaaatc gctccagggc aaactggaaa gattgctgat   1260
tataattata aattaccaga tgattttaca ggctgcgtta tagcttggaa ttctaacaat   1320
cttgattcta aggttggtgg taattataat tacctgtata gattgtttag gaagtctaat   1380
ctcaaacctt ttgagagaga tatttcaact gaaatctatc aggccggtag cacaccttgt   1440
aatggtgttg aaggttttaa ttgttacttt cctttacaat catatggttt ccaacccact   1500
aatggtgttg gttaccaacc atacagagta gtagtacttt cttttgaact tctacatgca   1560
ccagcaactg tttgtggacc taaaaagtct actaatttgg ttaaaaacaa atgtgtcaat   1620
ttcaacttca atggtttaac aggcacaggt gttcttactg agtctaacaa aaagtttctg   1680
cctttccaac aatttggcag agacattgct gacactactg atgctgtccg tgatccacag   1740
acacttgaga ttcttgacat tacaccatgt tcttttggtg gtgtcagtgt tataacacca   1800
ggaacaaata cttctaacca ggttgctgtt ctttatcagg atgttaactg cacagaagtc   1860
cctgttgcta ttcatgcaga tcaacttact cctacttggc gtgtttattc tacaggttct   1920
aatgtttttc aaacacgtgc aggctgttta ataggggctg aacatgtcaa caactcatat   1980
gagtgtgaca tacccattgg tgcaggtata tgcgctagtt atcagactca gactaattct   2040
cctcggcggg cacgtagtgt agctagtcaa tccatcattg cctacactat gtcacttggt   2100
gcagaaaatt cagttgctta ctctaataac tctattgcca tacccacaaa ttttactatt   2160
agtgttacca cagaaattct accagtgtct atgaccaaga catcagtaga ttgtacaatg   2220
tacatttgtg gtgattcaac tgaatgcagc aatcttttgt tgcaatatgg cagtttttgt   2280
acacaattaa accgtgcttt aactggaata gctgttgaac aagacaaaaa cacccaagaa   2340
gtttttgcac aagtcaaaca aatttacaaa acaccaccaa ttaaagattt tggtggtttt   2400
aatttttcac aaatattacc agatccatca aaaccaagca agaggtcatt tattgaagat   2460
```

-continued

```
ctacttttca acaaagtgac acttgcagat gctggcttca tcaaacaata tggtgattgc   2520

cttggtgata ttgctgctag agacctcatt tgtgcacaaa agtttaacgg ccttactgtt   2580

ttgccacctt tgctcacaga tgaaatgatt gctcaataca cttctgcact gttagcgggt   2640

acaatcactt ctggttggac ctttggtgca ggtgctgcat tacaaatacc atttgctatg   2700

caaatggctt ataggtttaa tggtattgga gttacacaga atgttctcta tgagaaccaa   2760

aaattgattg ccaaccaatt taatagtgct attggcaaaa ttcaagactc actttcttcc   2820

acagcaagtg cacttggaaa acttcaagat gtggtcaacc aaaatgcaca agctttaaac   2880

acgcttgtta aacaacttag ctccaatttt ggtgcaattt caagtgtttt aaatgatatc   2940

ctttcacgtc ttgacaaagt tgaggctgaa gtgcaaattg ataggttgat cacaggcaga   3000

cttcaaagtt tgcagacata tgtgactcaa caattaatta gagctgcaga aatcagagct   3060

tctgctaatc ttgctgctac taaaatgtca gagtgtgtac ttggacaatc aaaaagagtt   3120

gatttttgtg gaaagggcta tcatcttatg tccttccctc agtcagcacc tcatggtgta   3180

gtcttcttgc atgtgactta tgtccctgca caagaaaaga acttcacaac tgctcctgcc   3240

atttgtcatg atggaaaagc acactttcct cgtgaaggtg tctttgtttc aaatggcaca   3300

cactggtttg taacacaaag gaatttttat gaaccacaaa tcattactac agacaacaca   3360

tttgtgtctg gtaactgtga tgttgtaata ggaattgtca acaacacagt ttatgatcct   3420

ttgcaacctg aattagactc attcaaggag gagttagata aatattttaa gaatcataca   3480

tcaccagatg ttgatttagg tgacatctct ggcattaatg cttcagttgt aaacattcaa   3540

aaagaaattg accgcctcaa tgaggttgcc aagaatttaa atgaatctct catcgatctc   3600

caagaacttg gaaagtatga gcagtatata aaatggccat ggtacatttg gctaggtttt   3660

atagctggct tgattgccat agtaatggtg acaattatgc tttgctgtat gaccagttgc   3720

tgtagttgtc tcaagggctg ttgttcttgt ggatcctgct gcaaatttga tgaagacgac   3780

tctgagccag tgctcaaagg agtcaaatta cattacaca                          3819
```

<210> SEQ ID NO 17
<211> LENGTH: 19
<212> TYPE: DNA
<213> ORGANISM: SARS-CoV2 Coronavirus
<220> FEATURE:
<221> NAME/KEY: misc_feature
<222> LOCATION: (1)..(19)
<223> OTHER INFORMATION: Illustrative Variant Forward ORF1ab Primer

<400> SEQUENCE: 17
atggtagagt tgatggtca 19

<210> SEQ ID NO 18
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: Illustrative Variant Forward ORF1ab Primer

<400> SEQUENCE: 18
atggtagagt tgatggtc 18

<210> SEQ ID NO 19
<211> LENGTH: 17
<212> TYPE: DNA

<213> ORGANISM: SARS-CoV2 Coronavirus
<220> FEATURE:
<221> NAME/KEY: misc_feature
<222> LOCATION: (1)..(17)
<223> OTHER INFORMATION: Illustrative Variant Forward ORF1ab Primer

<400> SEQUENCE: 19
atggtagagt tgatggt 17

<210> SEQ ID NO 20
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)
<223> OTHER INFORMATION: Illustrative Variant Forward ORF1ab Primer

<400> SEQUENCE: 20
atggtagagt tgatgg 16

<210> SEQ ID NO 21
<211> LENGTH: 15
<212> TYPE: DNA
<213> ORGANISM: SARS-CoV2 Coronavirus
<220> FEATURE:
<221> NAME/KEY: misc_feature
<222> LOCATION: (1)..(15)
<223> OTHER INFORMATION: Illustrative Variant Forward ORF1ab Primer

<400> SEQUENCE: 21
atggtagagt tgatg 15

<210> SEQ ID NO 22
<211> LENGTH: 19
<212> TYPE: DNA
<213> ORGANISM: SARS-CoV2 Coronavirus
<220> FEATURE:
<221> NAME/KEY: misc_feature
<222> LOCATION: (1)..(19)
<223> OTHER INFORMATION: Illustrative Variant Forward ORF1ab Primer

<400> SEQUENCE: 22
tggtagagtt gatggtcaa 19

<210> SEQ ID NO 23
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: Illustrative Variant Forward ORF1ab Primer

<400> SEQUENCE: 23
ggtagagttg atggtcaa 18

<210> SEQ ID NO 24
<211> LENGTH: 17
<212> TYPE: DNA
<213> ORGANISM: SARS-CoV2 Coronavirus
<220> FEATURE:
<221> NAME/KEY: misc_feature
<222> LOCATION: (1)..(17)
<223> OTHER INFORMATION: Illustrative Variant Forward ORF1ab Primer

<400> SEQUENCE: 24
gtagagttga tggtcaa 17

<210> SEQ ID NO 25
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)
<223> OTHER INFORMATION: Illustrative Variant Forward ORF1ab Primer

<400> SEQUENCE: 25
tagagttgat ggtcaa 16

<210> SEQ ID NO 26
<211> LENGTH: 15
<212> TYPE: DNA
<213> ORGANISM: SARS-CoV2 Coronavirus
<220> FEATURE:
<221> NAME/KEY: misc_feature
<222> LOCATION: (1)..(15)
<223> OTHER INFORMATION: Illustrative Variant Forward ORF1ab Primer

<400> SEQUENCE: 26
agagttgatg gtcaa 15

<210> SEQ ID NO 27
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: Illustrative Variant Forward ORF1ab Primer

<400> SEQUENCE: 27
tggtagagtt gatggtca 18

<210> SEQ ID NO 28
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)
<223> OTHER INFORMATION: Illustrative Variant Forward ORF1ab Primer

<400> SEQUENCE: 28
ggtagagttg atggtc 16

<210> SEQ ID NO 29
<211> LENGTH: 19
<212> TYPE: DNA
<213> ORGANISM: SARS-CoV2 Coronavirus
<220> FEATURE:
<221> NAME/KEY: misc_feature
<222> LOCATION: (1)..(19)
<223> OTHER INFORMATION: Illustrative Variant Reverse ORF1ab Primer

<400> SEQUENCE: 29
taagactagc ttgtttggg 19

<210> SEQ ID NO 30
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(19)

<223> OTHER INFORMATION: Illustrative Variant Reverse ORF1ab Primer

<400> SEQUENCE: 30
taagactagc ttgtttgg 18

<210> SEQ ID NO 31
<211> LENGTH: 17
<212> TYPE: DNA
<213> ORGANISM: SARS-CoV2 Coronavirus
<220> FEATURE:
<221> NAME/KEY: misc_feature
<222> LOCATION: (1)..(17)
<223> OTHER INFORMATION: Illustrative Variant Reverse ORF1ab Primer

<400> SEQUENCE: 31
taagactagc ttgtttg 17

<210> SEQ ID NO 32
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)
<223> OTHER INFORMATION: Illustrative Variant Reverse ORF1ab Primer

<400> SEQUENCE: 32
taagactagc ttgttt 16

<210> SEQ ID NO 33
<211> LENGTH: 15
<212> TYPE: DNA
<213> ORGANISM: SARS-CoV2 Coronavirus
<220> FEATURE:
<221> NAME/KEY: misc_feature
<222> LOCATION: (1)..(15)
<223> OTHER INFORMATION: Illustrative Variant Reverse ORF1ab Primer

<400> SEQUENCE: 33
taagactagc ttgtt 15

<210> SEQ ID NO 34
<211> LENGTH: 19
<212> TYPE: DNA
<213> ORGANISM: SARS-CoV2 Coronavirus
<220> FEATURE:
<221> NAME/KEY: misc_feature
<222> LOCATION: (1)..(19)
<223> OTHER INFORMATION: Illustrative Variant Reverse ORF1ab Primer

<400> SEQUENCE: 34
aagactagct tgtttggga 19

<210> SEQ ID NO 35
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: Illustrative Variant Reverse ORF1ab Primer

<400> SEQUENCE: 35
agactagctt gtttggga 18

<210> SEQ ID NO 36
<211> LENGTH: 17

<212> TYPE: DNA
<213> ORGANISM: SARS-CoV2 Coronavirus
<220> FEATURE:
<221> NAME/KEY: misc_feature
<222> LOCATION: (1)..(17)
<223> OTHER INFORMATION: Illustrative Variant Reverse ORF1ab Primer

<400> SEQUENCE: 36
gactagcttg tttggga 17

<210> SEQ ID NO 37
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)
<223> OTHER INFORMATION: Illustrative Variant Reverse ORF1ab Primer

<400> SEQUENCE: 37
actagcttgt ttggga 16

<210> SEQ ID NO 38
<211> LENGTH: 15
<212> TYPE: DNA
<213> ORGANISM: SARS-CoV2 Coronavirus
<220> FEATURE:
<221> NAME/KEY: misc_feature
<222> LOCATION: (1)..(15)
<223> OTHER INFORMATION: Illustrative Variant Reverse ORF1ab Primer

<400> SEQUENCE: 38
ctagcttgtt tggga 15

<210> SEQ ID NO 39
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: Illustrative Variant Reverse ORF1ab Primer

<400> SEQUENCE: 39
aagactagct tgtttggg 18

<210> SEQ ID NO 40
<211> LENGTH: 17
<212> TYPE: DNA
<213> ORGANISM: SARS-CoV2 Coronavirus
<220> FEATURE:
<221> NAME/KEY: misc_feature
<222> LOCATION: (1)..(17)
<223> OTHER INFORMATION: Illustrative Variant Reverse ORF1ab Primer

<400> SEQUENCE: 40
agactagctt gtttggg 17

<210> SEQ ID NO 41
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)
<223> OTHER INFORMATION: Illustrative Variant Reverse ORF1ab Primer

<400> SEQUENCE: 41

-continued agactagctt gtttgg 16

<210> SEQ ID NO 42
<211> LENGTH: 15
<212> TYPE: DNA
<213> ORGANISM: SARS-CoV2 Coronavirus
<220> FEATURE:
<221> NAME/KEY: misc_feature
<222> LOCATION: (1)..(15)
<223> OTHER INFORMATION: Illustrative Variant Reverse ORF1ab Primer

<400> SEQUENCE: 42
gactagcttg tttgg 15

<210> SEQ ID NO 43
<211> LENGTH: 28
<212> TYPE: DNA
<213> ORGANISM: SARS-CoV2 Coronavirus
<220> FEATURE:
<221> NAME/KEY: misc_feature
<222> LOCATION: (1)..(28)
<223> OTHER INFORMATION: Illustrative Variant Forward S Gene Primer

<400> SEQUENCE: 43
ctaaccaggt tgctgttctt tatcagga 28

<210> SEQ ID NO 44
<211> LENGTH: 28
<212> TYPE: DNA
<213> ORGANISM: SARS-CoV2 Coronavirus
<220> FEATURE:
<221> NAME/KEY: misc_feature
<222> LOCATION: (1)..(28)
<223> OTHER INFORMATION: Illustrative Variant Forward S Gene Primer

<400> SEQUENCE: 44
ctaaccaggt tgctgttctt tatcaggg 28

<210> SEQ ID NO 45
<211> LENGTH: 27
<212> TYPE: DNA
<213> ORGANISM: SARS-CoV2 Coronavirus
<220> FEATURE:
<221> NAME/KEY: misc_feature
<222> LOCATION: (1)..(27)
<223> OTHER INFORMATION: Illustrative Variant Forward S Gene Primer

<400> SEQUENCE: 45
taaccaggtt gctgttcttt atcagga 27

<210> SEQ ID NO 46
<211> LENGTH: 27
<212> TYPE: DNA
<213> ORGANISM: SARS-CoV2 Coronavirus
<220> FEATURE:
<221> NAME/KEY: misc_feature
<222> LOCATION: (1)..(27)
<223> OTHER INFORMATION: Illustrative Variant Forward S Gene Primer

<400> SEQUENCE: 46
taaccaggtt gctgttcttt atcaggg 27

<210> SEQ ID NO 47
<211> LENGTH: 26
<212> TYPE: DNA
<213> ORGANISM: SARS-CoV2 Coronavirus
<220> FEATURE:
<221> NAME/KEY: misc_feature
<222> LOCATION: (1)..(26)
<223> OTHER INFORMATION: Illustrative Variant Forward S Gene Primer

<400> SEQUENCE: 47
aaccaggttg ctgttcttta tcagga 26

<210> SEQ ID NO 48
<211> LENGTH: 26
<212> TYPE: DNA
<213> ORGANISM: SARS-CoV2 Coronavirus
<220> FEATURE:
<221> NAME/KEY: misc_feature
<222> LOCATION: (1)..(26)
<223> OTHER INFORMATION: Illustrative Variant Forward S Gene Primer

<400> SEQUENCE: 48
aaccaggttg ctgttcttta tcaggg 26

<210> SEQ ID NO 49
<211> LENGTH: 25
<212> TYPE: DNA
<213> ORGANISM: SARS-CoV2 Coronavirus
<220> FEATURE:
<221> NAME/KEY: misc_feature
<222> LOCATION: (1)..(25)
<223> OTHER INFORMATION: Illustrative Variant Forward S Gene Primer

<400> SEQUENCE: 49
accaggttgc tgttctttat cagga 25

<210> SEQ ID NO 50
<211> LENGTH: 25
<212> TYPE: DNA
<213> ORGANISM: SARS-CoV2 Coronavirus
<220> FEATURE:
<221> NAME/KEY: misc_feature
<222> LOCATION: (1)..(25)
<223> OTHER INFORMATION: Illustrative Variant Forward S Gene Primer

<400> SEQUENCE: 50
accaggttgc tgttctttat caggg 25

<210> SEQ ID NO 51
<211> LENGTH: 24
<212> TYPE: DNA
<213> ORGANISM: SARS-CoV2 Coronavirus
<220> FEATURE:
<221> NAME/KEY: misc_feature
<222> LOCATION: (1)..(24)
<223> OTHER INFORMATION: Illustrative Variant Forward S Gene Primer

<400> SEQUENCE: 51
ccaggttgct gttctttatc agga 24

<210> SEQ ID NO 52
<211> LENGTH: 24
<212> TYPE: DNA
<213> ORGANISM: SARS-CoV2 Coronavirus
<220> FEATURE:
<221> NAME/KEY: misc_feature
<222> LOCATION: (1)..(24)
<223> OTHER INFORMATION: Illustrative Variant Forward S Gene Primer

<400> SEQUENCE: 52
ccaggttgct gttctttatc aggg 24

<210> SEQ ID NO 53

<211> LENGTH: 23
<212> TYPE: DNA
<213> ORGANISM: SARS-CoV2 Coronavirus
<220> FEATURE:
<221> NAME/KEY: misc_feature
<222> LOCATION: (1)..(23)
<223> OTHER INFORMATION: Illustrative Variant Forward S Gene Primer

<400> SEQUENCE: 53
caggttgctg ttctttatca gga 23

<210> SEQ ID NO 54
<211> LENGTH: 23
<212> TYPE: DNA
<213> ORGANISM: SARS-CoV2 Coronavirus
<220> FEATURE:
<221> NAME/KEY: misc_feature
<222> LOCATION: (1)..(23)
<223> OTHER INFORMATION: Illustrative Variant Forward S Gene Primer

<400> SEQUENCE: 54
caggttgctg ttctttatca ggg 23

<210> SEQ ID NO 55
<211> LENGTH: 22
<212> TYPE: DNA
<213> ORGANISM: SARS-CoV2 Coronavirus
<220> FEATURE:
<221> NAME/KEY: misc_feature
<222> LOCATION: (1)..(22)
<223> OTHER INFORMATION: Illustrative Variant Forward S Gene Primer

<400> SEQUENCE: 55
aggttgctgt tctttatcag ga 22

<210> SEQ ID NO 56
<211> LENGTH: 22
<212> TYPE: DNA
<213> ORGANISM: SARS-CoV2 Coronavirus
<220> FEATURE:
<221> NAME/KEY: misc_feature
<222> LOCATION: (1)..(22)
<223> OTHER INFORMATION: Illustrative Variant Forward S Gene Primer

<400> SEQUENCE: 56
aggttgctgt tctttatcag gg 22

<210> SEQ ID NO 57
<211> LENGTH: 21
<212> TYPE: DNA
<213> ORGANISM: SARS-CoV2 Coronavirus
<220> FEATURE:
<221> NAME/KEY: misc_feature
<222> LOCATION: (1)..(21)
<223> OTHER INFORMATION: Illustrative Variant Forward S Gene Primer

<400> SEQUENCE: 57
ggttgctgtt ctttatcagg a 21

<210> SEQ ID NO 58
<211> LENGTH: 21
<212> TYPE: DNA
<213> ORGANISM: SARS-CoV2 Coronavirus
<220> FEATURE:
<221> NAME/KEY: misc_feature
<222> LOCATION: (1)..(21)
<223> OTHER INFORMATION: Illustrative Variant Forward S Gene Primer

<400> SEQUENCE: 58
ggttgctgtt ctttatcagg g 21

<210> SEQ ID NO 59
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: Illustrative Variant Forward S Gene Primer

<400> SEQUENCE: 59
gttgctgttc tttatcagga 20

<210> SEQ ID NO 60
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: Illustrative Variant Forward S Gene Primer

<400> SEQUENCE: 60
gttgctgttc tttatcaggg 20

<210> SEQ ID NO 61
<211> LENGTH: 19
<212> TYPE: DNA
<213> ORGANISM: SARS-CoV2 Coronavirus
<220> FEATURE:
<221> NAME/KEY: misc_feature
<222> LOCATION: (1)..(19)
<223> OTHER INFORMATION: Illustrative Variant Forward S Gene Primer

<400> SEQUENCE: 61
ttgctgttct ttatcagga 19

<210> SEQ ID NO 62
<211> LENGTH: 19
<212> TYPE: DNA
<213> ORGANISM: SARS-CoV2 Coronavirus
<220> FEATURE:
<221> NAME/KEY: misc_feature
<222> LOCATION: (1)..(19)
<223> OTHER INFORMATION: Illustrative Variant Forward S Gene Primer

<400> SEQUENCE: 62
ttgctgttct ttatcaggg 19

<210> SEQ ID NO 63
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: Illustrative Variant Forward S Gene Primer

<400> SEQUENCE: 63
tgctgttctt tatcagga 18

<210> SEQ ID NO 64
<211> LENGTH: 18
<212> TYPE: DNA
<213> ORGANISM: SARS-CoV2 Coronavirus
<220> FEATURE:

-continued

```
<221> NAME/KEY: misc_feature
<222> LOCATION: (1)..(18)
<223> OTHER INFORMATION: Illustrative Variant Forward S Gene Primer

<400> SEQUENCE: 64

tgctgttctt tatcaggg                                                    18


<210> SEQ ID NO 65
<211> LENGTH: 17
<212> TYPE: DNA
<213> ORGANISM: SARS-CoV2 Coronavirus
<220> FEATURE:
<221> NAME/KEY: misc_feature
<222> LOCATION: (1)..(17)
<223> OTHER INFORMATION: Illustrative Variant Forward S Gene Primer

<400> SEQUENCE: 65

gctgttcttt atcagga                                                     17


<210> SEQ ID NO 66
<211> LENGTH: 17
<212> TYPE: DNA
<213> ORGANISM: SARS-CoV2 Coronavirus
<220> FEATURE:
<221> NAME/KEY: misc_feature
<222> LOCATION: (1)..(17)
<223> OTHER INFORMATION: Illustrative Variant Forward S Gene Primer

<400> SEQUENCE: 66

gctgttcttt atcaggg                                                     17


<210> SEQ ID NO 67
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)
<223> OTHER INFORMATION: Illustrative Variant Forward S Gene Primer

<400> SEQUENCE: 67

ctgttcttta tcagga                                                      16


<210> SEQ ID NO 68
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)
<223> OTHER INFORMATION: Illustrative Variant Forward S Gene Primer

<400> SEQUENCE: 68

ctgttcttta tcaggg                                                      16


<210> SEQ ID NO 69
<211> LENGTH: 15
<212> TYPE: DNA
<213> ORGANISM: SARS-CoV2 Coronavirus
<220> FEATURE:
<221> NAME/KEY: misc_feature
<222> LOCATION: (1)..(15)
<223> OTHER INFORMATION: Illustrative Variant Forward S Gene Primer

<400> SEQUENCE: 69

tgttctttat cagga                                                       15
```

-continued

<210> SEQ ID NO 70
<211> LENGTH: 15
<212> TYPE: DNA
<213> ORGANISM: SARS-CoV2 Coronavirus
<220> FEATURE:
<221> NAME/KEY: misc_feature
<222> LOCATION: (1)..(15)
<223> OTHER INFORMATION: Illustrative Variant Forward S Gene Primer

<400> SEQUENCE: 70
tgttctttat caggg 15

<210> SEQ ID NO 71
<211> LENGTH: 19
<212> TYPE: DNA
<213> ORGANISM: SARS-CoV2 Coronavirus
<220> FEATURE:
<221> NAME/KEY: misc_feature
<222> LOCATION: (1)..(19)
<223> OTHER INFORMATION: Illustrative Variant Forward S Gene Primer

<400> SEQUENCE: 71
ctaaccaggt tgctgttct 19

<210> SEQ ID NO 72
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: Illustrative Variant Forward S Gene Primer

<400> SEQUENCE: 72
ctaaccaggt tgctgttc 18

<210> SEQ ID NO 73
<211> LENGTH: 17
<212> TYPE: DNA
<213> ORGANISM: SARS-CoV2 Coronavirus
<220> FEATURE:
<221> NAME/KEY: misc_feature
<222> LOCATION: (1)..(17)
<223> OTHER INFORMATION: Illustrative Variant Forward S Gene Primer

<400> SEQUENCE: 73
ctaaccaggt tgctgtt 17

<210> SEQ ID NO 74
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)
<223> OTHER INFORMATION: Illustrative Variant Forward S Gene Primer

<400> SEQUENCE: 74
ctaaccaggt tgctgt 16

<210> SEQ ID NO 75
<211> LENGTH: 15
<212> TYPE: DNA
<213> ORGANISM: SARS-CoV2 Coronavirus
<220> FEATURE:
<221> NAME/KEY: misc_feature
<222> LOCATION: (1)..(15)
<223> OTHER INFORMATION: Illustrative Variant Forward S Gene Primer

<400> SEQUENCE: 75
ctaaccaggt tgctg 15

<210> SEQ ID NO 76
<211> LENGTH: 19
<212> TYPE: DNA
<213> ORGANISM: SARS-CoV2 Coronavirus
<220> FEATURE:
<221> NAME/KEY: misc_feature
<222> LOCATION: (1)..(19)
<223> OTHER INFORMATION: Illustrative Variant Forward S Gene Primer

<400> SEQUENCE: 76
taaccaggtt gctgttctt 19

<210> SEQ ID NO 77
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: Illustrative Variant Forward S Gene Primer

<400> SEQUENCE: 77
aaccaggttg ctgttctt 18

<210> SEQ ID NO 78
<211> LENGTH: 17
<212> TYPE: DNA
<213> ORGANISM: SARS-CoV2 Coronavirus
<220> FEATURE:
<221> NAME/KEY: misc_feature
<222> LOCATION: (1)..(17)
<223> OTHER INFORMATION: Illustrative Variant Forward S Gene Primer

<400> SEQUENCE: 78
accaggttgc tgttctt 17

<210> SEQ ID NO 79
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)
<223> OTHER INFORMATION: Illustrative Variant Forward S Gene Primer

<400> SEQUENCE: 79
ccaggttgct gttctt 16

<210> SEQ ID NO 80
<211> LENGTH: 15
<212> TYPE: DNA
<213> ORGANISM: SARS-CoV2 Coronavirus
<220> FEATURE:
<221> NAME/KEY: misc_feature
<222> LOCATION: (1)..(15)
<223> OTHER INFORMATION: Illustrative Variant Forward S Gene Primer

<400> SEQUENCE: 80
caggttgctg ttctt 15

<210> SEQ ID NO 81
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: Illustrative Variant Forward S Gene Primer

<400> SEQUENCE: 81
taaccaggtt gctgttct 18

<210> SEQ ID NO 82
<211> LENGTH: 17
<212> TYPE: DNA
<213> ORGANISM: SARS-CoV2 Coronavirus
<220> FEATURE:
<221> NAME/KEY: misc_feature
<222> LOCATION: (1)..(17)
<223> OTHER INFORMATION: Illustrative Variant Forward S Gene Primer

<400> SEQUENCE: 82
aaccaggttg ctgttct 17

<210> SEQ ID NO 83
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)
<223> OTHER INFORMATION: Illustrative Variant Forward S Gene Primer

<400> SEQUENCE: 83
aaccaggttg ctgttc 16

<210> SEQ ID NO 84
<211> LENGTH: 15
<212> TYPE: DNA
<213> ORGANISM: SARS-CoV2 Coronavirus
<220> FEATURE:
<221> NAME/KEY: misc_feature
<222> LOCATION: (1)..(15)
<223> OTHER INFORMATION: Illustrative Variant Forward S Gene Primer

<400> SEQUENCE: 84
accaggttgc tgttc 15

<210> SEQ ID NO 85
<211> LENGTH: 28
<212> TYPE: DNA
<213> ORGANISM: SARS-CoV2 Coronavirus
<220> FEATURE:
<221> NAME/KEY: misc_feature
<222> LOCATION: (1)..(28)
<223> OTHER INFORMATION: Illustrative Variant Reverse S Gene Primer

<400> SEQUENCE: 85
gcaacaggga cttctgtgca gttaacat 28

<210> SEQ ID NO 86
<211> LENGTH: 28
<212> TYPE: DNA
<213> ORGANISM: SARS-CoV2 Coronavirus
<220> FEATURE:
<221> NAME/KEY: misc_feature
<222> LOCATION: (1)..(28)
<223> OTHER INFORMATION: Illustrative Variant Reverse S Gene Primer

<400> SEQUENCE: 86
gcaacaggga cttctgtgca gttaacac 28

<210> SEQ ID NO 87
<211> LENGTH: 27
<212> TYPE: DNA
<213> ORGANISM: SARS-CoV2 Coronavirus
<220> FEATURE:
<221> NAME/KEY: misc_feature
<222> LOCATION: (1)..(27)
<223> OTHER INFORMATION: Illustrative Variant Reverse S Gene Primer

<400> SEQUENCE: 87
caacagggac ttctgtgcag ttaacat 27

<210> SEQ ID NO 88
<211> LENGTH: 27
<212> TYPE: DNA
<213> ORGANISM: SARS-CoV2 Coronavirus
<220> FEATURE:
<221> NAME/KEY: misc_feature
<222> LOCATION: (1)..(27)
<223> OTHER INFORMATION: Illustrative Variant Reverse S Gene Primer

<400> SEQUENCE: 88
caacagggac ttctgtgcag ttaacac 27

<210> SEQ ID NO 89
<211> LENGTH: 26
<212> TYPE: DNA
<213> ORGANISM: SARS-CoV2 Coronavirus
<220> FEATURE:
<221> NAME/KEY: misc_feature
<222> LOCATION: (1)..(26)
<223> OTHER INFORMATION: Illustrative Variant Reverse S Gene Primer

<400> SEQUENCE: 89
aacagggact tctgtgcagt taacat 26

<210> SEQ ID NO 90
<211> LENGTH: 26
<212> TYPE: DNA
<213> ORGANISM: SARS-CoV2 Coronavirus
<220> FEATURE:
<221> NAME/KEY: misc_feature
<222> LOCATION: (1)..(26)
<223> OTHER INFORMATION: Illustrative Variant Reverse S Gene Primer

<400> SEQUENCE: 90
aacagggact tctgtgcagt taacac 26

<210> SEQ ID NO 91
<211> LENGTH: 25
<212> TYPE: DNA
<213> ORGANISM: SARS-CoV2 Coronavirus
<220> FEATURE:
<221> NAME/KEY: misc_feature
<222> LOCATION: (1)..(25)
<223> OTHER INFORMATION: Illustrative Variant Reverse S Gene Primer

<400> SEQUENCE: 91
acagggactt ctgtgcagtt aacat 25

<210> SEQ ID NO 92
<211> LENGTH: 25
<212> TYPE: DNA
<213> ORGANISM: SARS-CoV2 Coronavirus
<220> FEATURE:
<221> NAME/KEY: misc_feature
<222> LOCATION: (1)..(25)
<223> OTHER INFORMATION: Illustrative Variant Reverse S Gene Primer

<400> SEQUENCE: 92
acagggactt ctgtgcagtt aacac 25

<210> SEQ ID NO 93
<211> LENGTH: 24
<212> TYPE: DNA
<213> ORGANISM: SARS-CoV2 Coronavirus
<220> FEATURE:
<221> NAME/KEY: misc_feature
<222> LOCATION: (1)..(24)
<223> OTHER INFORMATION: Illustrative Variant Reverse S Gene Primer

<400> SEQUENCE: 93
cagggacttc tgtgcagtta acat 24

<210> SEQ ID NO 94
<211> LENGTH: 24
<212> TYPE: DNA
<213> ORGANISM: SARS-CoV2 Coronavirus
<220> FEATURE:
<221> NAME/KEY: misc_feature
<222> LOCATION: (1)..(24)
<223> OTHER INFORMATION: Illustrative Variant Reverse S Gene Primer

<400> SEQUENCE: 94
cagggacttc tgtgcagtta acac 24

<210> SEQ ID NO 95
<211> LENGTH: 23
<212> TYPE: DNA
<213> ORGANISM: SARS-CoV2 Coronavirus
<220> FEATURE:
<221> NAME/KEY: misc_feature
<222> LOCATION: (1)..(23)
<223> OTHER INFORMATION: Illustrative Variant Reverse S Gene Primer

<400> SEQUENCE: 95
agggacttct gtgcagttaa cat 23

<210> SEQ ID NO 96
<211> LENGTH: 23
<212> TYPE: DNA
<213> ORGANISM: SARS-CoV2 Coronavirus
<220> FEATURE:
<221> NAME/KEY: misc_feature
<222> LOCATION: (1)..(23)
<223> OTHER INFORMATION: Illustrative Variant Reverse S Gene Primer

<400> SEQUENCE: 96
agggacttct gtgcagttaa cac 23

<210> SEQ ID NO 97
<211> LENGTH: 22
<212> TYPE: DNA
<213> ORGANISM: SARS-CoV2 Coronavirus
<220> FEATURE:
<221> NAME/KEY: misc_feature
<222> LOCATION: (1)..(22)
<223> OTHER INFORMATION: Illustrative Variant Reverse S Gene Primer

<400> SEQUENCE: 97
gggacttctg tgcagttaac at 22

<210> SEQ ID NO 98
<211> LENGTH: 22
<212> TYPE: DNA

-continued

<213> ORGANISM: SARS-CoV2 Coronavirus
<220> FEATURE:
<221> NAME/KEY: misc_feature
<222> LOCATION: (1)..(22)
<223> OTHER INFORMATION: Illustrative Variant Reverse S Gene Primer

<400> SEQUENCE: 98
gggacttctg tgcagttaac ac 22

<210> SEQ ID NO 99
<211> LENGTH: 21
<212> TYPE: DNA
<213> ORGANISM: SARS-CoV2 Coronavirus
<220> FEATURE:
<221> NAME/KEY: misc_feature
<222> LOCATION: (1)..(21)
<223> OTHER INFORMATION: Illustrative Variant Reverse S Gene Primer

<400> SEQUENCE: 99
ggacttctgt gcagttaaca t 21

<210> SEQ ID NO 100
<211> LENGTH: 21
<212> TYPE: DNA
<213> ORGANISM: SARS-CoV2 Coronavirus
<220> FEATURE:
<221> NAME/KEY: misc_feature
<222> LOCATION: (1)..(21)
<223> OTHER INFORMATION: Illustrative Variant Reverse S Gene Primer

<400> SEQUENCE: 100
ggacttctgt gcagttaaca c 21

<210> SEQ ID NO 101
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: Illustrative Variant Reverse S Gene Primer

<400> SEQUENCE: 101
gacttctgtg cagttaacat 20

<210> SEQ ID NO 102
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: Illustrative Variant Reverse S Gene Primer

<400> SEQUENCE: 102
gacttctgtg cagttaacac 20

<210> SEQ ID NO 103
<211> LENGTH: 19
<212> TYPE: DNA
<213> ORGANISM: SARS-CoV2 Coronavirus
<220> FEATURE:
<221> NAME/KEY: misc_feature
<222> LOCATION: (1)..(19)
<223> OTHER INFORMATION: Illustrative Variant Reverse S Gene Primer

<400> SEQUENCE: 103
acttctgtgc agttaacat 19

<210> SEQ ID NO 104
<211> LENGTH: 19
<212> TYPE: DNA
<213> ORGANISM: SARS-CoV2 Coronavirus
<220> FEATURE:
<221> NAME/KEY: misc_feature
<222> LOCATION: (1)..(19)
<223> OTHER INFORMATION: Illustrative Variant Reverse S Gene Primer

<400> SEQUENCE: 104
acttctgtgc agttaacac 19

<210> SEQ ID NO 105
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: Illustrative Variant Reverse S Gene Primer

<400> SEQUENCE: 105
cttctgtgca gttaacat 18

<210> SEQ ID NO 106
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: Illustrative Variant Reverse S Gene Primer

<400> SEQUENCE: 106
cttctgtgca gttaacac 18

<210> SEQ ID NO 107
<211> LENGTH: 17
<212> TYPE: DNA
<213> ORGANISM: SARS-CoV2 Coronavirus
<220> FEATURE:
<221> NAME/KEY: misc_feature
<222> LOCATION: (1)..(17)
<223> OTHER INFORMATION: Illustrative Variant Reverse S Gene Primer

<400> SEQUENCE: 107
ttctgtgcag ttaacat 17

<210> SEQ ID NO 108
<211> LENGTH: 17
<212> TYPE: DNA
<213> ORGANISM: SARS-CoV2 Coronavirus
<220> FEATURE:
<221> NAME/KEY: misc_feature
<222> LOCATION: (1)..(17)
<223> OTHER INFORMATION: Illustrative Variant Reverse S Gene Primer

<400> SEQUENCE: 108
ttctgtgcag ttaacac 17

<210> SEQ ID NO 109
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)

<223> OTHER INFORMATION: Illustrative Variant Reverse S Gene Primer

<400> SEQUENCE: 109
tctgtgcagt taacat 16

<210> SEQ ID NO 110
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)
<223> OTHER INFORMATION: Illustrative Variant Reverse S Gene Primer

<400> SEQUENCE: 110
tctgtgcagt taacac 16

<210> SEQ ID NO 111
<211> LENGTH: 15
<212> TYPE: DNA
<213> ORGANISM: SARS-CoV2 Coronavirus
<220> FEATURE:
<221> NAME/KEY: misc_feature
<222> LOCATION: (1)..(15)
<223> OTHER INFORMATION: Illustrative Variant Reverse S Gene Primer

<400> SEQUENCE: 111
ctgtgcagtt aacat 15

<210> SEQ ID NO 112
<211> LENGTH: 15
<212> TYPE: DNA
<213> ORGANISM: SARS-CoV2 Coronavirus
<220> FEATURE:
<221> NAME/KEY: misc_feature
<222> LOCATION: (1)..(15)
<223> OTHER INFORMATION: Illustrative Variant Reverse S Gene Primer

<400> SEQUENCE: 112
ctgtgcagtt aacac 15

<210> SEQ ID NO 113
<211> LENGTH: 19
<212> TYPE: DNA
<213> ORGANISM: SARS-CoV2 Coronavirus
<220> FEATURE:
<221> NAME/KEY: misc_feature
<222> LOCATION: (1)..(19)
<223> OTHER INFORMATION: Illustrative Variant Reverse S Gene Primer

<400> SEQUENCE: 113
cctgtagaat aaacacgcc 19

<210> SEQ ID NO 114
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: Illustrative Variant Reverse S Gene Primer

<400> SEQUENCE: 114
cctgtagaat aaacacgc 18

<210> SEQ ID NO 115
<211> LENGTH: 17

<212> TYPE: DNA
<213> ORGANISM: SARS-CoV2 Coronavirus
<220> FEATURE:
<221> NAME/KEY: misc_feature
<222> LOCATION: (1)..(17)
<223> OTHER INFORMATION: Illustrative Variant Reverse S Gene Primer

<400> SEQUENCE: 115
cctgtagaat aaacacg 17

<210> SEQ ID NO 116
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)
<223> OTHER INFORMATION: Illustrative Variant Reverse S Gene Primer

<400> SEQUENCE: 116
cctgtagaat aaacac 16

<210> SEQ ID NO 117
<211> LENGTH: 15
<212> TYPE: DNA
<213> ORGANISM: SARS-CoV2 Coronavirus
<220> FEATURE:
<221> NAME/KEY: misc_feature
<222> LOCATION: (1)..(15)
<223> OTHER INFORMATION: Illustrative Variant Reverse S Gene Primer

<400> SEQUENCE: 117
cctgtagaat aaaca 15

<210> SEQ ID NO 118
<211> LENGTH: 19
<212> TYPE: DNA
<213> ORGANISM: SARS-CoV2 Coronavirus
<220> FEATURE:
<221> NAME/KEY: misc_feature
<222> LOCATION: (1)..(19)
<223> OTHER INFORMATION: Illustrative Variant Reverse S Gene Primer

<400> SEQUENCE: 118
ctgtagaata aacacgcca 19

<210> SEQ ID NO 119
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: Illustrative Variant Reverse S Gene Primer

<400> SEQUENCE: 119
tgtagaataa acacgcca 18

<210> SEQ ID NO 120
<211> LENGTH: 17
<212> TYPE: DNA
<213> ORGANISM: SARS-CoV2 Coronavirus
<220> FEATURE:
<221> NAME/KEY: misc_feature
<222> LOCATION: (1)..(17)
<223> OTHER INFORMATION: Illustrative Variant Reverse S Gene Primer

<400> SEQUENCE: 120

-continued gtagaataaa cacgcca 17

<210> SEQ ID NO 121
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)
<223> OTHER INFORMATION: Illustrative Variant Reverse S Gene Primer

<400> SEQUENCE: 121
tagaataaac acgcca 16

<210> SEQ ID NO 122
<211> LENGTH: 15
<212> TYPE: DNA
<213> ORGANISM: SARS-CoV2 Coronavirus
<220> FEATURE:
<221> NAME/KEY: misc_feature
<222> LOCATION: (1)..(15)
<223> OTHER INFORMATION: Illustrative Variant Reverse S Gene Primer

<400> SEQUENCE: 122
agaataaaca cgcca 15

<210> SEQ ID NO 123
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: Illustrative Variant Reverse S Gene Primer

<400> SEQUENCE: 123
ctgtagaata aacacgcc 18

<210> SEQ ID NO 124
<211> LENGTH: 17
<212> TYPE: DNA
<213> ORGANISM: SARS-CoV2 Coronavirus
<220> FEATURE:
<221> NAME/KEY: misc_feature
<222> LOCATION: (1)..(17)
<223> OTHER INFORMATION: Illustrative Variant Reverse S Gene Primer

<400> SEQUENCE: 124
tgtagaataa acacgcc 17

<210> SEQ ID NO 125
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)
<223> OTHER INFORMATION: Illustrative Variant Reverse S Gene Primer

<400> SEQUENCE: 125
tgtagaataa acacgc 16

<210> SEQ ID NO 126
<211> LENGTH: 15
<212> TYPE: DNA
<213> ORGANISM: SARS-CoV2 Coronavirus
<220> FEATURE:
<221> NAME/KEY: misc_feature -continued

```
<222> LOCATION: (1)..(15)
<223> OTHER INFORMATION: Illustrative Variant Reverse S Gene Primer

<400> SEQUENCE: 126

gtagaataaa cacgc                                                        15


<210> SEQ ID NO 127
<211> LENGTH: 26
<212> TYPE: DNA
<213> ORGANISM: SARS-CoV2 Coronavirus
<220> FEATURE:
<221> NAME/KEY: misc_feature
<222> LOCATION: (1)..(26)
<223> OTHER INFORMATION: SARS-CoV-2 Polynucleotide Domain of
      Illustrative Sense-Strand Probe for Detecting SARS-CoV-2 ORF1ab

<400> SEQUENCE: 127

tgcccgtaat ggtgttctta ttacag                                            26


<210> SEQ ID NO 128
<211> LENGTH: 25
<212> TYPE: DNA
<213> ORGANISM: SARS-CoV2 Coronavirus
<220> FEATURE:
<221> NAME/KEY: misc_feature
<222> LOCATION: (1)..(25)
<223> OTHER INFORMATION: SARS-CoV-2 Polynucleotide Domain of
      Illustrative Sense-Strand Probe for Detecting SARS-CoV-2 ORF1ab

<400> SEQUENCE: 128

tgcccgtaat ggtgttctta ttaca                                             25


<210> SEQ ID NO 129
<211> LENGTH: 24
<212> TYPE: DNA
<213> ORGANISM: SARS-CoV2 Coronavirus
<220> FEATURE:
<221> NAME/KEY: misc_feature
<222> LOCATION: (1)..(24)
<223> OTHER INFORMATION: SARS-CoV-2 Polynucleotide Domain of
      Illustrative Sense-Strand Probe for Detecting SARS-CoV-2 ORF1ab

<400> SEQUENCE: 129

tgcccgtaat ggtgttctta ttac                                              24


<210> SEQ ID NO 130
<211> LENGTH: 23
<212> TYPE: DNA
<213> ORGANISM: SARS-CoV2 Coronavirus
<220> FEATURE:
<221> NAME/KEY: misc_feature
<222> LOCATION: (1)..(23)
<223> OTHER INFORMATION: SARS-CoV-2 Polynucleotide Domain of
      Illustrative Sense-Strand Probe for Detecting SARS-CoV-2 ORF1ab

<400> SEQUENCE: 130

tgcccgtaat ggtgttctta tta                                               23


<210> SEQ ID NO 131
<211> LENGTH: 22
<212> TYPE: DNA
<213> ORGANISM: SARS-CoV2 Coronavirus
<220> FEATURE:
<221> NAME/KEY: misc_feature
<222> LOCATION: (1)..(22)
<223> OTHER INFORMATION: SARS-CoV-2 Polynucleotide Domain of
      Illustrative Sense-Strand Probe for Detecting SARS-CoV-2 ORF1ab

<400> SEQUENCE: 131
```

-continued

```
tgcccgtaat ggtgttctta tt                                            22


<210> SEQ ID NO 132
<211> LENGTH: 21
<212> TYPE: DNA
<213> ORGANISM: SARS-CoV2 Coronavirus
<220> FEATURE:
<221> NAME/KEY: misc_feature
<222> LOCATION: (1)..(21)
<223> OTHER INFORMATION: SARS-CoV-2 Polynucleotide Domain of
      Illustrative Sense-Strand Probe for Detecting SARS-CoV-2 ORF1ab

<400> SEQUENCE: 132

tgcccgtaat ggtgttctta t                                             21


<210> SEQ ID NO 133
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of
      Illustrative Sense-Strand Probe for Detecting SARS-CoV-2 ORF1ab

<400> SEQUENCE: 133

tgcccgtaat ggtgttctta                                               20


<210> SEQ ID NO 134
<211> LENGTH: 26
<212> TYPE: DNA
<213> ORGANISM: SARS-CoV2 Coronavirus
<220> FEATURE:
<221> NAME/KEY: misc_feature
<222> LOCATION: (1)..(26)
<223> OTHER INFORMATION: SARS-CoV-2 Polynucleotide Domain of
      Illustrative Sense-Strand Probe for Detecting SARS-CoV-2 ORF1ab

<400> SEQUENCE: 134

gcccgtaatg gtgttcttat tacaga                                        26


<210> SEQ ID NO 135
<211> LENGTH: 25
<212> TYPE: DNA
<213> ORGANISM: SARS-CoV2 Coronavirus
<220> FEATURE:
<221> NAME/KEY: misc_feature
<222> LOCATION: (1)..(25)
<223> OTHER INFORMATION: SARS-CoV-2 Polynucleotide Domain of
      Illustrative Sense-Strand Probe for Detecting SARS-CoV-2 ORF1ab

<400> SEQUENCE: 135

cccgtaatgg tgttcttatt acaga                                         25


<210> SEQ ID NO 136
<211> LENGTH: 24
<212> TYPE: DNA
<213> ORGANISM: SARS-CoV2 Coronavirus
<220> FEATURE:
<221> NAME/KEY: misc_feature
<222> LOCATION: (1)..(24)
<223> OTHER INFORMATION: SARS-CoV-2 Polynucleotide Domain of
      Illustrative Sense-Strand Probe for Detecting SARS-CoV-2 ORF1ab

<400> SEQUENCE: 136

ccgtaatggt gttcttatta caga                                          24
```

-continued

<210> SEQ ID NO 137
<211> LENGTH: 23
<212> TYPE: DNA
<213> ORGANISM: SARS-CoV2 Coronavirus
<220> FEATURE:
<221> NAME/KEY: misc_feature
<222> LOCATION: (1)..(23)
<223> OTHER INFORMATION: SARS-CoV-2 Polynucleotide Domain of Illustrative Sense-Strand Probe for Detecting SARS-CoV-2 ORF1ab

<400> SEQUENCE: 137
cgtaatggtg ttcttattac aga 23

<210> SEQ ID NO 138
<211> LENGTH: 22
<212> TYPE: DNA
<213> ORGANISM: SARS-CoV2 Coronavirus
<220> FEATURE:
<221> NAME/KEY: misc_feature
<222> LOCATION: (1)..(22)
<223> OTHER INFORMATION: SARS-CoV-2 Polynucleotide Domain of Illustrative Sense-Strand Probe for Detecting SARS-CoV-2 ORF1ab

<400> SEQUENCE: 138
gtaatggtgt tcttattaca ga 22

<210> SEQ ID NO 139
<211> LENGTH: 21
<212> TYPE: DNA
<213> ORGANISM: SARS-CoV2 Coronavirus
<220> FEATURE:
<221> NAME/KEY: misc_feature
<222> LOCATION: (1)..(21)
<223> OTHER INFORMATION: SARS-CoV-2 Polynucleotide Domain of Illustrative Sense-Strand Probe for Detecting SARS-CoV-2 ORF1ab

<400> SEQUENCE: 139
taatggtgtt cttattacag a 21

<210> SEQ ID NO 140
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of Illustrative Sense-Strand Probe for Detecting SARS-CoV-2 ORF1ab

<400> SEQUENCE: 140
aatggtgttc ttattacaga 20

<210> SEQ ID NO 141
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of Illustrative Sense-Strand Probe for Detecting SARS-CoV-2 ORF1ab

<400> SEQUENCE: 141
ttcttattac agaaggtagt 20

<210> SEQ ID NO 142
<211> LENGTH: 24
<212> TYPE: DNA
<213> ORGANISM: SARS-CoV2 Coronavirus

```
<220> FEATURE:
<221> NAME/KEY: misc_feature
<222> LOCATION: (1)..(24)
<223> OTHER INFORMATION: SARS-CoV-2 Polynucleotide Domain of
      Illustrative Sense-Strand Probe for Detecting SARS-CoV-2 ORF1ab

<400> SEQUENCE: 142

gcccgtaatg gtgttcttat taca                                          24


<210> SEQ ID NO 143
<211> LENGTH: 23
<212> TYPE: DNA
<213> ORGANISM: SARS-CoV2 Coronavirus
<220> FEATURE:
<221> NAME/KEY: misc_feature
<222> LOCATION: (1)..(23)
<223> OTHER INFORMATION: SARS-CoV-2 Polynucleotide Domain of
      Illustrative Sense-Strand Probe for Detecting SARS-CoV-2 ORF1ab

<400> SEQUENCE: 143

gcccgtaatg gtgttcttat tac                                           23


<210> SEQ ID NO 144
<211> LENGTH: 22
<212> TYPE: DNA
<213> ORGANISM: SARS-CoV2 Coronavirus
<220> FEATURE:
<221> NAME/KEY: misc_feature
<222> LOCATION: (1)..(22)
<223> OTHER INFORMATION: SARS-CoV-2 Polynucleotide Domain of
      Illustrative Sense-Strand Probe for Detecting SARS-CoV-2 ORF1ab

<400> SEQUENCE: 144

cccgtaatgg tgttcttatt ac                                            22


<210> SEQ ID NO 145
<211> LENGTH: 21
<212> TYPE: DNA
<213> ORGANISM: SARS-CoV2 Coronavirus
<220> FEATURE:
<221> NAME/KEY: misc_feature
<222> LOCATION: (1)..(21)
<223> OTHER INFORMATION: SARS-CoV-2 Polynucleotide Domain of
      Illustrative Sense-Strand Probe for Detecting SARS-CoV-2 ORF1ab

<400> SEQUENCE: 145

cccgtaatgg tgttcttatt a                                             21


<210> SEQ ID NO 146
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of
      Illustrative Sense-Strand Probe for Detecting SARS-CoV-2 ORF1ab

<400> SEQUENCE: 146

ccgtaatggt gttcttatta                                               20


<210> SEQ ID NO 147
<211> LENGTH: 26
<212> TYPE: DNA
<213> ORGANISM: SARS-CoV2 Coronavirus
<220> FEATURE:
<221> NAME/KEY: misc_feature
<222> LOCATION: (1)..(26)
<223> OTHER INFORMATION: SARS-CoV-2 Polynucleotide Domain of
```

Illustrative Antisense-Strand Probe for Detecting SARS-CoV-2 ORF1ab

<400> SEQUENCE: 147
tctgtaataa gaacaccatt acgggc 26

<210> SEQ ID NO 148
<211> LENGTH: 25
<212> TYPE: DNA
<213> ORGANISM: SARS-CoV2 Coronavirus
<220> FEATURE:
<221> NAME/KEY: misc_feature
<222> LOCATION: (1)..(25)
<223> OTHER INFORMATION: SARS-CoV-2 Polynucleotide Domain of Illustrative Antisense-Strand Probe for Detecting SARS-CoV-2 ORF1ab

<400> SEQUENCE: 148
tctgtaataa gaacaccatt acggg 25

<210> SEQ ID NO 149
<211> LENGTH: 24
<212> TYPE: DNA
<213> ORGANISM: SARS-CoV2 Coronavirus
<220> FEATURE:
<221> NAME/KEY: misc_feature
<222> LOCATION: (1)..(24)
<223> OTHER INFORMATION: SARS-CoV-2 Polynucleotide Domain of Illustrative Antisense-Strand Probe for Detecting SARS-CoV-2 ORF1ab

<400> SEQUENCE: 149
tctgtaataa gaacaccatt acgg 24

<210> SEQ ID NO 150
<211> LENGTH: 23
<212> TYPE: DNA
<213> ORGANISM: SARS-CoV2 Coronavirus
<220> FEATURE:
<221> NAME/KEY: misc_feature
<222> LOCATION: (1)..(23)
<223> OTHER INFORMATION: SARS-CoV-2 Polynucleotide Domain of Illustrative Antisense-Strand Probe for Detecting SARS-CoV-2 ORF1ab

<400> SEQUENCE: 150
tctgtaataa gaacaccatt acg 23

<210> SEQ ID NO 151
<211> LENGTH: 22
<212> TYPE: DNA
<213> ORGANISM: SARS-CoV2 Coronavirus
<220> FEATURE:
<221> NAME/KEY: misc_feature
<222> LOCATION: (1)..(22)
<223> OTHER INFORMATION: SARS-CoV-2 Polynucleotide Domain of Illustrative Antisense-Strand Probe for Detecting SARS-CoV-2 ORF1ab

<400> SEQUENCE: 151
tctgtaataa gaacaccatt ac 22

<210> SEQ ID NO 152
<211> LENGTH: 21
<212> TYPE: DNA
<213> ORGANISM: SARS-CoV2 Coronavirus
<220> FEATURE:
<221> NAME/KEY: misc_feature
<222> LOCATION: (1)..(21)

<223> OTHER INFORMATION: SARS-CoV-2 Polynucleotide Domain of
      Illustrative Antisense-Strand Probe for Detecting SARS-Cov-2
      ORF1ab

<400> SEQUENCE: 152
tctgtaataa gaacaccatt a                                              21

<210> SEQ ID NO 153
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of
      Illustrative Antisense-Strand Probe for Detecting SARS-CoV-2
      ORF1ab

<400> SEQUENCE: 153
tctgtaataa gaacaccatt                                                20

<210> SEQ ID NO 154
<211> LENGTH: 26
<212> TYPE: DNA
<213> ORGANISM: SARS-CoV2 Coronavirus
<220> FEATURE:
<221> NAME/KEY: misc_feature
<222> LOCATION: (1)..(26)
<223> OTHER INFORMATION: SARS-CoV-2 Polynucleotide Domain of
      Illustrative Antisense-Strand Probe for Detecting SARS-CoV-2
      ORF1ab

<400> SEQUENCE: 154
ctgtaataag aacaccatta cgggca                                         26

<210> SEQ ID NO 155
<211> LENGTH: 25
<212> TYPE: DNA
<213> ORGANISM: SARS-CoV2 Coronavirus
<220> FEATURE:
<221> NAME/KEY: misc_feature
<222> LOCATION: (1)..(25)
<223> OTHER INFORMATION: SARS-CoV-2 Polynucleotide Domain of
      Illustrative Antisense-Strand Probe for Detecting SARS-CoV-2
      ORF1ab

<400> SEQUENCE: 155
tgtaataaga acaccattac gggca                                          25

<210> SEQ ID NO 156
<211> LENGTH: 24
<212> TYPE: DNA
<213> ORGANISM: SARS-CoV2 Coronavirus
<220> FEATURE:
<221> NAME/KEY: misc_feature
<222> LOCATION: (1)..(24)
<223> OTHER INFORMATION: SARS-CoV-2 Polynucleotide Domain of
      Illustrative Antisense-Strand Probe for Detecting SARS-CoV-2
      ORF1ab

<400> SEQUENCE: 156
gtaataagaa caccattacg ggca                                           24

<210> SEQ ID NO 157
<211> LENGTH: 23
<212> TYPE: DNA
<213> ORGANISM: SARS-CoV2 Coronavirus
<220> FEATURE:
<221> NAME/KEY: misc_feature

```
<222> LOCATION: (1)..(23)
<223> OTHER INFORMATION: SARS-CoV-2 Polynucleotide Domain of
      Illustrative Antisense-Strand Probe for Detecting SARS-CoV-2
      ORF1ab

<400> SEQUENCE: 157

taataagaac accattacgg gca                                          23


<210> SEQ ID NO 158
<211> LENGTH: 22
<212> TYPE: DNA
<213> ORGANISM: SARS-CoV2 Coronavirus
<220> FEATURE:
<221> NAME/KEY: misc_feature
<222> LOCATION: (1)..(22)
<223> OTHER INFORMATION: SARS-CoV-2 Polynucleotide Domain of
      Illustrative Antisense-Strand Probe for Detecting SARS-CoV-2
      ORF1ab

<400> SEQUENCE: 158

aataagaaca ccattacggg ca                                           22


<210> SEQ ID NO 159
<211> LENGTH: 21
<212> TYPE: DNA
<213> ORGANISM: SARS-CoV2 Coronavirus
<220> FEATURE:
<221> NAME/KEY: misc_feature
<222> LOCATION: (1)..(21)
<223> OTHER INFORMATION: SARS-CoV-2 Polynucleotide Domain of
      Illustrative Antisense-Strand Probe for Detecting SARS-CoV-2
      ORF1ab

<400> SEQUENCE: 159

ataagaacac cattacgggc a                                            21


<210> SEQ ID NO 160
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of
      Illustrative Antisense-Strand Probe for Detecting SARS-CoV-2
      ORF1ab

<400> SEQUENCE: 160

taagaacacc attacgggca                                              20


<210> SEQ ID NO 161
<211> LENGTH: 25
<212> TYPE: DNA
<213> ORGANISM: SARS-CoV2 Coronavirus
<220> FEATURE:
<221> NAME/KEY: misc_feature
<222> LOCATION: (1)..(25)
<223> OTHER INFORMATION: SARS-CoV-2 Polynucleotide Domain of
      Illustrative Antisense-Strand Probe for Detecting SARS-CoV-2
      ORF1ab

<400> SEQUENCE: 161

ctgtaataag aacaccatta cgggc                                        25


<210> SEQ ID NO 162
<211> LENGTH: 24
<212> TYPE: DNA
<213> ORGANISM: SARS-CoV2 Coronavirus
<220> FEATURE:
```

<221> NAME/KEY: misc_feature
<222> LOCATION: (1)..(24)
<223> OTHER INFORMATION: SARS-CoV-2 Polynucleotide Domain of
      Illustrative Antisense-Strand Probe for Detecting SARS-CoV-2
      ORF1ab

<400> SEQUENCE: 162
tgtaataaga acaccattac gggc 24

<210> SEQ ID NO 163
<211> LENGTH: 23
<212> TYPE: DNA
<213> ORGANISM: SARS-CoV2 Coronavirus
<220> FEATURE:
<221> NAME/KEY: misc_feature
<222> LOCATION: (1)..(23)
<223> OTHER INFORMATION: SARS-CoV-2 Polynucleotide Domain of
      Illustrative Antisense-Strand Probe for Detecting SARS-CoV-2
      ORF1ab

<400> SEQUENCE: 163
gtaataagaa caccattacg ggc 23

<210> SEQ ID NO 164
<211> LENGTH: 22
<212> TYPE: DNA
<213> ORGANISM: SARS-CoV2 Coronavirus
<220> FEATURE:
<221> NAME/KEY: misc_feature
<222> LOCATION: (1)..(22)
<223> OTHER INFORMATION: SARS-CoV-2 Polynucleotide Domain of
      Illustrative Antisense-Strand Probe for Detecting SARS-CoV-2
      ORF1ab

<400> SEQUENCE: 164
gtaataagaa caccattacg gg 22

<210> SEQ ID NO 165
<211> LENGTH: 21
<212> TYPE: DNA
<213> ORGANISM: SARS-CoV2 Coronavirus
<220> FEATURE:
<221> NAME/KEY: misc_feature
<222> LOCATION: (1)..(21)
<223> OTHER INFORMATION: SARS-CoV-2 Polynucleotide Domain of
      Illustrative Antisense-Strand Probe for Detecting SARS-CoV-2
      ORF1ab

<400> SEQUENCE: 165
taataagaac accattacgg g 21

<210> SEQ ID NO 166
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of
      Illustrative Antisense-Strand Probe for Detecting SARS-CoV-2
      ORF1ab

<400> SEQUENCE: 166
taataagaac accattacgg 20

<210> SEQ ID NO 167
<211> LENGTH: 31
<212> TYPE: DNA
<213> ORGANISM: SARS-CoV2 Coronavirus
<220> FEATURE:
<221> NAME/KEY: misc_feature
<222> LOCATION: (1)..(31)
<223> OTHER INFORMATION: SARS-CoV-2 Polynucleotide Domain of Illustrative Sense-Strand Probe for Detecting the SARS-CoV-2 S Gene

<400> SEQUENCE: 167
ctgttcttta tcaggatgtt aactgcacag a 31

<210> SEQ ID NO 168
<211> LENGTH: 31
<212> TYPE: DNA
<213> ORGANISM: SARS-CoV2 Coronavirus
<220> FEATURE:
<221> NAME/KEY: misc_feature
<222> LOCATION: (1)..(31)
<223> OTHER INFORMATION: SARS-CoV-2 Polynucleotide Domain of Illustrative Sense-Strand Probe for Detecting the SARS-CoV-2 S Gene

<400> SEQUENCE: 168
ctgttcttta tcagggtgtt aactgcacag a 31

<210> SEQ ID NO 169
<211> LENGTH: 30
<212> TYPE: DNA
<213> ORGANISM: SARS-CoV2 Coronavirus
<220> FEATURE:
<221> NAME/KEY: misc_feature
<222> LOCATION: (1)..(30)
<223> OTHER INFORMATION: SARS-CoV-2 Polynucleotide Domain of Illustrative Sense-Strand Probe for Detecting the SARS-CoV-2 S Gene

<400> SEQUENCE: 169
tgttctttat caggatgtta actgcacaga 30

<210> SEQ ID NO 170
<211> LENGTH: 30
<212> TYPE: DNA
<213> ORGANISM: SARS-CoV2 Coronavirus
<220> FEATURE:
<221> NAME/KEY: misc_feature
<222> LOCATION: (1)..(30)
<223> OTHER INFORMATION: SARS-CoV-2 Polynucleotide Domain of Illustrative Sense-Strand Probe for Detecting the SARS-CoV-2 S Gene

<400> SEQUENCE: 170
tgttctttat cagggtgtta actgcacaga 30

<210> SEQ ID NO 171
<211> LENGTH: 29
<212> TYPE: DNA
<213> ORGANISM: SARS-CoV2 Coronavirus
<220> FEATURE:
<221> NAME/KEY: misc_feature
<222> LOCATION: (1)..(29)
<223> OTHER INFORMATION: SARS-CoV-2 Polynucleotide Domain of Illustrative Sense-Strand Probe for Detecting the SARS-CoV-2 S Gene

<400> SEQUENCE: 171
gttctttatc aggatgttaa ctgcacaga 29

<210> SEQ ID NO 172
<211> LENGTH: 29
<212> TYPE: DNA

<213> ORGANISM: SARS-CoV2 Coronavirus
<220> FEATURE:
<221> NAME/KEY: misc_feature
<222> LOCATION: (1)..(29)
<223> OTHER INFORMATION: SARS-CoV-2 Polynucleotide Domain of Illustrative Sense-Strand Probe for Detecting the SARS-CoV-2 S Gene

<400> SEQUENCE: 172
gttctttatc agggtgttaa ctgcacaga 29

<210> SEQ ID NO 173
<211> LENGTH: 28
<212> TYPE: DNA
<213> ORGANISM: SARS-CoV2 Coronavirus
<220> FEATURE:
<221> NAME/KEY: misc_feature
<222> LOCATION: (1)..(28)
<223> OTHER INFORMATION: SARS-CoV-2 Polynucleotide Domain of Illustrative Sense-Strand Probe for Detecting the SARS-CoV-2 S Gene

<400> SEQUENCE: 173
ttctttatca ggatgttaac tgcacaga 28

<210> SEQ ID NO 174
<211> LENGTH: 28
<212> TYPE: DNA
<213> ORGANISM: SARS-CoV2 Coronavirus
<220> FEATURE:
<221> NAME/KEY: misc_feature
<222> LOCATION: (1)..(28)
<223> OTHER INFORMATION: SARS-CoV-2 Polynucleotide Domain of Illustrative Sense-Strand Probe for Detecting the SARS-CoV-2 S Gene

<400> SEQUENCE: 174
ttctttatca gggtgttaac tgcacaga 28

<210> SEQ ID NO 175
<211> LENGTH: 27
<212> TYPE: DNA
<213> ORGANISM: SARS-CoV2 Coronavirus
<220> FEATURE:
<221> NAME/KEY: misc_feature
<222> LOCATION: (1)..(27)
<223> OTHER INFORMATION: SARS-CoV-2 Polynucleotide Domain of Illustrative Sense-Strand Probe for Detecting the SARS-CoV-2 S Gene

<400> SEQUENCE: 175
tctttatcag gatgttaact gcacaga 27

<210> SEQ ID NO 176
<211> LENGTH: 27
<212> TYPE: DNA
<213> ORGANISM: SARS-CoV2 Coronavirus
<220> FEATURE:
<221> NAME/KEY: misc_feature
<222> LOCATION: (1)..(27)
<223> OTHER INFORMATION: SARS-CoV-2 Polynucleotide Domain of Illustrative Sense-Strand Probe for Detecting the SARS-CoV-2 S Gene

<400> SEQUENCE: 176
tctttatcag ggtgttaact gcacaga 27

<210> SEQ ID NO 177
<211> LENGTH: 26

<212> TYPE: DNA
<213> ORGANISM: SARS-CoV2 Coronavirus
<220> FEATURE:
<221> NAME/KEY: misc_feature
<222> LOCATION: (1)..(26)
<223> OTHER INFORMATION: SARS-CoV-2 Polynucleotide Domain of Illustrative Sense-Strand Probe for Detecting the SARS-CoV-2 S Gene

<400> SEQUENCE: 177
ctttatcagg atgttaactg cacaga 26

<210> SEQ ID NO 178
<211> LENGTH: 26
<212> TYPE: DNA
<213> ORGANISM: SARS-CoV2 Coronavirus
<220> FEATURE:
<221> NAME/KEY: misc_feature
<222> LOCATION: (1)..(26)
<223> OTHER INFORMATION: SARS-CoV-2 Polynucleotide Domain of Illustrative Sense-Strand Probe for Detecting the SARS-CoV-2 S Gene

<400> SEQUENCE: 178
ctttatcagg gtgttaactg cacaga 26

<210> SEQ ID NO 179
<211> LENGTH: 25
<212> TYPE: DNA
<213> ORGANISM: SARS-CoV2 Coronavirus
<220> FEATURE:
<221> NAME/KEY: misc_feature
<222> LOCATION: (1)..(25)
<223> OTHER INFORMATION: SARS-CoV-2 Polynucleotide Domain of Illustrative Sense-Strand Probe for Detecting the SARS-CoV-2 S Gene

<400> SEQUENCE: 179
tttatcagga tgttaactgc acaga 25

<210> SEQ ID NO 180
<211> LENGTH: 25
<212> TYPE: DNA
<213> ORGANISM: SARS-CoV2 Coronavirus
<220> FEATURE:
<221> NAME/KEY: misc_feature
<222> LOCATION: (1)..(25)
<223> OTHER INFORMATION: SARS-CoV-2 Polynucleotide Domain of Illustrative Sense-Strand Probe for Detecting the SARS-CoV-2 S Gene

<400> SEQUENCE: 180
tttatcaggg tgttaactgc acaga 25

<210> SEQ ID NO 181
<211> LENGTH: 24
<212> TYPE: DNA
<213> ORGANISM: SARS-CoV2 Coronavirus
<220> FEATURE:
<221> NAME/KEY: misc_feature
<222> LOCATION: (1)..(24)
<223> OTHER INFORMATION: SARS-CoV-2 Polynucleotide Domain of Illustrative Sense-Strand Probe for Detecting the SARS-CoV-2 S Gene

<400> SEQUENCE: 181
ttatcaggat gttaactgca caga 24

<210> SEQ ID NO 182

<211> LENGTH: 24
<212> TYPE: DNA
<213> ORGANISM: SARS-CoV2 Coronavirus
<220> FEATURE:
<221> NAME/KEY: misc_feature
<222> LOCATION: (1)..(24)
<223> OTHER INFORMATION: SARS-CoV-2 Polynucleotide Domain of Illustrative Sense-Strand Probe for Detecting the SARS-CoV-2 S Gene

<400> SEQUENCE: 182
ttatcagggt gttaactgca caga 24

<210> SEQ ID NO 183
<211> LENGTH: 23
<212> TYPE: DNA
<213> ORGANISM: SARS-CoV2 Coronavirus
<220> FEATURE:
<221> NAME/KEY: misc_feature
<222> LOCATION: (1)..(23)
<223> OTHER INFORMATION: SARS-CoV-2 Polynucleotide Domain of Illustrative Sense-Strand Probe for Detecting the SARS-CoV-2 S Gene

<400> SEQUENCE: 183
tatcaggatg ttaactgcac aga 23

<210> SEQ ID NO 184
<211> LENGTH: 23
<212> TYPE: DNA
<213> ORGANISM: SARS-CoV2 Coronavirus
<220> FEATURE:
<221> NAME/KEY: misc_feature
<222> LOCATION: (1)..(23)
<223> OTHER INFORMATION: SARS-CoV-2 Polynucleotide Domain of Illustrative Sense-Strand Probe for Detecting the SARS-CoV-2 S Gene

<400> SEQUENCE: 184
tatcagggtg ttaactgcac aga 23

<210> SEQ ID NO 185
<211> LENGTH: 22
<212> TYPE: DNA
<213> ORGANISM: SARS-CoV2 Coronavirus
<220> FEATURE:
<221> NAME/KEY: misc_feature
<222> LOCATION: (1)..(22)
<223> OTHER INFORMATION: SARS-CoV-2 Polynucleotide Domain of Illustrative Sense-Strand Probe for Detecting the SARS-CoV-2 S Gene

<400> SEQUENCE: 185
atcaggatgt taactgcaca ga 22

<210> SEQ ID NO 186
<211> LENGTH: 22
<212> TYPE: DNA
<213> ORGANISM: SARS-CoV2 Coronavirus
<220> FEATURE:
<221> NAME/KEY: misc_feature
<222> LOCATION: (1)..(22)
<223> OTHER INFORMATION: SARS-CoV-2 Polynucleotide Domain of Illustrative Sense-Strand Probe for Detecting the SARS-CoV-2 S Gene

<400> SEQUENCE: 186
atcagggtgt taactgcaca ga 22

```
<210> SEQ ID NO 187
<211> LENGTH: 21
<212> TYPE: DNA
<213> ORGANISM: SARS-CoV2 Coronavirus
<220> FEATURE:
<221> NAME/KEY: misc_feature
<222> LOCATION: (1)..(21)
<223> OTHER INFORMATION: SARS-CoV-2 Polynucleotide Domain of
      Illustrative Sense-Strand Probe for Detecting the SARS-CoV-2 S
      Gene

<400> SEQUENCE: 187

tcaggatgtt aactgcacag a                                            21


<210> SEQ ID NO 188
<211> LENGTH: 21
<212> TYPE: DNA
<213> ORGANISM: SARS-CoV2 Coronavirus
<220> FEATURE:
<221> NAME/KEY: misc_feature
<222> LOCATION: (1)..(21)
<223> OTHER INFORMATION: SARS-CoV-2 Polynucleotide Domain of
      Illustrative Sense-Strand Probe for Detecting the SARS-CoV-2 S
      Gene

<400> SEQUENCE: 188

tcagggtgtt aactgcacag a                                            21


<210> SEQ ID NO 189
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of
      Illustrative Sense-Strand Probe for Detecting the SARS-CoV-2 S
      Gene

<400> SEQUENCE: 189

caggatgtta actgcacaga                                              20


<210> SEQ ID NO 190
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of
      Illustrative Sense-Strand Probe for Detecting the SARS-CoV-2 S
      Gene

<400> SEQUENCE: 190

cagggtgtta actgcacaga                                              20


<210> SEQ ID NO 191
<211> LENGTH: 30
<212> TYPE: DNA
<213> ORGANISM: SARS-CoV2 Coronavirus
<220> FEATURE:
<221> NAME/KEY: misc_feature
<222> LOCATION: (1)..(30)
<223> OTHER INFORMATION: SARS-CoV-2 Polynucleotide Domain of
      Illustrative Sense-Strand Probe for Detecting the SARS-CoV-2 S
      Gene

<400> SEQUENCE: 191

ctgttcttta tcaggatgtt aactgcacag                                   30
```

<210> SEQ ID NO 192
<211> LENGTH: 30
<212> TYPE: DNA
<213> ORGANISM: SARS-CoV2 Coronavirus
<220> FEATURE:
<221> NAME/KEY: misc_feature
<222> LOCATION: (1)..(30)
<223> OTHER INFORMATION: SARS-CoV-2 Polynucleotide Domain of Illustrative Sense-Strand Probe for Detecting the SARS-CoV-2 S Gene

<400> SEQUENCE: 192
ctgttcttta tcagggtgtt aactgcacag 30

<210> SEQ ID NO 193
<211> LENGTH: 29
<212> TYPE: DNA
<213> ORGANISM: SARS-CoV2 Coronavirus
<220> FEATURE:
<221> NAME/KEY: misc_feature
<222> LOCATION: (1)..(29)
<223> OTHER INFORMATION: SARS-CoV-2 Polynucleotide Domain of Illustrative Sense-Strand Probe for Detecting the SARS-CoV-2 S Gene

<400> SEQUENCE: 193
ctgttcttta tcaggatgtt aactgcaca 29

<210> SEQ ID NO 194
<211> LENGTH: 29
<212> TYPE: DNA
<213> ORGANISM: SARS-CoV2 Coronavirus
<220> FEATURE:
<221> NAME/KEY: misc_feature
<222> LOCATION: (1)..(29)
<223> OTHER INFORMATION: SARS-CoV-2 Polynucleotide Domain of Illustrative Sense-Strand Probe for Detecting the SARS-CoV-2 S Gene

<400> SEQUENCE: 194
ctgttcttta tcagggtgtt aactgcaca 29

<210> SEQ ID NO 195
<211> LENGTH: 28
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of Illustrative Sense-Strand Probe for Detecting the SARS-CoV-2 S Gene

<400> SEQUENCE: 195
ctgttcttta tcaggatgtt aactgcac 28

<210> SEQ ID NO 196
<211> LENGTH: 28
<212> TYPE: DNA
<213> ORGANISM: SARS-CoV2 Coronavirus
<220> FEATURE:
<221> NAME/KEY: misc_feature
<222> LOCATION: (1)..(28)
<223> OTHER INFORMATION: SARS-CoV-2 Polynucleotide Domain of Illustrative Sense-Strand Probe for Detecting the SARS-CoV-2 S Gene

<400> SEQUENCE: 196
ctgttcttta tcagggtgtt aactgcac 28

<210> SEQ ID NO 197
<211> LENGTH: 27
<212> TYPE: DNA
<213> ORGANISM: SARS-CoV2 Coronavirus
<220> FEATURE:
<221> NAME/KEY: misc_feature
<222> LOCATION: (1)..(27)
<223> OTHER INFORMATION: SARS-CoV-2 Polynucleotide Domain of Illustrative Sense-Strand Probe for Detecting the SARS-CoV-2 S Gene

<400> SEQUENCE: 197
ctgttcttta tcaggatgtt aactgca 27

<210> SEQ ID NO 198
<211> LENGTH: 27
<212> TYPE: DNA
<213> ORGANISM: SARS-CoV2 Coronavirus
<220> FEATURE:
<221> NAME/KEY: misc_feature
<222> LOCATION: (1)..(27)
<223> OTHER INFORMATION: SARS-CoV-2 Polynucleotide Domain of Illustrative Sense-Strand Probe for Detecting the SARS-CoV-2 S Gene

<400> SEQUENCE: 198
ctgttcttta tcagggtgtt aactgca 27

<210> SEQ ID NO 199
<211> LENGTH: 26
<212> TYPE: DNA
<213> ORGANISM: SARS-CoV2 Coronavirus
<220> FEATURE:
<221> NAME/KEY: misc_feature
<222> LOCATION: (1)..(26)
<223> OTHER INFORMATION: SARS-CoV-2 Polynucleotide Domain of Illustrative Sense-Strand Probe for Detecting the SARS-CoV-2 S Gene

<400> SEQUENCE: 199
ctgttcttta tcaggatgtt aactgc 26

<210> SEQ ID NO 200
<211> LENGTH: 26
<212> TYPE: DNA
<213> ORGANISM: SARS-CoV2 Coronavirus
<220> FEATURE:
<221> NAME/KEY: misc_feature
<222> LOCATION: (1)..(26)
<223> OTHER INFORMATION: SARS-CoV-2 Polynucleotide Domain of Illustrative Sense-Strand Probe for Detecting the SARS-CoV-2 S Gene

<400> SEQUENCE: 200
ctgttcttta tcagggtgtt aactgc 26

<210> SEQ ID NO 201
<211> LENGTH: 25
<212> TYPE: DNA
<213> ORGANISM: SARS-CoV2 Coronavirus
<220> FEATURE:
<221> NAME/KEY: misc_feature
<222> LOCATION: (1)..(25)
<223> OTHER INFORMATION: SARS-CoV-2 Polynucleotide Domain of Illustrative Sense-Strand Probe for Detecting the SARS-CoV-2 S Gene

<400> SEQUENCE: 201

```
ctgttcttta tcaggatgtt aactg                                      25


<210> SEQ ID NO 202
<211> LENGTH: 25
<212> TYPE: DNA
<213> ORGANISM: SARS-CoV2 Coronavirus
<220> FEATURE:
<221> NAME/KEY: misc_feature
<222> LOCATION: (1)..(25)
<223> OTHER INFORMATION: SARS-CoV-2 Polynucleotide Domain of
      Illustrative Sense-Strand Probe for Detecting the SARS-CoV-2 S
      Gene

<400> SEQUENCE: 202

ctgttcttta tcagggtgtt aactg                                      25


<210> SEQ ID NO 203
<211> LENGTH: 24
<212> TYPE: DNA
<213> ORGANISM: SARS-CoV2 Coronavirus
<220> FEATURE:
<221> NAME/KEY: misc_feature
<222> LOCATION: (1)..(24)
<223> OTHER INFORMATION: SARS-CoV-2 Polynucleotide Domain of
      Illustrative Sense-Strand Probe for Detecting the SARS-CoV-2 S
      Gene

<400> SEQUENCE: 203

ctgttcttta tcaggatgtt aact                                       24


<210> SEQ ID NO 204
<211> LENGTH: 24
<212> TYPE: DNA
<213> ORGANISM: SARS-CoV2 Coronavirus
<220> FEATURE:
<221> NAME/KEY: misc_feature
<222> LOCATION: (1)..(24)
<223> OTHER INFORMATION: SARS-CoV-2 Polynucleotide Domain of
      Illustrative Sense-Strand Probe for Detecting the SARS-CoV-2 S
      Gene

<400> SEQUENCE: 204

ctgttcttta tcagggtgtt aact                                       24


<210> SEQ ID NO 205
<211> LENGTH: 23
<212> TYPE: DNA
<213> ORGANISM: SARS-CoV2 Coronavirus
<220> FEATURE:
<221> NAME/KEY: misc_feature
<222> LOCATION: (1)..(23)
<223> OTHER INFORMATION: SARS-CoV-2 Polynucleotide Domain of
      Illustrative Sense-Strand Probe for Detecting the SARS-CoV-2 S
      Gene

<400> SEQUENCE: 205

ctgttcttta tcaggatgtt aac                                        23


<210> SEQ ID NO 206
<211> LENGTH: 23
<212> TYPE: DNA
<213> ORGANISM: SARS-CoV2 Coronavirus
<220> FEATURE:
<221> NAME/KEY: misc_feature
<222> LOCATION: (1)..(23)
<223> OTHER INFORMATION: SARS-CoV-2 Polynucleotide Domain of
      Illustrative Sense-Strand Probe for Detecting the SARS-CoV-2 S
      Gene

<400> SEQUENCE: 206
```

ctgttcttta tcagggtgtt aac 23

<210> SEQ ID NO 207
<211> LENGTH: 22
<212> TYPE: DNA
<213> ORGANISM: SARS-CoV2 Coronavirus
<220> FEATURE:
<221> NAME/KEY: misc_feature
<222> LOCATION: (1)..(22)
<223> OTHER INFORMATION: SARS-CoV-2 Polynucleotide Domain of Illustrative Sense-Strand Probe for Detecting the SARS-CoV-2 S Gene

<400> SEQUENCE: 207
ctgttcttta tcaggatgtt aa 22

<210> SEQ ID NO 208
<211> LENGTH: 22
<212> TYPE: DNA
<213> ORGANISM: SARS-CoV2 Coronavirus
<220> FEATURE:
<221> NAME/KEY: misc_feature
<222> LOCATION: (1)..(22)
<223> OTHER INFORMATION: SARS-CoV-2 Polynucleotide Domain of Illustrative Sense-Strand Probe for Detecting the SARS-CoV-2 S Gene

<400> SEQUENCE: 208
ctgttcttta tcagggtgtt aa 22

<210> SEQ ID NO 209
<211> LENGTH: 21
<212> TYPE: DNA
<213> ORGANISM: SARS-CoV2 Coronavirus
<220> FEATURE:
<221> NAME/KEY: misc_feature
<222> LOCATION: (1)..(21)
<223> OTHER INFORMATION: SARS-CoV-2 Polynucleotide Domain of Illustrative Sense-Strand Probe for Detecting the SARS-CoV-2 S Gene

<400> SEQUENCE: 209
ctgttcttta tcaggatgtt a 21

<210> SEQ ID NO 210
<211> LENGTH: 21
<212> TYPE: DNA
<213> ORGANISM: SARS-CoV2 Coronavirus
<220> FEATURE:
<221> NAME/KEY: misc_feature
<222> LOCATION: (1)..(21)
<223> OTHER INFORMATION: SARS-CoV-2 Polynucleotide Domain of Illustrative Sense-Strand Probe for Detecting the SARS-CoV-2 S Gene

<400> SEQUENCE: 210
ctgttcttta tcagggtgtt a 21

<210> SEQ ID NO 211
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of Illustrative Sense-Strand Probe for Detecting the SARS-CoV-2 S Gene

<400> SEQUENCE: 211
ctgttcttta tcaggatgtt 20

<210> SEQ ID NO 212
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of Illustrative Sense-Strand Probe for Detecting the SARS-CoV-2 S Gene

<400> SEQUENCE: 212
ctgttcttta tcagggtgtt 20

<210> SEQ ID NO 213
<211> LENGTH: 30
<212> TYPE: DNA
<213> ORGANISM: SARS-CoV2 Coronavirus
<220> FEATURE:
<221> NAME/KEY: misc_feature
<222> LOCATION: (1)..(30)
<223> OTHER INFORMATION: SARS-CoV-2 Polynucleotide Domain of Illustrative Sense-Strand Probe for Detecting the SARS-CoV-2 S Gene

<400> SEQUENCE: 213
tgttctttat caggatgtta actgcacaga 30

<210> SEQ ID NO 214
<211> LENGTH: 30
<212> TYPE: DNA
<213> ORGANISM: SARS-CoV2 Coronavirus
<220> FEATURE:
<221> NAME/KEY: misc_feature
<222> LOCATION: (1)..(30)
<223> OTHER INFORMATION: SARS-CoV-2 Polynucleotide Domain of Illustrative Sense-Strand Probe for Detecting the SARS-CoV-2 S Gene

<400> SEQUENCE: 214
tgttctttat cagggtgtta actgcacaga 30

<210> SEQ ID NO 215
<211> LENGTH: 29
<212> TYPE: DNA
<213> ORGANISM: SARS-CoV2 Coronavirus
<220> FEATURE:
<221> NAME/KEY: misc_feature
<222> LOCATION: (1)..(29)
<223> OTHER INFORMATION: SARS-CoV-2 Polynucleotide Domain of Illustrative Sense-Strand Probe for Detecting the SARS-CoV-2 S Gene

<400> SEQUENCE: 215
tgttctttat caggatgtta actgcacag 29

<210> SEQ ID NO 216
<211> LENGTH: 29
<212> TYPE: DNA
<213> ORGANISM: SARS-CoV2 Coronavirus
<220> FEATURE:
<221> NAME/KEY: misc_feature
<222> LOCATION: (1)..(29)
<223> OTHER INFORMATION: SARS-CoV-2 Polynucleotide Domain of Illustrative Sense-Strand Probe for Detecting the SARS-CoV-2 S Gene

<400> SEQUENCE: 216
tgttctttat cagggtgtta actgcacag 29

<210> SEQ ID NO 217
<211> LENGTH: 28
<212> TYPE: DNA
<213> ORGANISM: SARS-CoV2 Coronavirus
<220> FEATURE:
<221> NAME/KEY: misc_feature
<222> LOCATION: (1)..(28)
<223> OTHER INFORMATION: SARS-CoV-2 Polynucleotide Domain of Illustrative Sense-Strand Probe for Detecting the SARS-CoV-2 S Gene

<400> SEQUENCE: 217
gttctttatc aggatgttaa ctgcacag 28

<210> SEQ ID NO 218
<211> LENGTH: 28
<212> TYPE: DNA
<213> ORGANISM: SARS-CoV2 Coronavirus
<220> FEATURE:
<221> NAME/KEY: misc_feature
<222> LOCATION: (1)..(28)
<223> OTHER INFORMATION: SARS-CoV-2 Polynucleotide Domain of Illustrative Sense-Strand Probe for Detecting the SARS-CoV-2 S Gene

<400> SEQUENCE: 218
gttctttatc agggtgttaa ctgcacag 28

<210> SEQ ID NO 219
<211> LENGTH: 27
<212> TYPE: DNA
<213> ORGANISM: SARS-CoV2 Coronavirus
<220> FEATURE:
<221> NAME/KEY: misc_feature
<222> LOCATION: (1)..(27)
<223> OTHER INFORMATION: SARS-CoV-2 Polynucleotide Domain of Illustrative Sense-Strand Probe for Detecting the SARS-CoV-2 S Gene

<400> SEQUENCE: 219
gttctttatc aggatgttaa ctgcaca 27

<210> SEQ ID NO 220
<211> LENGTH: 27
<212> TYPE: DNA
<213> ORGANISM: SARS-CoV2 Coronavirus
<220> FEATURE:
<221> NAME/KEY: misc_feature
<222> LOCATION: (1)..(27)
<223> OTHER INFORMATION: SARS-CoV-2 Polynucleotide Domain of Illustrative Sense-Strand Probe for Detecting the SARS-CoV-2 S Gene

<400> SEQUENCE: 220
gttctttatc agggtgttaa ctgcaca 27

<210> SEQ ID NO 221
<211> LENGTH: 26
<212> TYPE: DNA
<213> ORGANISM: SARS-CoV2 Coronavirus
<220> FEATURE:
<221> NAME/KEY: misc_feature
<222> LOCATION: (1)..(26)
<223> OTHER INFORMATION: SARS-CoV-2 Polynucleotide Domain of Illustrative Sense-Strand Probe for Detecting the SARS-CoV-2 S Gene

<400> SEQUENCE: 221
ttctttatca ggatgttaac tgcaca 26

<210> SEQ ID NO 222
<211> LENGTH: 26
<212> TYPE: DNA
<213> ORGANISM: SARS-CoV2 Coronavirus
<220> FEATURE:
<221> NAME/KEY: misc_feature
<222> LOCATION: (1)..(26)
<223> OTHER INFORMATION: SARS-CoV-2 Polynucleotide Domain of Illustrative Sense-Strand Probe for Detecting the SARS-CoV-2 S Gene

<400> SEQUENCE: 222
ttctttatca gggtgttaac tgcaca 26

<210> SEQ ID NO 223
<211> LENGTH: 25
<212> TYPE: DNA
<213> ORGANISM: SARS-CoV2 Coronavirus
<220> FEATURE:
<221> NAME/KEY: misc_feature
<222> LOCATION: (1)..(25)
<223> OTHER INFORMATION: SARS-CoV-2 Polynucleotide Domain of Illustrative Sense-Strand Probe for Detecting the SARS-CoV-2 S Gene

<400> SEQUENCE: 223
ttctttatca ggatgttaac tgcac 25

<210> SEQ ID NO 224
<211> LENGTH: 25
<212> TYPE: DNA
<213> ORGANISM: SARS-CoV2 Coronavirus
<220> FEATURE:
<221> NAME/KEY: misc_feature
<222> LOCATION: (1)..(25)
<223> OTHER INFORMATION: SARS-CoV-2 Polynucleotide Domain of Illustrative Sense-Strand Probe for Detecting the SARS-CoV-2 S Gene

<400> SEQUENCE: 224
ttctttatca gggtgttaac tgcac 25

<210> SEQ ID NO 225
<211> LENGTH: 24
<212> TYPE: DNA
<213> ORGANISM: SARS-CoV2 Coronavirus
<220> FEATURE:
<221> NAME/KEY: misc_feature
<222> LOCATION: (1)..(24)
<223> OTHER INFORMATION: SARS-CoV-2 Polynucleotide Domain of Illustrative Sense-Strand Probe for Detecting the SARS-CoV-2 S Gene

<400> SEQUENCE: 225
tctttatcag gatgttaact gcac 24

<210> SEQ ID NO 226
<211> LENGTH: 24
<212> TYPE: DNA
<213> ORGANISM: SARS-CoV2 Coronavirus
<220> FEATURE:
<221> NAME/KEY: misc_feature
<222> LOCATION: (1)..(24)
<223> OTHER INFORMATION: SARS-CoV-2 Polynucleotide Domain of Illustrative Sense-Strand Probe for Detecting the SARS-CoV-2 S Gene

<400> SEQUENCE: 226
tctttatcag ggtgttaact gcac 24

<210> SEQ ID NO 227
<211> LENGTH: 23
<212> TYPE: DNA
<213> ORGANISM: SARS-CoV2 Coronavirus
<220> FEATURE:
<221> NAME/KEY: misc_feature
<222> LOCATION: (1)..(23)
<223> OTHER INFORMATION: SARS-CoV-2 Polynucleotide Domain of Illustrative Sense-Strand Probe for Detecting the SARS-CoV-2 S Gene

<400> SEQUENCE: 227
tctttatcag gatgttaact gca 23

<210> SEQ ID NO 228
<211> LENGTH: 23
<212> TYPE: DNA
<213> ORGANISM: SARS-CoV2 Coronavirus
<220> FEATURE:
<221> NAME/KEY: misc_feature
<222> LOCATION: (1)..(23)
<223> OTHER INFORMATION: SARS-CoV-2 Polynucleotide Domain of Illustrative Sense-Strand Probe for Detecting the SARS-CoV-2 S Gene

<400> SEQUENCE: 228
tctttatcag ggtgttaact gca 23

<210> SEQ ID NO 229
<211> LENGTH: 22
<212> TYPE: DNA
<213> ORGANISM: SARS-CoV2 Coronavirus
<220> FEATURE:
<221> NAME/KEY: misc_feature
<222> LOCATION: (1)..(22)
<223> OTHER INFORMATION: SARS-CoV-2 Polynucleotide Domain of Illustrative Sense-Strand Probe for Detecting the SARS-CoV-2 S Gene

<400> SEQUENCE: 229
ctttatcagg atgttaactg ca 22

<210> SEQ ID NO 230
<211> LENGTH: 22
<212> TYPE: DNA
<213> ORGANISM: SARS-CoV2 Coronavirus
<220> FEATURE:
<221> NAME/KEY: misc_feature
<222> LOCATION: (1)..(22)
<223> OTHER INFORMATION: SARS-CoV-2 Polynucleotide Domain of Illustrative Sense-Strand Probe for Detecting the SARS-CoV-2 S Gene

<400> SEQUENCE: 230
ctttatcagg gtgttaactg ca 22

<210> SEQ ID NO 231
<211> LENGTH: 21
<212> TYPE: DNA
<213> ORGANISM: SARS-CoV2 Coronavirus
<220> FEATURE:
<221> NAME/KEY: misc_feature
<222> LOCATION: (1)..(21)

```
<223> OTHER INFORMATION: SARS-CoV-2 Polynucleotide Domain of
      Illustrative Sense-Strand Probe for Detecting the SARS-CoV-2 S
      Gene

<400> SEQUENCE: 231

ctttatcagg atgttaactg c                                            21


<210> SEQ ID NO 232
<211> LENGTH: 21
<212> TYPE: DNA
<213> ORGANISM: SARS-CoV2 Coronavirus
<220> FEATURE:
<221> NAME/KEY: misc_feature
<222> LOCATION: (1)..(21)
<223> OTHER INFORMATION: SARS-CoV-2 Polynucleotide Domain of
      Illustrative Sense-Strand Probe for Detecting the SARS-CoV-2 S
      Gene

<400> SEQUENCE: 232

ctttatcagg gtgttaactg c                                            21


<210> SEQ ID NO 233
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of
      Illustrative Sense-Strand Probe for Detecting the SARS-CoV-2 S
      Gene

<400> SEQUENCE: 233

tttatcagga tgttaactgc                                              20


<210> SEQ ID NO 234
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of
      Illustrative Sense-Strand Probe for Detecting the SARS-CoV-2 S
      Gene

<400> SEQUENCE: 234

tttatcaggg tgttaactgc                                              20


<210> SEQ ID NO 235
<211> LENGTH: 19
<212> TYPE: DNA
<213> ORGANISM: SARS-CoV2 Coronavirus
<220> FEATURE:
<221> NAME/KEY: misc_feature
<222> LOCATION: (1)..(19)
<223> OTHER INFORMATION: SARS-CoV-2 Polynucleotide Domain of
      Illustrative Sense-Strand Probe for Detecting the SARS-CoV-2 S
      Gene

<400> SEQUENCE: 235

tttatcagga tgttaactg                                               19


<210> SEQ ID NO 236
<211> LENGTH: 19
<212> TYPE: DNA
<213> ORGANISM: SARS-CoV2 Coronavirus
<220> FEATURE:
<221> NAME/KEY: misc_feature
```

<222> LOCATION: (1)..(19)
<223> OTHER INFORMATION: SARS-CoV-2 Polynucleotide Domain of Illustrative Sense-Strand Probe for Detecting the SARS-CoV-2 S Gene

<400> SEQUENCE: 236
tttatcaggg tgttaactg 19

<210> SEQ ID NO 237
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: SARS-CoV-2 Polynucleotide Domain of Illustrative Sense-Strand Probe for Detecting the SARS-CoV-2 S Gene

<400> SEQUENCE: 237
ttatcaggat gttaactg 18

<210> SEQ ID NO 238
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: SARS-CoV-2 Polynucleotide Domain of Illustrative Sense-Strand Probe for Detecting the SARS-CoV-2 S Gene

<400> SEQUENCE: 238
ttatcagggt gttaactg 18

<210> SEQ ID NO 239
<211> LENGTH: 17
<212> TYPE: DNA
<213> ORGANISM: SARS-CoV2 Coronavirus
<220> FEATURE:
<221> NAME/KEY: misc_feature
<222> LOCATION: (1)..(17)
<223> OTHER INFORMATION: SARS-CoV-2 Polynucleotide Domain of Illustrative Sense-Strand Probe for Detecting the SARS-CoV-2 S Gene

<400> SEQUENCE: 239
tatcaggatg ttaactg 17

<210> SEQ ID NO 240
<211> LENGTH: 17
<212> TYPE: DNA
<213> ORGANISM: SARS-CoV2 Coronavirus
<220> FEATURE:
<221> NAME/KEY: misc_feature
<222> LOCATION: (1)..(17)
<223> OTHER INFORMATION: SARS-CoV-2 Polynucleotide Domain of Illustrative Sense-Strand Probe for Detecting the SARS-CoV-2 S Gene

<400> SEQUENCE: 240
tatcagggtg ttaactg 17

<210> SEQ ID NO 241
<211> LENGTH: 16
<212> TYPE: DNA
<213> ORGANISM: SARS-CoV2 Coronavirus
<220> FEATURE:

<221> NAME/KEY: misc_feature
<222> LOCATION: (1)..(16)
<223> OTHER INFORMATION: SARS-CoV-2 Polynucleotide Domain of Illustrative Sense-Strand Probe for Detecting the SARS-CoV-2 S Gene

<400> SEQUENCE: 241
tatcaggatg ttaact 16

<210> SEQ ID NO 242
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)
<223> OTHER INFORMATION: SARS-CoV-2 Polynucleotide Domain of Illustrative Sense-Strand Probe for Detecting the SARS-CoV-2 S Gene

<400> SEQUENCE: 242
tatcagggtg ttaact 16

<210> SEQ ID NO 243
<211> LENGTH: 15
<212> TYPE: DNA
<213> ORGANISM: SARS-CoV2 Coronavirus
<220> FEATURE:
<221> NAME/KEY: misc_feature
<222> LOCATION: (1)..(15)
<223> OTHER INFORMATION: SARS-CoV-2 Polynucleotide Domain of Illustrative Sense-Strand Probe for Detecting the SARS-CoV-2 S Gene

<400> SEQUENCE: 243
atcaggatgt taact 15

<210> SEQ ID NO 244
<211> LENGTH: 15
<212> TYPE: DNA
<213> ORGANISM: SARS-CoV2 Coronavirus
<220> FEATURE:
<221> NAME/KEY: misc_feature
<222> LOCATION: (1)..(15)
<223> OTHER INFORMATION: SARS-CoV-2 Polynucleotide Domain of Illustrative Sense-Strand Probe for Detecting the SARS-CoV-2 S Gene

<400> SEQUENCE: 244
atcagggtgt taact 15

<210> SEQ ID NO 245
<211> LENGTH: 14
<212> TYPE: DNA
<213> ORGANISM: SARS-CoV2 Coronavirus
<220> FEATURE:
<221> NAME/KEY: misc_feature
<222> LOCATION: (1)..(14)
<223> OTHER INFORMATION: SARS-CoV-2 Polynucleotide Domain of Illustrative Sense-Strand Probe for Detecting the SARS-CoV-2 S Gene

<400> SEQUENCE: 245
tcaggatgtt aact 14

<210> SEQ ID NO 246
<211> LENGTH: 14
<212> TYPE: DNA
<213> ORGANISM: SARS-CoV2 Coronavirus

```
<220> FEATURE:
<221> NAME/KEY: misc_feature
<222> LOCATION: (1)..(14)
<223> OTHER INFORMATION: SARS-CoV-2 Polynucleotide Domain of
      Illustrative Sense-Strand Probe for Detecting the SARS-CoV-2 S
      Gene

<400> SEQUENCE: 246

tcagggtgtt aact                                                      14


<210> SEQ ID NO 247
<211> LENGTH: 13
<212> TYPE: DNA
<213> ORGANISM: SARS-CoV2 Coronavirus
<220> FEATURE:
<221> NAME/KEY: misc_feature
<222> LOCATION: (1)..(13)
<223> OTHER INFORMATION: SARS-CoV-2 Polynucleotide Domain of
      Illustrative Sense-Strand Probe for Detecting the SARS-CoV-2 S
      Gene

<400> SEQUENCE: 247

tcaggatgtt aac                                                       13


<210> SEQ ID NO 248
<211> LENGTH: 13
<212> TYPE: DNA
<213> ORGANISM: SARS-CoV2 Coronavirus
<220> FEATURE:
<221> NAME/KEY: misc_feature
<222> LOCATION: (1)..(13)
<223> OTHER INFORMATION: SARS-CoV-2 Polynucleotide Domain of
      Illustrative Sense-Strand Probe for Detecting the SARS-CoV-2 S
      Gene

<400> SEQUENCE: 248

tcagggtgtt aac                                                       13


<210> SEQ ID NO 249
<211> LENGTH: 12
<212> TYPE: DNA
<213> ORGANISM: SARS-CoV2 Coronavirus
<220> FEATURE:
<221> NAME/KEY: misc_feature
<222> LOCATION: (1)..(12)
<223> OTHER INFORMATION: SARS-CoV-2 Polynucleotide Domain of
      Illustrative Sense-Strand Probe for Detecting the SARS-CoV-2 S
      Gene

<400> SEQUENCE: 249

tcaggatgtt aa                                                        12


<210> SEQ ID NO 250
<211> LENGTH: 12
<212> TYPE: DNA
<213> ORGANISM: SARS-CoV2 Coronavirus
<220> FEATURE:
<221> NAME/KEY: misc_feature
<222> LOCATION: (1)..(12)
<223> OTHER INFORMATION: SARS-CoV-2 Polynucleotide Domain of
      Illustrative Sense-Strand Probe for Detecting the SARS-CoV-2 S
      Gene

<400> SEQUENCE: 250

tcagggtgtt aa                                                        12


<210> SEQ ID NO 251
<211> LENGTH: 11
<212> TYPE: DNA
```

<213> ORGANISM: SARS-CoV2 Coronavirus
<220> FEATURE:
<221> NAME/KEY: misc_feature
<222> LOCATION: (1)..(11)
<223> OTHER INFORMATION: SARS-CoV-2 Polynucleotide Domain of Illustrative Sense-Strand Probe for Detecting the SARS-CoV-2 S Gene

<400> SEQUENCE: 251
tcaggatgtt a 11

<210> SEQ ID NO 252
<211> LENGTH: 11
<212> TYPE: DNA
<213> ORGANISM: SARS-CoV2 Coronavirus
<220> FEATURE:
<221> NAME/KEY: misc_feature
<222> LOCATION: (1)..(11)
<223> OTHER INFORMATION: SARS-CoV-2 Polynucleotide Domain of Illustrative Sense-Strand Probe for Detecting the SARS-CoV-2 S Gene

<400> SEQUENCE: 252
tcagggtgtt a 11

<210> SEQ ID NO 253
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of Illustrative Sense-Strand Probe for Detecting the SARS-CoV-2 S Gene

<400> SEQUENCE: 253
gcacagaagt ccctgttgct 20

<210> SEQ ID NO 254
<211> LENGTH: 19
<212> TYPE: DNA
<213> ORGANISM: SARS-CoV2 Coronavirus
<220> FEATURE:
<221> NAME/KEY: misc_feature
<222> LOCATION: (1)..(19)
<223> OTHER INFORMATION: SARS-CoV-2 Polynucleotide Domain of Illustrative Sense-Strand Probe for Detecting the SARS-CoV-2 S Gene

<400> SEQUENCE: 254
cacagaagtc cctgttgct 19

<210> SEQ ID NO 255
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: SARS-CoV-2 Polynucleotide Domain of Illustrative Sense-Strand Probe for Detecting the SARS-CoV-2 S Gene

<400> SEQUENCE: 255
acagaagtcc ctgttgct 18

<210> SEQ ID NO 256
<211> LENGTH: 17

```
<212> TYPE: DNA
<213> ORGANISM: SARS-CoV2 Coronavirus
<220> FEATURE:
<221> NAME/KEY: misc_feature
<222> LOCATION: (1)..(17)
<223> OTHER INFORMATION: SARS-CoV-2 Polynucleotide Domain of
      Illustrative Sense-Strand Probe for Detecting the SARS-CoV-2 S
      Gene

<400> SEQUENCE: 256

cagaagtccc tgttgct                                                   17


<210> SEQ ID NO 257
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of
      Illustrative Sense-Strand Probe for Detecting the SARS-CoV-2 S
      Gene

<400> SEQUENCE: 257

cagaagtccc tgttgctatt                                                20


<210> SEQ ID NO 258
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)
<223> OTHER INFORMATION: SARS-CoV-2 Polynucleotide Domain of
      Illustrative Sense-Strand Probe for Detecting the SARS-CoV-2 S
      Gene

<400> SEQUENCE: 258

agaagtccct gttgct                                                    16


<210> SEQ ID NO 259
<211> LENGTH: 15
<212> TYPE: DNA
<213> ORGANISM: SARS-CoV2 Coronavirus
<220> FEATURE:
<221> NAME/KEY: misc_feature
<222> LOCATION: (1)..(15)
<223> OTHER INFORMATION: SARS-CoV-2 Polynucleotide Domain of
      Illustrative Sense-Strand Probe for Detecting the SARS-CoV-2 S
      Gene

<400> SEQUENCE: 259

gaagtccctg ttgct                                                     15


<210> SEQ ID NO 260
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of
      Illustrative Sense-Strand Probe for Detecting the SARS-CoV-2 S
      Gene

<400> SEQUENCE: 260

tgcacagaag tccctgttgc                                                20


<210> SEQ ID NO 261
```

<211> LENGTH: 19
<212> TYPE: DNA
<213> ORGANISM: SARS-CoV2 Coronavirus
<220> FEATURE:
<221> NAME/KEY: misc_feature
<222> LOCATION: (1)..(19)
<223> OTHER INFORMATION: SARS-CoV-2 Polynucleotide Domain of Illustrative Sense-Strand Probe for Detecting the SARS-CoV-2 S Gene

<400> SEQUENCE: 261
tgcacagaag tccctgttg 19

<210> SEQ ID NO 262
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: SARS-CoV-2 Polynucleotide Domain of Illustrative Sense-Strand Probe for Detecting the SARS-CoV-2 S Gene

<400> SEQUENCE: 262
tgcacagaag tccctgtt 18

<210> SEQ ID NO 263
<211> LENGTH: 17
<212> TYPE: DNA
<213> ORGANISM: SARS-CoV2 Coronavirus
<220> FEATURE:
<221> NAME/KEY: misc_feature
<222> LOCATION: (1)..(17)
<223> OTHER INFORMATION: SARS-CoV-2 Polynucleotide Domain of Illustrative Sense-Strand Probe for Detecting the SARS-CoV-2 S Gene

<400> SEQUENCE: 263
tgcacagaag tccctgt 17

<210> SEQ ID NO 264
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)
<223> OTHER INFORMATION: SARS-CoV-2 Polynucleotide Domain of Illustrative Sense-Strand Probe for Detecting the SARS-CoV-2 S Gene

<400> SEQUENCE: 264
tgcacagaag tccctg 16

<210> SEQ ID NO 265
<211> LENGTH: 15
<212> TYPE: DNA
<213> ORGANISM: SARS-CoV2 Coronavirus
<220> FEATURE:
<221> NAME/KEY: misc_feature
<222> LOCATION: (1)..(15)
<223> OTHER INFORMATION: SARS-CoV-2 Polynucleotide Domain of Illustrative Sense-Strand Probe for Detecting the SARS-CoV-2 S Gene

<400> SEQUENCE: 265
tgcacagaag tccct 15

<210> SEQ ID NO 266
<211> LENGTH: 19
<212> TYPE: DNA
<213> ORGANISM: SARS-CoV2 Coronavirus
<220> FEATURE:
<221> NAME/KEY: misc_feature
<222> LOCATION: (1)..(19)
<223> OTHER INFORMATION: SARS-CoV-2 Polynucleotide Domain of Illustrative Sense-Strand Probe for Detecting the SARS-CoV-2 S Gene

<400> SEQUENCE: 266
gcacagaagt ccctgttgc 19

<210> SEQ ID NO 267
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: SARS-CoV-2 Polynucleotide Domain of Illustrative Sense-Strand Probe for Detecting the SARS-CoV-2 S Gene

<400> SEQUENCE: 267
cacagaagtc cctgttgc 18

<210> SEQ ID NO 268
<211> LENGTH: 17
<212> TYPE: DNA
<213> ORGANISM: SARS-CoV2 Coronavirus
<220> FEATURE:
<221> NAME/KEY: misc_feature
<222> LOCATION: (1)..(17)
<223> OTHER INFORMATION: SARS-CoV-2 Polynucleotide Domain of Illustrative Sense-Strand Probe for Detecting the SARS-CoV-2 S Gene

<400> SEQUENCE: 268
cacagaagtc cctgttg 17

<210> SEQ ID NO 269
<211> LENGTH: 17
<212> TYPE: DNA
<213> ORGANISM: SARS-CoV2 Coronavirus
<220> FEATURE:
<221> NAME/KEY: misc_feature
<222> LOCATION: (1)..(17)
<223> OTHER INFORMATION: SARS-CoV-2 Polynucleotide Domain of Illustrative Sense-Strand Probe for Detecting the SARS-CoV-2 S Gene

<400> SEQUENCE: 269
acagaagtcc ctgttgc 17

<210> SEQ ID NO 270
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)
<223> OTHER INFORMATION: SARS-CoV-2 Polynucleotide Domain of Illustrative Sense-Strand Probe for Detecting the SARS-CoV-2 S Gene

<400> SEQUENCE: 270
acagaagtcc ctgttg 16

<210> SEQ ID NO 271
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)
<223> OTHER INFORMATION: SARS-CoV-2 Polynucleotide Domain of Illustrative Sense-Strand Probe for Detecting the SARS-CoV-2 S Gene

<400> SEQUENCE: 271
cagaagtccc tgttgc 16

<210> SEQ ID NO 272
<211> LENGTH: 15
<212> TYPE: DNA
<213> ORGANISM: SARS-CoV2 Coronavirus
<220> FEATURE:
<221> NAME/KEY: misc_feature
<222> LOCATION: (1)..(15)
<223> OTHER INFORMATION: SARS-CoV-2 Polynucleotide Domain of Illustrative Sense-Strand Probe for Detecting the SARS-CoV-2 S Gene

<400> SEQUENCE: 272
cagaagtccc tgttg 15

<210> SEQ ID NO 273
<211> LENGTH: 31
<212> TYPE: DNA
<213> ORGANISM: SARS-CoV2 Coronavirus
<220> FEATURE:
<221> NAME/KEY: misc_feature
<222> LOCATION: (1)..(31)
<223> OTHER INFORMATION: SARS-CoV-2 Polynucleotide Domain of Illustrative Antisense-Strand Probe for Detecting the SARS-CoV-2 S Gene

<400> SEQUENCE: 273
tctgtgcagt taacatcctg ataaagaaca g 31

<210> SEQ ID NO 274
<211> LENGTH: 31
<212> TYPE: DNA
<213> ORGANISM: SARS-CoV2 Coronavirus
<220> FEATURE:
<221> NAME/KEY: misc_feature
<222> LOCATION: (1)..(31)
<223> OTHER INFORMATION: SARS-CoV-2 Polynucleotide Domain of Illustrative Antisense-Strand Probe for Detecting the SARS-CoV-2 S Gene

<400> SEQUENCE: 274
tctgtgcagt taacatcctg ataaagaaca g 31

<210> SEQ ID NO 275
<211> LENGTH: 31
<212> TYPE: DNA
<213> ORGANISM: SARS-CoV2 Coronavirus
<220> FEATURE:
<221> NAME/KEY: misc_feature
<222> LOCATION: (1)..(31)
<223> OTHER INFORMATION: SARS-CoV-2 Polynucleotide Domain of Illustrative Antisense-Strand Probe for Detecting the SARS-CoV-2 S Gene

<400> SEQUENCE: 275
tctgtgcagt taacaccctg ataaagaaca g 31

<210> SEQ ID NO 276
<211> LENGTH: 30
<212> TYPE: DNA
<213> ORGANISM: SARS-CoV2 Coronavirus
<220> FEATURE:
<221> NAME/KEY: misc_feature
<222> LOCATION: (1)..(30)
<223> OTHER INFORMATION: SARS-CoV-2 Polynucleotide Domain of Illustrative Antisense-Strand Probe for Detecting the SARS-CoV-2 S Gene

<400> SEQUENCE: 276
ctgtgcagtt aacatcctga taaagaacag 30

<210> SEQ ID NO 277
<211> LENGTH: 30
<212> TYPE: DNA
<213> ORGANISM: SARS-CoV2 Coronavirus
<220> FEATURE:
<221> NAME/KEY: misc_feature
<222> LOCATION: (1)..(30)
<223> OTHER INFORMATION: SARS-CoV-2 Polynucleotide Domain of Illustrative Antisense-Strand Probe for Detecting the SARS-CoV-2 S Gene

<400> SEQUENCE: 277
ctgtgcagtt aacaccctga taaagaacag 30

<210> SEQ ID NO 278
<211> LENGTH: 29
<212> TYPE: DNA
<213> ORGANISM: SARS-CoV2 Coronavirus
<220> FEATURE:
<221> NAME/KEY: misc_feature
<222> LOCATION: (1)..(29)
<223> OTHER INFORMATION: SARS-CoV-2 Polynucleotide Domain of Illustrative Antisense-Strand Probe for Detecting the SARS-CoV-2 S Gene

<400> SEQUENCE: 278
tgtgcagtta acatcctgat aaagaacag 29

<210> SEQ ID NO 279
<211> LENGTH: 29
<212> TYPE: DNA
<213> ORGANISM: SARS-CoV2 Coronavirus
<220> FEATURE:
<221> NAME/KEY: misc_feature
<222> LOCATION: (1)..(29)
<223> OTHER INFORMATION: SARS-CoV-2 Polynucleotide Domain of Illustrative Antisense-Strand Probe for Detecting the SARS-CoV-2 S Gene

<400> SEQUENCE: 279
tgtgcagtta acaccctgat aaagaacag 29

<210> SEQ ID NO 280
<211> LENGTH: 28
<212> TYPE: DNA
<213> ORGANISM: SARS-CoV2 Coronavirus
<220> FEATURE:
<221> NAME/KEY: misc_feature
<222> LOCATION: (1)..(28)
<223> OTHER INFORMATION: SARS-CoV-2 Polynucleotide Domain of Illustrative Antisense-Strand Probe for Detecting the SARS-CoV-2 S Gene

<400> SEQUENCE: 280
gtgcagttaa catcctgata aagaacag 28

<210> SEQ ID NO 281
<211> LENGTH: 28
<212> TYPE: DNA
<213> ORGANISM: SARS-CoV2 Coronavirus
<220> FEATURE:
<221> NAME/KEY: misc_feature
<222> LOCATION: (1)..(28)
<223> OTHER INFORMATION: SARS-CoV-2 Polynucleotide Domain of Illustrative Antisense-Strand Probe for Detecting the SARS-CoV-2 S Gene

<400> SEQUENCE: 281
gtgcagttaa caccctgata aagaacag 28

<210> SEQ ID NO 282
<211> LENGTH: 27
<212> TYPE: DNA
<213> ORGANISM: SARS-CoV2 Coronavirus
<220> FEATURE:
<221> NAME/KEY: misc_feature
<222> LOCATION: (1)..(27)
<223> OTHER INFORMATION: SARS-CoV-2 Polynucleotide Domain of Illustrative Antisense-Strand Probe for Detecting the SARS-CoV-2 S Gene

<400> SEQUENCE: 282
tgcagttaac atcctgataa agaacag 27

<210> SEQ ID NO 283
<211> LENGTH: 27
<212> TYPE: DNA
<213> ORGANISM: SARS-CoV2 Coronavirus
<220> FEATURE:
<221> NAME/KEY: misc_feature
<222> LOCATION: (1)..(27)
<223> OTHER INFORMATION: SARS-CoV-2 Polynucleotide Domain of Illustrative Antisense-Strand Probe for Detecting the SARS-CoV-2 S Gene

<400> SEQUENCE: 283
tgcagttaac accctgataa agaacag 27

<210> SEQ ID NO 284
<211> LENGTH: 26
<212> TYPE: DNA
<213> ORGANISM: SARS-CoV2 Coronavirus
<220> FEATURE:
<221> NAME/KEY: misc_feature
<222> LOCATION: (1)..(26)
<223> OTHER INFORMATION: SARS-CoV-2 Polynucleotide Domain of Illustrative Antisense-Strand Probe for Detecting the SARS-CoV-2 S Gene

<400> SEQUENCE: 284
gcagttaaca tcctgataaa gaacag 26

<210> SEQ ID NO 285
<211> LENGTH: 26
<212> TYPE: DNA
<213> ORGANISM: SARS-CoV2 Coronavirus
<220> FEATURE:
<221> NAME/KEY: misc_feature
<222> LOCATION: (1)..(26)
<223> OTHER INFORMATION: SARS-CoV-2 Polynucleotide Domain of Illustrative Antisense-Strand Probe for Detecting the SARS-CoV-2 S Gene

<400> SEQUENCE: 285
gcagttaaca ccctgataaa gaacag 26

<210> SEQ ID NO 286
<211> LENGTH: 25
<212> TYPE: DNA
<213> ORGANISM: SARS-CoV2 Coronavirus
<220> FEATURE:
<221> NAME/KEY: misc_feature
<222> LOCATION: (1)..(25)
<223> OTHER INFORMATION: SARS-CoV-2 Polynucleotide Domain of Illustrative Antisense-Strand Probe for Detecting the SARS-CoV-2 S Gene

<400> SEQUENCE: 286
cagttaacat cctgataaag aacag 25

<210> SEQ ID NO 287
<211> LENGTH: 25
<212> TYPE: DNA
<213> ORGANISM: SARS-CoV2 Coronavirus
<220> FEATURE:
<221> NAME/KEY: misc_feature
<222> LOCATION: (1)..(25)
<223> OTHER INFORMATION: SARS-CoV-2 Polynucleotide Domain of Illustrative Antisense-Strand Probe for Detecting the SARS-CoV-2 S Gene

<400> SEQUENCE: 287
cagttaacac cctgataaag aacag 25

<210> SEQ ID NO 288
<211> LENGTH: 24
<212> TYPE: DNA
<213> ORGANISM: SARS-CoV2 Coronavirus
<220> FEATURE:
<221> NAME/KEY: misc_feature
<222> LOCATION: (1)..(24)
<223> OTHER INFORMATION: SARS-CoV-2 Polynucleotide Domain of Illustrative Antisense-Strand Probe for Detecting the SARS-CoV-2 S Gene

<400> SEQUENCE: 288
agttaacatc ctgataaaga acag 24

<210> SEQ ID NO 289
<211> LENGTH: 24
<212> TYPE: DNA
<213> ORGANISM: SARS-CoV2 Coronavirus
<220> FEATURE:
<221> NAME/KEY: misc_feature
<222> LOCATION: (1)..(24)
<223> OTHER INFORMATION: SARS-CoV-2 Polynucleotide Domain of Illustrative Antisense-Strand Probe for Detecting the SARS-CoV-2 S Gene

<400> SEQUENCE: 289
agttaacacc ctgataaaga acag 24

<210> SEQ ID NO 290
<211> LENGTH: 23
<212> TYPE: DNA
<213> ORGANISM: SARS-CoV2 Coronavirus
<220> FEATURE:
<221> NAME/KEY: misc_feature
<222> LOCATION: (1)..(23)
<223> OTHER INFORMATION: SARS-CoV-2 Polynucleotide Domain of Illustrative Antisense-Strand Probe for Detecting the SARS-CoV-2 S Gene

<400> SEQUENCE: 290
gttaacatcc tgataaagaa cag 23

<210> SEQ ID NO 291
<211> LENGTH: 23
<212> TYPE: DNA
<213> ORGANISM: SARS-CoV2 Coronavirus
<220> FEATURE:
<221> NAME/KEY: misc_feature
<222> LOCATION: (1)..(23)
<223> OTHER INFORMATION: SARS-CoV-2 Polynucleotide Domain of Illustrative Antisense-Strand Probe for Detecting the SARS-CoV-2 S Gene

<400> SEQUENCE: 291
gttaacaccc tgataaagaa cag 23

<210> SEQ ID NO 292
<211> LENGTH: 22
<212> TYPE: DNA
<213> ORGANISM: SARS-CoV2 Coronavirus
<220> FEATURE:
<221> NAME/KEY: misc_feature
<222> LOCATION: (1)..(22)
<223> OTHER INFORMATION: SARS-CoV-2 Polynucleotide Domain of Illustrative Antisense-Strand Probe for Detecting the SARS-CoV-2 S Gene

<400> SEQUENCE: 292
ttaacatcct gataaagaac ag 22

<210> SEQ ID NO 293
<211> LENGTH: 22
<212> TYPE: DNA
<213> ORGANISM: SARS-CoV2 Coronavirus
<220> FEATURE:
<221> NAME/KEY: misc_feature
<222> LOCATION: (1)..(22)
<223> OTHER INFORMATION: SARS-CoV-2 Polynucleotide Domain of Illustrative Antisense-Strand Probe for Detecting the SARS-CoV-2 S Gene

<400> SEQUENCE: 293
ttaacaccct gataaagaac ag 22

<210> SEQ ID NO 294
<211> LENGTH: 21
<212> TYPE: DNA
<213> ORGANISM: SARS-CoV2 Coronavirus
<220> FEATURE:
<221> NAME/KEY: misc_feature
<222> LOCATION: (1)..(21)
<223> OTHER INFORMATION: SARS-CoV-2 Polynucleotide Domain of Illustrative Antisense-Strand Probe for Detecting the SARS-CoV-2 S Gene

<400> SEQUENCE: 294
taacatcctg ataaagaaca g 21

<210> SEQ ID NO 295
<211> LENGTH: 21
<212> TYPE: DNA
<213> ORGANISM: SARS-CoV2 Coronavirus
<220> FEATURE:
<221> NAME/KEY: misc_feature
<222> LOCATION: (1)..(21)
<223> OTHER INFORMATION: SARS-CoV-2 Polynucleotide Domain of Illustrative Antisense-Strand Probe for Detecting the SARS-CoV-2 S Gene

<400> SEQUENCE: 295
taacaccctg ataaagaaca g 21

<210> SEQ ID NO 296
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of Illustrative Antisense-Strand Probe for Detecting the SARS-CoV-2 S Gene

<400> SEQUENCE: 296
aacatcctga taaagaacag 20

<210> SEQ ID NO 297
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of Illustrative Antisense-Strand Probe for Detecting the SARS-CoV-2 S Gene

<400> SEQUENCE: 297
aacaccctga taaagaacag 20

<210> SEQ ID NO 298
<211> LENGTH: 30
<212> TYPE: DNA
<213> ORGANISM: SARS-CoV2 Coronavirus
<220> FEATURE:
<221> NAME/KEY: misc_feature
<222> LOCATION: (1)..(30)
<223> OTHER INFORMATION: SARS-CoV-2 Polynucleotide Domain of Illustrative Antisense-Strand Probe for Detecting the SARS-CoV-2 S Gene

<400> SEQUENCE: 298
tctgtgcagt taacatcctg ataaagaaca 30

<210> SEQ ID NO 299
<211> LENGTH: 30
<212> TYPE: DNA
<213> ORGANISM: SARS-CoV2 Coronavirus
<220> FEATURE:
<221> NAME/KEY: misc_feature
<222> LOCATION: (1)..(30)
<223> OTHER INFORMATION: SARS-CoV-2 Polynucleotide Domain of Illustrative Antisense-Strand Probe for Detecting the SARS-CoV-2 S Gene

<400> SEQUENCE: 299
tctgtgcagt taacaccctg ataaagaaca 30

<210> SEQ ID NO 300
<211> LENGTH: 29
<212> TYPE: DNA
<213> ORGANISM: SARS-CoV2 Coronavirus
<220> FEATURE:
<221> NAME/KEY: misc_feature
<222> LOCATION: (1)..(29)
<223> OTHER INFORMATION: SARS-CoV-2 Polynucleotide Domain of Illustrative Antisense-Strand Probe for Detecting the SARS-CoV-2 S Gene

<400> SEQUENCE: 300
tctgtgcagt taacatcctg ataaagaac 29

<210> SEQ ID NO 301
<211> LENGTH: 29
<212> TYPE: DNA
<213> ORGANISM: SARS-CoV2 Coronavirus
<220> FEATURE:
<221> NAME/KEY: misc_feature
<222> LOCATION: (1)..(29)
<223> OTHER INFORMATION: SARS-CoV-2 Polynucleotide Domain of Illustrative Antisense-Strand Probe for Detecting the SARS-CoV-2 S Gene

<400> SEQUENCE: 301
tctgtgcagt taacaccctg ataaagaac 29

<210> SEQ ID NO 302
<211> LENGTH: 28
<212> TYPE: DNA
<213> ORGANISM: SARS-CoV2 Coronavirus
<220> FEATURE:
<221> NAME/KEY: misc_feature
<222> LOCATION: (1)..(28)
<223> OTHER INFORMATION: SARS-CoV-2 Polynucleotide Domain of Illustrative Antisense-Strand Probe for Detecting the SARS-CoV-2 S Gene

<400> SEQUENCE: 302
tctgtgcagt taacatcctg ataaagaa 28

<210> SEQ ID NO 303
<211> LENGTH: 28
<212> TYPE: DNA
<213> ORGANISM: SARS-CoV2 Coronavirus
<220> FEATURE:
<221> NAME/KEY: misc_feature
<222> LOCATION: (1)..(28)
<223> OTHER INFORMATION: SARS-CoV-2 Polynucleotide Domain of Illustrative Antisense-Strand Probe for Detecting the SARS-CoV-2 S Gene

<400> SEQUENCE: 303
tctgtgcagt taacaccctg ataaagaa 28

<210> SEQ ID NO 304
<211> LENGTH: 27
<212> TYPE: DNA
<213> ORGANISM: SARS-CoV2 Coronavirus
<220> FEATURE:
<221> NAME/KEY: misc_feature
<222> LOCATION: (1)..(27)
<223> OTHER INFORMATION: SARS-CoV-2 Polynucleotide Domain of Illustrative Antisense-Strand Probe for Detecting the SARS-CoV-2 S Gene

<400> SEQUENCE: 304
tctgtgcagt taacatcctg ataaaga 27

<210> SEQ ID NO 305
<211> LENGTH: 27
<212> TYPE: DNA
<213> ORGANISM: SARS-CoV2 Coronavirus
<220> FEATURE:
<221> NAME/KEY: misc_feature
<222> LOCATION: (1)..(27)
<223> OTHER INFORMATION: SARS-CoV-2 Polynucleotide Domain of Illustrative Antisense-Strand Probe for Detecting the SARS-CoV-2 S Gene

<400> SEQUENCE: 305
tctgtgcagt taacaccctg ataaaga 27

<210> SEQ ID NO 306
<211> LENGTH: 26
<212> TYPE: DNA
<213> ORGANISM: SARS-CoV2 Coronavirus
<220> FEATURE:
<221> NAME/KEY: misc_feature
<222> LOCATION: (1)..(26)
<223> OTHER INFORMATION: SARS-CoV-2 Polynucleotide Domain of Illustrative Antisense-Strand Probe for Detecting the SARS-CoV-2 S Gene

<400> SEQUENCE: 306
tctgtgcagt taacatcctg ataaag 26

<210> SEQ ID NO 307
<211> LENGTH: 26
<212> TYPE: DNA
<213> ORGANISM: SARS-CoV2 Coronavirus
<220> FEATURE:
<221> NAME/KEY: misc_feature
<222> LOCATION: (1)..(26)
<223> OTHER INFORMATION: SARS-CoV-2 Polynucleotide Domain of Illustrative Antisense-Strand Probe for Detecting the SARS-CoV-2 S Gene

<400> SEQUENCE: 307
tctgtgcagt taacaccctg ataaag 26

<210> SEQ ID NO 308
<211> LENGTH: 25
<212> TYPE: DNA
<213> ORGANISM: SARS-CoV2 Coronavirus
<220> FEATURE:
<221> NAME/KEY: misc_feature
<222> LOCATION: (1)..(25)
<223> OTHER INFORMATION: SARS-CoV-2 Polynucleotide Domain of Illustrative Antisense-Strand Probe for Detecting the SARS-CoV-2 S Gene

<400> SEQUENCE: 308
tctgtgcagt taacatcctg ataaa 25

<210> SEQ ID NO 309
<211> LENGTH: 25
<212> TYPE: DNA
<213> ORGANISM: SARS-CoV2 Coronavirus
<220> FEATURE:
<221> NAME/KEY: misc_feature
<222> LOCATION: (1)..(25)
<223> OTHER INFORMATION: SARS-CoV-2 Polynucleotide Domain of Illustrative Antisense-Strand Probe for Detecting the SARS-CoV-2 S Gene

<400> SEQUENCE: 309
tctgtgcagt taacaccctg ataaa 25

<210> SEQ ID NO 310
<211> LENGTH: 24
<212> TYPE: DNA
<213> ORGANISM: SARS-CoV2 Coronavirus
<220> FEATURE:
<221> NAME/KEY: misc_feature
<222> LOCATION: (1)..(24)

<223> OTHER INFORMATION: SARS-CoV-2 Polynucleotide Domain of
      Illustrative Antisense-Strand Probe for Detecting the SARS-CoV-2 S
      Gene

<400> SEQUENCE: 310
tctgtgcagt taacatcctg ataa 24

<210> SEQ ID NO 311
<211> LENGTH: 24
<212> TYPE: DNA
<213> ORGANISM: SARS-CoV2 Coronavirus
<220> FEATURE:
<221> NAME/KEY: misc_feature
<222> LOCATION: (1)..(24)
<223> OTHER INFORMATION: SARS-CoV-2 Polynucleotide Domain of
      Illustrative Antisense-Strand Probe for Detecting the SARS-CoV-2 S
      Gene

<400> SEQUENCE: 311
tctgtgcagt taacaccctg ataa 24

<210> SEQ ID NO 312
<211> LENGTH: 23
<212> TYPE: DNA
<213> ORGANISM: SARS-CoV2 Coronavirus
<220> FEATURE:
<221> NAME/KEY: misc_feature
<222> LOCATION: (1)..(23)
<223> OTHER INFORMATION: SARS-CoV-2 Polynucleotide Domain of
      Illustrative Antisense-Strand Probe for Detecting the SARS-CoV-2 S
      Gene

<400> SEQUENCE: 312
tctgtgcagt taacatcctg ata 23

<210> SEQ ID NO 313
<211> LENGTH: 23
<212> TYPE: DNA
<213> ORGANISM: SARS-CoV2 Coronavirus
<220> FEATURE:
<221> NAME/KEY: misc_feature
<222> LOCATION: (1)..(23)
<223> OTHER INFORMATION: SARS-CoV-2 Polynucleotide Domain of
      Illustrative Antisense-Strand Probe for Detecting the SARS-CoV-2 S
      Gene

<400> SEQUENCE: 313
tctgtgcagt taacaccctg ata 23

<210> SEQ ID NO 314
<211> LENGTH: 22
<212> TYPE: DNA
<213> ORGANISM: SARS-CoV2 Coronavirus
<220> FEATURE:
<221> NAME/KEY: misc_feature
<222> LOCATION: (1)..(22)
<223> OTHER INFORMATION: SARS-CoV-2 Polynucleotide Domain of
      Illustrative Antisense-Strand Probe for Detecting the SARS-CoV-2 S
      Gene

<400> SEQUENCE: 314
tctgtgcagt taacatcctg at 22

<210> SEQ ID NO 315
<211> LENGTH: 22
<212> TYPE: DNA
<213> ORGANISM: SARS-CoV2 Coronavirus
<220> FEATURE:
<221> NAME/KEY: misc_feature
<222> LOCATION: (1)..(22)
<223> OTHER INFORMATION: SARS-CoV-2 Polynucleotide Domain of
      Illustrative Antisense-Strand Probe for Detecting the SARS-CoV-2 S
      Gene

<400> SEQUENCE: 315
tctgtgcagt taacaccctg at 22

<210> SEQ ID NO 316
<211> LENGTH: 21
<212> TYPE: DNA
<213> ORGANISM: SARS-CoV2 Coronavirus
<220> FEATURE:
<221> NAME/KEY: misc_feature
<222> LOCATION: (1)..(21)
<223> OTHER INFORMATION: SARS-CoV-2 Polynucleotide Domain of
      Illustrative Antisense-Strand Probe for Detecting the SARS-CoV-2 S
      Gene

<400> SEQUENCE: 316
tctgtgcagt taacatcctg a 21

<210> SEQ ID NO 317
<211> LENGTH: 21
<212> TYPE: DNA
<213> ORGANISM: SARS-CoV2 Coronavirus
<220> FEATURE:
<221> NAME/KEY: misc_feature
<222> LOCATION: (1)..(21)
<223> OTHER INFORMATION: SARS-CoV-2 Polynucleotide Domain of
      Illustrative Antisense-Strand Probe for Detecting the SARS-CoV-2 S
      Gene

<400> SEQUENCE: 317
tctgtgcagt taacaccctg a 21

<210> SEQ ID NO 318
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of
      Illustrative Antisense-Strand Probe for Detecting the SARS-CoV-2 S
      Gene

<400> SEQUENCE: 318
tctgtgcagt taacatcctg 20

<210> SEQ ID NO 319
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of
      Illustrative Antisense-Strand Probe for Detecting the SARS-CoV-2 S
      Gene

<400> SEQUENCE: 319
tctgtgcagt taacaccctg 20

<210> SEQ ID NO 320
<211> LENGTH: 30
<212> TYPE: DNA
<213> ORGANISM: SARS-CoV2 Coronavirus
<220> FEATURE:

<221> NAME/KEY: misc_feature
<222> LOCATION: (1)..(30)
<223> OTHER INFORMATION: SARS-CoV-2 Polynucleotide Domain of
      Illustrative Antisense-Strand Probe for Detecting the SARS-CoV-2 S
      Gene

<400> SEQUENCE: 320
ctgtgcagtt aacatcctga taaagaacag 30

<210> SEQ ID NO 321
<211> LENGTH: 30
<212> TYPE: DNA
<213> ORGANISM: SARS-CoV2 Coronavirus
<220> FEATURE:
<221> NAME/KEY: misc_feature
<222> LOCATION: (1)..(30)
<223> OTHER INFORMATION: SARS-CoV-2 Polynucleotide Domain of
      Illustrative Antisense-Strand Probe for Detecting the SARS-CoV-2 S
      Gene

<400> SEQUENCE: 321
ctgtgcagtt aacaccctga taaagaacag 30

<210> SEQ ID NO 322
<211> LENGTH: 29
<212> TYPE: DNA
<213> ORGANISM: SARS-CoV2 Coronavirus
<220> FEATURE:
<221> NAME/KEY: misc_feature
<222> LOCATION: (1)..(29)
<223> OTHER INFORMATION: SARS-CoV-2 Polynucleotide Domain of
      Illustrative Antisense-Strand Probe for Detecting the SARS-CoV-2 S
      Gene

<400> SEQUENCE: 322
ctgtgcagtt aacatcctga taaagaaca 29

<210> SEQ ID NO 323
<211> LENGTH: 29
<212> TYPE: DNA
<213> ORGANISM: SARS-CoV2 Coronavirus
<220> FEATURE:
<221> NAME/KEY: misc_feature
<222> LOCATION: (1)..(29)
<223> OTHER INFORMATION: SARS-CoV-2 Polynucleotide Domain of
      Illustrative Antisense-Strand Probe for Detecting the SARS-CoV-2 S
      Gene

<400> SEQUENCE: 323
ctgtgcagtt aacaccctga taaagaaca 29

<210> SEQ ID NO 324
<211> LENGTH: 28
<212> TYPE: DNA
<213> ORGANISM: SARS-CoV2 Coronavirus
<220> FEATURE:
<221> NAME/KEY: misc_feature
<222> LOCATION: (1)..(28)
<223> OTHER INFORMATION: SARS-CoV-2 Polynucleotide Domain of
      Illustrative Antisense-Strand Probe for Detecting the SARS-CoV-2 S
      Gene

<400> SEQUENCE: 324
tgtgcagtta acatcctgat aaagaaca 28

<210> SEQ ID NO 325
<211> LENGTH: 28
<212> TYPE: DNA
<213> ORGANISM: SARS-CoV2 Coronavirus -continued
<220> FEATURE:
<221> NAME/KEY: misc_feature
<222> LOCATION: (1)..(28)
<223> OTHER INFORMATION: SARS-CoV-2 Polynucleotide Domain of
      Illustrative Antisense-Strand Probe for Detecting the SARS-CoV-2 S
      Gene

<400> SEQUENCE: 325
tgtgcagtta acaccctgat aaagaaca 28

<210> SEQ ID NO 326
<211> LENGTH: 27
<212> TYPE: DNA
<213> ORGANISM: SARS-CoV2 Coronavirus
<220> FEATURE:
<221> NAME/KEY: misc_feature
<222> LOCATION: (1)..(27)
<223> OTHER INFORMATION: SARS-CoV-2 Polynucleotide Domain of
      Illustrative Antisense-Strand Probe for Detecting the SARS-CoV-2 S
      Gene

<400> SEQUENCE: 326
tgtgcagtta acatcctgat aaagaac 27

<210> SEQ ID NO 327
<211> LENGTH: 27
<212> TYPE: DNA
<213> ORGANISM: SARS-CoV2 Coronavirus
<220> FEATURE:
<221> NAME/KEY: misc_feature
<222> LOCATION: (1)..(27)
<223> OTHER INFORMATION: SARS-CoV-2 Polynucleotide Domain of
      Illustrative Antisense-Strand Probe for Detecting the SARS-CoV-2 S
      Gene

<400> SEQUENCE: 327
tgtgcagtta acaccctgat aaagaac 27

<210> SEQ ID NO 328
<211> LENGTH: 26
<212> TYPE: DNA
<213> ORGANISM: SARS-CoV2 Coronavirus
<220> FEATURE:
<221> NAME/KEY: misc_feature
<222> LOCATION: (1)..(26)
<223> OTHER INFORMATION: SARS-CoV-2 Polynucleotide Domain of
      Illustrative Antisense-Strand Probe for Detecting the SARS-CoV-2 S
      Gene

<400> SEQUENCE: 328
gtgcagttaa catcctgata aagaac 26

<210> SEQ ID NO 329
<211> LENGTH: 26
<212> TYPE: DNA
<213> ORGANISM: SARS-CoV2 Coronavirus
<220> FEATURE:
<221> NAME/KEY: misc_feature
<222> LOCATION: (1)..(26)
<223> OTHER INFORMATION: SARS-CoV-2 Polynucleotide Domain of
      Illustrative Antisense-Strand Probe for Detecting the SARS-CoV-2 S
      Gene

<400> SEQUENCE: 329
gtgcagttaa caccctgata aagaac 26

<210> SEQ ID NO 330
<211> LENGTH: 25
<212> TYPE: DNA

<213> ORGANISM: SARS-CoV2 Coronavirus
<220> FEATURE:
<221> NAME/KEY: misc_feature
<222> LOCATION: (1)..(25)
<223> OTHER INFORMATION: SARS-CoV-2 Polynucleotide Domain of Illustrative Antisense-Strand Probe for Detecting the SARS-CoV-2 S Gene

<400> SEQUENCE: 330
gtgcagttaa catcctgata aagaa 25

<210> SEQ ID NO 331
<211> LENGTH: 25
<212> TYPE: DNA
<213> ORGANISM: SARS-CoV2 Coronavirus
<220> FEATURE:
<221> NAME/KEY: misc_feature
<222> LOCATION: (1)..(25)
<223> OTHER INFORMATION: SARS-CoV-2 Polynucleotide Domain of Illustrative Antisense-Strand Probe for Detecting the SARS-CoV-2 S Gene

<400> SEQUENCE: 331
gtgcagttaa caccctgata aagaa 25

<210> SEQ ID NO 332
<211> LENGTH: 24
<212> TYPE: DNA
<213> ORGANISM: SARS-CoV2 Coronavirus
<220> FEATURE:
<221> NAME/KEY: misc_feature
<222> LOCATION: (1)..(24)
<223> OTHER INFORMATION: SARS-CoV-2 Polynucleotide Domain of Illustrative Antisense-Strand Probe for Detecting the SARS-CoV-2 S Gene

<400> SEQUENCE: 332
tgcagttaac atcctgataa agaa 24

<210> SEQ ID NO 333
<211> LENGTH: 24
<212> TYPE: DNA
<213> ORGANISM: SARS-CoV2 Coronavirus
<220> FEATURE:
<221> NAME/KEY: misc_feature
<222> LOCATION: (1)..(24)
<223> OTHER INFORMATION: SARS-CoV-2 Polynucleotide Domain of Illustrative Antisense-Strand Probe for Detecting the SARS-CoV-2 S Gene

<400> SEQUENCE: 333
tgcagttaac accctgataa agaa 24

<210> SEQ ID NO 334
<211> LENGTH: 23
<212> TYPE: DNA
<213> ORGANISM: SARS-CoV2 Coronavirus
<220> FEATURE:
<221> NAME/KEY: misc_feature
<222> LOCATION: (1)..(23)
<223> OTHER INFORMATION: SARS-CoV-2 Polynucleotide Domain of Illustrative Antisense-Strand Probe for Detecting the SARS-CoV-2 S Gene

<400> SEQUENCE: 334
tgcagttaac atcctgataa aga 23

<210> SEQ ID NO 335
<211> LENGTH: 23

```
<212> TYPE: DNA
<213> ORGANISM: SARS-CoV2 Coronavirus
<220> FEATURE:
<221> NAME/KEY: misc_feature
<222> LOCATION: (1)..(23)
<223> OTHER INFORMATION: SARS-CoV-2 Polynucleotide Domain of
      Illustrative Antisense-Strand Probe for Detecting the SARS-CoV-2 S
      Gene

<400> SEQUENCE: 335

tgcagttaac accctgataa aga                                          23


<210> SEQ ID NO 336
<211> LENGTH: 22
<212> TYPE: DNA
<213> ORGANISM: SARS-CoV2 Coronavirus
<220> FEATURE:
<221> NAME/KEY: misc_feature
<222> LOCATION: (1)..(22)
<223> OTHER INFORMATION: SARS-CoV-2 Polynucleotide Domain of
      Illustrative Antisense-Strand Probe for Detecting the SARS-CoV-2 S
      Gene

<400> SEQUENCE: 336

gcagttaaca tcctgataaa ga                                           22


<210> SEQ ID NO 337
<211> LENGTH: 22
<212> TYPE: DNA
<213> ORGANISM: SARS-CoV2 Coronavirus
<220> FEATURE:
<221> NAME/KEY: misc_feature
<222> LOCATION: (1)..(22)
<223> OTHER INFORMATION: SARS-CoV-2 Polynucleotide Domain of
      Illustrative Antisense-Strand Probe for Detecting the SARS-CoV-2 S
      Gene

<400> SEQUENCE: 337

gcagttaaca ccctgataaa ga                                           22


<210> SEQ ID NO 338
<211> LENGTH: 21
<212> TYPE: DNA
<213> ORGANISM: SARS-CoV2 Coronavirus
<220> FEATURE:
<221> NAME/KEY: misc_feature
<222> LOCATION: (1)..(21)
<223> OTHER INFORMATION: SARS-CoV-2 Polynucleotide Domain of
      Illustrative Antisense-Strand Probe for Detecting the SARS-CoV-2 S
      Gene

<400> SEQUENCE: 338

cagttaacat cctgataaag a                                            21


<210> SEQ ID NO 339
<211> LENGTH: 21
<212> TYPE: DNA
<213> ORGANISM: SARS-CoV2 Coronavirus
<220> FEATURE:
<221> NAME/KEY: misc_feature
<222> LOCATION: (1)..(21)
<223> OTHER INFORMATION: SARS-CoV-2 Polynucleotide Domain of
      Illustrative Antisense-Strand Probe for Detecting the SARS-CoV-2 S
      Gene

<400> SEQUENCE: 339

cagttaacac cctgataaag a                                            21


<210> SEQ ID NO 340
```

-continued

<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of Illustrative Antisense-Strand Probe for Detecting the SARS-CoV-2 S Gene

<400> SEQUENCE: 340
agttaacatc ctgataaaga 20

<210> SEQ ID NO 341
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of Illustrative Antisense-Strand Probe for Detecting the SARS-CoV-2 S Gene

<400> SEQUENCE: 341
agttaacacc ctgataaaga 20

<210> SEQ ID NO 342
<211> LENGTH: 19
<212> TYPE: DNA
<213> ORGANISM: SARS-CoV2 Coronavirus
<220> FEATURE:
<221> NAME/KEY: misc_feature
<222> LOCATION: (1)..(19)
<223> OTHER INFORMATION: SARS-CoV-2 Polynucleotide Domain of Illustrative Antisense-Strand Probe for Detecting the SARS-CoV-2 S Gene

<400> SEQUENCE: 342
agttaacatc ctgataaag 19

<210> SEQ ID NO 343
<211> LENGTH: 19
<212> TYPE: DNA
<213> ORGANISM: SARS-CoV2 Coronavirus
<220> FEATURE:
<221> NAME/KEY: misc_feature
<222> LOCATION: (1)..(19)
<223> OTHER INFORMATION: SARS-CoV-2 Polynucleotide Domain of Illustrative Antisense-Strand Probe for Detecting the SARS-CoV-2 S Gene

<400> SEQUENCE: 343
agttaacacc ctgataaag 19

<210> SEQ ID NO 344
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: SARS-CoV-2 Polynucleotide Domain of Illustrative Antisense-Strand Probe for Detecting the SARS-CoV-2 S Gene

<400> SEQUENCE: 344
gttaacatcc tgataaag 18

<210> SEQ ID NO 345
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: SARS-CoV-2 Polynucleotide Domain of Illustrative Antisense-Strand Probe for Detecting the SARS-CoV-2 S Gene

<400> SEQUENCE: 345
gttaacaccc tgataaag 18

<210> SEQ ID NO 346
<211> LENGTH: 17
<212> TYPE: DNA
<213> ORGANISM: SARS-CoV2 Coronavirus
<220> FEATURE:
<221> NAME/KEY: misc_feature
<222> LOCATION: (1)..(17)
<223> OTHER INFORMATION: SARS-CoV-2 Polynucleotide Domain of Illustrative Antisense-Strand Probe for Detecting the SARS-CoV-2 S Gene

<400> SEQUENCE: 346
gttaacatcc tgataaa 17

<210> SEQ ID NO 347
<211> LENGTH: 17
<212> TYPE: DNA
<213> ORGANISM: SARS-CoV2 Coronavirus
<220> FEATURE:
<221> NAME/KEY: misc_feature
<222> LOCATION: (1)..(17)
<223> OTHER INFORMATION: SARS-CoV-2 Polynucleotide Domain of Illustrative Antisense-Strand Probe for Detecting the SARS-CoV-2 S Gene

<400> SEQUENCE: 347
gttaacaccc tgataaa 17

<210> SEQ ID NO 348
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)
<223> OTHER INFORMATION: SARS-CoV-2 Polynucleotide Domain of Illustrative Antisense-Strand Probe for Detecting the SARS-CoV-2 S Gene

<400> SEQUENCE: 348
ttaacatcct gataaa 16

<210> SEQ ID NO 349
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)
<223> OTHER INFORMATION: SARS-CoV-2 Polynucleotide Domain of Illustrative Antisense-Strand Probe for Detecting the SARS-CoV-2 S Gene

<400> SEQUENCE: 349
ttaacaccct gataaa 16

<210> SEQ ID NO 350
<211> LENGTH: 15
<212> TYPE: DNA
<213> ORGANISM: SARS-CoV2 Coronavirus
<220> FEATURE:
<221> NAME/KEY: misc_feature
<222> LOCATION: (1)..(15)
<223> OTHER INFORMATION: SARS-CoV-2 Polynucleotide Domain of Illustrative Antisense-Strand Probe for Detecting the SARS-CoV-2 S Gene

<400> SEQUENCE: 350
ttaacatcct gataa 15

<210> SEQ ID NO 351
<211> LENGTH: 15
<212> TYPE: DNA
<213> ORGANISM: SARS-CoV2 Coronavirus
<220> FEATURE:
<221> NAME/KEY: misc_feature
<222> LOCATION: (1)..(15)
<223> OTHER INFORMATION: SARS-CoV-2 Polynucleotide Domain of Illustrative Antisense-Strand Probe for Detecting the SARS-CoV-2 S Gene

<400> SEQUENCE: 351
ttaacaccct gataa 15

<210> SEQ ID NO 352
<211> LENGTH: 14
<212> TYPE: DNA
<213> ORGANISM: SARS-CoV2 Coronavirus
<220> FEATURE:
<221> NAME/KEY: misc_feature
<222> LOCATION: (1)..(14)
<223> OTHER INFORMATION: SARS-CoV-2 Polynucleotide Domain of Illustrative Antisense-Strand Probe for Detecting the SARS-CoV-2 S Gene

<400> SEQUENCE: 352
taacatcctg ataa 14

<210> SEQ ID NO 353
<211> LENGTH: 14
<212> TYPE: DNA
<213> ORGANISM: SARS-CoV2 Coronavirus
<220> FEATURE:
<221> NAME/KEY: misc_feature
<222> LOCATION: (1)..(14)
<223> OTHER INFORMATION: SARS-CoV-2 Polynucleotide Domain of Illustrative Antisense-Strand Probe for Detecting the SARS-CoV-2 S Gene

<400> SEQUENCE: 353
taacaccctg ataa 14

<210> SEQ ID NO 354
<211> LENGTH: 13
<212> TYPE: DNA
<213> ORGANISM: SARS-CoV2 Coronavirus
<220> FEATURE:
<221> NAME/KEY: misc_feature
<222> LOCATION: (1)..(13)
<223> OTHER INFORMATION: SARS-CoV-2 Polynucleotide Domain of Illustrative Antisense-Strand Probe for Detecting the SARS-CoV-2 S Gene

<400> SEQUENCE: 354
taacatcctg ata 13

<210> SEQ ID NO 355
<211> LENGTH: 13
<212> TYPE: DNA
<213> ORGANISM: SARS-CoV2 Coronavirus
<220> FEATURE:
<221> NAME/KEY: misc_feature
<222> LOCATION: (1)..(13)
<223> OTHER INFORMATION: SARS-CoV-2 Polynucleotide Domain of Illustrative Antisense-Strand Probe for Detecting the SARS-CoV-2 S Gene

<400> SEQUENCE: 355
taacaccctg ata 13

<210> SEQ ID NO 356
<211> LENGTH: 12
<212> TYPE: DNA
<213> ORGANISM: SARS-CoV2 Coronavirus
<220> FEATURE:
<221> NAME/KEY: misc_feature
<222> LOCATION: (1)..(12)
<223> OTHER INFORMATION: SARS-CoV-2 Polynucleotide Domain of Illustrative Antisense-Strand Probe for Detecting the SARS-CoV-2 S Gene

<400> SEQUENCE: 356
taacatcctg at 12

<210> SEQ ID NO 357
<211> LENGTH: 12
<212> TYPE: DNA
<213> ORGANISM: SARS-CoV2 Coronavirus
<220> FEATURE:
<221> NAME/KEY: misc_feature
<222> LOCATION: (1)..(12)
<223> OTHER INFORMATION: SARS-CoV-2 Polynucleotide Domain of Illustrative Antisense-Strand Probe for Detecting the SARS-CoV-2 S Gene

<400> SEQUENCE: 357
taacaccctg at 12

<210> SEQ ID NO 358
<211> LENGTH: 10
<212> TYPE: DNA
<213> ORGANISM: SARS-CoV2 Coronavirus
<220> FEATURE:
<221> NAME/KEY: misc_feature
<222> LOCATION: (1)..(10)
<223> OTHER INFORMATION: SARS-CoV-2 Polynucleotide Domain of Illustrative Antisense-Strand Probe for Detecting the SARS-CoV-2 S Gene

<400> SEQUENCE: 358
taacatcctg 10

<210> SEQ ID NO 359
<211> LENGTH: 10
<212> TYPE: DNA
<213> ORGANISM: SARS-CoV2 Coronavirus
<220> FEATURE:
<221> NAME/KEY: misc_feature
<222> LOCATION: (1)..(10)
<223> OTHER INFORMATION: SARS-CoV-2 Polynucleotide Domain of Illustrative Antisense-Strand Probe for Detecting the SARS-CoV-2 S Gene

<400> SEQUENCE: 359
taacaccctg 10

<210> SEQ ID NO 360
<211> LENGTH: 11
<212> TYPE: DNA
<213> ORGANISM: SARS-CoV2 Coronavirus
<220> FEATURE:
<221> NAME/KEY: misc_feature
<222> LOCATION: (1)..(11)
<223> OTHER INFORMATION: SARS-CoV-2 Polynucleotide Domain of Illustrative Antisense-Strand Probe for Detecting the SARS-CoV-2 S Gene

<400> SEQUENCE: 360
aacatcctga t 11

<210> SEQ ID NO 361
<211> LENGTH: 11
<212> TYPE: DNA
<213> ORGANISM: SARS-CoV2 Coronavirus
<220> FEATURE:
<221> NAME/KEY: misc_feature
<222> LOCATION: (1)..(11)
<223> OTHER INFORMATION: SARS-CoV-2 Polynucleotide Domain of Illustrative Antisense-Strand Probe for Detecting the SARS-CoV-2 S Gene

<400> SEQUENCE: 361
aacaccctga t 11

<210> SEQ ID NO 362
<211> LENGTH: 10
<212> TYPE: DNA
<213> ORGANISM: SARS-CoV2 Coronavirus
<220> FEATURE:
<221> NAME/KEY: misc_feature
<222> LOCATION: (1)..(10)
<223> OTHER INFORMATION: SARS-CoV-2 Polynucleotide Domain of Illustrative Antisense-Strand Probe for Detecting the SARS-CoV-2 S Gene

<400> SEQUENCE: 362
aacatcctga 10

<210> SEQ ID NO 363
<211> LENGTH: 10
<212> TYPE: DNA
<213> ORGANISM: SARS-CoV2 Coronavirus
<220> FEATURE:
<221> NAME/KEY: misc_feature
<222> LOCATION: (1)..(10)
<223> OTHER INFORMATION: SARS-CoV-2 Polynucleotide Domain of Illustrative Antisense-Strand Probe for Detecting the SARS-CoV-2 S Gene

<400> SEQUENCE: 363
aacaccctga 10

<210> SEQ ID NO 364
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of Illustrative Antisense-Strand Probe for Detecting the SARS-CoV-2 S Gene

<400> SEQUENCE: 364
gcaacaggga cttctgtgca 20

<210> SEQ ID NO 365
<211> LENGTH: 19
<212> TYPE: DNA
<213> ORGANISM: SARS-CoV2 Coronavirus
<220> FEATURE:
<221> NAME/KEY: misc_feature
<222> LOCATION: (1)..(19)
<223> OTHER INFORMATION: SARS-CoV-2 Polynucleotide Domain of Illustrative Antisense-Strand Probe for Detecting the SARS-CoV-2 S Gene

<400> SEQUENCE: 365
caacagggac ttctgtgca 19

<210> SEQ ID NO 366
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: SARS-CoV-2 Polynucleotide Domain of Illustrative Antisense-Strand Probe for Detecting the SARS-CoV-2 S Gene

<400> SEQUENCE: 366
aacagggact tctgtgca 18

<210> SEQ ID NO 367
<211> LENGTH: 17
<212> TYPE: DNA
<213> ORGANISM: SARS-CoV2 Coronavirus
<220> FEATURE:
<221> NAME/KEY: misc_feature
<222> LOCATION: (1)..(17)
<223> OTHER INFORMATION: SARS-CoV-2 Polynucleotide Domain of Illustrative Antisense-Strand Probe for Detecting the SARS-CoV-2 S Gene

<400> SEQUENCE: 367
acagggactt ctgtgca 17

<210> SEQ ID NO 368
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)
<223> OTHER INFORMATION: SARS-CoV-2 Polynucleotide Domain of Illustrative Antisense-Strand Probe for Detecting the SARS-CoV-2 S Gene

<400> SEQUENCE: 368
cagggacttc tgtgca 16

<210> SEQ ID NO 369
<211> LENGTH: 15
<212> TYPE: DNA
<213> ORGANISM: SARS-CoV2 Coronavirus
<220> FEATURE:
<221> NAME/KEY: misc_feature
<222> LOCATION: (1)..(15)
<223> OTHER INFORMATION: SARS-CoV-2 Polynucleotide Domain of Illustrative Antisense-Strand Probe for Detecting the SARS-CoV-2 S Gene

<400> SEQUENCE: 369
agggacttct gtgca 15

<210> SEQ ID NO 370
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of Illustrative Antisense-Strand Probe for Detecting the SARS-CoV-2 S Gene

<400> SEQUENCE: 370
agcaacaggg acttctgtgc 20

<210> SEQ ID NO 371
<211> LENGTH: 19
<212> TYPE: DNA
<213> ORGANISM: SARS-CoV2 Coronavirus
<220> FEATURE:
<221> NAME/KEY: misc_feature
<222> LOCATION: (1)..(19)
<223> OTHER INFORMATION: SARS-CoV-2 Polynucleotide Domain of Illustrative Antisense-Strand Probe for Detecting the SARS-CoV-2 S Gene

<400> SEQUENCE: 371
agcaacaggg acttctgtg 19

<210> SEQ ID NO 372
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: SARS-CoV-2 Polynucleotide Domain of Illustrative Antisense-Strand Probe for Detecting the SARS-CoV-2 S Gene

<400> SEQUENCE: 372
agcaacaggg acttctgt 18

<210> SEQ ID NO 373
<211> LENGTH: 17
<212> TYPE: DNA
<213> ORGANISM: SARS-CoV2 Coronavirus
<220> FEATURE:
<221> NAME/KEY: misc_feature
<222> LOCATION: (1)..(17)
<223> OTHER INFORMATION: SARS-CoV-2 Polynucleotide Domain of Illustrative Antisense-Strand Probe for Detecting the SARS-CoV-2 S Gene

<400> SEQUENCE: 373
agcaacaggg acttctg 17

<210> SEQ ID NO 374
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)
<223> OTHER INFORMATION: SARS-CoV-2 Polynucleotide Domain of Illustrative Antisense-Strand Probe for Detecting the SARS-CoV-2 S Gene

<400> SEQUENCE: 374
agcaacaggg acttct 16

<210> SEQ ID NO 375
<211> LENGTH: 15
<212> TYPE: DNA
<213> ORGANISM: SARS-CoV2 Coronavirus
<220> FEATURE:
<221> NAME/KEY: misc_feature
<222> LOCATION: (1)..(15)
<223> OTHER INFORMATION: SARS-CoV-2 Polynucleotide Domain of Illustrative Antisense-Strand Probe for Detecting the SARS-CoV-2 S Gene

<400> SEQUENCE: 375
agcaacaggg acttc 15

<210> SEQ ID NO 376
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: SARS-CoV-2 Polynucleotide Domain of Illustrative Antisense-Strand Probe for Detecting the SARS-CoV-2 S Gene

<400> SEQUENCE: 376
gcaacaggga cttctgtgca 20

<210> SEQ ID NO 377
<211> LENGTH: 19
<212> TYPE: DNA
<213> ORGANISM: SARS-CoV2 Coronavirus
<220> FEATURE:
<221> NAME/KEY: misc_feature
<222> LOCATION: (1)..(19)
<223> OTHER INFORMATION: SARS-CoV-2 Polynucleotide Domain of Illustrative Antisense-Strand Probe for Detecting the SARS-CoV-2 S Gene

<400> SEQUENCE: 377
gcaacaggga cttctgtgc 19

<210> SEQ ID NO 378
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: SARS-CoV-2 Polynucleotide Domain of Illustrative Antisense-Strand Probe for Detecting the SARS-CoV-2 S Gene

<400> SEQUENCE: 378
caacagggac ttctgtgc 18

<210> SEQ ID NO 379
<211> LENGTH: 17
<212> TYPE: DNA
<213> ORGANISM: SARS-CoV2 Coronavirus
<220> FEATURE:
<221> NAME/KEY: misc_feature
<222> LOCATION: (1)..(17)
<223> OTHER INFORMATION: SARS-CoV-2 Polynucleotide Domain of Illustrative Antisense-Strand Probe for Detecting the SARS-CoV-2 S Gene

<400> SEQUENCE: 379
caacagggac ttctgtg 17

<210> SEQ ID NO 380
<211> LENGTH: 16
<212> TYPE: DNA
<213> ORGANISM: SARS-CoV2 Coronavirus
<220> FEATURE:
<221> NAME/KEY: misc_feature
<222> LOCATION: (1)..(16)
<223> OTHER INFORMATION: SARS-CoV-2 Polynucleotide Domain of Illustrative Antisense-Strand Probe for Detecting the SARS-CoV-2 S Gene

<400> SEQUENCE: 380
aacagggact tctgtg 16

<210> SEQ ID NO 381
<211> LENGTH: 15
<212> TYPE: DNA
<213> ORGANISM: SARS-CoV2 Coronavirus
<220> FEATURE:
<221> NAME/KEY: misc_feature
<222> LOCATION: (1)..(15)
<223> OTHER INFORMATION: SARS-CoV-2 Polynucleotide Domain of Illustrative Antisense-Strand Probe for Detecting the SARS-CoV-2 S Gene

<400> SEQUENCE: 381
aacagggact tctgt 15

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

<210> SEQ ID NO 393

<400> SEQUENCE: 393

000

<210> SEQ ID NO 394

<400> SEQUENCE: 394

000

<210> SEQ ID NO 395

<400> SEQUENCE: 395

000

<210> SEQ ID NO 396

<400> SEQUENCE: 396

000

<210> SEQ ID NO 397

<400> SEQUENCE: 397

000

<210> SEQ ID NO 398
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)

<223> OTHER INFORMATION: PCR Primer Oligonucleotide of Illustrative
      SARS-CoV-2 ORF1ab Scorpion Primer-Probe

<400> SEQUENCE: 398
gagttgatgg tcaagtagac 20

<210> SEQ ID NO 399
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: PCR Primer Oligonucleotide of Illustrative
      SARS-CoV-2 ORF1ab Scorpion Primer-Probe

<400> SEQUENCE: 399
gtagacttat ttagaaatgc 20

<210> SEQ ID NO 400
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: PCR Primer Oligonucleotide of Illustrative
      SARS-CoV-2 S Gene Scorpion Primer-Probe

<400> SEQUENCE: 400
ccaggttgct gttctttatc 20

<210> SEQ ID NO 401
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: PCR Primer Oligonucleotide of Illustrative
      SARS-CoV-2 S Gene Scorpion Primer-Probe

<400> SEQUENCE: 401
gttgctgttc tttatcagga 20

<210> SEQ ID NO 402
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: PCR Primer Oligonucleotide of Illustrative
      SARS-CoV-2 S Gene Scorpion Primer-Probe

<400> SEQUENCE: 402
gttgctgttc tttatcaggg 20

<210> SEQ ID NO 403
<211> LENGTH: 45
<212> TYPE: DNA
<213> ORGANISM: SARS-CoV2 Coronavirus
<220> FEATURE:
<221> NAME/KEY: misc_feature
<222> LOCATION: (1)..(45)
<223> OTHER INFORMATION: Illustrative LAMP ORF1ab FIP Primer

<400> SEQUENCE: 403
gaacaccatt acgggcattt ctatcttttt tgatggtaga gttga 45

<210> SEQ ID NO 404
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: Illustrative LAMP ORF1ab F3 Primer

<400> SEQUENCE: 404
tttgtgcacc actcactg 18

<210> SEQ ID NO 405
<211> LENGTH: 50
<212> TYPE: DNA
<213> ORGANISM: SARS-CoV2 Coronavirus
<220> FEATURE:
<221> NAME/KEY: misc_feature
<222> LOCATION: (1)..(50)
<223> OTHER INFORMATION: Illustrative LAMP ORF1ab BIP Primer

<400> SEQUENCE: 405
aggtagtgtt aaaggtttac aaccacaatt aatgtgactc cattaagact 50

<210> SEQ ID NO 406
<211> LENGTH: 20
<212> TYPE: DNA
<213> ORGANISM: SARS-CoV2 Coronavirus
<220> FEATURE:
<221> NAME/KEY: misc_feature
<222> LOCATION: (1)..(20)
<223> OTHER INFORMATION: Illustrative LAMP ORF1ab B3 Primer

<400> SEQUENCE: 406
ctgtgttttt acggcttctc 20

<210> SEQ ID NO 407
<211> LENGTH: 47
<212> TYPE: DNA
<213> ORGANISM: SARS-CoV2 Coronavirus
<220> FEATURE:
<221> NAME/KEY: misc_feature
<222> LOCATION: (1)..(47)
<223> OTHER INFORMATION: Illustrative LAMP S Gene FIP Primer

<400> SEQUENCE: 407
ctgtgcagtt aacatcctga taaagagtgt tataacacca ggaacaa 47

<210> SEQ ID NO 408
<211> LENGTH: 19
<212> TYPE: DNA
<213> ORGANISM: SARS-CoV2 Coronavirus
<220> FEATURE:
<221> NAME/KEY: misc_feature
<222> LOCATION: (1)..(19)
<223> OTHER INFORMATION: Illustrative LAMP S Gene F3 Primer

<400> SEQUENCE: 408
tgttcttttg gtggtgtca 19

<210> SEQ ID NO 409
<211> LENGTH: 46
<212> TYPE: DNA
<213> ORGANISM: SARS-CoV2 Coronavirus
<220> FEATURE:
<221> NAME/KEY: misc_feature
<222> LOCATION: (1)..(46)
<223> OTHER INFORMATION: Illustrative LAMP S Gene BIP Primer

<400> SEQUENCE: 409
gaagtccctg ttgctattca tgcgtgtttg aaaaacatta gaacct 46

<210> SEQ ID NO 410
<211> LENGTH: 18
<212> TYPE: DNA
<213> ORGANISM: SARS-CoV2 Coronavirus
<220> FEATURE:
<221> NAME/KEY: misc_feature
<222> LOCATION: (1)..(18)
<223> OTHER INFORMATION: Illustrative LAMP S Gene B3 Primer

<400> SEQUENCE: 410
gcccctatta aacagcct 18

<210> SEQ ID NO 411
<211> LENGTH: 144
<212> TYPE: DNA
<213> ORGANISM: SARS-CoV2 Coronavirus
<220> FEATURE:
<221> NAME/KEY: misc_feature
<222> LOCATION: (1)..(144)
<223> OTHER INFORMATION: SARS-CoV-2 ORF1ab Domain Amplified by
Illustrative ORF1ab LAMP Primers

<400> SEQUENCE: 411
tcttttttga tggtagagtt gatggtcaag tagacttatt tagaaatgcc cgtaatggtg 60
ttcttattac agaaggtagt gttaaaggtt tacaaccatc tgtaggtccc aaacaagcta 120
gtcttaatgg agtcacatta attg 144

<210> SEQ ID NO 412
<211> LENGTH: 144
<212> TYPE: DNA
<213> ORGANISM: SARS-CoV2 Coronavirus
<220> FEATURE:
<221> NAME/KEY: misc_feature
<222> LOCATION: (1)..(154)
<223> OTHER INFORMATION: Complement SARS-CoV-2 ORF1ab Domain Amplified
by Illustrative ORF1ab LAMP Primers

<400> SEQUENCE: 412
caattaatgt gactccatta agactagctt gtttgggacc tacagatggt tgtaaacctt 60
taacactacc ttctgtaata agaacaccat tacgggcatt tctaaataag tctacttgac 120
catcaactct accatcaaaa aaga 144

<210> SEQ ID NO 413
<211> LENGTH: 154
<212> TYPE: DNA
<213> ORGANISM: SARS-CoV2 Coronavirus
<220> FEATURE:
<221> NAME/KEY: misc_feature
<222> LOCATION: (1)..(154)
<223> OTHER INFORMATION: SARS-CoV-2 S Gene Domain Amplified by
Illustrative S Gene LAMP Primers

<400> SEQUENCE: 413
gtgttataac accaggaaca aatacttcta accaggttgc tgttctttat caggatgtta 60
actgcacaga agtccctgtt gctattcatg cagatcaact tactcctact tggcgtgttt 120
attctacagg ttctaatgtt tttcaaacac gtgc 154

<210> SEQ ID NO 414
<211> LENGTH: 154
<212> TYPE: DNA
<213> ORGANISM: SARS-CoV2 Coronavirus
<220> FEATURE:
<221> NAME/KEY: misc_feature
<222> LOCATION: (1)..(154)
<223> OTHER INFORMATION: Complement SARS-CoV-2 S Gene Domain Amplified by Illustrative S Gene LAMP Primers

<400> SEQUENCE: 414

```
gcacgtgttt gaaaaacatt agaacctgta gaataaacac gccaagtagg agtaagttga     60

tctgcatgaa tagcaacagg gacttctgtg cagttaacat cctgataaag aacagcaacc    120

tggttagaag tatttgttcc tggtgttata acac                                154
```

<210> SEQ ID NO 415
<211> LENGTH: 21290
<212> TYPE: DNA
<213> ORGANISM: SARS-CoV2 Coronavirus
<220> FEATURE:
<221> NAME/KEY: misc_feature
<222> LOCATION: (1)..(21290)
<223> OTHER INFORMATION: ORF1ab of SARS-CoV-2 of of GenBank NC_045512

<400> SEQUENCE: 415

```
atggagagcc ttgtccctgg tttcaacgag aaaacacacg tccaactcag tttgcctgtt     60

ttacaggttc gcgacgtgct cgtacgtggc tttggagact ccgtggagga ggtcttatca    120

gaggcacgtc aacatcttaa agatggcact tgtggcttag tagaagttga aaaaggcgtt    180

ttgcctcaac ttgaacagcc ctatgtgttc atcaaacgtt cggatgctcg aactgcacct    240

catggtcatg ttatggttga gctggtagca gaactcgaag gcattcagta cggtcgtagt    300

ggtgagacac ttggtgtcct tgtccctcat gtgggcgaaa taccagtggc ttaccgcaag    360

gttcttcttc gtaagaacgg taataaagga gctggtggcc atagttacgg cgccgatcta    420

aagtcatttg acttaggcga cgagcttggc actgatcctt atgaagattt tcaagaaaac    480

tggaacacta aacatagcag tggtgttacc cgtgaactca tgcgtgagct taacggaggg    540

gcatacactc gctatgtcga taacaacttc tgtggccctg atggctaccc tcttgagtgc    600

attaaagacc ttctagcacg tgctggtaaa gcttcatgca ctttgtccga acaactggac    660

tttattgaca ctaagagggg tgtatactgc tgccgtgaac atgagcatga aattgcttgg    720

tacacggaac gttctgaaaa gagctatgaa ttgcagacac cttttgaaat taaattggca    780

aagaaatttg acaccttcaa tggggaatgt ccaaattttg tatttccctt aaattccata    840

atcaagacta ttcaaccaag ggttgaaaag aaaaagcttg atggctttat gggtagaatt    900

cgatctgtct atccagttgc gtcaccaaat gaatgcaacc aaatgtgcct ttcaactctc    960

atgaagtgtg atcattgtgg tgaaacttca tggcagacgg gcgattttgt taaagccact   1020

tgcgaatttt gtggcactga gaatttgact aaagaaggtg ccactacttg tggttactta   1080

ccccaaaatg ctgttgttaa aatttattgt ccagcatgtc acaattcaga agtaggacct   1140

gagcatagtc ttgccgaata ccataatgaa tctggcttga aaaccattct tcgtaagggt   1200

ggtcgcacta ttgcctttgg aggctgtgtg ttctcttatg ttggttgcca taacaagtgt   1260

gcctattggg ttccacgtgc tagcgctaac ataggttgta accatacagg tgttgttgga   1320

gaaggttccg aaggtcttaa tgacaacctt cttgaaatac tccaaaaaga gaaagtcaac   1380

atcaatattg ttggtgactt taaacttaat gaagagatcg ccattatttt ggcatctttt   1440

tctgcttcca caagtgcttt tgtggaaact gtgaaaggtt tggattataa agcattcaaa   1500
```

-continued

```
caaattgttg aatcctgtgg taattttaaa gttacaaaag gaaaagctaa aaaaggtgcc   1560
tggaatattg gtgaacagaa atcaatactg agtcctcttt atgcatttgc atcagaggct   1620
gctcgtgttg tacgatcaat tttctcccgc actcttgaaa ctgctcaaaa ttctgtgcgt   1680
gttttacaga aggccgctat aacaatacta gatggaattt cacagtattc actgagactc   1740
attgatgcta tgatgttcac atctgatttg gctactaaca atctagttgt aatggcctac   1800
attacaggtg gtgttgttca gttgacttcg cagtggctaa ctaacatctt tggcactgtt   1860
tatgaaaaac tcaaacccgt ccttgattgg cttgaagaga agtttaagga aggtgtagag   1920
tttcttagag acggttggga aattgttaaa tttatctcaa cctgtgcttg tgaaattgtc   1980
ggtggacaaa ttgtcacctg tgcaaaggaa attaaggaga gtgttcagac attctttaag   2040
cttgtaaata aatttttggc tttgtgtgct gactctatca ttattggtgg agctaaactt   2100
aaagccttga atttaggtga aacatttgtc acgcactcaa agggattgta cagaaagtgt   2160
gttaaatcca gagaagaaac tggcctactc atgcctctaa aagccccaaa agaaattatc   2220
ttcttagagg gagaaacact tcccacagaa gtgttaacag aggaagttgt cttgaaaact   2280
ggtgatttac aaccattaga acaacctact agtgaagctg ttgaagctcc attggttggt   2340
acaccagttt gtattaacgg gcttatgttg ctcgaaatca aagacacaga aaagtactgt   2400
gcccttgcac ctaatatgat ggtaacaaac aataccttca cactcaaagg cggtgcacca   2460
acaaaggtta cttttggtga tgacactgtg atagaagtgc aaggttacaa gagtgtgaat   2520
atcacttttg aacttgatga aaggattgat aaagtactta atgagaagtg ctctgcctat   2580
acagttgaac tcggtacaga agtaaatgag ttcgcctgtg ttgtggcaga tgctgtcata   2640
aaaactttgc aaccagtatc tgaattactt acaccactgg gcattgattt agatgagtgg   2700
agtatggcta catactactt atttgatgag tctggtgagt ttaaattggc ttcacatatg   2760
tattgttctt tctaccctcc agatgaggat gaagaagaag gtgattgtga agaagaagag   2820
tttgagccat caactcaata tgagtatggt actgaagatg attaccaagg taaacctttg   2880
gaatttggtg ccacttctgc tgctcttcaa cctgaagaag agcaagaaga agattggtta   2940
gatgatgata gtcaacaaac tgttggtcaa caagacggca gtgaggacaa tcagacaact   3000
actattcaaa caattgttga ggttcaacct caattagaga tggaacttac accagttgtt   3060
cagactattg aagtgaatag ttttagtggt tatttaaaac ttactgacaa tgtatacatt   3120
aaaaatgcag acattgtgga agaagctaaa aaggtaaaac caacagtggt tgttaatgca   3180
gccaatgttt accttaaaca tggaggaggt gttgcaggag ccttaaataa ggctactaac   3240
aatgccatgc aagttgaatc tgatgattac atagctacta atggaccact taaagtgggt   3300
ggtagttgtg ttttaagcgg acacaatctt gctaaacact gtcttcatgt tgtcggccca   3360
aatgttaaca aaggtgaaga cattcaactt cttaagagtg cttatgaaaa ttttaatcag   3420
cacgaagttc tacttgcacc attattatca gctggtattt ttggtgctga ccctatacat   3480
tctttaagag tttgtgtaga tactgttcgc acaaatgtct acttagctgt ctttgataaa   3540
aatctctatg acaaacttgt ttcaagcttt ttggaaatga agagtgaaaa gcaagttgaa   3600
caaaagatcg ctgagattcc taaagaggaa gttaagccat ttataactga aagtaaacct   3660
tcagttgaac agagaaaaca agatgataag aaaatcaaag cttgtgttga agaagttaca   3720
acaactctgg aagaaactaa gttcctcaca gaaaacttgt tactttatat tgacattaat   3780
ggcaatcttc atccagattc tgccactctt gttagtgaca ttgacatcac tttcttaaag   3840
```

-continued

```
aaagatgctc catatatagt gggtgatgtt gttcaagagg gtgttttaac tgctgtggtt   3900
atacctacta aaaaggctgg tggcactact gaaatgctag cgaaagcttt gagaaaagtg   3960
ccaacagaca attatataac cacttacccg ggtcagggtt taaatggtta cactgtagag   4020
gaggcaaaga cagtgcttaa aaagtgtaaa agtgcctttt acattctacc atctattatc   4080
tctaatgaga agcaagaaat tcttggaact gtttcttgga atttgcgaga aatgcttgca   4140
catgcagaag aaacacgcaa attaatgcct gtctgtgtgg aaactaaagc catagtttca   4200
actatacagc gtaaatataa gggtattaaa atacaagagg gtgtggttga ttatggtgct   4260
agattttact tttacaccag taaaacaact gtagcgtcac ttatcaacac acttaacgat   4320
ctaaatgaaa ctcttgttac aatgccactt ggctatgtaa cacatggctt aaatttggaa   4380
gaagctgctc ggtatatgag atctctcaaa gtgccagcta cagtttctgt ttcttcacct   4440
gatgctgtta cagcgtataa tggttatctt acttcttctt ctaaaacacc tgaagaacat   4500
tttattgaaa ccatctcact tgctggttcc tataaagatt ggtcctattc tggacaatct   4560
acacaactag gtatagaatt tcttaagaga ggtgataaaa gtgtatatta cactagtaat   4620
cctaccacat tccacctaga tggtgaagtt atcacctttg acaatcttaa gacacttctt   4680
tctttgagag aagtgaggac tattaaggtg tttacaacag tagacaacat taacctccac   4740
acgcaagttg tggacatgtc aatgacatat ggacaacagt ttggtccaac ttatttggat   4800
ggagctgatg ttactaaaat aaaacctcat aattcacatg aaggtaaaac attttatgtt   4860
ttacctaatg atgacactct acgtgttgag gcttttgagt actaccacac aactgatcct   4920
agttttctgg gtaggtacat gtcagcatta aatcacacta aaaagtggaa atacccacaa   4980
gttaatggtt taacttctat taaatgggca gataacaact gttatcttgc cactgcattg   5040
ttaacactcc aacaaataga gttgaagttt aatccacctg ctctacaaga tgcttattac   5100
agagcaaggg ctggtgaagc tgctaacttt tgtgcactta tcttagccta ctgtaataag   5160
acagtaggtg agttaggtga tgttagagaa acaatgagtt acttgtttca acatgccaat   5220
ttagattctt gcaaaagagt cttgaacgtg gtgtgtaaaa cttgtggaca acagcagaca   5280
acccttaagg gtgtagaagc tgttatgtac atgggcacac tttcttatga acaatttaag   5340
aaaggtgttc agataccttg tacgtgtggt aaacaagcta caaaatatct agtacaacag   5400
gagtcacctt ttgttatgat gtcagcacca cctgctcagt atgaacttaa gcatggtaca   5460
tttacttgtg ctagtgagta cactggtaat taccagtgtg gtcactataa acatataact   5520
tctaaagaaa ctttgtattg catagacggt gctttactta caaagtcctc agaatacaaa   5580
ggtcctatta cggatgtttt ctacaaagaa aacagttaca caacaaccat aaaaccagtt   5640
acttataaat tggatggtgt tgtttgtaca gaaattgacc ctaagttgga caattattat   5700
aagaaagaca attcttattt cacagagcaa ccaattgatc ttgtaccaaa ccaaccatat   5760
ccaaacgcaa gcttcgataa ttttaagttt gtatgtgata atatcaaatt tgctgatgat   5820
ttaaaccagt taactggtta taagaaacct gcttcaagag agcttaaagt tacatttttc   5880
cctgacttaa atggtgatgt ggtggctatt gattataaac actacacacc ctcttttaag   5940
aaaggagcta aattgttaca taaacctatt gtttggcatg ttaacaatgc aactaataaa   6000
gccacgtata aaccaaatac ctggtgtata cgttgtcttt ggagcacaaa accagttgaa   6060
acatcaaatt cgtttgatgt actgaagtca gaggacgcgc agggaatgga taatcttgcc   6120
tgcgaagatc taaaaccagt ctctgaagaa gtagtggaaa atcctaccat acagaaagac   6180
gttcttgagt gtaatgtgaa aactaccgaa gttgtaggag acattatact taaaccagca   6240
```

aataatagtt taaaaattac agaagaggtt ggccacacag atctaatggc tgcttatgta 6300
gacaattcta gtcttactat taagaaacct aatgaattat ctagagtatt aggtttgaaa 6360
acccttgcta ctcatggttt agctgctgtt aatagtgtcc cttgggatac tatagctaat 6420
tatgctaagc cttttcttaa caaagttgtt agtacaacta ctaacatagt tacacggtgt 6480
ttaaaccgtg tttgtactaa ttatatgcct tatttcttta ctttattgct acaattgtgt 6540
acttttacta gaagtacaaa ttctagaatt aaagcatcta tgccgactac tatagcaaag 6600
aatactgtta agagtgtcgg taaattttgt ctagaggctt catttaatta tttgaagtca 6660
cctaattttt ctaaactgat aaatattata atttggtttt tactattaag tgtttgccta 6720
ggttctttaa tctactcaac cgctgcttta ggtgttttaa tgtctaattt aggcatgcct 6780
tcttactgta ctggttacag agaaggctat ttgaactcta ctaatgtcac tattgcaacc 6840
tactgtactg gttctatacc ttgtagtgtt tgtcttagtg gtttagattc tttagacacc 6900
tatccttctt tagaaactat acaaattacc atttcatctt ttaaatggga tttaactgct 6960
tttggcttag ttgcagagtg gtttttggca tatattcttt tcactaggtt tttctatgta 7020
cttggattgg ctgcaatcat gcaattgttt ttcagctatt ttgcagtaca ttttattagt 7080
aattcttggc ttatgtggtt aataattaat cttgtacaaa tggccccgat ttcagctatg 7140
gttagaatgt acatcttctt tgcatcattt tattatgtat ggaaaagtta tgtgcatgtt 7200
gtagacggtt gtaattcatc aacttgtatg atgtgttaca aacgtaatag agcaacaaga 7260
gtcgaatgta caactattgt taatggtgtt agaaggtcct tttatgtcta tgctaatgga 7320
ggtaaaggct tttgcaaact acacaattgg aattgtgtta attgtgatac attctgtgct 7380
ggtagtacat ttattagtga tgaagttgcg agagacttgt cactacagtt taaaagacca 7440
ataaatccta ctgaccagtc ttcttacatc gttgatagtg ttacagtgaa gaatggttcc 7500
atccatcttt actttgataa agctggtcaa aagacttatg aaagacattc tctctctcat 7560
tttgttaact tagacaacct gagagctaat aacactaaag gttcattgcc tattaatgtt 7620
atagtttttg atggtaaatc aaaatgtgaa gaatcatctg caaaatcagc gtctgtttac 7680
tacagtcagc ttatgtgtca acctatactg ttactagatc aggcattagt gtctgatgtt 7740
ggtgatagtg cggaagttgc agttaaaatg tttgatgctt acgttaatac gttttcatca 7800
acttttaacg taccaatgga aaaactcaaa acactagttg caactgcaga agctgaactt 7860
gcaaagaatg tgtccttaga caatgtctta tctactttta tttcagcagc tcggcaaggg 7920
tttgttgatt cagatgtaga aactaaagat gttgttgaat gtcttaaatt gtcacatcaa 7980
tctgacatag aagttactgg cgatagttgt aataactata tgctcaccta taacaaagtt 8040
gaaaacatga caccccgtga ccttggtgct tgtattgact gtagtgcgcg tcatattaat 8100
gcgcaggtag caaaaagtca caacattgct ttgatatgga acgttaaaga tttcatgtca 8160
ttgtctgaac aactacgaaa acaaatacgt agtgctgcta aaaagaataa cttacctttt 8220
aagttgacat gtgcaactac tagacaagtt gttaatgttg taacaacaaa gatagcactt 8280
aagggtggta aaattgttaa taattggttg aagcagttaa ttaaagttac acttgtgttc 8340
ctttttgttg ctgctatttt ctatttaata acacctgttc atgtcatgtc taaacatact 8400
gacttttcaa gtgaaatcat aggatacaag gctattgatg gtggtgtcac tcgtgacata 8460
gcatctacag atacttgttt tgctaacaaa catgctgatt ttgacacatg gtttagccag 8520
cgtggtggta gttatactaa tgacaaagct tgcccattga ttgctgcagt cataacaaga 8580
gaagtgggtt ttgtcgtgcc tggtttgcct ggcacgatat tacgcacaac taatggtgac 8640
tttttgcatt tcttacctag agtttttagt gcagttggta acatctgtta cacaccatca 8700
aaacttatag agtacactga ctttgcaaca tcagcttgtg ttttggctgc tgaatgtaca 8760
atttttaaag atgcttctgg taagccagta ccatattgtt atgataccaa tgtactagaa 8820
ggttctgttg cttatgaaag tttacgccct gacacacgtt atgtgctcat ggatggctct 8880
attattcaat ttcctaacac ctaccttgaa ggttctgtta gagtggtaac aacttttgat 8940
tctgagtact gtaggcacgg cacttgtgaa agatcagaag ctggtgtttg tgtatctact 9000
agtggtagat gggtacttaa caatgattat tacagatctt taccaggagt tttctgtggt 9060
gtagatgctg taaatttact tactaatatg tttacaccac taattcaacc tattggtgct 9120
ttggacatat cagcatctat agtagctggt ggtattgtag ctatcgtagt aacatgcctt 9180
gcctactatt ttatgaggtt tagaagagct tttggtgaat acagtcatgt agttgccttt 9240
aatactttac tattccttat gtcattcact gtactctgtt taacaccagt ttactcattc 9300
ttacctggtg tttattctgt tatttacttg tacttgacat tttatcttac taatgatgtt 9360 tctttttttag cacatattca gtggatggtt atgttcacac ctttagtacc tttctggata 9420
acaattgctt atatcatttg tatttccaca aagcatttct attggttctt tagtaattac 9480
ctaaagagac gtgtagtctt taatggtgtt tcctttagta cttttgaaga agctgcgctg 9540
tgcacctttt tgttaaataa agaaatgtat ctaaagttgc gtagtgatgt gctattacct 9600
cttacgcaat ataatagata cttagctctt tataataagt acaagtattt tagtggagca 9660
atggatacaa ctagctacag agaagctgct tgttgtcatc tcgcaaaggc tctcaatgac 9720
ttcagtaact caggttctga tgttctttac caaccaccac aaacctctat cacctcagct 9780
gttttgcaga gtggttttag aaaaatggca ttcccatctg gtaaagttga gggttgtatg 9840
gtacaagtaa cttgtggtac aactacactt aacggtcttt ggcttgatga cgtagtttac 9900
tgtccaagac atgtgatctg cacctctgaa gacatgctta accctaatta tgaagattta 9960
ctcattcgta agtctaatca taatttcttg gtacaggctg gtaatgttca actcagggtt 10020
attggacatt ctatgcaaaa ttgtgtactt aagcttaagg ttgatacagc caatcctaag 10080
acacctaagt ataagtttgt tcgcattcaa ccaggacaga ctttttcagt gttagcttgt 10140
tacaatggtt caccatctgg tgtttaccaa tgtgctatga ggcccaattt cactattaag 10200
ggttcattcc ttaatggttc atgtggtagt gttggtttta acatagatta tgactgtgtc 10260
tctttttgtt acatgcacca tatggaatta ccaactggag ttcatgctgg cacagactta 10320
gaaggtaact tttatggacc ttttgttgac aggcaaacag cacaagcagc tggtacggac 10380
acaactatta cagttaatgt tttagcttgg ttgtacgctg ctgttataaa tggagacagg 10440
tggtttctca atcgatttac cacaactctt aatgacttta accttgtggc tatgaagtac 10500
aattatgaac ctctaacaca agaccatgtt gacatactag gacctctttc tgctcaaact 10560
ggaattgccg ttttagatat gtgtgcttca ttaaaagaat tactgcaaaa tggtatgaat 10620
ggacgtacca tattgggtag tgctttatta gaagatgaat ttacaccttt tgatgttgtt 10680
agacaatgct caggtgttac tttccaaagt gcagtgaaaa gaacaatcaa gggtacacac 10740
cactggttgt tactcacaat tttgacttca cttttagttt tagtccagag tactcaatgg 10800
tctttgttct ttttttgta tgaaaatgcc tttttacctt ttgctatggg tattattgct 10860
atgtctgctt ttgcaatgat gtttgtcaaa cataagcatg catttctctg tttgtttttg 10920
ttaccttctc ttgccactgt agcttatttt aatatggtct atatgcctgc tagttgggtg 10980

```
atgcgtatta tgacatggtt ggatatggtt gatactagtt tgtctggttt taagctaaaa  11040
gactgtgtta tgtatgcatc agctgtagtg ttactaatcc ttatgacagc aagaactgtg  11100
tatgatgatg gtgctaggag agtgtggaca cttatgaatg tcttgacact cgtttataaa  11160
gtttattatg gtaatgcttt agatcaagcc atttccatgt gggctcttat aatctctgtt  11220
acttctaact actcaggtgt agttacaact gtcatgtttt tggccagagg tattgttttt  11280
atgtgtgttg agtattgccc tattttcttc ataactggta atacacttca gtgtataatg  11340
ctagtttatt gtttcttagg ctatttttgt acttgttact ttggcctctt ttgtttactc  11400
aaccgctact ttagactgac tcttggtgtt tatgattact tagtttctac acaggagttt  11460
agatatatga attcacaggg actactccca cccaagaata gcatagatgc cttcaaactc  11520
aacattaaat tgttgggtgt tggtggcaaa ccttgtatca aagtagccac tgtacagtct  11580
aaaatgtcag atgtaaagtg cacatcagta gtcttactct cagttttgca acaactcaga  11640
gtagaatcat catctaaatt gtgggctcaa tgtgtccagt tacacaatga cattctctta  11700
gctaaagata ctactgaagc ctttgaaaaa atggtttcac tactttctgt tttgctttcc  11760
atgcagggtg ctgtagacat aaacaagctt tgtgaagaaa tgctggacaa cagggcaacc  11820
ttacaagcta tagcctcaga gtttagttcc cttccatcat atgcagcttt tgctactgct  11880
caagaagctt atgagcaggc tgttgctaat ggtgattctg aagttgttct taaaaagttg  11940
aagaagtctt tgaatgtggc taaatctgaa tttgaccgtg atgcagccat gcaacgtaag  12000
ttggaaaaga tggctgatca agctatgacc caaatgtata aacaggctag atctgaggac  12060
aagagggcaa aagttactag tgctatgcag acaatgcttt tcactatgct tagaaagttg  12120
gataatgatg cactcaacaa cattatcaac aatgcaagag atggttgtgt tcccttgaac  12180
ataataccte ttacaacagc agccaaacta atggttgtca taccagacta taacacatat  12240
aaaaatacgt gtgatggtac aacatttact tatgcatcag cattgtggga aatccaacag  12300
gttgtagatg cagatagtaa aattgttcaa cttagtgaaa ttagtatgga caattcacct  12360
aatttagcat ggcctcttat tgtaacagct ttaagggcca attctgctgt caaattacag  12420
aataatgagc ttagtcctgt tgcactacga cagatgtctt gtgctgccgg tactacacaa  12480
actgcttgca ctgatgacaa tgcgttagct tactacaaca caacaaaggg aggtaggttt  12540
gtacttgcac tgttatccga tttacaggat ttgaaatggg ctagattccc taagagtgat  12600
ggaactggta ctatctatac agaactggaa ccaccttgta ggtttgttac agacacacct  12660
aaaggtccta aagtgaagta tttatacttt attaaaggat taaacaacct aaatagaggt  12720
atggtacttg gtagtttagc tgccacagta cgtctacaag ctggtaatgc aacagaagtg  12780
cctgccaatt caactgtatt atctttctgt gcttttgctg tagatgctgc taaagcttac  12840
aaagattatc tagctagtgg gggacaacca atcactaatt gtgttaagat gttgtgtaca  12900
cacactggta ctggtcaggc aataacagtt acaccggaag ccaatatgga tcaagaatcc  12960
tttggtggtg catcgtgttg tctgtactgc cgttgccaca tagatcatcc aaatcctaaa  13020
ggattttgtg acttaaaagg taagtatgta caaataccta caacttgtgc taatgaccct  13080
gtgggtttta cacttaaaaa cacagtctgt accgtctgcg gtatgtggaa aggttatggc  13140
tgtagttgtg atcaactccg cgaacccatg cttcagtcag ctgatgcaca atcgttttta  13200
aacgggtttg cggtgtaagt gcagcccgtc ttacaccgtg cggcacaggc actagtactg  13260
atgtcgtata cagggctttt gacatctaca atgataaagt agctggtttt gctaaattcc  13320
```

-continued

```
taaaaactaa ttgttgtcgc ttccaagaaa aggacgaaga tgacaattta attgattctt  13380
actttgtagt taagagacac actttctcta actaccaaca tgaagaaaca atttataatt  13440
tacttaagga ttgtccagct gttgctaaac atgacttctt taagtttaga atagacggtg  13500
acatggtacc acatatatca cgtcaacgtc ttactaaata cacaatggca gacctcgtct  13560
atgctttaag gcattttgat gaaggtaatt gtgacacatt aaaagaaata cttgtcacat  13620
acaattgttg tgatgatgat tatttcaata aaaaggactg gtatgatttt gtagaaaacc  13680
cagatatatt acgcgtatac gccaacttag gtgaacgtgt acgccaagct ttgttaaaaa  13740
cagtacaatt ctgtgatgcc atgcgaaatg ctggtattgt tggtgtactg acattagata  13800
atcaagatct caatggtaac tggtatgatt tcggtgattt catacaaacc acgccaggta  13860
gtggagttcc tgttgtagat tcttattatt cattgttaat gcctatatta accttgacca  13920
gggctttaac tgcagagtca catgttgaca ctgacttaac aaagccttac attaagtggg  13980
atttgttaaa atatgacttc acggaagaga ggttaaaact ctttgaccgt tattttaaat  14040
attgggatca gacataccac ccaaattgtg ttaactgttt ggatgacaga tgcattctgc  14100
attgtgcaaa ctttaatgtt ttattctcta cagtgttccc acctacaagt tttggaccac  14160
tagtgagaaa aatatttgtt gatggtgttc catttgtagt ttcaactgga taccacttca  14220
gagagctagg tgttgtacat aatcaggatg taaacttaca tagctctaga cttagtttta  14280
aggaattact tgtgtatgct gctgaccctg ctatgcacgc tgcttctggt aatctattac  14340
tagataaacg cactacgtgc ttttcagtag ctgcacttac taacaatgtt gcttttcaaa  14400
ctgtcaaacc cggtaatttt aacaaagact tctatgactt tgctgtgtct aagggtttct  14460
ttaaggaagg aagttctgtt gaattaaaac acttcttctt tgctcaggat ggtaatgctg  14520
ctatcagcga ttatgactac tatcgttata atctaccaac aatgtgtgat atcagacaac  14580
tactatttgt agttgaagtt gttgataagt actttgattg ttacgatggt ggctgtatta  14640
atgctaacca agtcatcgtc aacaacctag acaaatcagc tggttttcca tttaataaat  14700
ggggtaaggc tagactttat tatgattcaa tgagttatga ggatcaagat gcacttttcg  14760
catatacaaa acgtaatgtc atccctacta taactcaaat gaatcttaag tatgccatta  14820
gtgcaaagaa tagagctcgc accgtagctg gtgtctctat ctgtagtact atgaccaata  14880
gacagtttca tcaaaaatta ttgaaatcaa tagccgccac tagaggagct actgtagtaa  14940
ttggaacaag caaattctat ggtggttggc acaacatgtt aaaaactgtt tatagtgatg  15000
tagaaaaccc tcaccttatg ggttgggatt atcctaaatg tgatagagcc atgcctaaca  15060
tgcttagaat tatggcctca cttgttcttg ctcgcaaaca tacaacgtgt tgtagcttgt  15120
cacaccgttt ctatagatta gctaatgagt gtgctcaagt attgagtgaa atggtcatgt  15180
gtggcggttc actatatgtt aaaccaggtg gaacctcatc aggagatgcc acaactgctt  15240
atgctaatag tgtttttaac atttgtcaag ctgtcacggc caatgttaat gcacttttat  15300
ctactgatgg taacaaaatt gccgataagt atgtccgcaa tttacaacac agactttatg  15360
agtgtctcta tagaaataga gatgttgaca cagactttgt gaatgagttt tacgcatatt  15420
tgcgtaaaca tttctcaatg atgatactct ctgacgatgc tgttgtgtgt ttcaatagca  15480
cttatgcatc tcaaggtcta gtggctagca taaagaactt taagtcagtt ctttattatc  15540
aaaacaatgt ttttatgtct gaagcaaaat gttggactga gactgacctt actaaaggac  15600
ctcatgaatt ttgctctcaa catacaatgc tagttaaaca gggtgatgat tatgtgtacc  15660
ttccttaccc agatccatca agaatcctag ggccggctgt tttgtagat gatatcgtaa  15720
```

aaacagatgg tacacttatg attgaacggt tcgtgtcttt agctatagat gcttacccac 15780
ttactaaaca tcctaatcag gagtatgctg atgtctttca tttgtactta caatacataa 15840
gaaagctaca tgatgagtta acaggacaca tgttagacat gtattctgtt atgcttacta 15900
atgataacac ttcaaggtat tgggaacctg agttttatga ggctatgtac acaccgcata 15960
cagtcttaca ggctgttggg gcttgtgttc tttgcaattc acagacttca ttaagatgtg 16020
gtgcttgcat acgtagacca ttcttatgtt gtaaatgctg ttacgaccat gtcatatcaa 16080
catcacataa attagtcttg tctgttaatc cgtatgtttg caatgctcca ggttgtgatg 16140
tcacagatgt gactcaactt tacttaggag gtatgagcta ttattgtaaa tcacataaac 16200
cacccattag ttttccattg tgtgctaatg gacaagtttt tggtttatat aaaaatacat 16260
gtgttggtag cgataatgtt actgacttta atgcaattgc aacatgtgac tggacaaatg 16320
ctggtgatta cattttagct aacacctgta ctgaaagact caagcttttt gcagcagaaa 16380
cgctcaaagc tactgaggag acatttaaac tgtcttatgg tattgctact gtacgtgaag 16440
tgctgtctga cagagaatta catctttcat gggaagttgg taaacctaga ccaccactta 16500
accgaaatta tgtctttact ggttatcgtg taactaaaaa cagtaaagta caaataggag 16560
agtacacctt tgaaaaaggt gactatggtg atgctgttgt ttaccgaggt acaacaactt 16620
acaaattaaa tgttggtgat tattttgtgc tgacatcaca tacagtaatg ccattaagtg 16680
cacctacact agtgccacaa gagcactatg ttagaattac tggcttatac ccaacactca 16740
atatctcaga tgagttttct agcaatgttg caaattatca aaaggttggt atgcaaaagt 16800
attctacact ccagggacca cctggtactg gtaagagtca ttttgctatt ggcctagctc 16860
tctactaccc ttctgctcgc atagtgtata cagcttgctc tcatgccgct gttgatgcac 16920
tatgtgagaa ggcattaaaa tatttgccta tagataaatg tagtagaatt atacctgcac 16980
gtgctcgtgt agagtgtttt gataaattca aagtgaattc aacattagaa cagtatgtct 17040
tttgtactgt aaatgcattg cctgagacga cagcagatat agttgtcttt gatgaaattt 17100
caatggccac aaattatgat ttgagtgttg tcaatgccag attacgtgct aagcactatg 17160
tgtacattgg cgaccctgct caattacctg caccacgcac attgctaact aagggcacac 17220
tagaaccaga atatttcaat tcagtgtgta gacttatgaa aactataggt ccagacatgt 17280
tcctcggaac ttgtcggcgt tgtcctgctg aaattgttga cactgtgagt gctttggttt 17340
atgataataa gcttaaagca cataaagaca aatcagctca atgctttaaa atgttttata 17400
agggtgttat cacgcatgat gtttcatctg caattaacag gccacaaata ggcgtggtaa 17460
gagaattcct tacacgtaac cctgcttgga gaaaagctgt ctttatttca ccttataatt 17520
cacagaatgc tgtagcctca aagattttgg gactaccaac tcaaactgtt gattcatcac 17580
agggctcaga atatgactat gtcatattca ctcaaaccac tgaaacagct cactcttgta 17640
atgtaaacag atttaatgtt gctattacca gagcaaaagt aggcatactt tgcataatgt 17700
ctgatagaga cctttatgac aagttgcaat ttacaagtct tgaaattcca cgtaggaatg 17760
tggcaacttt acaagctgaa aatgtaacag gactctttaa agattgtagt aaggtaatca 17820
ctgggttaca tcctacacag gcacctacac acctcagtgt tgacactaaa ttcaaaactg 17880
aaggtttatg tgttgacata cctggcatac ctaaggacat gacctataga agactcatct 17940
ctatgatggg ttttaaaatg aattatcaag ttaatggtta ccctaacatg tttatcaccc 18000
gcgaagaagc tataagacat gtacgtgcat ggattggctt cgatgtcgag ggtgtcatg 18060 ctactagaga agctgttggt accaatttac ctttacagct aggtttttct acaggtgtta 18120
acctagttgc tgtacctaca ggttatgttg atacacctaa taatacagat ttttccagag 18180
ttagtgctaa accaccgcct ggagatcaat ttaaacacct cataccactt atgtacaaag 18240
gacttccttg gaatgtagtg cgtataaaga ttgtacaaat gttaagtgac acacttaaaa 18300
atctctctga cagagtcgta tttgtcttat gggcacatgg ctttgagttg acatctatga 18360
agtattttgt gaaaatagga cctgagcgca cctgttgtct atgtgataga cgtgccacat 18420
gcttttccac tgcttcagac acttatgcct gttggcatca ttctattgga tttgattacg 18480
tctataatcc gtttatgatt gatgttcaac aatggggttt tacaggtaac ctacaaagca 18540
accatgatct gtattgtcaa gtccatggta atgcacatgt agctagttgt gatgcaatca 18600
tgactaggtg tctagctgtc cacgagtgct ttgttaagcg tgttgactgg actattgaat 18660
atcctataat tggtgatgaa ctgaagatta atgcggcttg tagaaaggtt caacacatgg 18720
ttgttaaagc tgcattatta gcagacaaat tcccagttct tcacgacatt ggtaacccta 18780
aagctattaa gtgtgtacct caagctgatg tagaatggaa gttctatgat gcacagcctt 18840
gtagtgacaa agcttataaa atagaagaat tattctattc ttatgccaca cattctgaca 18900
aattcacaga tggtgtatgc ctattttgga attgcaatgt cgatagatat cctgctaatt 18960
ccattgtttg tagatttgac actagagtgc tatctaacct taacttgcct ggttgtgatg 19020
gtggcagttt gtatgtaaat aaacatgcat tccacacacc agcttttgat aaaagtgctt 19080
ttgttaattt aaaacaatta ccatttttct attactctga cagtccatgt gagtctcatg 19140
gaaaacaagt agtgtcagat atagattatg taccactaaa gtctgctacg tgtataacac 19200
gttgcaattt aggtggtgct gtctgtagac atcatgctaa tgagtacaga ttgtatctcg 19260
atgcttataa catgatgatc tcagctggct ttagcttgtg ggtttacaaa caatttgata 19320
cttataacct ctggaacact tttacaagac ttcagagttt agaaaatgtg gcttttaatg 19380
ttgtaaataa gggacacttt gatggacaac agggtgaagt accagtttct atcattaata 19440
acactgttta cacaaaagtt gatggtgttg atgtagaatt gtttgaaaat aaaacaacat 19500
tacctgttaa tgtagcattt gagctttggg ctaagcgcaa cattaaacca gtaccagagg 19560
tgaaaatact caataatttg ggtgtggaca ttgctgctaa tactgtgatc tgggactaca 19620
aaagagatgc tccagcacat atatctacta ttggtgtttg ttctatgact gacatagcca 19680
agaaaccaac tgaaacgatt tgtgcaccac tcactgtctt ttttgatggt agagttgatg 19740
gtcaagtaga cttatttaga aatgcccgta atggtgttct tattacagaa ggtagtgtta 19800
aaggtttaca accatctgta ggtcccaaac aagctagtct taatggagtc acattaattg 19860
gagaagccgt aaaaacacag ttcaattatt ataagaaagt tgatggtgtt gtccaacaat 19920
tacctgaaac ttactttact cagagtagaa atttacaaga atttaaaccc aggagtcaaa 19980
tggaaattga tttcttagaa ttagctatgg atgaattcat tgaacggtat aaattagaag 20040
gctatgcctt cgaacatatc gtttatggag attttagtca tagtcagtta ggtggtttac 20100
atctactgat tggactagct aaacgtttta aggaatcacc ttttgaatta gaagatttta 20160
ttcctatgga cagtacagtt aaaaactatt tcataacaga tgcgcaaaca ggttcatcta 20220
agtgtgtgtg ttctgttatt gatttattac ttgatgattt tgttgaaata ataaaatccc 20280
aagatttatc tgtagtttct aaggttgtca aagtgactat tgactataca gaaatttcat 20340
ttatgctttg gtgtaaagat ggccatgtag aaacatttta cccaaaatta caatctagtc 20400
aagcgtggca accgggtgtt gctatgccta atctttacaa aatgcaaaga atgctattag 20460

-continued

```
aaaagtgtga ccttcaaaat tatggtgata gtgcaacatt acctaaaggc ataatgatga  20520

atgtcgcaaa atatactcaa ctgtgtcaat atttaaacac attaacatta gctgtaccct  20580

ataatatgag agttatacat tttggtgctg gttctgataa aggagttgca ccaggtacag  20640

ctgttttaag acagtggttg cctacgggta cgctgcttgt cgattcagat cttaatgact  20700

ttgtctctga tgcagattca actttgattg gtgattgtgc aactgtacat acagctaata  20760

aatgggatct cattattagt gatatgtacg accctaagac taaaaatgtt acaaaagaaa  20820

atgactctaa agagggtttt ttcacttaca tttgtgggtt tatacaacaa aagctagctc  20880

ttggaggttc cgtggctata aagataacag aacattcttg gaatgctgat ctttataagc  20940

tcatgggaca cttcgcatgg tggacagcct ttgttactaa tgtgaatgcg tcatcatctg  21000

aagcattttt aattggatgt aattatcttg gcaaaccacg cgaacaaata gatggttatg  21060

tcatgcatgc aaattacata ttttggagga atacaaatcc aattcagttg tcttcctatt  21120

ctttatttga catgagtaaa tttcccctta aattaagggg tactgctgtt atgtctttaa  21180

aagaaggtca aatcaatgat atgattttat ctcttcttag taaaggtaga cttataatta  21240

gagaaaacaa cagagttgtt atttctagtg atgttcttgt taacaactaa             21290
```